(12) United States Patent
Whitehouse et al.

(10) Patent No.: US 7,498,356 B2
(45) Date of Patent: Mar. 3, 2009

(54) SUBSTITUTED AMINO CARBOXYLIC ACIDS

(75) Inventors: Darren Whitehouse, Westbrook, CT (US); Shaojing Hu, Hamden, CT (US); Michael C. Van Zandt, Guilford, CT (US); Garrett Parker, Branford, CT (US)

(73) Assignee: The Institutes for Pharmaceutical Discovery LLC, Branford, CT (US)

( * ) Notice: Subject to any disclaimer, the term of this patent is extended or adjusted under 35 U.S.C. 154(b) by 145 days.

(21) Appl. No.: 11/283,456

(22) Filed: Nov. 18, 2005

(65) Prior Publication Data

US 2006/0122223 A1    Jun. 8, 2006

Related U.S. Application Data

(60) Provisional application No. 60/628,977, filed on Nov. 18, 2004.

(51) Int. Cl.
*A61K 31/343* (2006.01)
*C07D 307/91* (2006.01)

(52) U.S. Cl. .................. 514/468; 549/460; 549/461
(58) Field of Classification Search .............. 514/468; 549/460, 461
See application file for complete search history.

(56) References Cited

U.S. PATENT DOCUMENTS

| 5,968,980 | A | 10/1999 | Kawashima et al. |
| 6,232,322 | B1 | 5/2001 | Malamas et al. |
| 6,855,843 | B2 * | 2/2005 | Sircar et al. ............ 560/38 |
| 7,358,248 | B2 | 4/2008 | Whitehouse et al. |

FOREIGN PATENT DOCUMENTS

| DE | 3322574 | 12/1983 |
| EP | 327335 | 8/1989 |
| JP | 9118662 | 5/1997 |
| WO | WO99/36393 | 7/1999 |
| WO | WO01/12183 | 2/2001 |
| WO | WO2004/099170 | 11/2004 |
| WO | WO2004/099171 | 11/2004 |
| WO | WO2006/055725 | 5/2006 |

OTHER PUBLICATIONS

Probert Encyclopedia, on-line ediction of definition of alkanoyl.*
David E. Moller, Nature, 2001, vol. 44, No. 13, p. 821-827.*
Nature, 2001, vol. 44, No. 13, pp. 821-827. (This reference was provided with the previous Notice of Allowance Office action).*
Malamas, M.S. et al., "Novel Benzofuran and Benzothiophene Biphenyls as Inhibitors of Protein Tyrosine Phosphatase 1B with Antihyperglycemic Properties", Journal of Medicinal Chemistry, American Chemical Society, vol. 43, No. 7, Apr. 6, 2000, pp. 1293-1310.
Database Caplus Chemical Abstracts Service, Columbus, Ohio, XP002300704, Database Accession No. 1997:440050, "Prepartion of Urea Moiety-Containing Peptide Derivatives as Neutral Endopeptidase and Angiotensin Converting Enzyme Inhibitors".
International Search Report PCT/US2004/013700 dated Feb. 10, 2005.
Macor, John E. et al., "The 5-HT3 Antagonist Tropisetron (ICS 205-930) is a Potent and Selective a7 Nicotinic Receptor Partial Agonist", Bioorganic & Medicinal Chemistry Letters, vol. 11, 2001, pp. 319-321.
International Search Report PCT/US2005/041706 dated Jul. 7, 2006.

* cited by examiner

*Primary Examiner*—Kamal A Saeed
*Assistant Examiner*—Yong Chu
(74) *Attorney, Agent, or Firm*—McDonnell Boehnen Hulbert & Berghoff LLP

(57) ABSTRACT

Disclosed are compound and pharmaceutically acceptable salts of formula (I):

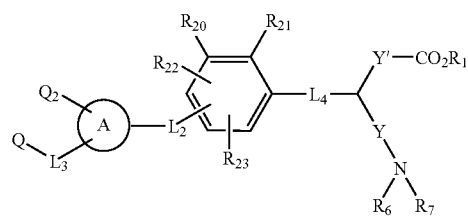

which are useful in the treatment of metabolic disorders related to insulin resistance, leptin resistance, or hyperglycemia. Compound of the invention include inhibitors of protein tyrosine phosphatase, in particular protein tyrosine phosphatase-1B (PTP-1B), that are useful in the treatment of diabetes and other PTP mediated diseases, such as cancer, neurodegenerative diseases and the like. Also disclosed are pharmaceutical compositions comprising aforementioned conditions using such compounds.

11 Claims, No Drawings

SUBSTITUTED AMINO CARBOXYLIC ACIDS

This application claims priority from U.S. Provisional Application Ser. No. 60/628,977, which was filed Nov. 18, 2004, the disclosure of which is incorporated herein by reference in its entirety.

BACKGROUND OF THE INVENTION

1. Field of the Invention

The invention relates to substituted carboxylic acids and more specifically to such compounds that are useful in the treatment of syndrome X (consisting of such abnormalities as obesity, dyslipidemia, hypercoagulation, hypertension, insulin resistance and leading to heart disease and diabetes), obesity, diabetes, immunological disease, bleeding disorders and/or cancer. More specifically, it relates to such compounds that are capable of inhibiting Protein tyrosine phosphatases (PTPs), in particular Protein tyrosine phosphatase-1B (PTP-1B) which is a negative regulator of the insulin and leptin signaling pathway and improves insulin-sensitivity.

2. Description of the Related Art

This invention relates to a class of heterocycle substituted carboxylic acids that are inhibitors of various PTPs, in particular PTP-1B.

Protein tyrosine phosphatases are a large family of trans-membrane or intracellular enzymes that dephosphorylate substrates involved in a variety of regulatory processes (Fischer et al., 1991, Science 253:401-406). Protein tyrosine phosphatase-1B (PTP-1B) is an approximately 50 kd intracellular protein, which is present in abundant amounts in various human tissues (Charbonneau et al., 1989, Proc. Natl. Acad. Sci. USA 86:5252-5256; Goldstein, 1993, Receptor 3:1-15).

Determining which proteins are substrates of PTP-1B has been of considerable interest. One substrate which has aroused especial interest is the insulin receptor. The binding of insulin to its receptor results in autophosphorylation of the domain. This causes activation of the insulin receptor tyrosine kinase, which phosphorylates the various insulin receptor substrate (IRS) proteins that propagate the insulin signaling event further downstream to mediate insulin's various biological effects.

Seely et al., 1996, Diabetes 45:1379-1385 ("Seely") studied the relationship of PTP-1B and the insulin receptor in vitro. Seely constructed a glutathione S-transferase (GST) fusion protein of PTP-1B that had a point mutation in the PTP-1B catalytic domain. Although catalytically inactive, this fusion protein was able to bind to the insulin receptor, as demonstrated by its ability to precipitate the insulin receptor from purified receptor preparations and from whole cell lysates derived from cells expressing the insulin receptor.

Ahmad et al., 1995, J. Biol. Chem. 270:20503-20508 used osmotic loading to introduce PTP-1B neutralizing antibodies into rat KRC-7 hepatoma cells. The presence of the antibody in the cells resulted in an increase of 42% and 38%, respectively, in insulin stimulated DNA synthesis and phosphatidyinositol 3' kinase activity. Insulin receptor autophosphorylation and insulin receptor substrate-1 tyrosine phosphorylation were increased 2.2 and 2.0-fold, respectively, in the antibody-loaded cells. The antibody-loaded cells also showed a 57% increase in insulin stimulated insulin receptor kinase activity toward exogenous peptide substrates.

Kennedy et al., 1999, Science 283: 1544-1548 showed that protein tyrosine phosphatase PTP-1B is a negative regulator of the insulin signaling pathway, indicating that inhibitors of this enzyme are beneficial in the treatment of Type 2 diabetes, which appears to involve a defect in an early process in insulin signal transduction rather than a structural defect in the insulin receptor itself. (J. M. Olefsky, W. T. Garvey, R. R. Henry, D. Brillon, S. Matthai and G. R. Freidenberg, G. R. (1988).) Cellular mechanisms of insulin resistance in non-insulindependent (Type II) diabetes. (Am. J. Med. 85: Suppl. 5A, 86-105.) A drug that improved insulin sensitivity would have several advantages over traditional therapy of NIDDM using sulfonylureas, which do not alleviate insulin resistance but instead compensate by increasing insulin secretion.

Ragab et al (2003, J. Biol. Chem 278(42), 40923-32) showed that PTP 1B is involved in regulating platelet aggregation. Hence, inhibition of PTP 1B can be predicted to have an effect on bleeding disorder, and cardiovascular disease.

Romsicki et al., (2003, Arch Biochem. Biophys 414(1), 40-50) showed that TC PTP is structurally and functionally very similar. A PTP 1B inhibitor is very likely to also inhibit TC PTP. A knockout of the TC PTP gene produces a phenotype with impaired immune function. (You-Ten et al., 1997, J. Exp. Med. 186(5), 683-93). Hence, inhibitors of PTP 1B can be predict to inhibit TC PTP and modulate immune response.

It has also been demonstrated that PT-P1B is a negative regulator of leptin signaling (Kaszua et al. MolCell. Endocrinology, 195:109-118, 2002). PTP-1B deficient mice show enhanced potency for exogenous leptin to suppress food intake (Cheng, et al. Developmental Cell 2:497-503, 2002). Thus, inhibitors of PTP-1B augment the beneficial effects of leptin on food intake, body weight regulation and metabolism, in normal individuals and leptin resistant individuals.

Therefore, inhibitors of PTPs, and inhibitors of PTP-1B in particular, are useful in controlling or treating obesity, syndrome X, Type 2 diabetes, in improving glucose tolerance, and in improving insulin sensitivity in patients in need thereof. Such compounds are also useful in treating or controlling other PTP mediated diseases, such as the treatment of cancer, neurodegenerative diseases, immunological disorders, bleeding and cardiovascular disorders, and the like.

SUMMARY OF THE INVENTION

In a broad aspect, the invention encompasses the compounds of formula (I) shown below, pharmaceutical compositions containing the compounds and methods employing such compounds or compositions in the treatment of diabetes and/or cancer.

The invention provides compounds of formula I:

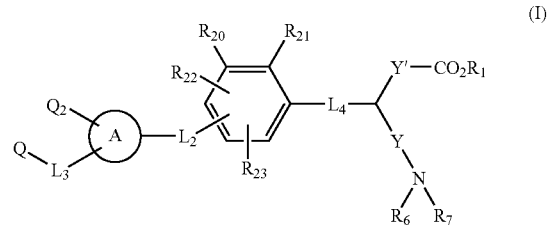

and pharmaceutically acceptable salts thereof, wherein
$R_1$ is H, $C_1$-$C_6$ alkyl, phenyl($C_1$-$C_6$)alkyl, or $C_3$-$C_6$ alkenyl;
$R_6$ and $R_7$ are independently H, $C_1$-$C_6$ alkyl, aryl($C_1$-$C_6$) alkyl, ($C_1$-$C_6$) alkanoyl optionally substituted with 1 or 2 groups independently selected from amino, mono or dialkylamino, —NHaryl, —N($C_1$-$C_6$ alkyl)aryl, and $CO_2H$, aryl($C_1$-$C_6$)alkanoyl, ($C_1$-$C_6$) alkoxycarbonyl, arylalkoxycarbonyl, heteroarylcarbonyl, heteroaryl, heterocycloalkylcarbonyl, —C(O)NH$_2$, —C(O)NH(C$_1$-C$_6$)alkyl, —C(O)N(C$_1$-C$_6$)alkyl(C$_1$-C$_6$)alkyl, —C(=NH)NH$_2$, —C(=N—C(O)C$_1$-C$_6$ alkoxy)NH—C(O)C$_1$-C$_6$ alkoxy, or —SO$_2$-aryl, wherein the cyclic portions of each of the above are optionally substituted with 1, 2, 3, or 4 groups that are independently halogen, C$_1$-C$_6$ alkyl, C$_1$-C$_6$ alkoxy, NO$_2$, OH, CO$_2$H, CN, C$_2$-C$_6$ alkanoyl, NH$_2$, NH(C$_1$-C$_6$)alkyl, N(C$_1$-C$_6$)alkyl(C$_1$-C$_6$)alkyl, haloalkyl or haloalkoxy;

R$_8$ is H, (C$_1$-C$_6$)alkyl, aryl(C$_1$-C$_6$)alkyl, aryl(C$_1$-C$_6$)alkanoyl, wherein the aryl group is optionally substituted with C$_1$-C$_4$ alkyl, C$_1$-C$_4$ alkoxy, halogen, NO$_2$, C$_1$-C$_4$ haloalkyl, or C$_1$-C$_4$ haloalkoxy;

R$_{20}$, R$_{21}$, R$_{22}$, and R$_{23}$ are independently selected from H, arylalkoxy, arylalkyl, halogen, alkyl, OH, alkoxy, NO$_2$, NH$_2$, NH(C$_1$-C$_6$)alkyl, N(C$_1$-C$_6$)alkyl(C$_1$-C$_6$)alkyl, NH-aryl, N(C$_1$-C$_4$)alkyl-aryl, —NHSO$_2$-aryl, —N(C$_1$-C$_4$alkyl)SO$_2$aryl, wherein the aryl group is optionally substituted with 1, 2, 3, or 4 groups that are independently C$_1$-C$_6$ alkyl, C$_1$-C$_6$ alkoxy, halogen, OH, NO$_2$, C$_1$-C$_4$ haloalkyl, C$_1$-C$_4$ haloalkoxy;

L$_2$ is a bond, —O—(C$_1$-C$_6$)alkyl-, —(C$_1$-C$_6$)alkyl-O—, —N(R$_8$)C(O)—(C$_1$-C$_4$)alkyl-, —(C$_1$-C$_4$)alkyl-C(O)N(R$_8$)—, —CO—, or —SO$_2$—;

L$_3$ is a bond, —(C$_1$-C$_4$)alkyl-O—, —O—(C$_1$-C$_4$)alkyl, —(C$_1$-C$_4$)alkyl-, —C$_2$-C$_6$ alkenyl-, —C(O)—, (C$_1$-C$_4$)alkyl-O—, —C(O)NH—, or —NHC(O)—;

L$_4$ is —(C$_1$-C$_4$)alkyl-, —S(O)$_u$—(C$_1$-C$_4$)alkyl-, —(C$_1$-C$_4$)alkyl-S(O)$_u$—(C$_1$-C$_4$)alkyl-, —C$_2$-C$_6$ alkenyl-, —C$_2$-C$_6$ alkynyl-, —C$_1$-C$_6$ alkyl-O—C$_1$-C$_6$ alkyl-, —O—C$_1$-C$_6$ alkyl-, —C(O)—(C$_1$-C$_4$)alkyl-, —(C$_1$-C$_4$)alkyl-C(O)—, C$_1$-C$_6$alkyl-O—, —(C$_1$-C$_4$)alkyl-C(O)—(C$_1$-C$_4$)alkyl-, or —(C$_1$-C$_4$)alkyl-NR$_N$—(C$_1$-C$_4$)alkyl-;

wherein R$_N$ represents (C$_1$-C$_6$)alkyl or hydrogen;

wherein u is 0, 1, or 2;

the A-ring is phenyl, naphthyl, isoindolyl, indolyl, pyridyl, thiazolyl, pyrimidyl, benzofuranyl, benzimidazolyl, or 1H-indazolyl each of which is optionally substituted with 1, 2, 3, or 4 groups that are independently, halogen, C$_1$-C$_4$ alkyl, C$_1$-C$_4$ alkoxy, C$_1$-C$_4$ haloalkyl, C$_1$-C$_4$ haloalkoxy, NO$_2$, NH$_2$, NH(C$_1$-C$_6$)alkyl, or N(C$_1$-C$_6$)alkyl(C$_1$-C$_6$)alkyl;

Q is -heteroaryl-(C$_1$-C$_4$)alkyl-aryl, -aryl-(C$_1$-C$_4$)alkyl-heteroaryl, -aryl-O-aryl, heteroaryl, heterocycloalkyl, cycloalkyl, or aryl, each of which is optionally substituted with 1, 2, 3, 4, or 5 groups that are independently alkoxycarbonyl, C$_1$-C$_6$ alkyl, C$_1$-C$_6$ alkoxy, halogen, C$_1$-C$_6$ alkanoyl, C$_1$-C$_4$ haloalkyl, C$_1$-C$_4$ haloalkoxy, NH$_2$, NH(C$_1$-C$_6$)alkyl, N(C$_1$-C$_6$)alkyl(C$_1$-C$_6$)alkyl, phenyl, C$_1$-C$_6$ alkanoyl;

Q$_2$ is and H or aryl, wherein the aryl is optionally substituted with 1, 2, or 3 groups that are independently C$_1$-C$_6$ alkyl, C$_1$-C$_6$ alkoxy, or halogen; and Y and Y' are independently a bond or —(C$_1$-C$_4$)alkyl-.

The compounds of formula I bind to PTPs, and in particular to PTP-1B. The interaction with the enzyme, specifically PTP-1B, preferably results in inhibition of the enzyme.

The invention also includes intermediates that are useful in making the compounds of the invention.

The invention also provides pharmaceutical compositions comprising a compound or salt of formula I and at least one pharmaceutically acceptable carrier, solvent, adjuvant or diluent.

The invention further provides methods of treating disease such as diabetes, syndrome X, cancer, immunological disease, bleeding disorders, or cardiovascular disease in a patient in need of such treatment, comprising administering to the patient a compound or pharmaceutically acceptable salt of formula I, or a pharmaceutical composition comprising a compound or salt of formula I.

In another aspect, the invention provides a method for inhibiting protein tyrosine phosphatases, preferably PTP-1B, comprising administering a therapeutically effective amount of a compound of formula I.

In another aspect, the invention provides a method for treating metabolic disorders related to insulin resistance or hyperglycemia, comprising administering to a patient in need of such treatment a therapeutically effective amount of a compound of formula I.

The invention also provides the use of a compound or salt according to formula I for the manufacture of a medicament for use in treating diabetes or cancer or other diseases related to PTP.

The invention also provides methods of preparing the compounds of the invention and the intermediates used in those methods.

The invention also provides methods and compositions for combination therapy of Type I and Type II diabetes. In these embodiments, the invention provides formulations and pharmaceutical compositions, as well as methods for treating Type I and Type II diabetes with the compounds of formula I plus additional compounds and medicaments as disclosed in more detail below. In these embodiments, the methods of the invention can comprise treatment methods for Type I and Type II diabetes where the compounds of formula I are formulated with a therapeutically-effective amount of said additional compounds and medicaments. In alternative embodiments, treatment methods of the invention for Type I and Type II diabetes comprise administration of the inventive compounds of formula I as disclosed herein concomitantly, simultaneously or together with a therapeutically-effective amount of said additional compounds and medicaments.

DETAILED DESCRIPTION OF THE INVENTION

In another aspect, the invention provides compounds of formula I-a, i.e., compounds of formula I, wherein, R$_6$ and R$_7$ are independently H, C$_1$-C$_6$ alkyl, phenyl(C$_1$-C$_6$)alkyl, C$_1$-C$_6$ alkanoyl optionally substituted with 1 or 2 groups independently selected from amino, mono or dialkylamino, —NHphenyl, —N(C$_1$-C$_6$ alkyl)aryl, and CO$_2$H, phenyl(C$_1$-C$_6$)alkanoyl, (C$_1$-C$_6$) alkoxycarbonyl, benzyloxycarbonyl, benzimidazolylcarbonyl, benzofuranylcarbonyl, furanylcarbonyl, thiazolylcarbonyl, indolylcarbonyl, pyridyl, pyrimidyl, morpholinylcarbonyl, thiomorpholinylcarbonyl, thiomorpholinyl S,S dioxide-carbonyl, piperazinylcarbonyl, piperidinylcarbonyl, pyrrolidinylcarbonyl, pyridylcarbonyl, pyrazolylcarbonyl, —C(O)NH$_2$, —C(O)NH(C$_1$-C$_6$)alkyl, —C(O)N(C$_1$-C$_6$)alkyl(C$_1$-C$_6$)alkyl, —C(=NH)NH$_2$, —C(=N—C(O)C$_1$-C$_4$ alkoxy)NH—C(O)C$_1$-C$_4$ alkoxy, —SO$_2$-phenyl, or —SO$_2$-naphthyl wherein the cyclic portions of each of the above are optionally substituted with 1, 2, 3, or 4 groups that are independently halogen, C$_1$-C$_6$ alkyl, C$_1$-C$_6$ alkoxy, NO$_2$, OH, CO$_2$H, CN, C$_1$-C$_6$ alkanoyl, NH$_2$, NH(C$_1$-C$_6$)alkyl, N(C$_1$-C$_6$)alkyl(C$_1$-C$_6$)alkyl, C$_1$-C$_4$ haloalkyl or C$_1$-C$_4$ haloalkoxy; and Q is -benzofuranyl-(C$_1$-C$_4$)alkyl-phenyl, -pyridyl-(C$_1$-C$_4$)alkyl-phenyl, -dibenzofuranyl-(C$_1$-C$_4$)alkyl-phenyl, indolyl-(C$_1$-C$_4$)alkyl-phenyl, benzo[b]thienyl-(C$_1$-C$_4$)alkyl-phenyl, -phenyl-(C$_1$-C$_4$)alkyl-benzofuranyl, indolyl, phenyl, benzo[d][1,3]dioxolyl, 2,3-dihydrobenzo[b][1,4]dioxinyl, dibenzothienyl, indolinyl, benzofuranyl, benzimidazolyl, diphenylether, adamantyl, 1,2,3,4-tetrahydroquinolinyl, 1,2,3,4-tetrahydroisoquinolinyl, or dibenzofuranyl, each of which is optionally substituted with 1, 2, 3, 4, or 5 groups that are independently alkoxycarbonyl, $C_1$-$C_6$ alkyl, $C_1$-$C_6$ alkoxy, halogen, $C_1$-$C_4$ haloalkyl, $C_1$-$C_4$ haloalkoxy, $NH_2$, $NH(C_1$-$C_6)$alkyl, $N(C_1$-$C_6)$alkyl$(C_1$-$C_6)$alkyl, phenyl or $C_1$-$C_6$ alkanoyl; and $Q_2$ is H or phenyl.

In another aspect, the invention provides compounds of formula I-b, i.e., compounds of formula I-a, wherein, $R_1$ is H, $C_1$-$C_6$ alkyl, benzyl, or allyl;

$R_{20}$, $R_{21}$, $R_{22}$, and $R_{23}$ are independently selected from H, benzyloxy, benzyl, halogen, $C_1$-$C_6$ alkyl, OH, $C_1$-$C_6$ alkoxy, $NO_2$, $NH_2$, $NH(C_1$-$C_6)$alkyl, $N(C_1$-$C_6)$alkyl$(C_1$-$C_6)$alkyl, NH-aryl, $N(C_1$-$C_4)$alkyl-aryl, —$NHSO_2$-phenyl, —$N(C_1$-$C_4$ alkyl)$SO_2$phenyl, wherein the phenyl group is optionally substituted with 1, 2, 3, or 4 groups that are independently $C_1$-$C_6$ alkyl, $C_1$-$C_6$ alkoxy, halogen, OH, $NO_2$, $C_1$-$C_2$ haloalkyl, $C_1$-$C_2$ haloalkoxy;

the A-ring is phenyl, naphthyl, pyridyl, thiazolyl, pyrimidyl, isoindolyl, indolyl, benzofuranyl, benzimidazolyl, or 1H-indazolyl each of which is optionally substituted with 1, 2, 3, or 4 groups that are independently, halogen, $C_1$-$C_4$ alkyl, $C_1$-$C_4$ alkoxy, $C_1$-$C_4$ haloalkyl, $C_1$-$C_4$ haloalkoxy, $NO_2$, $NH_2$, $NH(C_1$-$C_6)$alkyl, or $N(C_1$-$C_6)$alkyl$(C_1$-$C_6)$alkyl;

$L_2$ is a bond, —O—$(C_1$-$C_6)$alkyl-, —$(C_1$-$C_6)$alkyl-O—, —$N(R_8)C(O)$—$(C_1$-$C_4)$ alkyl-, —$(C_1$-$C_4)$alkyl-$C(O)N(R_8)$—, —CO—, —$SO_2$—; wherein $R_8$ is H, $(C_1$-$C_6)$alkyl, phenyl$(C_1$-$C_6)$alkyl, phenyl$(C_1$-$C_6)$alkanoyl, wherein the phenyl groups are optionally substituted with 1, 2, 3, 4, or 5 groups that are independently $C_1$-$C_4$ alkyl, $C_1$-$C_4$ alkoxy, halogen, $NO_2$, $C_1$-$C_2$ haloalkyl, or $C_1$-$C_2$ haloalkoxy; and $L_3$ is a bond, —$(C_1$-$C_4)$alkyl-O—, —O—$(C_1$-$C_4)$alkyl, —$(C_1$-$C_4)$alkyl-, or C(O).

In one aspect, the invention provides compounds of formula I-b-1, i.e., compounds of formula I-b wherein $L_4$ is —$(C_1$-$C_4)$alkyl-, —$S(O)_u$—$(C_1$-$C_4)$alkyl-, or —$(C_1$-$C_4)$alkyl-$S(O)_u$—$(C_1$-$C_4)$alkyl-$S(O)_u$—$(C_1$-$C_4)$alkyl; and wherein u is 0, 1, or 2.

In another aspect, the invention provides compounds of formula I-b-2, i.e., compounds of formula I-b wherein $L_4$ is —$C_2$-$C_6$ alkenyl-, —$C_1$-$C_4$ alkoxy $C_1$-$C_4$ alkyl-, —O—$C_1$-$C_4$ alkyl-, or $C_1$-$C_4$ alkyl-O—.

In still another aspect, the invention provides compounds of formula I-b-3, i.e., compounds of formula I-b wherein $L_4$ is —$(C_1$-$C_4)$alkyl-C(O)—, $C_1$-$C_6$alkyl-O—, —$(C_1$-$C_4)$alkyl-C(O)—$(C_1$-$C_4)$alkyl-, or —$(C_1$-$C_4)$alkyl-$NR_N$—$(C_1$-$C_4)$alkyl-; wherein $R_N$ represents $(C_1$-$C_6)$alkyl or hydrogen.

In yet another aspect, the invention provides compounds of formula I-c, i.e., compounds according to any one of formulas I-b, I-b-1, I-b-2, or I-b-3 wherein, the A-ring is isoindolyl, indolyl, benzofuranyl, benzimidazolyl, or 1H-indazolyl each of which is optionally substituted with 1, 2, 3, or 4 groups that are independently, halogen, $C_1$-$C_4$ alkyl, $C_1$-$C_4$ alkoxy, $C_1$-$C_4$ haloalkyl, $C_1$-$C_4$ haloalkoxy, $NO_2$, $NH_2$, $NH(C_1$-$C_6)$alkyl, or $N(C_1$-$C_6)$alkyl$(C_1$-$C_6)$alkyl. In another aspect, the A-ring is unsubstituted.

In yet another aspect, the invention provides compounds of formula I-c-1, i.e., compounds according to any one of formulas I-b, I-b-1, I-b-2, or I-b-3 wherein, the A-ring is pyridyl, thiazolyl, or pyrimidyl, each of which is optionally substituted with 1, 2, 3, or 4 groups that are independently, halogen, $C_1$-$C_4$ alkyl, $C_1$-$C_4$ alkoxy, $C_1$-$C_4$ haloalkyl, $C_1$-$C_4$ haloalkoxy, $NO_2$, $NH_2$, $NH(C_1$-$C_6)$alkyl, or $N(C_1$-$C_6)$alkyl $(C_1$-$C_6)$alkyl. In another aspect, the A-ring is unsubstituted.

In still another aspect, the invention provides compounds of formula I-d, i.e., compounds according to any one of formulas I-b, I-b-1, I-b-2, I-c, or I-c-1, wherein $R_1$ is H.

In yet another aspect, the invention provides compounds of formula I-e, i.e., compounds of formula I-d, wherein $R_{20}$ and $R_{21}$ are both hydrogen.

In another aspect, the invention provides compounds of formula I-f, i.e., compounds according to any one of formulas I-b, I-b-1, I-b-2, I-c, I-d, or I-e, wherein $Q_2$ is hydrogen.

In another aspect, the invention provides compounds of formula I-f-1, i.e., compounds according to any one of formulas I-b, I-b-1, I-b-2, I-c, I-d, or I-e, wherein $Q_2$ is phenyl.

In still another aspect, the invention provides compounds of formula I-g, i.e., compounds according to any one of formulas I-b, I-b-1, I-b-2, I-c, I-d, I-e, I-f, or I-f-1, wherein Y' is a bond; and one of $R_{22}$ and $R_{23}$ is hydrogen, while the other is hydrogen, $NO_2$, halogen, $CF_3$ or phenylalkoxy. In yet still another aspect, both $R_{22}$ and $R_{23}$ are hydrogen.

In another aspect, the invention provides compounds of formula II, i.e., compounds of either formula I or formula I-b are compounds of formula II,

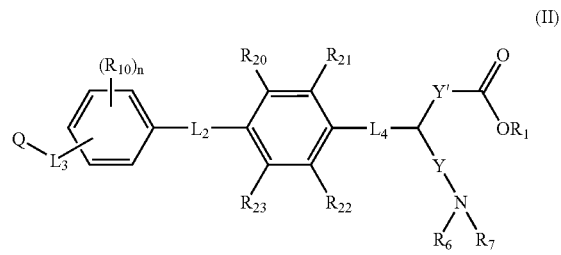

(II)

wherein n is 0, 1, 2, 3, or 4;

each $R_{10}$ is independently H, halogen, $C_1$-$C_4$ alkyl, $C_1$-$C_4$ alkoxy, $C_1$-$C_4$ haloalkyl, $C_1$-$C_4$ haloalkoxy, $NO_2$, $NH_2$, $NH(C_1$-$C_6)$alkyl, or $N(C_1$-$C_6)$alkyl$(C_1$-$C_6)$alkyl;

Q is -benzofuranyl-$(C_1$-$C_4)$alkyl-phenyl, -pyridyl-$(C_1$-$C_4)$alkyl-phenyl, -dibenzofuranyl-$(C_1$-$C_4)$alkyl-phenyl, indolyl-$(C_1$-$C_4)$alkyl-phenyl, -phenyl-$(C_1$-$C_4)$alkyl-benzofuranyl, indolyl, phenyl, indolinyl, benzofuranyl, benzimidazolyl, 1,2,3,4-tetrahydroquinolinyl, 1,2,3,4-tetrahydroisoquinolinyl, or dibenzofuranyl, each of which is optionally substituted with 1, 2, 3, 4, or 5 groups that are independently $C_1$-$C_6$ alkoxycarbonyl, $C_1$-$C_6$ alkyl, $C_1$-$C_6$ alkoxy, halogen, $C_1$-$C_2$ haloalkyl, $C_1$-$C_2$ haloalkoxy, $NH_2$, $NH(C_1$-$C_6)$alkyl, $N(C_1$-$C_6)$alkyl$(C_1$-$C_6)$alkyl, or phenyl.

In another aspect, the invention provides compounds of formula II-a, i.e., compounds of formula II, wherein n is 0, 1, 2, or 3;

$L_3$ is a bond, —$(C_1$-$C_4)$alkyl-O—, —O—$(C_1$-$C_4)$alkyl, —$(C_1$-$C_4)$alkyl-, —$C_2$-$C_6$ alkenyl-, or —C(O)—;

$R_1$ is H, $C_1$-$C_6$ alkyl, phenyl$(C_1$-$C_4)$alkyl, or $C_3$-$C_6$ alkenyl; and $R_6$ and $R_7$ are independently H, $C_1$-$C_6$ alkyl, aryl$(C_1$-$C_6)$ alkyl, $(C_2$-$C_6)$ alkanoyl, phenyl$(C_1$-$C_6)$alkanoyl, $(C_1$-$C_6)$ alkoxycarbonyl, phenylalkoxycarbonyl, heteroarylcarbonyl, heteroaryl, heterocycloalkylcarbonyl, —$C(O)NH_2$, —$C(O)NH(C_1$-$C_6)$alkyl, —$C(O)N(C_1$-$C_6)$alkyl$(C_1$-$C_6)$ alkyl, or —$SO_2$-aryl, wherein the cyclic groups are optionally substituted with 1, 2, 3, or 4 groups that are independently halogen, $C_1$-$C_4$ alkyl, $C_1$-$C_4$ alkoxy, $NO_2$, OH, $NH_2$, $NH(C_1$-$C_6)$alkyl, $N(C_1$-$C_6)$alkyl$(C_1$-$C_6)$alkyl, haloalkyl or haloalkoxy.

In another aspect, the invention provides compounds of formula II-b, i.e., compounds of formula II-a, wherein $R_{20}$, $R_{21}$, $R_{22}$, and $R_{23}$ are independently selected from H, phenylalkoxy, phenylalkyl, halogen, $C_1$-$C_6$ alkyl, OH, $C_1$-$C_6$ alkoxy, $NO_2$, $NH_2$, $NH(C_1$-$C_6)$alkyl, or $N(C_1$-$C_6)$alkyl$(C_1$-$C_6)$alkyl.

In another aspect, the invention provides compounds of formula II-c, i.e., compounds of formula II, or II-b, wherein $R_1$ is H, $C_1$-$C_4$ alkyl, or benzyl, $R_6$ and $R_7$ are independently H, $C_1$-$C_6$ alkyl, phenyl$(C_1$-$C_6)$alkyl, $(C_2$-$C_6)$ alkanoyl, phenyl$(C_1$-$C_6)$alkanoyl, $(C_1$-$C_6)$ alkoxycarbonyl, benzyloxycarbonyl, benzimidazolylcarbonyl, benzofuranylcarbonyl, thiazolylcarbonyl, indolylcarbonyl, morpholinylcarbonyl, thiomorpholinylcarbonyl, thiomorpholinyl S,S dioxide-carbonyl, piperazinylcarbonyl, piperidinylcarbonyl, pyrrolidinylcarbonyl, pyridylcarbonyl, pyrazolylcarbonyl, —C(O)$NH_2$, —C(O)NH$(C_1$-$C_6)$alkyl, —C(O)N$(C_1$-$C_6)$alkyl$(C_1$-$C_6)$alkyl, or —$SO_2$-phenyl wherein the cyclic groups are optionally substituted with 1, 2, 3, or 4 groups that are independently halogen, $C_1$-$C_4$ alkyl, $C_1$-$C_4$ alkoxy, $NO_2$, OH, $NH_2$, $NH(C_1$-$C_6)$alkyl, $N(C_1$-$C_6)$alkyl$(C_1$-$C_6)$alkyl, $C_1$-$C_2$ haloalkyl or $C_1$-$C_2$ haloalkoxy.

In another aspect, the invention provides compounds of formula II-d, i.e., compounds of formula II-c, wherein $R_{23}$ is H.

In another aspect, the invention provides compounds of formula II-e, i.e., compounds of formula II-d, wherein $R_{22}$ and $R_{23}$ are both H.

In still another aspect, the invention provides compounds of formula II-f, i.e., compounds of formula II-c, II-d, or II-e, wherein $L_2$ is a bond or —$(C_1$-$C_4)$alkyl; and $L_3$ is a bond, —$(C_1$-$C_4)$alkyl-O—, or —O—$(C_1$-$C_4)$alkyl, or —$(C_1$-$C_4)$alkyl-.

In yet another aspect, the invention provides compounds of formula II-g, i.e., compounds of formula II-c, II-d, or II-e, $L_2$ is a bond or —$(C_1$-$C_4)$alkyl; and $L_3$ is a bond, —$C_2$-$C_6$ alkenyl-, or —C(O)—.

In still yet another aspect, the invention provides compounds of formula II-h, i.e., compounds of formula II-c, II-d, or II-e, wherein $L_2$ is —O—$(C_1$-$C_6)$alkyl-, or —$(C_1$-$C_6)$alkyl-O—; and $L_3$ is a bond, —$(C_1$-$C_4)$alkyl-O—, or —O—$(C_1$-$C_4)$alkyl, or —$(C_1$-$C_4)$alkyl-.

In another aspect, the invention provides compounds of formula II-i, i.e., compounds of formula II-c, II-d, or II-e, wherein $L_2$ is —O—$(C_1$-$C_6)$alkyl-, or —$(C_1$-$C_6)$alkyl-O—; and $L_3$ is a bond, —$C_2$-$C_6$ alkenyl-, or —C(O)—.

In yet another aspect, the invention provides compounds of formula II-j, i.e., compounds of formula II-c, II-d, or II-e, wherein $L_2$ is —N$(R_8)$C(O)—$(C_1$-$C_4)$alkyl-, or —$(C_1$-$C_4)$alkyl-C(O)N$(R_8)$—; wherein $R_8$ is H, $(C_1$-$C_6)$alkyl, benzyl, or phenyl-CO—, wherein the phenyl groups are optionally substituted with $C_1$-$C_4$ alkyl, $C_1$-$C_4$ alkoxy, halogen, $NO_2$, $CF_3$, or $OCF_3$; and $L_3$ is a bond, —$(C_1$-$C_4)$alkyl-O—, or —O—$(C_1$-$C_4)$alkyl, or —$(C_1$-$C_4)$alkyl-.

In still another aspect, the invention provides compounds of formula II-k, i.e., compounds of formula II-c, II-d, or II-e, wherein $L_2$ is —N$(R_8)$C(O)—$(C_1$-$C_4)$alkyl-, or —$(C_1$-$C_4)$alkyl-C(O)N$(R_8)$—; wherein $R_8$ is H, $(C_1$-$C_6)$alkyl, benzyl, or phenyl-CO—, wherein the phenyl groups are optionally substituted with $C_1$-$C_4$ alkyl, $C_1$-$C_4$ alkoxy, halogen, $NO_2$, $CF_3$, or $OCF_3$; and $L_3$ is a bond, —$C_2$-$C_6$ alkenyl-, or —C(O)—.

In yet another aspect, the invention provides compounds of formula II-l, i.e., compounds of formula II-f, II-g, II-h, II-I, II-j, or II-k, wherein $L_4$ is —$(C_1$-$C_4)$alkyl-.

In another aspect, the invention provides compounds of formula II-m, i.e., compounds of formula II-f, II-g, II-h, II-I, II-j, or II-k, wherein $L_4$ is —S(O)$_u$—$CH_2$—, wherein u is 0, 1, or 2.

In yet still another aspect, the invention provides compounds of formula II-n, i.e., compounds of formula II-f, II-g, II-h, II-I, II-j, or II-k, wherein $L_4$ is —$(C_1$-$C_4)$alkyl-S(O)$_u$—$(C_1$-$C_4)$alkyl, wherein u is 0, 1, or 2.

In another aspect, the invention provides compounds of formula II-o, i.e., compounds of formula II-e, wherein $L_2$ is a bond; and $L_3$ is a bond.

In another aspect, the invention provides compounds of formula II-p, i.e., compounds of formula II-e, wherein $L_4$ is —S(O)$_u$—$CH_2$—, or —$(C_1$-$C_4)$alkyl-S(O)$_u$—$CH_2$—; wherein u is 0, 1, or 2. In another aspect, u is 0. In yet another aspect, u is 2.

In another aspect, the invention provides compounds of formula III, i.e., compounds of formula II, II-a, II-b, II-c, II-d, II-e, or II-f, which has the following structure:

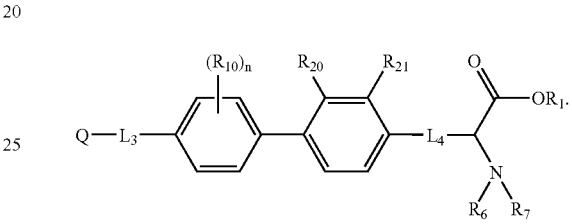

In still another aspect, the invention provides compounds of formula III-a, i.e., compounds of formula III, which has the formula:

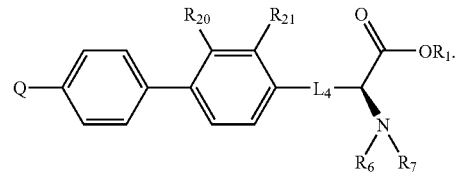

In still another aspect, the invention provides compounds of formula III-b, i.e., compounds of of formula III or III-a wherein Q is -benzofuranyl-$(C_1$-$C_4)$alkyl-phenyl, -dibenzofuranyl-$(C_1$-$C_4)$alkyl-phenyl, indolyl, phenyl, benzofuranyl, benzimidazolyl, 1,2,3,4-tetrahydroquinolinyl, 1,2,3,4-tetrahydroisoquinolinyl, or dibenzofuranyl, each of which is optionally substituted with 1, 2, 3, 4, or 5 groups that are independently $C_1$-$C_6$ alkoxycarbonyl, $C_1$-$C_6$ alkyl, $C_1$-$C_6$ alkoxy, halogen, $CF_3$, $OCF_3$, $NH_2$, $NH(C_1$-$C_6)$alkyl, $N(C_1$-$C_6)$alkyl$(C_1$-$C_6)$alkyl, or phenyl.

In another aspect, the invention provides compounds of formula III-c, i.e., compounds of formula III-b, wherein $R_1$ is H, or $C_1$-$C_6$ alkyl (preferably H); $R_6$ is H; at least one of $R_{20}$ and $R_{21}$ is H; and $L_4$ is —$(C_1$-$C_4)$alkyl-, —S(O)$_u$—$CH_2$—, or —$CH_2$—S(O)$_u$—$CH_2$—; wherein u is 0, 1, or 2.

In yet another aspect, the invention provides compounds of formula III-d, i.e., compounds of formula III-b or III-c, wherein $L_4$ is —$CH_2$—, —$CH_2$—S—$CH_2$— or —S—$CH_2$—. In another aspect, $L_4$ is —$CH_2$—S—$CH_2$— or —S—$CH_2$—.

In still another aspect, the invention provides compounds of formula III-e, i.e., compounds of formula III-b, III-c, or III-d, wherein $R_7$ is $C_1$-$C_6$ alkyl, $(C_2$-$C_6)$ alkanoyl, $(C_1$-$C_6)$ alkoxycarbonyl, —C(O)$NH_2$, —C(O)NH$(C_1$-$C_6)$alkyl, or —C(O)N$(C_1$-$C_6)$alkyl$(C_1$-$C_6)$alkyl.

In yet still another aspect, the invention provides compounds of formula III-f, i.e., compounds of formula III-e, wherein $R_7$ is $C_2$ alkanoyl or $C_4$ alkoxycarbonyl.

In yet another aspect, the invention provides compounds of formula III-g, i.e., compounds of formula III-b, III-c, or III-d, wherein $R_7$ is phenyl($C_1$-$C_4$)alkyl, phenyl($C_1$-$C_6$)alkanoyl, benzyloxycarbonyl, benzimidazolylcarbonyl, benzofuranylcarbonyl, thiazolylcarbonyl, indolylcarbonyl, morpholinylcarbonyl, piperazinylcarbonyl, piperidinylcarbonyl, pyrrolidinylcarbonyl, or —$SO_2$-phenyl wherein the cyclic groups are optionally substituted with 1, 2, 3, or 4 groups that are independently halogen, $C_1$-$C_4$ alkyl, $C_1$-$C_4$ alkoxy, $NO_2$, OH, $NH_2$, NH($C_1$-$C_6$)alkyl, N($C_1$-$C_6$)alkyl($C_1$-$C_6$)alkyl, $CF_3$ or $OCF_3$.

In yet another aspect, the invention provides compounds of formula III-h, i.e., compounds of formula III-g wherein $R_{21}$ is H or $NO_2$. In another aspect $R_{21}$, is H.

In another aspect, the invention provides compounds of formula III-h-1, i.e., compounds of formula III-a, III-b, III-c, III-d, III-e, III-f, III-g, or III-h, wherein Q is -benzofuranyl-$CH_2$-phenyl, -dibenzofuranyl-$CH_2$-phenyl, or dibenzofuranyl.

In another aspect, the invention provides compounds of formula III-h-2, i.e., compounds of formula III-a, III-b, III-c, III-d, III-e, III-f, III-g, or III-h, wherein Q is indolyl, phenyl, benzofuranyl, or benzimidazolyl.

In another aspect, the invention provides compounds of formula III-h-3, i.e., compounds of formula III, which have the formula:

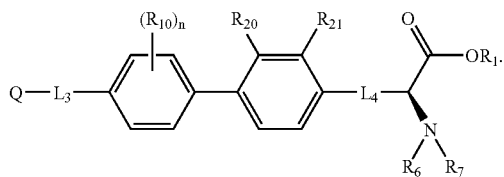

In another aspect, the invention provides compounds of formula III-h-4, i.e., compounds of formula III-h-3, wherein $R_1$ is H; n is 1, 2 or 3; $L_3$ is a bond, —$CH_2$—, or —($C_1$-$C_2$)alkyl-O—; and each $R_{10}$ is independently halogen, $C_1$-$C_4$ alkyl, $C_1$-$C_4$ alkoxy, $CF_3$, $OCF_3$, $NO_2$, $NH_2$, NH($C_1$-$C_6$)alkyl, or N($C_1$-$C_6$)alkyl($C_1$-$C_6$)alkyl.

In yet another aspect, the invention provides compounds of formula III-i, i.e., compounds of formula III-a, III-b, III-c, III-d, III-e, III-f, III-g, or III-h, wherein Q is -benzofuranyl-($C_1$-$C_4$)alkyl-phenyl, indolyl, phenyl, 1,2,3,4-tetrahydroquinolinyl, 1,2,3,4-tetrahydroisoquinolinyl, or dibenzofuranyl, each of which is optionally substituted with 1, 2, 3, 4, or 5 groups that are independently $C_1$-$C_6$ alkoxycarbonyl, $C_1$-$C_6$ alkyl, $C_1$-$C_6$ alkoxy, halogen, $CF_3$, $OCF_3$, $NH_2$, NH($C_1$-$C_6$) alkyl, or N($C_1$-$C_6$)alkyl($C_1$-$C_6$)alkyl.

In another aspect, the invention provides compounds of formula III-j, i.e., compounds of formula III-i, wherein Q is -benzofuranyl-$CH_2$-phenyl, indolyl, 1,2,3,4-tetrahydroquinolinyl, 1,2,3,4-tetrahydroisoquinolinyl, or dibenzofuranyl, each of which is optionally substituted with 1, 2, 3, 4, or 5 groups that are independently $C_1$-$C_6$ alkoxycarbonyl, $C_1$-$C_6$ alkyl, $C_1$-$C_6$ alkoxy, halogen, $CF_3$, $OCF_3$, $NH_2$, NH($C_1$-$C_6$) alkyl, or N($C_1$-$C_6$)alkyl($C_1$-$C_6$)alkyl. In another aspect, Q is unsubstituted.

In still another aspect, the invention provides compounds of formula III-k, i.e., compounds of formula III-j, wherein n is 0, 1, or 2; $L_3$ is a bond; $R_1$ is H; and $R_{20}$ is H.

In another aspect, the invention provides compounds of formula III-l, i.e., compounds of formula III-j wherein $L_4$ is —$CH_2$—, —$CH_2$—S—$CH_2$— or —S—$CH_2$—. In another aspect, $L_4$ is —$CH_2$—S—$CH_2$— or —S—$CH_2$—.

In another aspect, the invention provides compounds of formula III-m, i.e., compounds of formula III-i, wherein $R_7$ is benzyl, phenyl($C_1$-$C_4$)alkanoyl (in one aspect —C(O)phenyl, or —C(O)$CH_2$-phenyl, more preferably —C(O)phenyl), benzyloxycarbonyl, or —$SO_2$-phenyl wherein the cyclic groups are optionally substituted with 1, 2, or 3 groups that are independently halogen, $C_1$-$C_4$ alkyl, $C_1$-$C_4$ alkoxy, $NO_2$, OH, $NH_2$, NH($C_1$-$C_6$)alkyl, N($C_1$-$C_6$)alkyl($C_1$-$C_6$)alkyl, $CF_3$ or $OCF_3$.

In another aspect, the invention provides compounds of formula III-n, i.e., compounds of formula III-m, wherein $R_7$ is —$SO_2$-phenyl wherein the phenyl group is substituted at the para position with either an halogen, $C_1$-$C_4$ alkyl, $C_1$-$C_4$ alkoxy, $NO_2$, or OH group.

In another aspect, the invention provides compounds of formula III-o, i.e., compounds of formula III-n, wherein $R_7$ is benzyloxycarbonyl.

In another aspect, the invention provides compounds of formula IV, i.e., compounds of formula III, which have the formula:

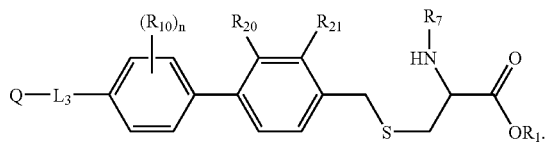

In another aspect, the invention provides compounds of formula IV, i.e. compounds of formula III, wherein $R_1$ is H or ($C_1$-$C_6$)alky; $R_7$ is H or ($C_1$-$C_6$)alkoxy; $R_{20}$ and $R_{21}$ are independently H, halogen, alkyl, OH, alkoxy, $NO_2$, $NH_2$, NH($C_1$-$C_6$)alkyl, or N($C_1$-$C_6$)alkyl($C_1$-$C_6$)alkyl; n is 0, 1, 2, 3, or 4; each $R_{10}$ is independently H, halogen, $C_1$-$C_4$ alkyl, $C_1$-$C_4$ alkoxy, $C_1$-$C_4$ haloalkyl, $C_1$-$C_4$ haloalkoxy, $NO_2$, $NH_2$, NH($C_1$-$C_6$)alkyl, or N($C_1$-$C_6$)alkyl($C_1$-$C_6$)alkyl; $L_3$ is a bond, —($C_1$-$C_4$)alkyl-O—, —O—($C_1$-$C_4$)alkyl, —($C_1$-$C_4$) alkyl-, —$C_2$-$C_6$ alkenyl-, —C(O)—, ($C_1$-$C_4$)alkyl-O—, —C(O)NH—, or —NHC(O)—; and Q is heterocycloalkyl optionally substituted with 1, 2, 3, 4, or 5 groups that are independently alkoxycarbonyl, $C_1$-$C_6$ alkyl, $C_1$-$C_6$ alkoxy, halogen, $C_1$-$C_6$ alkanoyl, $C_1$-$C_4$ haloalkyl, $C_1$-$C_4$ haloalkoxy, $NH_2$, NH($C_1$-$C_6$)alkyl, N($C_1$-$C_6$)alkyl($C_1$-$C_6$)alkyl, or phenyl.

In another aspect, the invention provides compounds of formula IV, i.e. compounds of formula III, wherein $R_1$ is H or ($C_1$-$C_6$)alky; $R_7$ is H or ($C_1$-$C_6$)alkoxy; $R_{20}$ and $R_{21}$ are independently H, halogen, alkyl, OH, alkoxy, $NO_2$, $NH_2$, NH($C_1$-$C_6$)alkyl, or N($C_1$-$C_6$)alkyl($C_1$-$C_6$)alkyl; n is 0, 1, 2, 3, or 4; each $R_{10}$ is independently H, halogen, $C_1$-$C_4$ alkyl, $C_1$-$C_4$ alkoxy, $C_1$-$C_4$ haloalkyl, $C_1$-$C_4$ haloalkoxy, $NO_2$, $NH_2$, NH($C_1$-$C_6$)alkyl, or N($C_1$-$C_6$)alkyl($C_1$-$C_6$)alkyl; $L_3$ is a bond, —($C_1$-$C_4$)alkyl-O—, —O—($C_1$-$C_4$)alkyl, —($C_1$-$C_4$) alkyl-, —$C_2$-$C_6$ alkenyl-, —C(O)—, ($C_1$-$C_4$)alkyl-O—, —C(O)NH—, or —NHC(O)—; and Q is 1,2,3,4-tetrahydroquinolinyl optionally substituted with 1, 2, 3, 4, or 5 groups that are independently alkoxycarbonyl, $C_1$-$C_6$ alkyl, $C_1$-$C_6$ alkoxy, halogen, $C_1$-$C_6$ alkanoyl, $C_1$-$C_4$ haloalkyl, $C_1$-$C_4$ haloalkoxy, $NH_2$, NH($C_1$-$C_6$)alkyl, N($C_1$-$C_6$)alkyl($C_1$-$C_6$) alkyl, or phenyl.

In another aspect, the invention provides compounds of formula IV, i.e. compounds of formula III, wherein $R_1$ is H or ($C_1$-$C_6$)alky; $R_7$ is H or ($C_1$-$C_6$)alkoxy; $R_{20}$ and $R_{21}$ are independently H, halogen, alkyl, OH, alkoxy, $NO_2$, $NH_2$, NH($C_1$-$C_6$)alkyl, or N($C_1$-$C_6$)alkyl($C_1$-$C_6$)alkyl; n is 0; $L_3$ is —($C_1$-$C_4$)alkyl-; and Q is 1,2,3,4-tetrahydroquinolinyl optionally substituted with $C_1$-$C_4$ haloalkyl.

In still another aspect, the invention provides compounds of formula IV-a, i.e., compounds of formula IV, which have the formula:

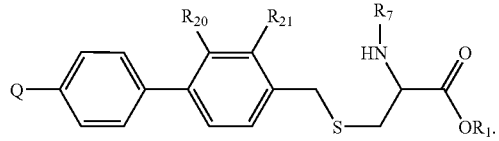

In yet another aspect, the invention provides compounds of formula IV-a-1, i.e., compounds of formula IV or IV-a, wherein $R_{20}$ and $R_{21}$ are independently selected from H, benzyloxy, benzyl, halogen, $C_1$-$C_6$ alkyl, OH, $C_1$-$C_6$ alkoxy, $NO_2$, $NH_2$, $NH(C_1$-$C_6)$alkyl, $N(C_1$-$C_6)$alkyl$(C_1$-$C_6)$alkyl, NH-phenyl, $N(C_1$-$C_4)$alkyl-aryl, —$NHSO_2$-phenyl, or —$N(C_1$-$C_4$ alkyl)$SO_2$phenyl, wherein the phenyl group is optionally substituted with 1, 2, 3, or 4 groups that are independently $C_1$-$C_6$ alkyl, $C_1$-$C_6$ alkoxy, halogen, OH, $NO_2$, $C_1$-$C_2$ haloalkyl, $C_1$-$C_2$ haloalkoxy.

In another aspect, the invention provides compounds of formula IV-b, i.e., compounds of formula IV, IV-a, or IV-a-1, wherein $R_1$ is H, $C_1$-$C_6$ alkyl or benzyl (in another aspect, $R_1$ is H); $R_7$ is phenyl$(C_1$-$C_4)$alkyl, phenyl$(C_1$-$C_6)$alkanoyl, benzyloxycarbonyl, benzimidazolylcarbonyl, benzofuranylcarbonyl, thiazolylcarbonyl, indolylcarbonyl, morpholinylcarbonyl, piperazinylcarbonyl, piperidinylcarbonyl, pyrrolidinylcarbonyl, or —$SO_2$-phenyl wherein the cyclic groups are optionally substituted with 1, 2, 3, or 4 groups that are independently halogen, $C_1$-$C_4$ alkyl, $C_1$-$C_4$ alkoxy, $NO_2$, OH, $NH_2$, $NH(C_1$-$C_6)$alkyl, $N(C_1$-$C_6)$alkyl$(C_1$-$C_6)$alkyl, $CF_3$ or $OCF_3$.

In still another aspect, the invention provides compounds of formula IV-c, i.e., compounds of formula IV-b, wherein $L_3$ is a bond, —$CH_2$—, or —$(C_1$-$C_2)$alkyl-O—; Q is -benzofuranyl-$(C_1$-$C_4)$alkyl-phenyl, -pyridyl-$(C_1$-$C_4)$alkyl-phenyl, -dibenzofuranyl-$(C_1$-$C_4)$alkyl-phenyl, indolyl-$(C_1$-$C_4)$alkyl-phenyl, -phenyl-$(C_1$-$C_4)$alkyl-benzofuranyl, indolyl, phenyl, benzofuranyl, benzimidazolyl, 1,2,3,4-tetrahydroquinolinyl, 1,2,3,4-tetrahydroisoquinolinyl, or dibenzofuranyl, each of which is optionally substituted with 1, 2, 3, 4, or 5 groups that are independently $C_1$-$C_6$ alkoxycarbonyl, $C_1$-$C_6$ alkyl, $C_1$-$C_6$ alkoxy, halogen, $C_1$-$C_2$ haloalkyl, $C_1$-$C_2$ haloalkoxy, $NH_2$, $NH(C_1$-$C_6)$alkyl, $N(C_1$-$C_6)$alkyl$(C_1$-$C_6)$alkyl, or phenyl; and $R_{20}$, and $R_{21}$ are independently selected from H, benzyloxy, benzyl, halogen, $C_1$-$C_6$ alkyl, OH, $C_1$-$C_6$ alkoxy, $NO_2$, $NH_2$, $NH(C_1$-$C_6)$alkyl, or $N(C_1$-$C_6)$alkyl$(C_1$-$C_6)$alkyl.

In still another aspect, the invention provides compounds of formula IV-d, i.e., compounds of formula IV-c, wherein wherein n is 0, 1, or 2; $L_3$ is a bond; $R_1$ is H; and $R_{20}$ is H.

In still another aspect, the invention provides compounds of formula IV-e, i.e., compounds of formula IV-d, wherein $R_7$ is benzyl, phenyl$(C_1$-$C_6)$alkanoyl, benzyloxycarbonyl, benzimidazolylcarbonyl, thiazolylcarbonyl, indolylcarbonyl, morpholinylcarbonyl, or —$SO_2$-phenyl wherein the cyclic groups are optionally substituted with 1, 2, 3, or 4 groups that are independently halogen, $C_1$-$C_4$ alkyl, $C_1$-$C_4$ alkoxy, $NO_2$, OH, $NH_2$, $NH(C_1$-$C_6)$alkyl, $N(C_1$-$C_6)$alkyl$(C_1$-$C_6)$alkyl, $CF_3$ or $OCF_3$.

In another aspect, the invention provides compounds of formula V, i.e., compounds and pharmaceutically acceptable salts of formula I that have the following formula,

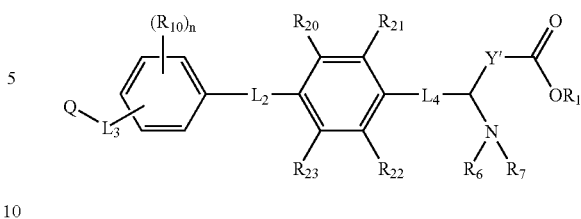

wherein n is 0, 1, 2, 3, or 4;

$L_2$ is a bond, —O—$(C_1$-$C_6)$alkyl-, —$(C_1$-$C_6)$alkyl-O—, or —$(C_1$-$C_4)$alkyl;

$L_3$ is a bond, —$(C_1$-$C_4)$alkyl-O—, —O—$(C_1$-$C_4)$alkyl, —$(C_1$-$C_4)$alkyl-, $C_2$-$C_6$ alkenyl, or C(O);

$L_4$ is —$S(O)_u$—$(C_1$-$C_4)$alkyl-, —$(C_1$-$C_4)$alkyl-$S(O)_u$—$(C_1$-$C_4)$alkyl-, —$(C_1$-$C_4)$alkyl-, —$C(O)$—$(C_1$-$C_4)$alkyl-, —$(C_1$-$C_4)$alkyl-$C(O)$—, —$(C_1$-$C_4)$alkyl-$C(O)$—$(C_1$-$C_4)$alkyl-, or —$(C_1$-$C_4)$alkyl-$NR_N$—$(C_1$-$C_4)$alkyl- where $R_N$ represents —$(C_1$-$C_6)$alkyl or hydrogen;

wherein u is 0, 1, or 2;

$R_1$ is H, $C_1$-$C_6$ alkyl, phenyl$(C_1$-$C_6)$alkyl, or $C_3$-$C_6$ alkenyl;

$R_6$ and $R_7$ are independently H, $C_1$-$C_6$ alkyl, aryl$(C_1$-$C_6)$alkyl, $(C_2$-$C_6)$ alkanoyl, aryl$(C_1$-$C_6)$alkanoyl, $(C_1$-$C_6)$ alkoxycarbonyl, arylalkoxycarbonyl, heteroarylcarbonyl, heteroaryl, heterocycloalkylcarbonyl, —$C(O)NH_2$, —$C(O)NH(C_1$-$C_6)$alkyl, —$C(O)N(C_1$-$C_6)$alkyl$(C_1$-$C_6)$ alkyl, or —$SO_2$-aryl, wherein the cyclic groups are optionally substituted with 1, 2, 3, or 4 groups that are independently halogen, $C_1$-$C_4$ alkyl, $C_1$-$C_4$ alkoxy, $NO_2$, OH, $NH_2$, $NH(C_1$-$C_6)$alkyl, $N(C_1$-$C_6)$alkyl$(C_1$-$C_6)$alkyl, haloalkyl or haloalkoxy;

each $R_{10}$ is independently H, halogen, $C_1$-$C_4$ alkyl, $C_1$-$C_4$ alkoxy, $C_1$-$C_4$ haloalkyl, $C_1$-$C_4$ haloalkoxy, $NO_2$, $NH_2$, $NH(C_1$-$C_6)$alkyl, or $N(C_1$-$C_6)$alkyl$(C_1$-$C_6)$alkyl;

$R_{20}$, $R_{21}$, $R_{22}$, and $R_{23}$ are independently selected from H, arylalkoxy, arylalkyl, halogen, alkyl, OH, alkoxy, $NO_2$, $NH_2$, $NH(C_1$-$C_6)$alkyl, or $N(C_1$-$C_6)$alkyl$(C_1$-$C_6)$alkyl;

Q is -benzofuranyl-$(C_1$-$C_4)$alkyl-phenyl, -pyridyl-$(C_1$-$C_4)$ alkyl-phenyl, -dibenzofuranyl-$(C_1$-$C_4)$alkyl-phenyl, indolyl-$(C_1$-$C_4)$alkyl-phenyl, -phenyl-$(C_1$-$C_4)$alkyl-benzofuranyl, indolyl, phenyl, indolinyl, benzofuranyl, benzimidazolyl, 1,2,3,4-tetrahydroquinolinyl, 1,2,3,4-tetrahydroisoquinolinyl, or dibenzofuranyl, each of which is optionally substituted with 1, 2, 3, 4, or 5 groups that are independently $C_1$-$C_6$ alkoxycarbonyl, $C_1$-$C_6$ alkyl, $C_1$-$C_6$ alkoxy, halogen, $C_1$-$C_2$ haloalkyl, $C_1$-$C_2$ haloalkoxy, $NH_2$, $NH(C_1$-$C_6)$alkyl, $N(C_1$-$C_6)$alkyl$(C_1$-$C_6)$alkyl, or phenyl; and Y' is a bond or —$(C_1$-$C_4)$alkyl-.

In still another aspect, the invention provides compounds of formula V-a, i.e., compounds of formula V, wherein $R_1$ is H, $C_1$-$C_6$ alkyl, benzyl, or allyl;

$R_{23}$ is H;

$R_6$ and $R_7$ are independently H, $C_1$-$C_6$ alkyl, phenyl$(C_1$-$C_6)$ alkyl, $(C_2$-$C_6)$ alkanoyl, phenyl$(C_1$-$C_6)$alkanoyl, $(C_1$-$C_6)$ alkoxycarbonyl, benzyloxycarbonyl, benzimidazolylcarbonyl, benzofuranylcarbonyl, thiazolylcarbonyl, indolylcarbonyl, morpholinylcarbonyl, thiomorpholinylcarbonyl, thiomorpholinyl S,S dioxide-carbonyl, piperazinylcarbonyl, piperidinylcarbonyl, pyrrolidinylcarbonyl, —$C(O)NH_2$, —$C(O)NH(C_1$-$C_6)$alkyl, —$C(O)N(C_1$-$C_6)$alkyl$(C_1$-$C_6)$alkyl, or —$SO_2$-phenyl wherein the cyclic groups are optionally substituted with 1, 2, 3, or 4 groups that are independently halogen, $C_1$-$C_4$ alkyl, $C_1$-$C_4$ alkoxy, $NO_2$, OH, $NH_2$, $NH(C_1$-$C_6)$alkyl, $N(C_1$-$C_6)$alkyl$(C_1$-$C_6)$alkyl, $C_1$-$C_2$ haloalkyl or $C_1$-$C_2$ haloalkoxy.

In still another aspect, the invention provides compounds of formula V-b, i.e., compounds of formula V-a, wherein
$L_2$ is a bond, —O—$(C_1$-$C_6)$alkyl-, —$(C_1$-$C_6)$alkyl-O—,
$L_3$ is a bond, —$(C_1$-$C_4)$alkyl-O—, —O—$(C_1$-$C_4)$alkyl, or —$(C_1$-$C_4)$alkyl-; and
$L_4$ is —$(C_1$-$C_4)$alkyl-, —S(O)$_u$—CH$_2$—, or —$(C_1$-$C_4)$alkyl-S(O)$_u$—CH$_2$—;
wherein u is 0, 1, or 2.

In yet still another aspect, the invention provides compounds of formula V-c, i.e., compounds of formula V-b of the formula

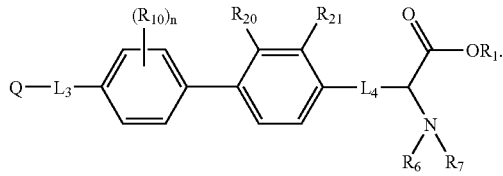

In still another aspect, the invention provides compounds of formula V-d, i.e., compounds of formula V-c, wherein Q is -benzofuranyl-$(C_1$-$C_4)$alkyl-phenyl, -dibenzofuranyl-$(C_1$-$C_4)$alkyl-phenyl, indolyl, phenyl, benzofuranyl, benzimidazolyl, 1,2,3,4-tetrahydroquinolinyl, 1,2,3,4-tetrahydroisoquinolinyl, or dibenzofuranyl, each of which is optionally substituted with 1, 2, 3, 4, or 5 groups that are independently $C_1$-$C_6$ alkoxycarbonyl, $C_1$-$C_6$ alkyl, $C_1$-$C_6$ alkoxy, halogen, CF$_3$, OCF$_3$, NH$_2$, NH$(C_1$-$C_6)$alkyl, N$(C_1$-$C_6)$alkyl$(C_1$-$C_6)$alkyl, or phenyl.

In still another aspect, the invention provides compounds of formula V-e, i.e., compounds of formula V-d, wherein $R_1$ is H, or $C_1$-$C_6$ alkyl; $R_6$ is H; at least one of $R_{20}$ and $R_{21}$ is H; and $L_4$ is —$(C_1$-$C_4)$alkyl-, —S(O)$_u$—CH$_2$—, S(O)$_u$—CH$_2$CH$_2$—, or —CH$_2$—S(O)$_u$—CH$_2$—; wherein u is 0, 1, or 2.

In yet another aspect, the invention provides compounds of formula V-f, i.e., compounds of formula V-e, wherein $R_7$ is $C_1$-$C_6$ alkyl, $(C_2$-$C_6)$ alkanoyl, $(C_1$-$C_6)$ alkoxycarbonyl, —C(O)NH$_2$, —C(O)NH$(C_1$-$C_6)$alkyl, or —C(O)N$(C_1$-$C_6)$alkyl$(C_1$-$C_6)$alkyl.

In yet another aspect, the invention provides compounds of formula V-g, i.e., compounds of formula V-e, wherein $R_7$ is phenyl$(C_1$-$C_4)$alkyl, phenyl$(C_1$-$C_6)$alkanoyl, benzyloxycarbonyl, benzimidazolylcarbonyl, benzofuranylcarbonyl, thiazolylcarbonyl, indolylcarbonyl, morpholinylcarbonyl, piperazinylcarbonyl, piperidinylcarbonyl, pyrrolidinylcarbonyl, or —SO$_2$-phenyl wherein the cyclic groups are optionally substituted with 1, 2, 3, or 4 groups that are independently halogen, $C_1$-$C_4$ alkyl, $C_1$-$C_4$ alkoxy, NO$_2$, OH, NH$_2$, NH$(C_1$-$C_6)$alkyl, N$(C_1$-$C_6)$alkyl$(C_1$-$C_6)$alkyl, CF$_3$ or OCF$_3$.

In yet another aspect, the invention provides compounds of formula V-f, i.e., compounds of formula V-e,

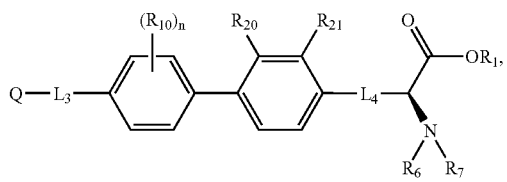

wherein n is 0, 1, or 2; $L_3$ is a bond, —CH$_2$—, or —$(C_1$-$C_2)$alkyl-O—; and each $R_{10}$ is independently H, halogen, $C_1$-$C_4$ alkyl, $C_1$-$C_4$ alkoxy, CF$_3$, OCF$_3$, NO$_2$, NH$_2$, NH$(C_1$-$C_6)$alkyl, or N$(C_1$-$C_6)$alkyl$(C_1$-$C_6)$alkyl.

In yet another aspect, the invention provides compounds of formula V-g, i.e., compounds of formula V-f, wherein Q is -benzofuranyl-$(C_1$-$C_4)$alkyl-phenyl, indolyl, phenyl, 1,2,3,4-tetrahydroquinolinyl, 1,2,3,4-tetrahydroisoquinolinyl, or dibenzofuranyl, each of which is optionally substituted with 1, 2, 3, 4, or 5 groups that are independently $C_1$-$C_6$ alkoxycarbonyl, $C_1$-$C_6$ alkyl, $C_1$-$C_6$ alkoxy, halogen, CF$_3$, OCF$_3$, NH$_2$, NH$(C_1$-$C_6)$alkyl, or N$(C_1$-$C_6)$alkyl$(C_1$-$C_6)$alkyl.

In yet another aspect, the invention provides compounds of formula V-h, i.e., compounds of formula V-g, wherein $R_7$ is benzyl, phenyl$(C_1$-$C_4)$alkanoyl, benzyloxycarbonyl, or —SO$_2$-phenyl wherein the cyclic groups are optionally substituted with 1, 2, or 3 groups that are independently halogen, $C_1$-$C_4$ alkyl, $C_1$-$C_4$ alkoxy, NO$_2$, OH, NH$_2$, NH$(C_1$-$C_6)$alkyl, N$(C_1$-$C_6)$alkyl$(C_1$-$C_6)$alkyl, CF$_3$ or OCF$_3$.

In still another aspect, the invention provides compounds of formula V-i, i.e., compounds of formula V-h, wherein Q is -benzofuranyl-CH$_2$-phenyl, indolyl, 1,2,3,4-tetrahydroquinolinyl, 1,2,3,4-tetrahydroisoquinolinyl, or dibenzofuranyl, each of which is optionally substituted with 1, 2, 3, 4, or 5 groups that are independently $C_1$-$C_6$ alkoxycarbonyl, $C_1$-$C_6$ alkyl, $C_1$-$C_6$ alkoxy, halogen, CF$_3$, OCF$_3$, NH$_2$, NH$(C_1$-$C_6)$ alkyl, or N$(C_1$-$C_6)$alkyl$(C_1$-$C_6)$alkyl.

In yet still another aspect, the invention provides compounds of formula V-j, i.e., compounds of formula V-i, wherein n is 0, 1, or 2; $L_3$ is a bond; $R_1$ is H; and $R_{20}$ is H.

In still yet another aspect, the invention provides compounds of formula V-k, i.e., compounds of formula V-i, wherein $L_4$ is —CH$_2$—, —CH$_2$—S—CH$_2$—, —S—CH$_2$CH$_2$—, or —S—CH$_2$—.

In another aspect, the invention provides compounds of formula V-l, i.e., compounds of formula V of the formula

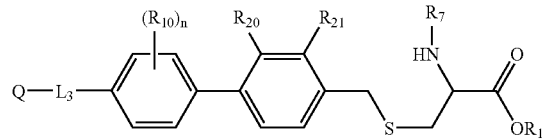

wherein $R_{20}$, and $R_2$, are independently selected from H, benzyloxy, benzyl, halogen, $C_1$-$C_6$ alkyl, OH, $C_1$-$C_6$ alkoxy, NO$_2$, NH$_2$, NH$(C_1$-$C_6)$alkyl, N$(C_1$-$C_6)$alkyl$(C_1$-$C_6)$alkyl, NH-phenyl, N$(C_1$-$C_4)$alkyl-aryl, —NHSO$_2$-phenyl, or —N$(C_1$-$C_4$ alkyl)SO$_2$phenyl, wherein the phenyl group is optionally substituted with 1, 2, 3, or 4 groups that are independently $C_1$-$C_6$ alkyl, $C_1$-$C_6$ alkoxy, halogen, OH, NO$_2$, $C_1$-$C_2$ haloalkyl, $C_1$-$C_2$ haloalkoxy.

In another aspect, the invention provides compounds of formula V-m, i.e., compounds of formula V-l wherein $R_1$ is H, $C_1$-$C_4$ alkyl or benzyl; $R_7$ is phenyl$(C_1$-$C_4)$alkyl, phenyl$(C_1$-$C_6)$alkanoyl, benzyloxycarbonyl, benzimidazolylcarbonyl, benzofuranylcarbonyl, thiazolylcarbonyl, indolylcarbonyl, morpholinylcarbonyl, piperazinylcarbonyl, piperidinylcarbonyl, pyrrolidinylcarbonyl, or —SO$_2$-phenyl wherein the cyclic groups are optionally substituted with 1, 2, 3, or 4 groups that are independently halogen, $C_1$-$C_4$ alkyl, $C_1$-$C_4$ alkoxy, NO$_2$, OH, NH$_2$, NH$(C_1$-$C_6)$alkyl, N$(C_1$-$C_6)$alkyl$(C_1$-$C_6)$alkyl, CF$_3$ or OCF$_3$.

In another aspect, the invention provides compounds of formula V-n, i.e., compounds of formula V-m, wherein $L_3$ is a bond, —CH$_2$—, —$(C_1$-$C_4)$alkyl-, or —$(C_1$-$C_2)$alkyl-O—; Q is -benzofuranyl-$(C_1$-$C_4)$alkyl-phenyl, -dibenzofuranyl-$(C_1$-$C_4)$alkyl-phenyl, indolyl, phenyl, benzofuranyl, benzimidazolyl, 1,2,3,4-tetrahydroquinolinyl, 1,2,3,4-tetrahydroisoquinolinyl, or dibenzofuranyl, each of which is optionally substituted with 1, 2, 3, 4, or 5 groups that are independently $C_1$-$C_6$ alkoxycarbonyl, $C_1$-$C_6$ alkyl, $C_1$-$C_6$ alkoxy, halogen, $CF_3$, $OCF_3$, $NH_2$, $NH(C_1-C_6)$alkyl, $N(C_1-C_6)$alkyl$(C_1-C_6)$alkyl, or phenyl; each $R_{10}$ is independently H, halogen, $C_1-C_4$ alkyl, $C_1-C_4$ alkoxy, $CF_3$, $OCF_3$, $NO_2$, $NH_2$, $NH(C_1-C_6)$alkyl, or $N(C_1-C_6)$alkyl$(C_1-C_6)$alkyl; and $R_{20}$, and $R_{21}$ are independently selected from H, benzyloxy, benzyl, halogen, $C_1-C_6$ alkyl, OH, $C_1-C_6$ alkoxy, $NO_2$, $NH_2$, $NH(C_1-C_6)$alkyl, or $N(C_1-C_6)$alkyl$(C_1-C_6)$alkyl.

In another aspect, the invention provides compounds of formula V-o, i.e., compounds of formula V-n, wherein n is 0, 1, or 2; $L_3$ is a bond; $R_1$ is H; and $R_{20}$ is H.

In another aspect, the invention provides compounds of formula V-p, i.e., compounds of formula V-o, wherein $R_7$ is benzyl, phenyl$(C_1-C_6)$alkanoyl, benzyloxycarbonyl, $C_1-C_4$ alkoxycarbonyl, pyridylcarbonyl, benzimidazolylcarbonyl, thiazolylcarbonyl, indolylcarbonyl, morpholinylcarbonyl, or —$SO_2$-phenyl, wherein each cyclic groups is optionally substituted with 1, 2, 3, or 4 groups that are independently halogen, $C_1-C_4$ alkyl, $C_1-C_4$ alkoxy, $NO_2$, OH, $NH_2$, $NH(C_1-C_6)$alkyl, $N(C_1-C_6)$alkyl$(C_1-C_6)$alkyl, $CF_3$ or $OCF_3$.

In another aspect, the invention provides compounds of Formula VI:

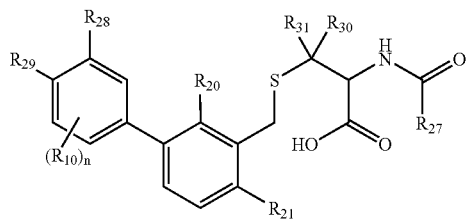

VI wherein
$R_{27}$ is $C_1-C_6$ alkoxy;
$R_{28}$ is (i) hydrogen, (ii) $C_1-C_2$ alkyl, (iii) adamantanyl, (iv) dibenzofuranyl, (v) $C_1-C_3$ alkyl, (vi) dibenzothiophenyl, or (vii) phenyl substituted with one or two $C_1-C_3$ alkoxy or $C_1-C_2$ acyl, or with one phenoxy;
$R_{29}$ is (i) hydrogen, (ii) $C_1-C_2$ alkyl, (iii) adamantanyl, (iv) dibenzofuranyl, (v) $C_1-C_3$ alkyl, (vi) dibenzothiophenyl, or (vii) phenyl substituted with one or two $C_1-C_3$ alkoxy or $C_1-C_2$ acyl, or with one phenoxy;
provided that at least one of $R_{28}$ and $R_{29}$ is hydrogen or $C_1-C_6$ alkyl;
$R_{20}$ and $R_{21}$ are hydrogen or halogen;
$R_{30}$ and $R_{31}$ are independently hydrogen or $C_1-C_2$ alkyl;
each $R_{10}$ is independently H, halogen, $C_1-C_4$ alkyl, $C_1-C_4$ alkoxy, $C_1-C_4$ haloalkyl, $C_1-C_4$ haloalkoxy, $NO_2$, $NH_2$, $NH(C_1-C_6)$alkyl, or $N(C_1-C_6)$alkyl$(C_1-C_6)$alkyl; and
n is 0, 1, or 2.

A preferred dibenzothiophenyl group is dibenzothiophen-4-yl.

In particular aspects of Formula VI, n is 0 or 1. In a preferred aspect, n is 0. In another preferred aspect of Formula VI, n is 1 and $R_{10}$ is chloro, fluoro, methyl, ethyl, methoxy, ethoxy, trifluoromethyl, or amino. In still another preferred aspect of Formula VI, n is 1 and $R_{10}$ is fluoro, methyl, methoxy, or trifluoromethyl.

Preferred compounds of Formula VI include those where $R_{20}$ is hydrogen and $R_{21}$ is halogen. More preferably $R_{21}$ is fluoro. In another aspect, both of $R_{20}$ and $R_{21}$ are halogen, preferably fluoro.

Other preferred compounds of Formula VI include those where $R_{28}$ is dibenzofuranyl or adamantanyl and $R_{29}$ is hydrogen or methyl. Other preferred compounds of Formula VI include those where $R_{29}$ is dibenzofuranyl or adamantanyl and $R_{28}$ is hydrogen or methyl.

Where one of $R_{28}$ and $R_{29}$ is hydrogen, the other is preferably adamantanyl or dibenzofuranyl, more preferably dibenzofuran-3-yl or dibenzofuran-4-yl, most preferably dibenzofuran-4-yl. Each of these preferred $R_{28}$ and $R_{29}$ groups is optionally substituted with from 1-4, more preferably 1-3, and most preferably 1-2 groups selected from $C_1-C_6$ alkyl, $C_1-C_4$ alkoxycarbonyl, $C_1-C_6$ alkoxy, halogen, haloalkyl, haloalkoxy, and $NR_6R_7$, where $R_6$ and $R_7$ are independently H, $C_1-C_6$ alkyl, $C_1-C_6$ alkanoyl, $C_1-C_6$ alkoxycarbonyl, piperidinyl, pyrrolidinylcarbonyl, —C(O)$NH_2$, —C(O)NH($C_1$-$C_6$)alkyl, or —C(O)N($C_1-C_6$)alkyl$(C_1-C_6)$alkyl.

A preferred dibenzothiophenyl group is dibenzothiophen-4-yl. Preferably, $R_{28}$ is hydrogen, $R_{29}$ is dibenzothiophen-4-yl, and each of $R_{30}$ and $R_{31}$ are hydrogen.

In a particular aspect of Formual VI, $R_{28}$ is hydrogen; $R_{29}$ is dibenzofuran-4-yl; and each of $R_{30}$ and $R_{31}$ is hydrogen. In a preferred aspect, $R_{20}$ is hydrogen and $R_{21}$ is halogen, more preferably fluoro. In another preferred aspect, both of $R_{20}$ and $R_{21}$ are halogen, preferably fluoro. In yet another preferred aspect, both of $R_{20}$ and $R_{21}$ are hydrogen.

In another particular aspect of Formual VI, $R_{29}$ is hydrogen; $R_{28}$ is dibenzofuran-4-yl; and each of $R_{30}$ and $R_{31}$ is hydrogen. Preferably, within this aspect both of $R_{20}$ and $R_{21}$ are halogen, preferably fluoro. More preferably, within this aspect, $R_{20}$ is hydrogen and $R_{21}$ is fluoro.

Still other preferred compounds of Formula VI include those where one of $R_{28}$ and $R_{29}$ is 3,4-dimethoxyphenyl, 3-methoxyphenyl, 3-formylphenyl, or 3-acetylphenyl.

Preferred compounds of Formula VI include those where $R_{30}$ and $R_{31}$ are (i) both hydrogen, (ii) hydrogen and methyl, or (iii) both methyl. More preferred compounds of Formula VI are those where $R_{30}$ and $R_{31}$ are both hydrogen.

In another aspect, the invention provides compounds of Formula VII:

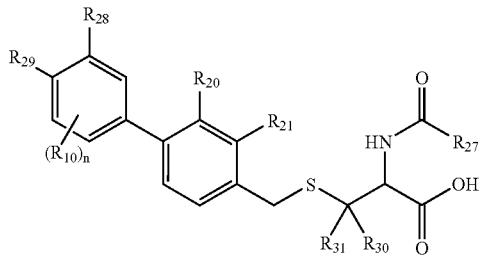

VII wherein
$R_{27}$ is $C_1-C_6$ alkoxy;
$R_{28}$ is (i) hydrogen, (ii) $C_1-C_2$ alkyl, (iii) adamantanyl, (iv) dibenzofuranyl, (v) $C_1-C_3$ alkyl, (vi) dibenzothiophenyl, or (vii) phenyl substituted with one or two $C_1-C_3$ alkoxy or $C_1-C_2$ acyl, or with one phenoxy;
$R_{29}$ is (i) hydrogen, (ii) $C_1-C_2$ alkyl, (iii) adamantanyl, (iv) dibenzofuranyl, (v) $C_1-C_3$ alkyl, (vi) dibenzothiophenyl, or (vii) phenyl substituted with one or two $C_1-C_3$ alkoxy or $C_1-C_2$ acyl, or with one phenoxy;
provided that at least one of $R_{28}$ and $R_{29}$ is hydrogen or $C_1-C_6$ alkyl;
$R_{20}$ and $R_{21}$ are hydrogen or halogen;
$R_{30}$ and $R_{31}$ are independently hydrogen or $C_1-C_2$ alkyl;
each $R_{10}$ is independently H; halogen, $C_1-C_4$ alkyl, $C_1-C_4$ alkoxy, $C_1-C_4$ haloalkyl, $C_1-C_4$ haloalkoxy, $NO_2$, $NH_2$, $NH(C_1-C_6)$alkyl, or $N(C_1-C_6)$alkyl$(C_1-C_6)$alkyl; and
n is 0, 1, or 2.

A preferred dibenzothiophenyl group is dibenzothiophen-4-yl. Preferably, $R_{28}$ is hydrogen, $R_{29}$ is dibenzothiophen-4-yl, and each of $R_{30}$ and $R_{31}$ are hydrogen.

In particular aspects of Formula VII, n is 0 or 1. In a preferred aspect, n is 0. In another preferred aspect of Formula VII, n is 1 and $R_{10}$ is chloro, fluoro, methyl, ethyl, methoxy, ethoxy, trifluoromethyl, or amino. In still another preferred aspect of Formula VII, n is 1 and $R_{10}$ is fluoro, methyl, methoxy, or trifluoromethyl.

Preferred compounds of Formula VII include those where $R_{20}$ is hydrogen and $R_{21}$ is halogen. More preferably $R_{21}$ is fluoro. In another aspect, both of $R_{20}$ and $R_{21}$ are halogen, preferably fluoro.

Other preferred compounds of Formula VII include those where $R_{28}$ is dibenzofuranyl or adamantanyl and $R_{29}$ is hydrogen or methyl. Other preferred compounds of Formula VII include those where $R_{29}$ is dibenzofuranyl or adamantanyl and $R_{28}$ is hydrogen or methyl.

Where one of $R_{28}$ and $R_{29}$ is hydrogen, the other is preferably adamantanyl or dibenzofuranyl, more preferably dibenzofuran-3-yl or dibenzofuran-4-yl, most preferably dibenzofuran-4-yl. Each of these preferred $R_{28}$ and $R_{29}$ groups is optionally substituted with from 1-4, more preferably 1-3, and most preferably 1-2 groups selected from $C_1$-$C_6$ alkyl, $C_1$-$C_4$ alkoxycarbonyl, $C_1$-$C_6$ alkoxy, halogen, haloalkyl, haloalkoxy, and $NR_6R_7$, where $R_6$ and $R_7$ are independently H, $C_1$-$C_6$ alkyl, $C_1$-$C_6$ alkanoyl, $C_1$-$C_6$ alkoxycarbonyl, piperidinyl, pyrrolidinylcarbonyl, —C(O)NH$_2$, —C(O)NH($C_1$-$C_6$)alkyl, or —C(O)N($C_1$-$C_6$)alkyl($C_1$-$C_6$)alkyl.

In a particular aspect of Formual VII, $R_{28}$ is hydrogen; $R_{29}$ is dibenzofuran-4-yl; and each of $R_{30}$ and $R_{31}$ is hydrogen. In a preferred aspect, $R_{20}$ is hydrogen and $R_{21}$ is halogen, more preferably fluoro. In another preferred aspect, both of $R_{20}$ and $R_{21}$ are halogen, preferably fluoro. In yet another preferred aspect, both of $R_{20}$ and $R_{21}$ are hydrogen.

In another particular aspect of Formual VII, $R_{29}$ is hydrogen; $R_{28}$ is dibenzofuran-4-yl; and each of $R_{30}$ and $R_{31}$ is hydrogen. In another preferred aspect, both of $R_{20}$ and $R_{21}$ are halogen, preferably fluoro.

In still another particular aspect of Formual VII, $R_{28}$ is hydrogen; $R_{29}$ is dibenzofuran-4-yl; and each of $R_{30}$ and $R_{31}$ is methyl.

Still other preferred compounds of Formula VII include those where one of $R_{28}$ and $R_{29}$ is 3,4-dimethoxyphenyl, 3-methoxyphenyl, 3-formylphenyl, or 3-acetylphenyl.

Preferred compounds of Formula VII include those where $R_{30}$ and $R_{31}$ are (i) both hydrogen, (ii) hydrogen and methyl, or (iii) both methyl. More preferred compounds of Formula VII are those where $R_{30}$ and $R_{31}$ are both hydrogen.

In another aspect, the invention provides compounds of Formula VIII-A:

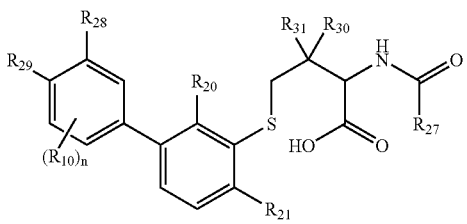

VIII-A wherein
$R_{27}$ is $C_1$-$C_6$ alkoxy;
$R_{28}$ is (i) hydrogen, (ii) $C_1$-$C_2$ alkyl, (iii) adamantanyl, (iv) dibenzofuranyl, (v) $C_1$-$C_3$ alkyl, (vi) dibenzothiophenyl, or (vii) phenyl substituted with one or two $C_1$-$C_3$ alkoxy or $C_1$-$C_2$ acyl, or with one phenoxy;

$R_{29}$ is (i) hydrogen, (ii) $C_1$-$C_2$ alkyl, (iii) adamantanyl, (iv) dibenzofuranyl, (v) $C_1$-$C_3$ alkyl, (vi) dibenzothiophenyl, or (vii) phenyl substituted with one or two $C_1$-$C_3$ alkoxy or $C_1$-$C_2$ acyl, or with one phenoxy;

provided that at least one of $R_{28}$ and $R_{29}$ is hydrogen or $C_1$-$C_6$ alkyl;

$R_{20}$ and $R_{21}$ are hydrogen or halogen;

$R_{30}$ and $R_{31}$ are independently hydrogen or $C_1$-$C_2$ alkyl;

each $R_{10}$ is independently H, halogen, $C_1$-$C_4$ alkyl, $C_1$-$C_4$ alkoxy, $C_1$-$C_4$ haloalkyl, $C_1$-$C_4$ haloalkoxy, NO$_2$, NH$_2$, NH($C_1$-$C_6$)alkyl, or N($C_1$-$C_6$)alkyl($C_1$-$C_6$)alkyl; and n is 0, 1, or 2.

In particular aspects of Formula VIII-A, n is 0 or 1. In a preferred aspect, n is 0. In another preferred aspect of Formula VIII-A, n is 1 and $R_{10}$ is chloro, fluoro, methyl, ethyl, methoxy, ethoxy, trifluoromethyl, or amino. In still another preferred aspect of Formula VIII-A, n is 1 and $R_{10}$ is fluoro, methyl, methoxy, or trifluoromethyl.

Preferred compounds of Formula VIII-A include those where $R_{20}$ is hydrogen and $R_{21}$ is halogen. More preferably $R_{21}$ is fluoro. In another aspect, both of $R_{20}$ and $R_{21}$ are halogen, preferably fluoro.

Other preferred compounds of Formula VIII-A include those where $R_{28}$ is dibenzofuranyl or adamantanyl and $R_{29}$ is hydrogen or methyl. Other preferred compounds of Formula VIII-A include those where $R_{29}$ is dibenzofuranyl or adamantanyl and $R_{28}$ is hydrogen or methyl.

Where one of $R_{28}$ and $R_{29}$ is hydrogen, the other is preferably adamantanyl or dibenzofuranyl, more preferably dibenzofuran-3-yl or dibenzofuran-4-yl, most preferably dibenzofuran-4-yl. Each of these preferred $R_{28}$ and $R_{29}$ groups is optionally substituted with from 1-4, more preferably 1-3, and most preferably 1-2 groups selected from $C_1$-$C_6$ alkyl, $C_1$-$C_4$ alkoxycarbonyl, $C_1$-$C_6$ alkoxy, halogen, haloalkyl, haloalkoxy, and $NR_6R_7$, where $R_6$ and $R_7$ are independently H, $C_1$-$C_6$ alkyl, $C_1$-$C_6$ alkanoyl, $C_1$-$C_6$ alkoxycarbonyl, piperidinyl, pyrrolidinylcarbonyl, —C(O)NH$_2$, —C(O)NH($C_1$-$C_6$)alkyl, or —C(O)N($C_1$-$C_6$)alkyl($C_1$-$C_6$)alkyl.

In a particular aspect of Formual VIII-A, $R_{28}$ is hydrogen; $R_{29}$ is dibenzofuran-4-yl; and each of $R_{30}$ and $R_{31}$ is hydrogen. In a preferred aspect, $R_{20}$ is hydrogen and $R_{21}$ is halogen, more preferably fluoro. In another preferred aspect, both of $R_{20}$ and $R_{21}$ are halogen, preferably fluoro. In yet another preferred aspect, both of $R_{20}$ and $R_{21}$ are hydrogen.

In another particular aspect of Formual VIII-A, $R_{29}$ is hydrogen; $R_{28}$ is dibenzofuran-4-yl; and each of $R_{30}$ and $R_{31}$ is hydrogen. In another preferred aspect, both of $R_{20}$ and $R_{21}$ are halogen, preferably fluoro.

In still another particular aspect of Formual VIII-A, $R_{28}$ is hydrogen; $R_{29}$ is dibenzofuran-4-yl; and each of $R_{30}$ and $R_{31}$ is methyl.

Still other preferred compounds of Formula VIII-A include those where one of $R_{28}$ and $R_{29}$ is 3,4-dimethoxyphenyl, 3-methoxyphenyl, 3-formylphenyl, or 3-acetylphenyl.

Preferred compounds of Formula VIII-A include those where $R_{30}$ and $R_{31}$ are (i) both hydrogen, (ii) hydrogen and methyl, or (iii) both methyl. More preferred compounds of Formula VIII-A are those where $R_{30}$ and $R_{31}$ are both hydrogen.

In another aspect, the invention provides compounds of Formula VIII-B:

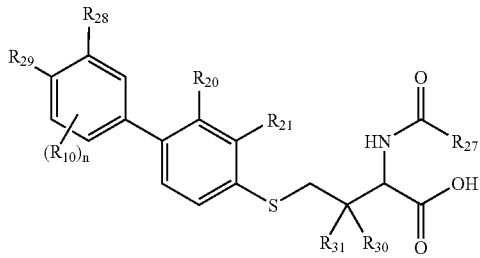

VIII-B wherein
$R_{27}$ is $C_1$-$C_6$ alkoxy;
$R_{28}$ is (i) hydrogen, (ii) $C_1$-$C_2$ alkyl, (iii) adamantanyl, (iv) dibenzofuranyl, (v) $C_1$-$C_3$ alkyl, (vi) dibenzothiophenyl, or (vii) phenyl substituted with one or two $C_1$-$C_3$ alkoxy or $C_1$-$C_2$ acyl, or with one phenoxy;
$R_{29}$ is (i) hydrogen, (ii) $C_1$-$C_2$ alkyl, (iii) adamantanyl, (iv) dibenzofuranyl, (v) $C_1$-$C_3$ alkyl, (vi) dibenzothiophenyl, or (vii) phenyl substituted with one or two $C_1$-$C_3$ alkoxy or $C_1$-$C_2$ acyl, or with one phenoxy; provided that at least one of $R_{28}$ and $R_{29}$ is hydrogen or $C_1$-$C_6$ alkyl;
$R_{20}$ and $R_{21}$ are hydrogen or halogen;
$R_{30}$ and $R_{31}$ are independently hydrogen or $C_1$-$C_2$ alkyl;
each $R_{10}$ is independently H, halogen, $C_1$-$C_4$ alkyl, $C_1$-$C_4$ alkoxy, $C_1$-$C_4$ haloalkyl, $C_1$-$C_4$ haloalkoxy, $NO_2$, $NH_2$, $NH(C_1$-$C_6)$alkyl, or $N(C_1$-$C_6)$alkyl$(C_1$-$C_6)$alkyl; and
n is 0, 1, or 2.

Preferred compounds of Formula VIII-B include those where $R_{20}$ is hydrogen and $R_{21}$ is halogen. More preferably $R_{21}$ is fluoro. In another aspect, both of $R_{20}$ and $R_{21}$ are halogen, preferably fluoro.

In particular aspects of Formula VIII-B, n is 0 or 1. In a preferred aspect, n is 0. In another preferred aspect of Formula VIII-B, n is 1 and $R_{10}$ is chloro, fluoro, methyl, ethyl, methoxy, ethoxy, trifluoromethyl, or amino. In still another preferred aspect of Formula VIII-B, n is 1 and $R_{10}$ is fluoro, methyl, methoxy, or trifluoromethyl.

Other preferred compounds of Formula VIII-B include those where $R_{28}$ is dibenzofuranyl or adamantanyl and $R_{29}$ is hydrogen or methyl. Other preferred compounds of Formula VIII-B include those where $R_{29}$ is dibenzofuranyl or adamantanyl and $R_{28}$ is hydrogen or methyl.

Where one of $R_{28}$ and $R_{29}$ is hydrogen, the other is preferably adamantanyl or dibenzofuranyl, more preferably dibenzofuran-3-yl or dibenzofuran-4-yl, most preferably dibenzofuran-4-yl. Each of these preferred $R_{28}$ and $R_{29}$ groups is optionally substituted with from 1-4, more preferably 1-3, and most preferably 1-2 groups selected from $C_1$-$C_6$ alkyl, $C_1$-$C_4$ alkoxycarbonyl, $C_1$-$C_6$ alkoxy, halogen, haloalkyl, haloalkoxy, and $NR_6R_7$, where $R_6$ and $R_7$ are independently H, $C_1$-$C_6$ alkyl, $C_1$-$C_6$ alkanoyl, $C_1$-$C_6$ alkoxycarbonyl, piperidinyl, pyrrolidinylcarbonyl, —$C(O)NH_2$, —$C(O)NH(C_1$-$C_6)$alkyl, or —$C(O)N(C_1$-$C_6)$alkyl$(C_1$-$C_6)$alkyl.

In a particular aspect of Formual VIII-B, $R_{28}$ is hydrogen; $R_{29}$ is dibenzofuran-4-yl; and each of $R_{30}$ and $R_{31}$ is hydrogen. In a preferred aspect, $R_{20}$ is hydrogen and $R_{21}$ is halogen, more preferably fluoro. In another preferred aspect, both of $R_{20}$ and $R_{21}$ are halogen, preferably fluoro. In yet another preferred aspect, both of $R_{20}$ and $R_{21}$ are hydrogen.

In another particular aspect of Formual VIII-B, $R_{29}$ is hydrogen; $R_{28}$ is dibenzofuran-4-yl; and each of $R_{30}$ and $R_{31}$ is hydrogen. In another preferred aspect, both of $R_{20}$ and $R_{21}$ are halogen, preferably fluoro.

In still another particular aspect of Formual VIII-B, $R_{28}$ is hydrogen; $R_{29}$ is dibenzofuran-4-yl; and each of $R_{30}$ and $R_{31}$ is methyl.

Still other preferred compounds of Formula VIII-B include those where one of $R_{28}$ and $R_{29}$ is 3,4-dimethoxyphenyl, 3-methoxyphenyl, 3-formylphenyl, or 3-acetylphenyl.

Preferred compounds of Formula VIII-B include those where $R_{30}$ and $R_{31}$ are (i) both hydrogen, (ii) hydrogen and methyl, or (iii) both methyl. More preferred compounds of Formula VIII-B are those where $R_{30}$ and $R_{31}$ are both hydrogen.

In another aspect, the invention provides compounds of Formula IX-A:

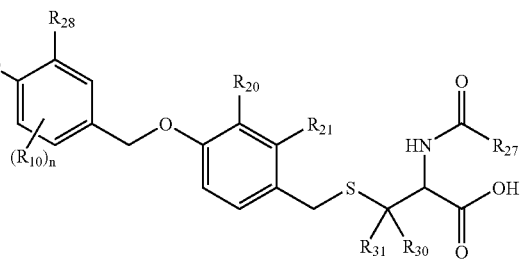

IX-A wherein
$R_{27}$ is $C_1$-$C_6$ alkoxy;
$R_{28}$ is (i) hydrogen, (ii) $C_1$-$C_2$ alkyl, (iii) adamantanyl, (iv) dibenzofuranyl, (v) $C_1$-$C_3$ alkyl, (vi) dibenzothiophenyl, or (vii) phenyl substituted with one or two $C_1$-$C_3$ alkoxy or $C_1$-$C_2$ acyl, or with one phenoxy;
$R_{29}$ is (i) hydrogen, (ii) $C_1$-$C_2$ alkyl, (iii) adamantanyl, (iv) dibenzofuranyl, (v) $C_1$-$C_3$ alkyl, (vi) dibenzothiophenyl, or (vii) phenyl substituted with one or two $C_1$-$C_3$ alkoxy or $C_1$-$C_2$ acyl, or with one phenoxy;
provided that at least one of $R_{28}$ and $R_{29}$ is hydrogen or $C_1$-$C_6$ alkyl;
$R_{20}$ and $R_{21}$ are hydrogen or halogen;
$R_{30}$ and $R_{31}$ are independently hydrogen or $C_1$-$C_2$ alkyl; each $R_{10}$ is independently H, halogen, $C_1$-$C_4$ alkyl, $C_1$-$C_4$ alkoxy, $C_1$-$C_4$ haloalkyl, $C_1$-$C_4$ haloalkoxy, $NO_2$, $NH_2$, $NH(C_1$-$C_6)$alkyl, or $N(C_1$-$C_6)$alkyl$(C_1$-$C_6)$alkyl; and
n is 0, 1, or 2.

Preferred compounds of Formula IX-A include those where $R_{20}$ is hydrogen and $R_{21}$ is halogen. More preferably $R_{21}$ is fluoro. In another aspect, both of $R_{20}$ and $R_{21}$ are halogen, preferably fluoro.

In particular aspects of Formula IX-A, n is 0 or 1. In a preferred aspect, n is 0. In another preferred aspect of Formula IX-A, n is 1 and $R_{10}$ is chloro, fluoro, methyl, ethyl, methoxy, ethoxy, trifluoromethyl, or amino. In still another preferred aspect of Formula IX-A, n is 1 and $R_{10}$ is fluoro, methyl, methoxy, or trifluoromethyl.

Other preferred compounds of Formula IX-A include those where $R_{28}$ is dibenzofuranyl or adamantanyl and $R_{29}$ is hydrogen or methyl. Other preferred compounds of Formula IX-A include those where $R_{29}$ is dibenzofuranyl or adamantanyl and $R_{28}$ is hydrogen or methyl.

Where one of $R_{28}$ and $R_{29}$ is hydrogen, the other is preferably adamantanyl or dibenzofuranyl, more preferably dibenzofuran-3-yl or dibenzofuran-4-yl, most preferably dibenzofuran-4-yl. Each of these preferred $R_{28}$ and $R_{29}$ groups is optionally substituted with from 1-4, more preferably 1-3, and most preferably 1-2 groups selected from $C_1$-$C_6$ alkyl, $C_1$-$C_4$ alkoxycarbonyl, $C_1$-$C_6$ alkoxy, halogen, haloalkyl, haloalkoxy, and $NR_6R_7$, where $R_6$ and $R_7$ are independently H, $C_1$-$C_6$ alkyl, $C_1$-$C_6$ alkanoyl, $C_1$-$C_6$ alkoxycarbonyl, piperidinyl, pyrrolidinylcarbonyl, —C(O)NH$_2$, —C(O)NH($C_1$-$C_6$)alkyl, or —C(O)N($C_1$-$C_6$)alkyl($C_1$-$C_6$)alkyl.

In a particular aspect of Formual IX-A, $R_{28}$ is hydrogen; $R_{29}$ is dibenzofuran-4-yl; and each of $R_{30}$ and $R_{31}$ is hydrogen. In a preferred aspect, $R_{20}$ is hydrogen and $R_{21}$ is halogen, more preferably fluoro. In another preferred aspect, both of $R_{20}$ and $R_{21}$ are halogen, preferably fluoro. In yet another preferred aspect, both of $R_{20}$ and $R_{21}$ are hydrogen.

In another particular aspect of Formual IX-A, $R_{29}$ is hydrogen; $R_{28}$ is dibenzofuran-4-yl; and each of $R_{30}$ and $R_{31}$ is hydrogen. In another preferred aspect, both of $R_{20}$ and $R_{21}$ are halogen, preferably fluoro.

In still another particular aspect of Formual IX-A, $R_{28}$ is hydrogen; $R_{29}$ is dibenzofuran-4-yl; and each of $R_{30}$ and $R_{31}$ is methyl.

Still other preferred compounds of Formula IX-A include those where one of $R_{28}$ and $R_{29}$ is 3,4-dimethoxyphenyl, 3-methoxyphenyl, 3-formylphenyl, or 3-acetylphenyl.

Preferred compounds of Formula IX-A include those where $R_{30}$ and $R_{31}$ are (i) both hydrogen, (ii) hydrogen and methyl, or (iii) both methyl. More preferred compounds of Formula IX-A are those where $R_{30}$ and $R_{31}$ are both hydrogen.

In another aspect, the invention provides compounds of Formula IX-B:

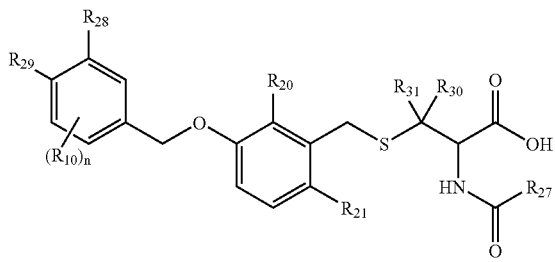

IX-B wherein
$R_{27}$ is $C_1$-$C_6$ alkoxy;
$R_{28}$ is (i) hydrogen, (ii) $C_1$-$C_2$ alkyl, (iii) adamantanyl, (iv) dibenzofuranyl, (v) $C_1$-$C_3$ alkyl, (vi) dibenzothiophenyl, or (vii) phenyl substituted with one or two $C_1$-$C_3$ alkoxy or $C_1$-$C_2$ acyl, or with one phenoxy;
$R_{29}$ is (i) hydrogen, (ii) $C_1$-$C_2$ alkyl, (iii) adamantanyl, (iv) dibenzofuranyl, (v) $C_1$-$C_3$ alkyl, (vi) dibenzothiophenyl, or (vii) phenyl substituted with one or two $C_1$-$C_3$ alkoxy or $C_1$-$C_2$ acyl, or with one phenoxy;
provided that at least one of $R_{28}$ and $R_{29}$ is hydrogen or $C_1$-$C_6$ alkyl;
$R_{20}$ and $R_{21}$ are hydrogen or halogen;
$R_{30}$ and $R_{31}$ are independently hydrogen or $C_1$-$C_2$ alkyl;
each $R_{10}$ is independently H, halogen, $C_1$-$C_4$ alkyl, $C_1$-$C_4$ alkoxy, $C_1$-$C_4$ haloalkyl, $C_1$-$C_4$ haloalkoxy, $NO_2$, $NH_2$, NH($C_1$-$C_6$)alkyl, or N($C_1$-$C_6$)alkyl($C_1$-$C_6$)alkyl; and
n is 0, 1, or 2.

Preferred compounds of Formula IX-B include those where $R_{20}$ is hydrogen and $R_{21}$ is halogen. More preferably $R_{21}$ is fluoro. In another aspect, both of $R_{20}$ and $R_{21}$ are halogen, preferably fluoro.

In particular aspects of Formula IX-B, n is 0 or 1. In a preferred aspect, n is 0. In another preferred aspect of Formula IX-B, n is 1 and $R_{10}$ is chloro, fluoro, methyl, ethyl, methoxy, ethoxy, trifluoromethyl, or amino. In still another preferred aspect of Formula IX-B, n is 1 and $R_{10}$ is fluoro, methyl, methoxy, or trifluoromethyl.

Other preferred compounds of Formula IX-B include those where $R_{28}$ is dibenzofuranyl or adamantanyl and $R_{29}$ is hydrogen or methyl. Other preferred compounds of Formula IX-B include those where $R_{29}$ is dibenzofuranyl or adamantanyl and $R_{28}$ is hydrogen or methyl.

Where one of $R_{28}$ and $R_{29}$ is hydrogen, the other is preferably adamantanyl or dibenzofuranyl, more preferably dibenzofuran-3-yl or dibenzofuran-4-yl, most preferably dibenzofuran-4-yl. Each of these preferred $R_{28}$ and $R_{29}$ groups is optionally substituted with from 1-4, more preferably 1-3, and most preferably 1-2 groups selected from $C_1$-$C_6$ alkyl, $C_1$-$C_4$ alkoxycarbonyl, $C_1$-$C_6$ alkoxy, halogen, haloalkyl, haloalkoxy, and $NR_6R_7$, where $R_6$ and $R_7$ are independently H, $C_1$-$C_6$ alkyl, $C_1$-$C_6$ alkanoyl, $C_1$-$C_6$ alkoxycarbonyl, piperidinyl, pyrrolidinylcarbonyl, —C(O)NH$_2$, —C(O)NH($C_1$-$C_6$)alkyl, or —C(O)N($C_1$-$C_6$)alkyl($C_1$-$C_6$)alkyl.

In a particular aspect of Formual IX-B, $R_{28}$ is hydrogen; $R_{29}$ is dibenzofuran-4-yl; and each of $R_{30}$ and $R_{31}$ is hydrogen. In a preferred aspect, $R_{20}$ is hydrogen and $R_{21}$ is halogen, more preferably fluoro. In another preferred aspect, both of $R_{20}$ and $R_{21}$ are halogen, preferably fluoro. In yet another preferred aspect, both of $R_{20}$ and $R_{21}$ are hydrogen.

In another particular aspect of Formual IX-B, $R_{29}$ is hydrogen; $R_{28}$ is dibenzofuran-4-yl; and each of $R_{30}$ and $R_{31}$ is hydrogen. In another preferred aspect, both of $R_{20}$ and $R_{21}$ are halogen, preferably fluoro.

In still another particular aspect of Formual IX-B, $R_{28}$ is hydrogen; $R_{29}$ is dibenzofuran-4-yl; and each of $R_{30}$ and $R_{31}$ is methyl.

Still other preferred compounds of Formula IX-B include those where one of $R_{28}$ and $R_{29}$ is 3,4-dimethoxyphenyl, 3-methoxyphenyl, 3-formylphenyl, or 3-acetylphenyl.

Preferred compounds of Formula IX-B include those where $R_{30}$ and $R_{31}$ are (i) both hydrogen, (ii) hydrogen and methyl, or (iii) both methyl. More preferred compounds of Formula IX-B are those where $R_{30}$ and $R_{31}$ are both hydrogen.

In another aspect, the invention provides compounds of Formula X-A:

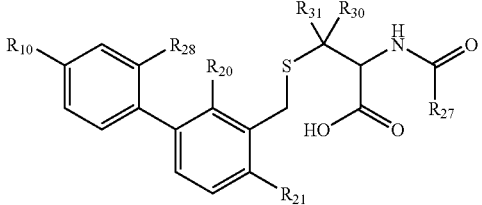

X-A wherein
$R_{27}$ is $C_1$-$C_6$ alkoxy;
$R_{28}$ is (i) hydrogen, (ii) $C_1$-$C_2$ alkyl, (iii) adamantanyl, (iv) dibenzofuranyl, (v) $C_1$-$C_3$ alkyl, (vi) dibenzothiophenyl, or (vii) phenyl substituted with one or two $C_1$-$C_3$ alkoxy or $C_1$-$C_2$ acyl, or with one phenoxy;
$R_{29}$ is (i) hydrogen, (ii) $C_1$-$C_2$ alkyl, (iii) adamantanyl, (iv) dibenzofuranyl, (v) $C_1$-$C_3$ alkyl, (vi) dibenzothiophenyl, or (vii) phenyl substituted with one or two $C_1$-$C_3$ alkoxy or $C_1$-$C_2$ acyl, or with one phenoxy;
provided that at least one of $R_{28}$ and $R_{29}$ is hydrogen or $C_1$-$C_6$ alkyl;
$R_{20}$ and $R_{21}$ are hydrogen or halogen;
$R_{30}$ and $R_{31}$ are independently hydrogen or $C_1$-$C_2$ alkyl;

each $R_{10}$ is independently H, halogen, $C_1$-$C_4$ alkyl, $C_1$-$C_4$ alkoxy, $C_1$-$C_4$ haloalkyl, $C_1$-$C_4$ haloalkoxy, $NO_2$, $NH_2$, $NH(C_1$-$C_6)$alkyl, or $N(C_1$-$C_6)$alkyl$(C_1$-$C_6)$alkyl; and n is 0, 1, or 2.

Preferred compounds of Formula X-A include those where $R_{20}$ is hydrogen and $R_{21}$ is halogen. More preferably $R_{21}$ is fluoro. In another aspect, both of $R_{20}$ and $R_{21}$ are halogen, preferably fluoro.

In particular aspects of Formula X-A, n is 0 or 1. In a preferred aspect, n is 0. In another preferred aspect of Formula X-A, n is 1 and $R_{10}$ is chloro, fluoro, methyl, ethyl, methoxy, ethoxy, trifluoromethyl, or amino. In still another preferred aspect of Formula X-A, n is 1 and $R_{10}$ is fluoro, methyl, methoxy, or trifluoromethyl.

Other preferred compounds of Formula X-A include those where $R_{28}$ is dibenzofuranyl or adamantanyl and $R_{10}$ is hydrogen or methyl.

In this aspect, $R_{28}$ is optionally substituted with from 1-4, more preferably 1-3, and most preferably 1-2 groups selected from $C_1$-$C_6$ alkyl, $C_1$-$C_4$ alkoxycarbonyl, $C_1$-$C_6$ alkoxy, halogen, haloalkyl, haloalkoxy, and $NR_6R_7$, where $R_6$ and $R_7$ are independently H, $C_1$-$C_6$ alkyl, $C_1$-$C_6$ alkanoyl, $C_1$-$C_6$ alkoxycarbonyl, piperidinyl, pyrrolidinylcarbonyl, —C(O)NH$_2$, —C(O)NH$(C_1$-$C_6)$alkyl, or —C(O)N$(C_1$-$C_6)$alkyl$(C_1$-$C_6)$alkyl.

In a particular aspect of Formual X-A, $R_{28}$ is adamantanyl or dibenzofuran-4-yl; $R_{10}$ is hydrogen, methyl, or ethyl; and each of $R_{30}$ and $R_{31}$ is hydrogen. In a preferred aspect, $R_{20}$ is hydrogen and $R_{21}$ is halogen, more preferably fluoro. In another preferred aspect, both of $R_{20}$ and $R_{21}$ are halogen, preferably fluoro. In yet another preferred aspect, both of $R_{20}$ and $R_{21}$ are hydrogen.

In another particular aspect of Formual X-A, $R_{10}$ is hydrogen; $R_{28}$ is dibenzofuran-4-yl; and each of $R_{30}$ and $R_{31}$ is hydrogen. In another preferred aspect, both of $R_{20}$ and $R_{21}$ are halogen, preferably fluoro.

In still another particular aspect of Formual X-A, $R_{10}$ is hydrogen, methyl, or ethyl; $R_{23}$ is dibenzofuran-4-yl or adamantanyl; and each of $R_{30}$ and $R_{31}$ is methyl.

Still other preferred compounds of Formula X-A include those where $R_{28}$ is 3,4-dimethoxyphenyl, 3-methoxyphenyl, 3-formylphenyl, or 3-acetylphenyl.

Preferred compounds of Formula X-A include those where $R_{30}$ and $R_{31}$ are (i) both hydrogen, (ii) hydrogen and methyl, or (iii) both methyl. More preferred compounds of Formula X-A are those where $R_{30}$ and $R_{31}$ are both hydrogen.

In another aspect, the invention provides compounds of Formula X-B:

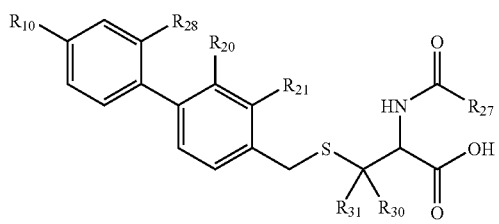

X-B wherein
$R_{27}$ is $C_1$-$C_6$ alkoxy;
$R_{28}$ is (i) hydrogen, (ii) $C_1$-$C_2$ alkyl, (iii) adamantanyl, (iv) dibenzofuranyl, (v) $C_1$-$C_3$ alkyl, (vi) dibenzothiophenyl, or (vii) phenyl substituted with one or two $C_1$-$C_3$ alkoxy or $C_1$-$C_2$ acyl, or with one phenoxy;

$R_{29}$ is (i) hydrogen, (ii) $C_1$-$C_2$ alkyl, (iii) adamantanyl, (iv) dibenzofuranyl, (v) $C_1$-$C_3$ alkyl, (vi) dibenzothiophenyl, or (vii) phenyl substituted with one or two $C_1$-$C_3$ alkoxy or $C_1$-$C_2$ acyl, or with one phenoxy;

provided that at least one of $R_{28}$ and $R_{29}$ is hydrogen or $C_1$-$C_6$ alkyl;

$R_{20}$ and $R_{21}$ are hydrogen or halogen;

$R_{30}$ and $R_{31}$ are independently hydrogen or $C_1$-$C_2$ alkyl;

each $R_{10}$ is independently H, halogen, $C_1$-$C_4$ alkyl, $C_1$-$C_4$ alkoxy, $C_1$-$C_4$ haloalkyl, $C_1$-$C_4$ haloalkoxy, $NO_2$, $NH_2$, $NH(C_1$-$C_6)$alkyl, or $N(C_1$-$C_6)$alkyl$(C_1$-$C_6)$alkyl; and n is 0, 1, or 2.

Preferred compounds of Formula X-B include those where $R_{20}$ is hydrogen and $R_{21}$ is halogen. More preferably $R_{21}$ is fluoro. In another aspect, both of $R_{20}$ and $R_{21}$ are halogen, preferably fluoro.

In particular aspects of Formula X-B, n is 0 or 1. In a preferred aspect, n is 0. In another preferred aspect of Formula X-B, n is 1 and $R_{10}$ is chloro, fluoro, methyl, ethyl, methoxy, ethoxy, trifluoromethyl, or amino. In still another preferred aspect of Formula X-B, n is 1 and $R_{10}$ is fluoro, methyl, methoxy, or trifluoromethyl.

Other preferred compounds of Formula X-B include those where $R_{28}$ is dibenzofuranyl or adamantanyl and $R_{29}$ is hydrogen or methyl. Other preferred compounds of Formula X-B include those where $R_{29}$ is dibenzofuranyl or adamantanyl and $R_{28}$ is hydrogen or methyl.

Where one of $R_{28}$ and $R_{29}$ is hydrogen, the other is preferably adamantanyl or dibenzofuranyl, more preferably dibenzofuran-3-yl or dibenzofuran-4-yl, most preferably dibenzofuran-4-yl. Each of these preferred $R_{28}$ and $R_{29}$ groups is optionally substituted with from 1-4, more preferably 1-3, and most preferably 1-2 groups selected from $C_1$-$C_6$ alkyl, $C_1$-$C_4$ alkoxycarbonyl, $C_1$-$C_6$ alkoxy, halogen, haloalkyl, haloalkoxy, and $NR_6R_7$, where $R_6$ and $R_7$ are independently H, $C_1$-$C_6$ alkyl, $C_1$-$C_6$ alkanoyl, $C_1$-$C_6$ alkoxycarbonyl, piperidinyl, pyrrolidinylcarbonyl, —C(O)NH$_2$, —C(O)NH$(C_1$-$C_6)$alkyl, or —C(O)N$(C_1$-$C_6)$alkyl$(C_1$-$C_6)$alkyl.

In a particular aspect of Formual X-B, $R_{28}$ is hydrogen; $R_{29}$ is dibenzofuran-4-yl; and each of $R_{30}$ and $R_{31}$ is hydrogen. In a preferred aspect, $R_{20}$ is hydrogen and $R_{21}$ is halogen, more preferably fluoro. In another preferred aspect, both of $R_{20}$ and $R_{21}$ are halogen, preferably fluoro. In yet another preferred aspect, both of $R_{20}$ and $R_{21}$ are hydrogen.

In another particular aspect of Formual X-B, $R_{29}$ is hydrogen; $R_{28}$ is dibenzofuran-4-yl; and each of $R_{30}$ and $R_{31}$ is hydrogen. In another preferred aspect, both of $R_{20}$ and $R_{21}$ are halogen, preferably fluoro.

In still another particular aspect of Formual X-B, $R_{28}$ is hydrogen; $R_{29}$ is dibenzofuran-4-yl; and each of $R_{30}$ and $R_{31}$ is methyl.

Still other preferred compounds of Formula X-B include those where one of $R_{28}$ and $R_{29}$ is 3,4-dimethoxyphenyl, 3-methoxyphenyl, 3-formylphenyl, or 3-acetylphenyl.

Preferred compounds of Formula X-B include those where $R_{30}$ and $R_{31}$ are (i) both hydrogen, (ii) hydrogen and methyl, or (iii) both methyl. More preferred compounds of Formula X-B are those where $R_{30}$ and $R_{31}$ are both hydrogen.

In another aspect, the invention provides compounds of Formula XI:

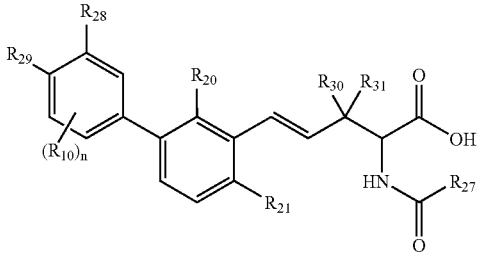

wherein
$R_{27}$ is $C_1$-$C_6$ alkoxy;
$R_{28}$ is (i) hydrogen, (ii) $C_1$-$C_2$ alkyl, (iii) adamantanyl, (iv) dibenzofuranyl, (v) $C_1$-$C_3$ alkyl, (vi) dibenzothiophenyl, or (vii) phenyl substituted with one or two $C_1$-$C_3$ alkoxy or $C_1$-$C_2$ acyl, or with one phenoxy;
$R_{29}$ is (i) hydrogen, (ii) $C_1$-$C_2$ alkyl, (iii) adamantanyl, (iv) dibenzofuranyl, (v) $C_1$-$C_3$ alkyl, (vi) dibenzothiophenyl, or (vii) phenyl substituted with one or two $C_1$-$C_3$ alkoxy or $C_1$-$C_2$ acyl, or with one phenoxy;
provided that at least one of $R_{28}$ and $R_{29}$ is hydrogen or $C_1$-$C_6$ alkyl;
$R_{20}$ and $R_{21}$ are hydrogen or halogen;
$R_{30}$ and $R_{31}$ are independently hydrogen or $C_1$-$C_2$ alkyl;
each $R_{10}$ is independently H, halogen, $C_1$-$C_4$ alkyl, $C_1$-$C_4$ alkoxy, $C_1$-$C_4$ haloalkyl, $C_1$-$C_4$ haloalkoxy, $NO_2$, $NH_2$, $NH(C_1$-$C_6)$alkyl, or $N(C_1$-$C_6)$alkyl$(C_1$-$C_6)$alkyl; and
n is 0, 1, or 2.

A preferred dibenzothiophenyl group is dibenzothiophen-4-yl.

Preferred compounds of Formula XI include those where $R_{20}$ is hydrogen and $R_{21}$ is halogen. More preferably $R_{21}$ is fluoro. In another aspect, both of $R_{20}$ and $R_{21}$ are halogen, preferably fluoro.

In particular aspects of Formula XI, n is 0 or 1. In a preferred aspect, n is 0. In another preferred aspect of Formula XI, n is 1 and $R_{10}$ is chloro, fluoro, methyl, ethyl, methoxy, ethoxy, trifluoromethyl, or amino. In still another preferred aspect of Formula XI, n is 1 and $R_{10}$ is fluoro, methyl, methoxy, or trifluoromethyl.

Other preferred compounds of Formula XI include those where $R_{28}$ is dibenzofuranyl or adamantanyl and $R_{29}$ is hydrogen or methyl. Other preferred compounds of Formula XI include those where $R_{29}$ is dibenzofuranyl or adamantanyl and $R_{28}$ is hydrogen or methyl.

Where one of $R_{28}$ and $R_{29}$ is hydrogen, the other is preferably adamantanyl or dibenzofuranyl, more preferably dibenzofuran-3-yl or dibenzofuran-4-yl, most preferably dibenzofuran-4-yl. Each of these preferred $R_{28}$ and $R_{29}$ groups is optionally substituted with from 1-4, more preferably 1-3, and most preferably 1-2 groups selected from $C_1$-$C_6$ alkyl, $C_1$-$C_4$ alkoxycarbonyl, $C_1$-$C_6$ alkoxy, halogen, haloalkyl, haloalkoxy, and $NR_6R_7$, where $R_6$ and $R_7$ are independently H, $C_1$-$C_6$ alkyl, $C_1$-$C_6$ alkanoyl, $C_1$-$C_6$ alkoxycarbonyl, piperidinyl, pyrrolidinylcarbonyl, —C(O)NH$_2$, —C(O)NH(C$_1$-C$_6$)alkyl, or —C(O)N(C$_1$-C$_6$)alkyl(C$_1$-C$_6$)alkyl.

A preferred dibenzothiophenyl group is dibenzothiophen-4-yl. Preferably, $R_{28}$ is hydrogen, $R_{29}$ is dibenzothiophen-4-yl, and each of $R_{30}$ and $R_{31}$ are hydrogen.

In a particular aspect of Formual XI, $R_{28}$ is hydrogen; $R_{29}$ is dibenzofuran-4-yl; and each of $R_{30}$ and $R_{31}$ is hydrogen. In a preferred aspect, $R_{20}$ is hydrogen and $R_{21}$ is halogen, more preferably fluoro. In another preferred aspect, both of $R_{20}$ and $R_{21}$ are halogen, preferably fluoro. In yet another preferred aspect, both of $R_{20}$ and $R_{21}$ are hydrogen.

In another particular aspect of Formual XI, $R_{29}$ is hydrogen; $R_{28}$ is dibenzofuran-4-yl; and each of $R_{30}$ and $R_{31}$ is hydrogen. Preferably, within this aspect both of $R_{20}$ and $R_{21}$ are halogen, preferably fluoro. More preferably, within this aspect, $R_{20}$ is hydrogen and $R_{21}$ is fluoro.

Still other preferred compounds of Formula XI include those where one of $R_{28}$ and $R_{29}$ is 3,4-dimethoxyphenyl, 3-methoxyphenyl, 3-formylphenyl, or 3-acetylphenyl.

Preferred compounds of Formula XI include those where $R_{30}$ and $R_{31}$ are (i) both hydrogen, (ii) hydrogen and methyl, or (iii) both methyl. More preferred compounds of Formula XI are those where $R_{30}$ and $R_{31}$ are both hydrogen.

In another aspect, the invention provides compounds of Formula XII:

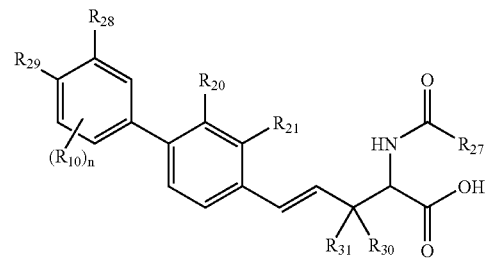

wherein
$R_{27}$ is $C_1$-$C_6$ alkoxy;
$R_{28}$ is (i) hydrogen, (ii) $C_1$-$C_2$ alkyl, (iii) adamantanyl, (iv) dibenzofuranyl, (v) $C_1$-$C_3$ alkyl, (vi) dibenzothiophenyl, or (vii) phenyl substituted with one or two $C_1$-$C_3$ alkoxy or $C_1$-$C_2$ acyl, or with one phenoxy;
$R_{29}$ is (i) hydrogen, (ii) $C_1$-$C_2$ alkyl, (iii) adamantanyl, (iv) dibenzofuranyl, (v) $C_1$-$C_3$ alkyl, (vi) dibenzothiophenyl, or (vii) phenyl substituted with one or two $C_1$-$C_3$ alkoxy or $C_1$-$C_2$ acyl, or with one phenoxy;
provided that at least one of $R_{28}$ and $R_{29}$ is hydrogen or $C_1$-$C_6$ alkyl;
$R_{20}$ and $R_{21}$ are hydrogen or halogen;
$R_{30}$ and $R_{31}$ are independently hydrogen or $C_1$-$C_2$ alkyl;
each $R_{10}$ is independently H, halogen, $C_1$-$C_4$ alkyl, $C_1$-$C_4$ alkoxy, $C_1$-$C_4$ haloalkyl, $C_1$-$C_4$ haloalkoxy, $NO_2$, $NH_2$, $NH(C_1$-$C_6)$alkyl, or $N(C_1$-$C_6)$alkyl$(C_1$-$C_6)$alkyl; and
n is 0, 1, or 2.

A preferred dibenzothiophenyl group is dibenzothiophen-4-yl. Preferably, $R_{28}$ is hydrogen, $R_{29}$ is dibenzothiophen-4-yl, and each of $R_{30}$ and $R_{31}$ are hydrogen.

In particular aspects of Formula XII, n is 0 or 1. In a preferred aspect, n is 0. In another preferred aspect of Formula XII, n is 1 and $R_{10}$ is chloro, fluoro, methyl, ethyl, methoxy, ethoxy, trifluoromethyl, or amino. In still another preferred aspect of Formula XII, n is 1 and $R_{10}$ is fluoro, methyl, methoxy, or trifluoromethyl.

Preferred compounds of Formula XII include those where $R_{20}$ is hydrogen and $R_{21}$ is halogen. More preferably $R_{21}$ is fluoro. In another aspect, both of $R_{20}$ and $R_{21}$ are halogen, preferably fluoro.

Other preferred compounds of Formula XII include those where $R_{28}$ is dibenzofuranyl or adamantanyl and $R_{29}$ is hydrogen or methyl. Other preferred compounds of Formula XII include those where $R_{29}$ is dibenzofuranyl or adamantanyl and $R_{28}$ is hydrogen or methyl.

Where one of $R_{28}$ and $R_{29}$ is hydrogen, the other is preferably adamantanyl or dibenzofuranyl, more preferably dibenzofuran-3-yl or dibenzofuran-4-yl, most preferably dibenzofuran-4-yl. Each of these preferred $R_{28}$ and $R_{29}$ groups is optionally substituted with from 1-4, more preferably 1-3, and most preferably 1-2 groups selected from $C_1$-$C_6$ alkyl, $C_1$-$C_4$ alkoxycarbonyl, $C_1$-$C_6$ alkoxy, halogen, haloalkyl, haloalkoxy, and $NR_6R_7$, where $R_6$ and $R_7$ are independently H, $C_1$-$C_6$ alkyl, $C_1$-$C_6$ alkanoyl, $C_1$-$C_6$ alkoxycarbonyl, piperidinyl, pyrrolidinylcarbonyl, —C(O)NH$_2$, —C(O)NH($C_1$-$C_6$)alkyl, or —C(O)N($C_1$-$C_6$)alkyl($C_1$-$C_6$)alkyl.

In a particular aspect of Formual XII, $R_{28}$ is hydrogen; $R_{29}$ is dibenzofuran-4-yl; and each of $R_{30}$ and $R_{31}$ is hydrogen. In a preferred aspect, $R_{20}$ is hydrogen and $R_{21}$ is halogen, more preferably fluoro. In another preferred aspect, both of $R_{20}$ and $R_{21}$ are halogen, preferably fluoro. In yet another preferred aspect, both of $R_{20}$ and $R_{21}$ are hydrogen.

In another particular aspect of Formual XII, $R_{29}$ is hydrogen; $R_{28}$ is dibenzofuran-4-yl; and each of $R_{30}$ and $R_{31}$ is hydrogen. In another preferred aspect, both of $R_{20}$ and $R_{21}$ are halogen, preferably fluoro.

In still another particular aspect of Formual XII, $R_{28}$ is hydrogen; $R_{29}$ is dibenzofuran-4-yl; and each of $R_{30}$ and $R_{31}$ is methyl.

Still other preferred compounds of Formula XII include those where one of $R_{28}$ and $R_{29}$ is 3,4-dimethoxyphenyl, 3-methoxyphenyl, 3-formylphenyl, or 3-acetylphenyl.

Preferred compounds of Formula XII include those where $R_{30}$ and $R_{31}$ are (i) both hydrogen, (ii) hydrogen and methyl, or (iii) both methyl. More preferred compounds of Formula XII are those where $R_{30}$ and $R_{31}$ are both hydrogen.

In another aspect, the invention provides compounds of Formula XIII:

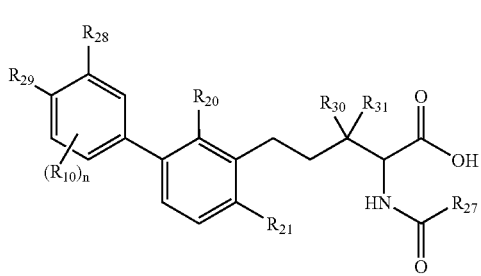

XIII wherein
$R_{27}$ is $C_1$-$C_6$ alkoxy;
$R_{28}$ is (i) hydrogen, (ii) $C_1$-$C_2$ alkyl, (iii) adamantanyl, (iv) dibenzofuranyl, (v) $C_1$-$C_3$ alkyl, (vi) dibenzothiophenyl, or (vii) phenyl substituted with one or two $C_1$-$C_3$ alkoxy or $C_1$-$C_2$ acyl, or with one phenoxy;
$R_{29}$ is (i) hydrogen, (ii) $C_1$-$C_2$ alkyl, (iii) adamantanyl, (iv) dibenzofuranyl, (v) $C_1$-$C_3$ alkyl, (vi) dibenzothiophenyl, or (vii) phenyl substituted with one or two $C_1$-$C_3$ alkoxy or $C_1$-$C_2$ acyl, or with one phenoxy;
provided that at least one of $R_{28}$ and $R_{29}$ is hydrogen or $C_1$-$C_6$ alkyl;
$R_{20}$ and $R_{21}$ are hydrogen or halogen;
$R_{30}$ and $R_{31}$ are independently hydrogen or $C_1$-$C_2$ alkyl;
each $R_{10}$ is independently H, halogen, $C_1$-$C_4$ alkyl, $C_1$-$C_4$ alkoxy, $C_1$-$C_4$ haloalkyl, $C_1$-$C_4$ haloalkoxy, NO$_2$, NH$_2$, NH($C_1$-$C_6$)alkyl, or N($C_1$-$C_6$)alkyl($C_1$-$C_6$)alkyl; and
n is 0, 1, or 2.

A preferred dibenzothiophenyl group is dibenzothiophen-4-yl.

In particular aspects of Formula XIII, n is 0 or 1. In a preferred aspect, n is 0. In another preferred aspect of Formula XIII, n is 1 and $R_{10}$ is chloro, fluoro, methyl, ethyl, methoxy, ethoxy, trifluoromethyl, or amino. In still another preferred aspect of Formula XIII, n is 1 and $R_{10}$ is fluoro, methyl, methoxy, or trifluoromethyl.

Preferred compounds of Formula XIII include those where $R_{20}$ is hydrogen and $R_{21}$ is halogen. More preferably $R_{21}$ is fluoro. In another aspect, both of $R_{20}$ and $R_{21}$ are halogen, preferably fluoro.

Other preferred compounds of Formula XIII include those where $R_{28}$ is dibenzofuranyl or adamantanyl and $R_{29}$ is hydrogen or methyl. Other preferred compounds of Formula XIII include those where $R_{29}$ is dibenzofuranyl or adamantanyl and $R_{28}$ is hydrogen or methyl.

Where one of $R_{28}$ and $R_{29}$ is hydrogen, the other is preferably adamantanyl or dibenzofuranyl, more preferably dibenzofuran-3-yl or dibenzofuran-4-yl, most preferably dibenzofuran-4-yl. Each of these preferred $R_{28}$ and $R_{29}$ groups is optionally substituted with from 1-4, more preferably 1-3, and most preferably 1-2 groups selected from $C_1$-$C_6$ alkyl, $C_1$-$C_4$ alkoxycarbonyl, $C_1$-$C_6$ alkoxy, halogen, haloalkyl, haloalkoxy, and $NR_6R_7$, where $R_6$ and $R_7$ are independently H, $C_1$-$C_6$ alkyl, $C_1$-$C_6$ alkanoyl, $C_1$-$C_6$ alkoxycarbonyl, piperidinyl, pyrrolidinylcarbonyl, —C(O)NH$_2$, —C(O)NH($C_1$-$C_6$)alkyl, or —C(O)N($C_1$-$C_6$)alkyl($C_1$-$C_6$)alkyl.

A preferred dibenzothiophenyl group is dibenzothiophen-4-yl. Preferably, $R_{28}$ is hydrogen, $R_{29}$ is dibenzothiophen-4-yl, and each of $R_{30}$ and $R_{31}$ are hydrogen.

In a particular aspect of Formual XIII, $R_{28}$ is hydrogen; $R_{29}$ is dibenzofuran-4-yl; and each of $R_{30}$ and $R_{31}$ is hydrogen. In a preferred aspect, $R_{20}$ is hydrogen and $R_{21}$ is halogen, more preferably fluoro. In another preferred aspect, both of $R_{20}$ and $R_{21}$ are halogen, preferably fluoro. In yet another preferred aspect, both of $R_{20}$ and $R_{21}$ are hydrogen.

In another particular aspect of Formual XIII, $R_{29}$ is hydrogen; $R_{28}$ is dibenzofuran-4-yl; and each of $R_{30}$ and $R_{31}$ is hydrogen. Preferably, within this aspect both of $R_{20}$ and $R_{21}$ are halogen, preferably fluoro. More preferably, within this aspect, $R_{20}$ is hydrogen and $R_{21}$ is fluoro.

Still other preferred compounds of Formula XIII include those where one of $R_{28}$ and $R_{29}$ is 3,4-dimethoxyphenyl, 3-methoxyphenyl, 3-formylphenyl, or 3-acetylphenyl.

Preferred compounds of Formula XIII include those where $R_{30}$ and $R_{31}$ are (i) both hydrogen, (ii) hydrogen and methyl, or (iii) both methyl. More preferred compounds of Formula XIII are those where $R_{30}$ and $R_{31}$ are both hydrogen.

In another aspect, the invention provides compounds of Formula XIV:

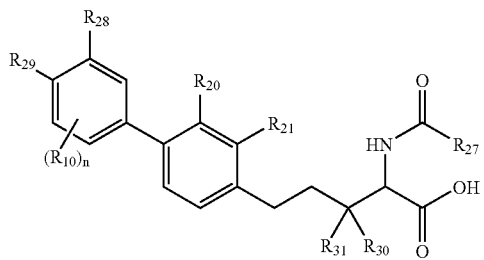

XIV wherein
$R_{27}$ is $C_1$-$C_6$ alkoxy;
$R_{28}$ is (i) hydrogen, (ii) $C_1$-$C_2$ alkyl, (iii) adamantanyl, (iv) dibenzofuranyl, (v) $C_1$-$C_3$ alkyl, (vi) dibenzothiophenyl, or (vii) phenyl substituted with one or two $C_1$-$C_3$ alkoxy or $C_1$-$C_2$ acyl, or with one phenoxy;

$R_{29}$ is (i) hydrogen, (ii) $C_1$-$C_2$ alkyl, (iii) adamantanyl, (iv) dibenzofuranyl, (v) $C_1$-$C_3$ alkyl, (vi) dibenzothiophenyl, or (vii) phenyl substituted with one or two $C_1$-$C_3$ alkoxy or $C_1$-$C_2$ acyl, or with one phenoxy;

provided that at least one of $R_{28}$ and $R_{29}$ is hydrogen or $C_1$-$C_6$ alkyl;

$R_{20}$ and $R_{21}$ are hydrogen or halogen;

$R_{30}$ and $R_{31}$ are independently hydrogen or $C_1$-$C_2$ alkyl; each $R_{10}$ is independently H, halogen, $C_1$-$C_4$ alkyl, $C_1$-$C_4$ alkoxy, $C_1$-$C_4$ haloalkyl, $C_1$-$C_4$ haloalkoxy, $NO_2$, $NH_2$, $NH(C_1$-$C_6)$alkyl, or $N(C_1$-$C_6)$alkyl$(C_1$-$C_6)$alkyl; and n is 0, 1, or 2.

A preferred dibenzothiophenyl group is dibenzothiophen-4-yl. Preferably, $R_{28}$ is hydrogen, $R_{29}$ is dibenzothiophen-4-yl, and each of $R_{30}$ and $R_{31}$ are hydrogen.

In particular aspects of Formula XIV, n is 0 or 1. In a preferred aspect, n is 0. In another preferred aspect of Formula XIV, n is 1 and $R_{10}$ is chloro, fluoro, methyl, ethyl, methoxy, ethoxy, trifluoromethyl, or amino. In still another preferred aspect of Formula XIV, n is 1 and $R_{10}$ is fluoro, methyl, methoxy, or trifluoromethyl.

Preferred compounds of Formula XIV include those where $R_{20}$ is hydrogen and $R_{21}$ is halogen. More preferably $R_{21}$ is fluoro. In another aspect, both of $R_{20}$ and $R_{21}$ are halogen, preferably fluoro.

Other preferred compounds of Formula XIV include those where $R_{28}$ is dibenzofuranyl or adamantanyl and $R_{29}$ is hydrogen or methyl. Other preferred compounds of Formula XIV include those where $R_{29}$ is dibenzofuranyl or adamantanyl and $R_{28}$ is hydrogen or methyl.

Where one of $R_{28}$ and $R_{29}$ is hydrogen, the other is preferably adamantanyl or dibenzofuranyl, more preferably dibenzofuran-3-yl or dibenzofuran-4-yl, most preferably dibenzofuran-4-yl. Each of these preferred $R_{28}$ and $R_{29}$ groups is optionally substituted with from 1-4, more preferably 1-3, and most preferably 1-2 groups selected from $C_1$-$C_6$ alkyl, $C_1$-$C_4$ alkoxycarbonyl, $C_1$-$C_6$ alkoxy, halogen, haloalkyl, haloalkoxy, and $NR_6R_7$, where $R_6$ and $R_7$ are independently H, $C_1$-$C_6$ alkyl, $C_1$-$C_6$ alkanoyl, $C_1$-$C_6$ alkoxycarbonyl, piperidinyl, pyrrolidinylcarbonyl, —C(O)NH_2, —C(O)NH($C_1$-$C_6$)alkyl, or —C(O)N($C_1$-$C_6$)alkyl($C_1$-$C_6$)alkyl.

In a particular aspect of Formual XIV, $R_{28}$ is hydrogen; $R_{29}$ is dibenzofuran-4-yl; and each of $R_{30}$ and $R_{31}$ is hydrogen. In a preferred aspect, $R_{20}$ is hydrogen and $R_{21}$ is halogen, more preferably fluoro. In another preferred aspect, both of $R_{20}$ and $R_{21}$ are halogen, preferably fluoro. In yet another preferred aspect, both of $R_{20}$ and $R_{21}$ are hydrogen.

In another particular aspect of Formual XIV, $R_{29}$ is hydrogen; $R_{28}$ is dibenzofuran-4-yl; and each of $R_{30}$ and $R_{31}$ is hydrogen. In another preferred aspect, both of $R_{20}$ and $R_{21}$ are halogen, preferably fluoro.

In still another particular aspect of Formual XIV, $R_{28}$ is hydrogen; $R_{29}$ is dibenzofuran-4-yl; and each of $R_{30}$ and $R_{31}$ is methyl.

Still other preferred compounds of Formula XIV include those where one of $R_{28}$ and $R_{29}$ is 3,4-dimethoxyphenyl, 3-methoxyphenyl, 3-formylphenyl, or 3-acetylphenyl.

Preferred compounds of Formula XIV include those where $R_{30}$ and $R_{31}$ are (i) both hydrogen, (ii) hydrogen and methyl, or (iii) both methyl. More preferred compounds of Formula XIV are those where $R_{30}$ and $R_{31}$ are both hydrogen.

In another aspect, the invention provides compounds of Formula XV:

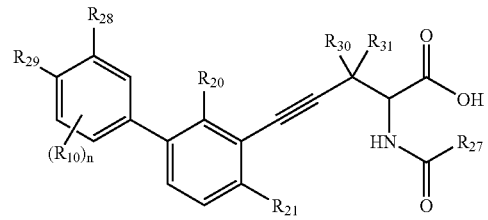

XV wherein $R_{27}$ is $C_1$-$C_6$ alkoxy;

$R_{28}$ is (i) hydrogen, (ii) $C_1$-$C_2$ alkyl, (iii) adamantanyl, (iv) dibenzofuranyl, (v) $C_1$-$C_3$ alkyl, (vi) dibenzothiophenyl, or (vii) phenyl substituted with one or two $C_1$-$C_3$ alkoxy or $C_1$-$C_2$ acyl, or with one phenoxy;

$R_{29}$ is (i) hydrogen, (ii) $C_1$-$C_2$ alkyl, (iii) adamantanyl, (iv) dibenzofuranyl, (v) $C_1$-$C_3$ alkyl, (vi) dibenzothiophenyl, or (vii) phenyl substituted with one or two $C_1$-$C_3$ alkoxy or $C_1$-$C_2$ acyl, or with one phenoxy;

provided that at least one of $R_{28}$ and $R_{29}$ is hydrogen or $C_1$-$C_6$ alkyl;

$R_{20}$ and $R_{21}$ are hydrogen or halogen;

$R_{30}$ and $R_{31}$ are independently hydrogen or $C_1$-$C_2$ alkyl; each $R_{10}$ is independently H, halogen, $C_1$-$C_4$ alkyl, $C_1$-$C_4$ alkoxy, $C_1$-$C_4$ haloalkyl, $C_1$-$C_4$ haloalkoxy, $NO_2$, $NH_2$, $NH(C_1$-$C_6)$alkyl, or $N(C_1$-$C_6)$alkyl$(C_1$-$C_6)$alkyl; and n is 0, 1, or 2.

A preferred dibenzothiophenyl group is dibenzothiophen-4-yl.

In particular aspects of Formula XV, n is 0 or 1. In a preferred aspect, n is 0. In another preferred aspect of Formula XV, n is 1 and $R_{10}$ is chloro, fluoro, methyl, ethyl, methoxy, ethoxy, trifluoromethyl, or amino. In still another preferred aspect of Formula XV, n is 1 and $R_{10}$ is fluoro, methyl, methoxy, or trifluoromethyl.

Preferred compounds of Formula XV include those where $R_{20}$ is hydrogen and $R_{21}$ is halogen. More preferably $R_{21}$ is fluoro. In another aspect, both of $R_{20}$ and $R_{21}$ are halogen, preferably fluoro.

Other preferred compounds of Formula XV include those where $R_{28}$ is dibenzofuranyl or adamantanyl and $R_{29}$ is hydrogen or methyl. Other preferred compounds of Formula XV include those where $R_{29}$ is dibenzofuranyl or adamantanyl and $R_{28}$ is hydrogen or methyl.

Where one of $R_{28}$ and $R_{29}$ is hydrogen, the other is preferably adamantanyl or dibenzofuranyl, more preferably dibenzofuran-3-yl or dibenzofuran-4-yl, most preferably dibenzofuran-4-yl. Each of these preferred $R_{28}$ and $R_{29}$ groups is optionally substituted with from 1-4, more preferably 1-3, and most preferably 1-2 groups selected from $C_1$-$C_6$ alkyl, $C_1$-$C_4$ alkoxycarbonyl, $C_1$-$C_6$ alkoxy, halogen, haloalkyl, haloalkoxy, and $NR_6R_7$, where $R_6$ and $R_7$ are independently H, $C_1$-$C_6$ alkyl, $C_1$-$C_6$ alkanoyl, $C_1$-$C_6$ alkoxycarbonyl, piperidinyl, pyrrolidinylcarbonyl, —C(O)NH_2, —C(O)NH($C_1$-$C_6$)alkyl, or —C(O)N($C_1$-$C_6$)alkyl($C_1$-$C_6$)alkyl.

A preferred dibenzothiophenyl group is dibenzothiophen-4-yl. Preferably, $R_{28}$ is hydrogen, $R_{29}$ is dibenzothiophen-4-yl, and each of $R_{30}$ and $R_{31}$ are hydrogen.

In a particular aspect of Formual XV, $R_{28}$ is hydrogen; $R_{29}$ is dibenzofuran-4-yl; and each of $R_{30}$ and $R_{31}$ is hydrogen. In a preferred aspect, $R_{20}$ is hydrogen and $R_{21}$ is halogen, more preferably fluoro. In another preferred aspect, both of $R_{20}$ and $R_{21}$ are halogen, preferably fluoro. In yet another preferred aspect, both of $R_{20}$ and $R_{21}$ are hydrogen.

In another particular aspect of Formual XV, $R_{29}$ is hydrogen; $R_{28}$ is dibenzofuran-4-yl; and each of $R_{30}$ and $R_{31}$ is hydrogen. Preferably, within this aspect both of $R_{20}$ and $R_{21}$ are halogen, preferably fluoro. More preferably, within this aspect, $R_{20}$ is hydrogen and $R_{21}$ is fluoro.

Still other preferred compounds of Formula XV include those where one of $R_{28}$ and $R_{29}$ is 3,4-dimethoxyphenyl, 3-methoxyphenyl, 3-formylphenyl, or 3-acetylphenyl.

Preferred compounds of Formula XV include those where $R_{30}$ and $R_{31}$ are (i) both hydrogen, (ii) hydrogen and methyl, or (iii) both methyl. More preferred compounds of Formula XV are those where $R_{30}$ and $R_{31}$ are both hydrogen.

In another aspect, the invention provides compounds of Formula XVI:

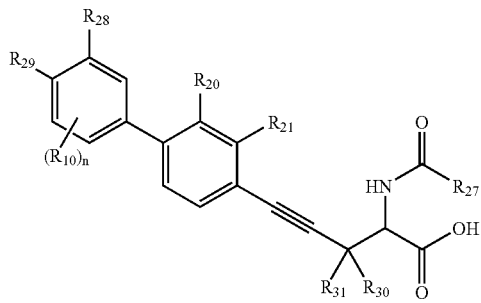

XVI wherein
$R_{27}$ is $C_1$-$C_6$ alkoxy;
$R_{28}$ is (i) hydrogen, (ii) $C_1$-$C_2$ alkyl, (iii) adamantanyl, (iv) dibenzofuranyl, (v) $C_1$-$C_3$ alkyl, (vi) dibenzothiophenyl, or (vii) phenyl substituted with one or two $C_1$-$C_3$ alkoxy or $C_1$-$C_2$ acyl, or with one phenoxy;
$R_{29}$ is (i) hydrogen, (ii) $C_1$-$C_2$ alkyl, (iii) adamantanyl, (iv) dibenzofuranyl, (v) $C_1$-$C_3$ alkyl, (vi) dibenzothiophenyl, or (vii) phenyl substituted with one or two $C_1$-$C_3$ alkoxy or $C_1$-$C_2$ acyl, or with one phenoxy;
provided that at least one of $R_{28}$ and $R_{29}$ is hydrogen or $C_1$-$C_6$ alkyl;
$R_{20}$ and $R_{21}$ are hydrogen or halogen;
$R_{30}$ and $R_{31}$ are independently hydrogen or $C_1$-$C_2$ alkyl; each $R_{10}$ is independently H, halogen, $C_1$-$C_4$ alkyl, $C_1$-$C_4$ alkoxy, $C_1$-$C_4$ haloalkyl, $C_1$-$C_4$ haloalkoxy, $NO_2$, $NH_2$, $NH(C_1$-$C_6)$alkyl, or $N(C_1$-$C_6)$alkyl$(C_1$-$C_6)$alkyl; and
n is 0, 1, or 2.

A preferred dibenzothiophenyl group is dibenzothiophen-4-yl. Preferably, $R_{28}$ is hydrogen, $R_{29}$ is dibenzothiophen-4-yl, and each of $R_{30}$ and $R_{31}$ are hydrogen.

In particular aspects of Formula XVI, n is 0 or 1. In a preferred aspect, n is 0. In another preferred aspect of Formula XVI, n is 1 and $R_{10}$ is chloro, fluoro, methyl, ethyl, methoxy, ethoxy, trifluoromethyl, or amino. In still another preferred aspect of Formula XVI, n is 1 and $R_{10}$ is fluoro, methyl, methoxy, or trifluoromethyl.

Preferred compounds of Formula XVI include those where $R_{20}$ is hydrogen and $R_{21}$ is halogen. More preferably $R_{21}$ is fluoro. In another aspect, both of $R_{20}$ and $R_{21}$ are halogen, preferably fluoro.

Other preferred compounds of Formula XVI include those where $R_{28}$ is dibenzofuranyl or adamantanyl and $R_{29}$ is hydrogen or methyl. Other preferred compounds of Formula XVI include those where $R_{29}$ is dibenzofuranyl or adamantanyl and $R_{28}$ is hydrogen or methyl.

Where one of $R_{28}$ and $R_{29}$ is hydrogen, the other is preferably adamantanyl or dibenzofuranyl, more preferably dibenzofuran-3-yl or dibenzofuran-4-yl, most preferably dibenzofuran-4-yl. Each of these preferred $R_{28}$ and $R_{29}$ groups is optionally substituted with from 1-4, more preferably 1-3, and most preferably 1-2 groups selected from $C_1$-$C_6$ alkyl, $C_1$-$C_4$ alkoxycarbonyl, $C_1$-$C_6$ alkoxy, halogen, haloalkyl, haloalkoxy, and $NR_6R_7$, where $R_6$ and $R_7$ are independently H, $C_1$-$C_6$ alkyl, $C_1$-$C_6$ alkanoyl, $C_1$-$C_6$ alkoxycarbonyl, piperidinyl, pyrrolidinylcarbonyl, —C(O)NH$_2$, —C(O)NH(C$_1$-C$_6$)alkyl, or —C(O)N(C$_1$-C$_6$)alkyl(C$_1$-C$_6$)alkyl.

In a particular aspect of Formual XVI, $R_{28}$ is hydrogen; $R_{29}$ is dibenzofuran-4-yl; and each of $R_{30}$ and $R_{31}$ is hydrogen. In a preferred aspect, $R_{20}$ is hydrogen and $R_{21}$ is halogen, more preferably fluoro. In another preferred aspect, both of $R_{20}$ and $R_{21}$ are halogen, preferably fluoro. In yet another preferred aspect, both of $R_{20}$ and $R_{21}$ are hydrogen.

In another particular aspect of Formual XVI, $R_{29}$ is hydrogen; $R_{28}$ is dibenzofuran-4-yl; and each of $R_{30}$ and $R_{31}$ is hydrogen. In another preferred aspect, both of $R_{20}$ and $R_{21}$ are halogen, preferably fluoro.

In still another particular aspect of Formual XVI, $R_{28}$ is hydrogen; $R_{29}$ is dibenzofuran-4-yl; and each of $R_{30}$ and $R_{31}$ is methyl.

Still other preferred compounds of Formula XVI include those where one of $R_{28}$ and $R_{29}$ is 3,4-dimethoxyphenyl, 3-methoxyphenyl, 3-formylphenyl, or 3-acetylphenyl.

Preferred compounds of Formula XVI include those where $R_{30}$ and $R_{31}$ are (i) both hydrogen, (ii) hydrogen and methyl, or (iii) both methyl. More preferred compounds of Formula XVI are those where $R_{30}$ and $R_{31}$ are both hydrogen.

In another aspect, the invention provides compounds of Formula XVII:

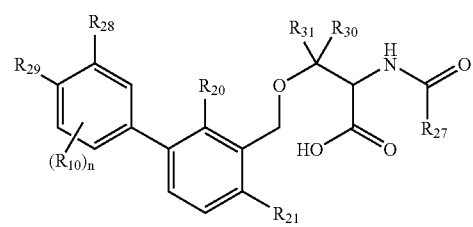

XVII wherein
$R_{27}$ is $C_1$-$C_6$ alkoxy;
$R_{28}$ is (i) hydrogen, (ii) $C_1$-$C_2$ alkyl, (iii) adamantanyl, (iv) dibenzofuranyl, (v) $C_1$-$C_3$ alkyl, (vi) dibenzothiophenyl, or (vii) phenyl substituted with one or two $C_1$-$C_3$ alkoxy or $C_1$-$C_2$ acyl, or with one phenoxy;
$R_{29}$ is (i) hydrogen, (ii) $C_1$-$C_2$ alkyl, (iii) adamantanyl, (iv) dibenzofuranyl, (v) $C_1$-$C_3$ alkyl, (vi) dibenzothiophenyl, or (vii) phenyl substituted with one or two $C_1$-$C_3$ alkoxy or $C_1$-$C_2$ acyl, or with one phenoxy;
provided that at least one of $R_{28}$ and $R_{29}$ is hydrogen or $C_1$-$C_6$ alkyl;
$R_{20}$ and $R_{21}$ are hydrogen or halogen;
$R_{30}$ and $R_{31}$ are independently hydrogen or $C_1$-$C_2$ alkyl;
each $R_{10}$ is independently H, halogen, $C_1$-$C_4$ alkyl, $C_1$-$C_4$ alkoxy, $C_1$-$C_4$ haloalkyl, $C_1$-$C_4$ haloalkoxy, $NO_2$, $NH_2$, $NH(C_1$-$C_6)$alkyl, or $N(C_1$-$C_6)$alkyl$(C_1$-$C_6)$alkyl; and
n is 0, 1, or 2.

A preferred dibenzothiophenyl group is dibenzothiophen-4-yl.

In particular aspects of Formula XVII, n is 0 or 1. In a preferred aspect, n is 0. In another preferred aspect of Formula XVII, n is 1 and $R_{10}$ is chloro, fluoro, methyl, ethyl, methoxy, ethoxy, trifluoromethyl, or amino. In still another preferred aspect of Formula XVII, n is 1 and $R_{10}$ is fluoro, methyl, methoxy, or trifluoromethyl.

Preferred compounds of Formula XVII include those where $R_{20}$ is hydrogen and $R_{21}$ is halogen. More preferably $R_{21}$ is fluoro. In another aspect, both of $R_{20}$ and $R_{21}$ are halogen, preferably fluoro.

Other preferred compounds of Formula XVII include those where $R_{28}$ is dibenzofuranyl or adamantanyl and $R_{29}$ is hydrogen or methyl. Other preferred compounds of Formula XVII include those where $R_{29}$ is dibenzofuranyl or adamantanyl and $R_{28}$ is hydrogen or methyl.

Where one of $R_{28}$ and $R_{29}$ is hydrogen, the other is preferably adamantanyl or dibenzofuranyl, more preferably dibenzofuran-3-yl or dibenzofuran-4-yl, most preferably dibenzofuran-4-yl. Each of these preferred $R_{28}$ and $R_{29}$ groups is optionally substituted with from 1-4, more preferably 1-3, and most preferably 1-2 groups selected from $C_1$-$C_6$ alkyl, $C_1$-$C_4$ alkoxycarbonyl, $C_1$-$C_6$ alkoxy, halogen, haloalkyl, haloalkoxy, and $NR_6R_7$, where $R_6$ and $R_7$ are independently H, $C_1$-$C_6$ alkyl, $C_1$-$C_6$ alkanoyl, $C_1$-$C_6$ alkoxycarbonyl, piperidinyl, pyrrolidinylcarbonyl, —C(O)NH$_2$, —C(O)NH($C_1$-$C_6$)alkyl, or —C(O)N($C_1$-$C_6$)alkyl($C_1$-$C_6$)alkyl.

A preferred dibenzothiophenyl group is dibenzothiophen-4-yl. Preferably, $R_{28}$ is hydrogen, $R_{29}$ is dibenzothiophen-4-yl, and each of $R_{30}$ and $R_{31}$ are hydrogen.

In a particular aspect of Formual XVII, $R_{28}$ is hydrogen; $R_{29}$ is dibenzofuran-4-yl; and each of $R_{30}$ and $R_{31}$ is hydrogen. In a preferred aspect, $R_{20}$ is hydrogen and $R_{21}$ is halogen, more preferably fluoro. In another preferred aspect, both of $R_{20}$ and $R_{21}$ are halogen, preferably fluoro. In yet another preferred aspect, both of $R_{20}$ and $R_{21}$ are hydrogen.

In another particular aspect of Formual XVII, $R_{29}$ is hydrogen; $R_{28}$ is dibenzofuran-4-yl; and each of $R_{30}$ and $R_{31}$ is hydrogen. Preferably, within this aspect both of $R_{20}$ and $R_{21}$ are halogen, preferably fluoro. More preferably, within this aspect, $R_{20}$ is hydrogen and $R_{21}$ is fluoro.

Still other preferred compounds of Formula XVII include those where one of $R_{28}$ and $R_{29}$ is 3,4-dimethoxyphenyl, 3-methoxyphenyl, 3-formylphenyl, or 3-acetylphenyl.

Preferred compounds of Formula XVII include those where $R_{30}$ and $R_{31}$ are (i) both hydrogen, (ii) hydrogen and methyl, or (iii) both methyl. More preferred compounds of Formula XVII are those where $R_{30}$ and $R_{31}$ are both hydrogen.

In another aspect, the invention provides compounds of Formula XVIII:

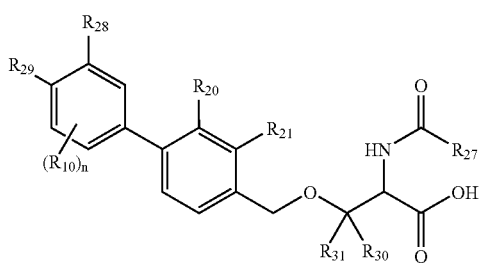

XVIII wherein $R_{27}$ is $C_1$-$C_6$ alkoxy;

$R_{28}$ is (i) hydrogen, (ii) $C_1$-$C_2$ alkyl, (iii) adamantanyl, (iv) dibenzofuranyl, (v) $C_1$-$C_3$ alkyl, (vi) dibenzothiophenyl, or (vii) phenyl substituted with one or two $C_1$-$C_3$ alkoxy or $C_1$-$C_2$ acyl, or with one phenoxy;

$R_{29}$ is (i) hydrogen, (ii) $C_1$-$C_2$ alkyl, (iii) adamantanyl, (iv) dibenzofuranyl, (v) $C_1$-$C_3$ alkyl, (vi) dibenzothiophenyl, or (vii) phenyl substituted with one or two $C_1$-$C_3$ alkoxy or $C_1$-$C_2$ acyl, or with one phenoxy;

provided that at least one of $R_{28}$ and $R_{29}$ is hydrogen or $C_1$-$C_6$ alkyl;

$R_{20}$ and $R_{21}$ are hydrogen or halogen;

$R_{30}$ and $R_{31}$ are independently hydrogen or $C_1$-$C_2$ alkyl;

each $R_{10}$ is independently H, halogen, $C_1$-$C_4$ alkyl, $C_1$-$C_4$ alkoxy, $C_1$-$C_4$ haloalkyl, $C_1$-$C_4$ haloalkoxy, $NO_2$, $NH_2$, $NH(C_1$-$C_6)$alkyl, or $N(C_1$-$C_6)$alkyl($C_1$-$C_6)$alkyl; and n is 0, 1, or 2.

A preferred dibenzothiophenyl group is dibenzothiophen-4-yl. Preferably, $R_{28}$ is hydrogen, $R_{29}$ is dibenzothiophen-4-yl, and each of $R_{30}$ and $R_{31}$ are hydrogen.

In particular aspects of Formula XVIII, n is 0 or 1. In a preferred aspect, n is 0. In another preferred aspect of Formula XVIII, n is 1 and $R_{10}$ is chloro, fluoro, methyl, ethyl, methoxy, ethoxy, trifluoromethyl, or amino. In still another preferred aspect of Formula XVIII, n is 1 and $R_{10}$ is fluoro, methyl, methoxy, or trifluoromethyl.

Preferred compounds of Formula XVIII include those where $R_{20}$ is hydrogen and $R_{21}$ is halogen. More preferably $R_{21}$ is fluoro. In another aspect, both of $R_{20}$ and $R_{21}$ are halogen, preferably fluoro.

Other preferred compounds of Formula XVIII include those where $R_{28}$ is dibenzofuranyl or adamantanyl and $R_{29}$ is hydrogen or methyl. Other preferred compounds of Formula XVIII include those where $R_{29}$ is dibenzofuranyl or adamantanyl and $R_{28}$ is hydrogen or methyl.

Where one of $R_{28}$ and $R_{29}$ is hydrogen, the other is preferably adamantanyl or dibenzofuranyl, more preferably dibenzofuran-3-yl or dibenzofuran-4-yl, most preferably dibenzofuran-4-yl. Each of these preferred $R_{28}$ and $R_{29}$ groups is optionally substituted with from 1-4, more preferably 1-3, and most preferably 1-2 groups selected from $C_1$-$C_6$ alkyl, $C_1$-$C_4$ alkoxycarbonyl, $C_1$-$C_6$ alkoxy, halogen, haloalkyl, haloalkoxy, and $NR_6R_7$, where $R_6$ and $R_7$ are independently H, $C_1$-$C_6$ alkyl, $C_1$-$C_6$ alkanoyl, $C_1$-$C_6$ alkoxycarbonyl, piperidinyl, pyrrolidinylcarbonyl, —C(O)NH$_2$, —C(O)NH($C_1$-$C_6$)alkyl, or —C(O)N($C_1$-$C_6$)alkyl($C_1$-$C_6$)alkyl.

In a particular aspect of Formual XVIII, $R_{28}$ is hydrogen; $R_{29}$ is dibenzofuran-4-yl; and each of $R_{30}$ and $R_{31}$ is hydrogen. In a preferred aspect, $R_{20}$ is hydrogen and $R_{21}$ is halogen, more preferably fluoro. In another preferred aspect, both of $R_{20}$ and $R_{21}$ are halogen, preferably fluoro. In yet another preferred aspect, both of $R_{20}$ and $R_{21}$ are hydrogen.

In another particular aspect of Formual XVIII, $R_{29}$ is hydrogen; $R_{28}$ is dibenzofuran-4-yl; and each of $R_{30}$ and $R_{31}$ is hydrogen. In another preferred aspect, both of $R_{20}$ and $R_{21}$ are halogen, preferably fluoro.

In still another particular aspect of Formual XVIII, $R_{28}$ is hydrogen; $R_{29}$ is dibenzofuran-4-yl; and each of $R_{30}$ and $R_{31}$ is methyl.

Still other preferred compounds of Formula XVIII include those where one of $R_{28}$ and $R_{29}$ is 3,4-dimethoxyphenyl, 3-methoxyphenyl, 3-formylphenyl, or 3-acetylphenyl.

Preferred compounds of Formula XVIII include those where $R_{30}$ and $R_{31}$ are (i) both hydrogen, (ii) hydrogen and methyl, or (iii) both methyl. More preferred compounds of Formula XVIII are those where $R_{30}$ and $R_{31}$ are both hydrogen.

In another aspect, the invention provides compounds of Formula XIX:

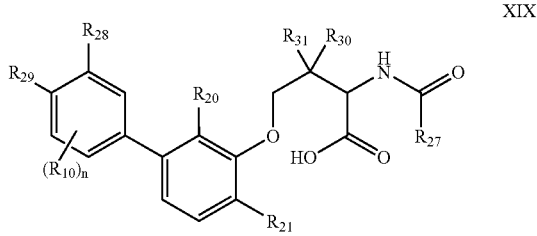

XIX wherein
$R_{27}$ is $C_1$-$C_6$ alkoxy;
$R_{28}$ is (i) hydrogen, (ii) $C_1$-$C_2$ alkyl, (iii) adamantanyl, (iv) dibenzofuranyl, (v) $C_1$-$C_3$ alkyl, (vi) dibenzothiophenyl, or (vii) phenyl substituted with one or two $C_1$-$C_3$ alkoxy or $C_1$-$C_2$ acyl, or with one phenoxy;
$R_{29}$ is (i) hydrogen, (ii) $C_1$-$C_2$ alkyl, (iii) adamantanyl, (iv) dibenzofuranyl, (v) $C_1$-$C_3$ alkyl, (vi) dibenzothiophenyl, or (vii) phenyl substituted with one or two $C_1$-$C_3$ alkoxy or $C_1$-$C_2$ acyl, or with one phenoxy;
provided that at least one of $R_{28}$ and $R_{29}$ is hydrogen or $C_1$-$C_6$ alkyl;
$R_{20}$ and $R_{21}$ are hydrogen or halogen;
$R_{30}$ and $R_{31}$ are independently hydrogen or $C_1$-$C_2$ alkyl;
each $R_{10}$ is independently H, halogen, $C_1$-$C_4$ alkyl, $C_1$-$C_4$ alkoxy, $C_1$-$C_4$ haloalkyl, $C_1$-$C_4$ haloalkoxy, $NO_2$, $NH_2$, $NH(C_1$-$C_6)$alkyl, or $N(C_1$-$C_6)$alkyl$(C_1$-$C_6)$alkyl; and
n is 0, 1, or 2.

A preferred dibenzothiophenyl group is dibenzothiophen-4-yl.

In particular aspects of Formula XIX, n is 0 or 1. In a preferred aspect, n is 0. In another preferred aspect of Formula XIX, n is 1 and $R_{10}$ is chloro, fluoro, methyl, ethyl, methoxy, ethoxy, trifluoromethyl, or amino. In still another preferred aspect of Formula XIX, n is 1 and $R_{10}$ is fluoro, methyl, methoxy, or trifluoromethyl.

Preferred compounds of Formula XIX include those where $R_{20}$ is hydrogen and $R_{21}$ is halogen. More preferably $R_{21}$ is fluoro. In another aspect, both of $R_{20}$ and $R_{21}$ are halogen, preferably fluoro.

Other preferred compounds of Formula XIX include those where $R_{28}$ is dibenzofuranyl or adamantanyl and $R_{29}$ is hydrogen or methyl. Other preferred compounds of Formula XIX include those where $R_{29}$ is dibenzofuranyl or adamantanyl and $R_{28}$ is hydrogen or methyl.

Where one of $R_{28}$ and $R_{29}$ is hydrogen, the other is preferably adamantanyl or dibenzofuranyl, more preferably dibenzofuran-3-yl or dibenzofuran-4-yl, most preferably dibenzofuran-4-yl. Each of these preferred $R_{28}$ and $R_{29}$ groups is optionally substituted with from 1-4, more preferably 1-3, and most preferably 1-2 groups selected from $C_1$-$C_6$ alkyl, $C_1$-$C_4$ alkoxycarbonyl, $C_1$-$C_6$ alkoxy, halogen, haloalkyl, haloalkoxy, and $NR_6R_7$, where $R_6$ and $R_7$ are independently H, $C_1$-$C_6$ alkyl, $C_1$-$C_6$ alkanoyl, $C_1$-$C_6$ alkoxycarbonyl, piperidinyl, pyrrolidinylcarbonyl, —C(O)NH$_2$, —C(O)NH(C$_1$-C$_6$)alkyl, or —C(O)N(C$_1$-C$_6$)alkyl(C$_1$-C$_6$)alkyl.

A preferred dibenzothiophenyl group is dibenzothiophen-4-yl. Preferably, $R_{28}$ is hydrogen, $R_{29}$ is dibenzothiophen-4-yl, and each of $R_{30}$ and $R_{31}$ are hydrogen.

In a particular aspect of Formual XIX, $R_{28}$ is hydrogen; $R_{29}$ is dibenzofuran-4-yl; and each of $R_{30}$ and $R_{31}$ is hydrogen. In a preferred aspect, $R_{20}$ is hydrogen and $R_{21}$ is halogen, more preferably fluoro. In another preferred aspect, both of $R_{20}$ and $R_{21}$ are halogen, preferably fluoro. In yet another preferred aspect, both of $R_{20}$ and $R_{21}$ are hydrogen.

In another particular aspect of Formual XIX, $R_{29}$ is hydrogen; $R_{28}$ is dibenzofuran-4-yl; and each of $R_{30}$ and $R_{31}$ is hydrogen. Preferably, within this aspect both of $R_{20}$ and $R_{21}$ are halogen, preferably fluoro. More preferably, within this aspect, $R_{20}$ is hydrogen and $R_{21}$ is fluoro.

Still other preferred compounds of Formula XIX include those where one of $R_{28}$ and $R_{29}$ is 3,4-dimethoxyphenyl, 3-methoxyphenyl, 3-formylphenyl, or 3-acetylphenyl.

Preferred compounds of Formula XIX include those where $R_{30}$ and $R_{31}$ are (i) both hydrogen, (ii) hydrogen and methyl, or (iii) both methyl. More preferred compounds of Formula XIX are those where $R_{30}$ and $R_{31}$ are both hydrogen.

In another aspect, the invention provides compounds of Formula XX:

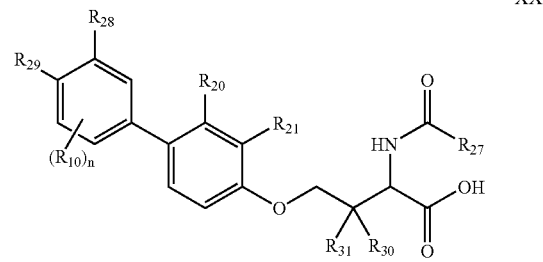

XX wherein
$R_{27}$ is $C_1$-$C_6$ alkoxy;
$R_{28}$ is (i) hydrogen, (ii) $C_1$-$C_2$ alkyl, (iii) adamantanyl, (iv) dibenzofuranyl, (v) $C_1$-$C_3$ alkyl, (vi) dibenzothiophenyl, or (vii) phenyl substituted with one or two $C_1$-$C_3$ alkoxy or $C_1$-$C_2$ acyl, or with one phenoxy;
$R_{29}$ is (i) hydrogen, (ii) $C_1$-$C_2$ alkyl, (iii) adamantanyl, (iv) dibenzofuranyl, (v) $C_1$-$C_3$ alkyl, (vi) dibenzothiophenyl, or (vii) phenyl substituted with one or two $C_1$-$C_3$ alkoxy or $C_1$-$C_2$ acyl, or with one phenoxy;
provided that at least one of $R_{28}$ and $R_{29}$ is hydrogen or $C_1$-$C_6$ alkyl;
$R_{20}$ and $R_{21}$ are hydrogen or halogen;
$R_{30}$ and $R_{31}$ are independently hydrogen or $C_1$-$C_2$ alkyl;
each $R_{10}$ is independently H, halogen, $C_1$-$C_4$ alkyl, $C_1$-$C_4$ alkoxy, $C_1$-$C_4$ haloalkyl, $C_1$-$C_4$ haloalkoxy, $NO_2$, $NH_2$, $NH(C_1$-$C_6)$alkyl, or $N(C_1$-$C_6)$alkyl$(C_1$-$C_6)$alkyl; and
n is 0, 1, or 2.

A preferred dibenzothiophenyl group is dibenzothiophen-4-yl. Preferably, $R_{28}$ is hydrogen, $R_{29}$ is dibenzothiophen-4-yl, and each of $R_{30}$ and $R_{31}$ are hydrogen.

In particular aspects of Formula XX, n is 0 or 1. In a preferred aspect, n is 0. In another preferred aspect of Formula XX, n is 1 and $R_{10}$ is chloro, fluoro, methyl, ethyl, methoxy, ethoxy, trifluoromethyl, or amino. In still another preferred aspect of Formula XX, n is 1 and $R_{10}$ is fluoro, methyl, methoxy, or trifluoromethyl.

Preferred compounds of Formula XX include those where $R_{20}$ is hydrogen and $R_{21}$ is halogen. More preferably $R_{21}$ is fluoro. In another aspect, both of $R_{20}$ and $R_{21}$ are halogen, preferably fluoro.

Other preferred compounds of Formula XX include those where $R_{28}$ is dibenzofuranyl or adamantanyl and $R_{29}$ is hydrogen or methyl. Other preferred compounds of Formula XX include those where $R_{29}$ is dibenzofuranyl or adamantanyl and $R_{28}$ is hydrogen or methyl.

Where one of $R_{28}$ and $R_{29}$ is hydrogen, the other is preferably adamantanyl or dibenzofuranyl, more preferably dibenzofuran-3-yl or dibenzofuran-4-yl, most preferably dibenzofuran-4-yl. Each of these preferred $R_{28}$ and $R_{29}$ groups is optionally substituted with from 1-4, more preferably 1-3, and most preferably 1-2 groups selected from $C_1$-$C_6$ alkyl, $C_1$-$C_4$ alkoxycarbonyl, $C_1$-$C_6$ alkoxy, halogen, haloalkyl, haloalkoxy, and $NR_6R_7$, where $R_6$ and $R_7$ are independently H, $C_1$-$C_6$ alkyl, $C_1$-$C_6$ alkanoyl, $C_1$-$C_6$ alkoxycarbonyl, piperidinyl, pyrrolidinylcarbonyl, —C(O)NH$_2$, —C(O)NH($C_1$-$C_6$)alkyl, or —C(O)N($C_1$-$C_6$)alkyl($C_1$-$C_6$)alkyl.

In a particular aspect of Formual XX, $R_{28}$ is hydrogen; $R_{29}$ is dibenzofuran-4-yl; and each of $R_{30}$ and $R_{31}$ is hydrogen. In a preferred aspect, $R_{20}$ is hydrogen and $R_{21}$ is halogen, more preferably fluoro. In another preferred aspect, both of $R_{20}$ and $R_{21}$ are halogen, preferably fluoro. In yet another preferred aspect, both of $R_{20}$ and $R_{21}$ are hydrogen.

In another particular aspect of Formual XX, $R_{29}$ is hydrogen; $R_{28}$ is dibenzofuran-4-yl; and each of $R_{30}$ and $R_{31}$ is hydrogen. In another preferred aspect, both of $R_{20}$ and $R_{21}$ are halogen, preferably fluoro.

In still another particular aspect of Formual XX, $R_{28}$ is hydrogen; $R_{29}$ is dibenzofuran-4-yl; and each of $R_{30}$ and $R_{31}$ is methyl.

Still other preferred compounds of Formula XVIII include those where one of $R_{28}$ and $R_{29}$ is 3,4-dimethoxyphenyl, 3-methoxyphenyl, 3-formylphenyl, or 3-acetylphenyl.

Preferred compounds of Formula XX include those where $R_{30}$ and $R_{31}$ are (i) both hydrogen, (ii) hydrogen and methyl, or (iii) both methyl. More preferred compounds of Formula XX are those where $R_{30}$ and $R_{31}$ are both hydrogen.

In another aspect, the invention provides a method of preparing a compound of formula (I)

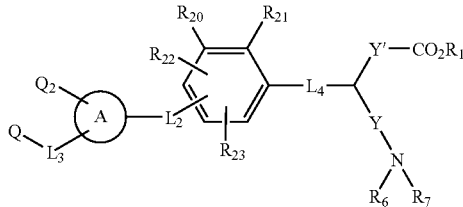
(I)

or a pharmaceutically acceptable salt thereof, wherein $L_2$ is a bond; $L_4$ is —S(O)$_u$—($C_1$-$C_4$)alkyl-, —($C_1$-$C_4$)alkyl-S(O)$_u$—($C_1$-$C_4$)alkyl-, —($C_1$-$C_6$)alkyl-O—($C_1$-$C_6$)alkyl-, —O—($C_1$-$C_6$)alkyl-, —($C_1$-$C_6$)alkyl-O—, or —($C_1$-$C_4$)alkyl-NR$_N$—($C_1$-$C_4$)alkyl-; $R_N$ is H or ($C_1$-$C_6$)alkyl; u is 0, 1, or 2; and A, Q, $Q_2$, Y, Y', $L_3$, $R_1$, $R_6$, $R_7$, $R_{20}$, $R_{21}$, $R_{22}$, and $R_{23}$ are as defined in claim 1;

comprising:

(1) treating a compound of formula

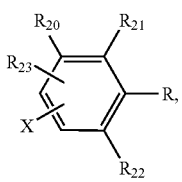

wherein R is (CH$_2$)$_n$OH, (CH$_2$)$_n$SH, or (CH$_2$)$_n$NH$_2$, n is 0, 1, 2, 3, or 4, and wherein X is Cl, Br, I, or OSO$_2$CF$_3$, with a metal catalyst, a base, and a compound of formula

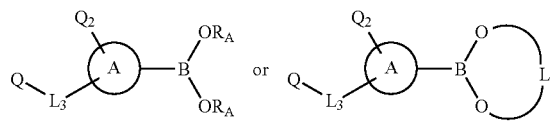

wherein $R_A$ is H or ($C_1$-$C_6$)alkyl, and
L is alkylene, to provide a compound of formula

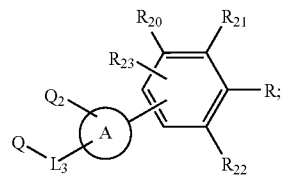

(2) treating the product of (1) with a base and a compound of formula

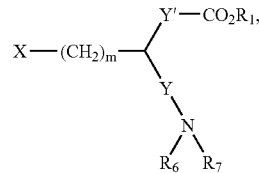

wherein X is Cl, Br, I, or OSO$_2$R',
R' is methyl, para-methylphenyl, or CF$_3$, and
m is 0, 1, 2, 3, or 4, to provide a compound of formula

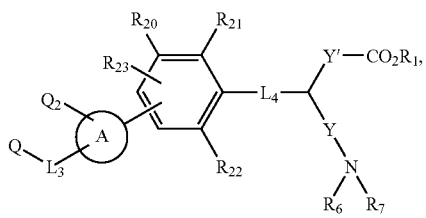

wherein $L_4$ is —S(O)$_u$—($C_1$-$C_4$)alkyl-, —($C_1$-$C_4$)alkyl-S(O)$_u$—($C_1$-$C_4$)alkyl-, —($C_1$-$C_6$)alkyl-O—($C_1$-$C_6$)alkyl-, —O—($C_1$-$C_6$)alkyl-, —($C_1$-$C_6$)alkyl-O—, or —($C_1$-$C_4$)alkyl-NR$_N$—($C_1$-$C_4$)alkyl-; $R_N$ is H or ($C_1$-$C_6$)alkyl; and u is 0, 1, or 2.

In another aspect, the invention provides a method of preparing a compound of formula (I)

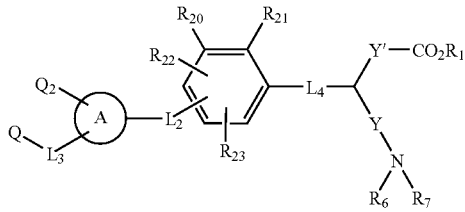

or a pharmaceutically acceptable salt thereof, wherein $L_2$ is a bond; $L_4$ is $-S(O)_u-(C_1-C_4)$alkyl-, $-(C_1-C_4)$alkyl-$S(O)_u$ $-(C_1-C_4)$alkyl-, $-(C_1-C_6)$alkyl-O-$(C_1-C_6)$alkyl-, $-O-(C_1-C_6)$alkyl-, $-(C_1-C_6)$alkyl-O-, or $-(C_1-C_4)$alkyl-$NR_N-(C_1-C_4)$alkyl-; $R_N$ is H or $(C_1-C_6)$alkyl; u is 0, 1, or 2; and A, Q, $Q_2$, Y, Y', $L_3$, $R_1$, $R_6$, $R_7$, $R_{20}$, $R_{21}$, $R_{22}$, and $R_{23}$ are as defined in claim 1;

comprising:

(1) treating a compound of formula

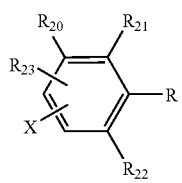

wherein R is $(CH_2)_nOH$, $(CH_2)_nSH$, or $(CH_2)_nNH_2$, n is 0, 1, 2, 3, or 4, and wherein X is Cl, Br, I, or $OSO_2CF_3$, with a base and a compound of formula

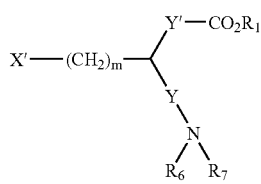

wherein X' is Cl, Br, I, or $OSO_2R'$,

R' is methyl, para-methylphenyl, or $CF_3$, and m is 0, 1, 2, 3, or 4, to provide a compound of formula

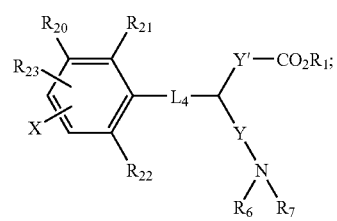

(2) treating the product of (1) with a metal catalyst, a base and a compound of formula

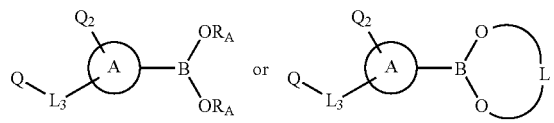

wherein $R_A$ is H or $(C_1-C_6)$alkyl, and

L is alkylene, to provide a compound of formula

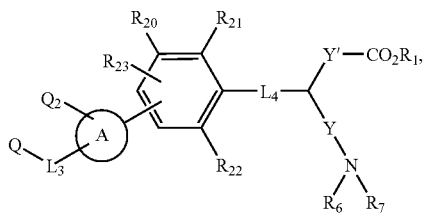

wherein $L_4$ is $-S(O)_u-(C_1-C_4)$alkyl-, $-(C_1-C_4)$alkyl-$S(O)_u-(C_1-C_4)$alkyl-, $-(C_1-C_6)$alkyl-O-$(C_1-C_6)$alkyl-, $-O-(C_1-C_6)$alkyl-, $-(C_1-C_6)$alkyl-O-, or $-(C_1-C_4)$alkyl-$NR_N-(C_1-C_4)$alkyl-; $R_N$ is H or $(C_1-C_6)$alkyl; and u is 0, 1, or 2.

In another aspect, the invention provides a method of preparing a compound of formula (I)

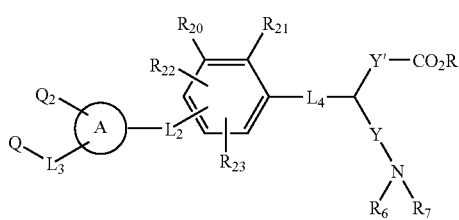

or a pharmaceutically acceptable salt thereof, wherein $L_4$ is $-S(O)_u-(C_1-C_4)$alkyl-, $-(C_1-C_4)$alkyl-$S(O)_u-(C_1-C_4)$alkyl-, $-(C_1-C_6)$alkyl-O-$(C_1-C_6)$alkyl-, $-O-(C_1-C_6)$alkyl-, $-(C_1-C_6)$alkyl-O-, or $-(C_1-C_4)$alkyl-$NR_N-(C_1-C_4)$alkyl-; $R_N$ is H or $(C_1-C_6)$alkyl; u is 0, 1, or 2; and A, Q, $Q_2$, Y, Y', $L_2$, $L_3$, $R_1$, $R_6$, $R_7$, $R_{20}$, $R_{21}$, $R_{22}$, and $R_{23}$ are as defined in claim 1;

comprising:

treating a compound of formula

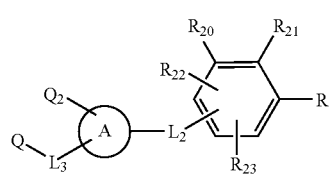

wherein R is $(CH_2)_nOH$, $(CH_2)_nSH$, or $(CH_2)_nNH_2$, n is 0, 1, 2, 3, or 4, with a base and a compound of formula

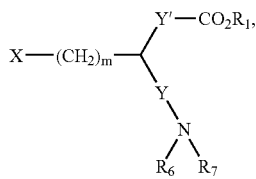

wherein X is Cl, Br, I, or $OSO_2R'$,
R' is methyl, para-methylphenyl, or $CF_3$, and
m is 0, 1, 2, 3, or 4, to provide a compound of formula (I) wherein $L_4$ is $-S(O)_u$-$(C_1-C_4)$alkyl-, $-(C_1-C_4)$alkyl-$S(O)_u$-$(C_1-C_4)$alkyl-, $-(C_1-C_6)$alkyl-O-$(C_1-C_6)$alkyl-, $-O-(C_1-C_6)$alkyl-, $-(C_1-C_6)$alkyl-O-, or $-(C_1-C_4)$alkyl-$NR_N$-$(C_1-C_4)$alkyl-; $R_N$ is H or $(C_1-C_6)$alkyl; and u is 0, 1, or 2.

In another aspect, the invention provides a method of preparing a compound of formula (I)

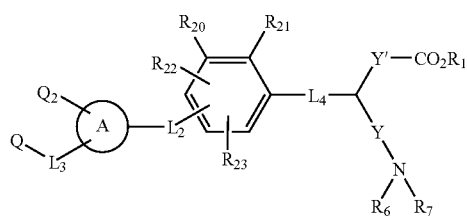

or a pharmaceutically acceptable salt thereof, wherein $L_2$ is a bond; and A, Q, $Q_2$, Y, Y', $L_3$, $L_4$, $R_1$, $R_6$, $R_7$, $R_{20}$, $R_{21}$, $R_{22}$, and $R_{23}$ are as defined in claim 1;

comprising:

treating a compound of formula

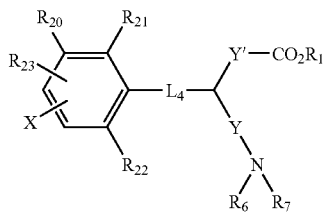

wherein X is Cl, Br, I, or $OSO_2CF_3$,
with a metal catalyst, a base, and a compound of formula

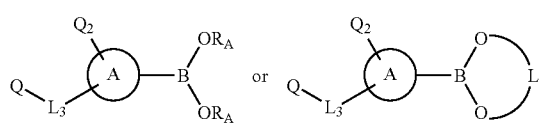

wherein $R_A$ is $(C_1-C_6)$alkyl, and
L is alkylene, to provide a compound of formula

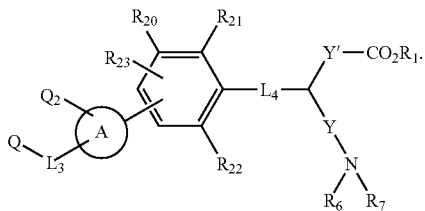

In another aspect, the invention provides a compound of formula (XXV)

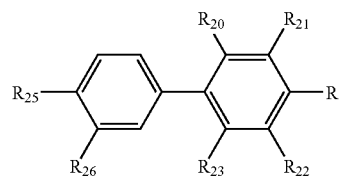

(XXV)

wherein
R is selected from the group consisting of $(CH_2)_nOH$, $(CH_2)_nSH$, $(CH_2)_nNH_2$, $(CH_2)_nOSO_2R'$, $(CH_2)_nX$, and $(CH_2)_nCHO$;
R' is methyl, para-methylphenyl, or $CF_3$;
X is Cl, Br, or I;
n is 0, 1, 2, 3, or 4;
$R_{20}$, $R_{21}$, $R_{22}$ and $R_{23}$ are independently selected from the group consisting of H, arylalkoxy, arylalkyl, halogen, alkyl, OH, alkoxy, $NO_2$, $NH_2$, $NH(C_1-C_6)$alkyl, $N(C_1-C_6)$alkyl$(C_1-C_6)$alkyl, NH-aryl, $N(C_1-C_4)$alkyl-aryl, $-NHSO_2$-aryl, and $-N(C_1-C_4$alkyl$)SO_2$aryl, wherein the aryl group is optionally substituted with 1, 2, 3, or 4 groups that are independently $C_1-C_6$ alkyl, $C_1-C_6$ alkoxy, halogen, OH, $NO_2$, $C_1-C_4$ haloalkyl, or $C_1-C_4$ haloalkoxy;
one of $R_{25}$ and $R_{26}$ is -$L_3$-Q and the other is H;
$L_3$ is a bond, $-(C_1-C_4)$alkyl-O-, $-O-(C_1-C_4)$alkyl, $-(C_1-C_4)$alkyl-, $-C_2-C_6$ alkenyl-, $-C(O)-$, $(C_1-C_4)$alkyl-O-, $-C(O)NH-$, or $-NHC(O)-$; and
Q is -heteroaryl-$(C_1-C_4)$alkyl-aryl, -aryl-$(C_1-C_4)$alkyl-heteroaryl, -aryl-O-aryl, heteroaryl, heterocycloalkyl, cycloalkyl, or aryl, each of which is optionally substituted with 1, 2, 3, 4, or 5 groups that are independently alkoxycarbonyl, $C_1-C_6$ alkyl, $C_1-C_6$ alkoxy, halogen, $C_1-C_6$ alkanoyl, $C_1-C_4$ haloalkyl, $C_1-C_4$ haloalkoxy, $NH_2$, $NH(C_1-C_6)$alkyl, $N(C_1-C_6)$alkyl$(C_1-C_6)$alkyl, phenyl, $(C_1-C_4)$phenyl, or $C_1-C_6$ alkanoyl.

In another aspect, the invention includes compounds of formula (XXV) wherein
R is selected from the group consisting of OH, SH, $(CH_2)_nOH$, $(CH_2)_nSH$, $(CH_2)_nOSO_2R'$, and $(CH_2)_nX$;
R' is methyl;
X is Cl, Br, or I;
n is 1, 2, 3, or 4;
$R_{20}$, $R_{21}$, $R_{22}$ and $R_{23}$ are are independently selected from the group consisting of H, halogen, alkyl, OH, alkoxy, $NO_2$, $NH_2$, $NH(C_1-C_6)$alkyl, and $N(C_1-C_6)$alkyl$(C_1-C_6)$alkyl;
one of $R_{25}$ and $R_{26}$ is -$L_3$-Q and the other is H;
$L_3$ is a bond or $-(C_1-C_4)$alkyl-; and
Q is heteroaryl or aryl wherein each is optionally substituted with 1 or 2 groups that are independently alkoxycarbonyl, $C_1-C_6$ alkyl, $C_1-C_6$ alkoxy, halogen, $C_1-C_6$ alkanoyl, $C_1-C_4$ haloalkyl, $C_1$-$C_4$ haloalkoxy, $NH_2$, $NH(C_1$-$C_6)$alkyl, $N(C_1$-$C_6)$alkyl$(C_1$-$C_6)$alkyl, phenyl, $(C_1$-$C_4)$phenyl, or $C_1$-$C_6$ alkanoyl.

In another aspect, the invention includes compounds of formula (XXV) wherein

R is selected from the group consisting of OH, SH, $(CH_2)_n$OH, $(CH_2)_nOSO_2R'$, and $(CH_2)_nX$;

R' is methyl;

X is Cl, Br, or I;

n is 1, 2, 3, or 4;

$R_{20}$, $R_{21}$, and $R_{23}$ are H;

$R_{22}$ is H, $NH_2$, or $NO_2$;

one of $R_{25}$ and $R_{26}$ is -$L_3$-Q and the other is H;

$L_3$ is a bond or —$(C_1$-$C_4)$alkyl-; and

Q is heteroaryl optionally substituted with $(C_1$-$C_4)$phenyl.

In another aspect the invention includes compounds of formula (XXV) wherein

R is selected from the group consisting of OH, SH, $(CH_2)_n$OH, $(CH_2)_nOSO_2R'$, and $(CH_2)_nX$;

R' is methyl;

X is Cl, Br, or I;

n is 1;

$R_{20}$, $R_{21}$, $R_{22}$, and $R_{23}$ are H;

$R_{25}$ is H;

$R_{26}$ is -$L_3$-Q;

$L_3$ is —$(C_1$-$C_4)$alkyl-; and

Q is 1,2,3,4-tetrahydroquinolinyl.

In another aspect the invention includes compounds of formula (XXV) wherein

R is selected from the group consisting of OH, SH, $(CH_2)_n$OH, $(CH_2)_nOSO_2R'$, and $(CH_2)_nX$;

R' is methyl;

X is Cl, Br, or I;

n is 1;

$R_{20}$, $R_{21}$, and $R_{23}$ are H;

$R_{22}$ is H, $NH_2$, or $NO_2$;

$R_{25}$ is H;

$R_{26}$ is -$L_3$-Q;

$L_3$ is a bond; and

Q is dibenzofuranyl, dibenzothiophenyl, indolinyl, or 2-benzylbenzofuranyl.

In another aspect the invention includes compounds of formula (XXV) wherein

R is selected from the group consisting of OH, SH, $(CH_2)_n$OH, $(CH_2)_nOSO_2R'$, and $(CH_2)_nX$;

R' is methyl;

X is Cl, Br, or I;

n is 1;

$R_{20}$, $R_{21}$, and $R_{23}$ are H;

$R_{22}$ is H, $NH_2$, or $NO_2$;

$R_{25}$ is -$L_3$-Q;

$R_{26}$ is H;

$L_3$ is a bond; and

Q is dibenzofuranyl, dibenzothiophenyl, indolinyl, or 2-benzylbenzofuranyl.

In another aspect, the invention includes a compound of formula (XXV) wherein

R is selected from the group consisting of OH, SH, $(CH_2)_n$OH, $(CH_2)_nOSO_2R'$, $(CH_2)_nX$, and $(CH_2)_nCHO$;

R' is methyl, para-methylphenyl, or $CF_3$;

X is Cl, Br, or I;

n is 1, 2, 3, or 4;

$R_{20}$, $R_{21}$, $R_{22}$, and $R_{23}$ are independently selected from the group consisting of H, arylalkoxy, arylalkyl, halogen, alkyl, OH, alkoxy, $NO_2$, $NH_2$, $NH(C_1$-$C_6)$alkyl, $N(C_1$-$C_6)$alkyl$(C_1$-$C_6)$alkyl, NH-aryl, $N(C_1$-$C_4)$alkyl-aryl, —$NHSO_2$-aryl, and —$N(C_1$-$C_4$alkyl)$SO_2$aryl, wherein the aryl group is optionally substituted with 1, 2, 3, or 4 groups that are independently $C_1$-$C_6$ alkyl, $C_1$-$C_6$ alkoxy, halogen, OH, $NO_2$, $C_1$-$C_4$ haloalkyl, or $C_1$-$C_4$ haloalkoxy;

one of $R_{25}$ and $R_{26}$ is -$L_3$-Q and the other is H;

$L_3$ is a bond, —$(C_1$-$C_4)$alkyl-O—, —O—$(C_1$-$C_4)$alkyl, —$(C_1$-$C_4)$alkyl-, —$C_2$-$C_6$ alkenyl-, —$C(O)$—, $(C_1$-$C_4)$alkyl-O—, —$C(O)NH$—, or —$NHC(O)$—; and Q is aryl optionally substituted with 1, 2, 3, 4, or 5 groups that are independently alkoxycarbonyl, $C_1$-$C_6$ alkyl, $C_1$-$C_6$ alkoxy, halogen, $C_1$-$C_6$ alkanoyl, $C_1$-$C_4$ haloalkyl, $C_1$-$C_4$ haloalkoxy, $NH_2$, $NH(C_1$-$C_6)$alkyl, $N(C_1$-$C_6)$alkyl$(C_1$-$C_6)$alkyl, phenyl, $(C_1$-$C_4)$phenyl, or $C_1$-$C_6$ alkanoyl.

In another aspect, the invention includes a compound of formula (XXV) wherein

R is selected from the group consisting of OH, SH, $(CH_2)_n$OH, $(CH_2)_nOSO_2R'$, $(CH_2)_nX$, and $(CH_2)_nCHO$;

R' is methyl, para-methylphenyl, or $CF_3$;

X is Cl, Br, or I;

n is 1, 2, 3, or 4;

$R_{20}$, $R_{21}$, $R_{22}$, or $R_{23}$ are independently selected from the group consisting of H, halogen, alkyl, OH, alkoxy, $NO_2$, $NH_2$, $NH(C_1$-$C_6)$alkyl, or $N(C_1$-$C_6)$alkyl$(C_1$-$C_6)$alkyl;

one of $R_{25}$ and $R_{26}$ is -$L_3$-Q and the other is H;

$L_3$ is a bond; and

Q is phenyl optionally substituted with 1 or 2 groups that are independently alkoxycarbonyl, $C_1$-$C_6$ alkyl, $C_1$-$C_6$ alkoxy, halogen, $C_1$-$C_6$ alkanoyl, $C_1$-$C_4$ haloalkyl, $C_1$-$C_4$ haloalkoxy, $NH_2$, $NH(C_1$-$C_6)$alkyl, or $N(C_1$-$C_6)$alkyl$(C_1$-$C_6)$alky.

In another aspect, the invention provides a compound of formula (XXVI) or formula (XXVII)

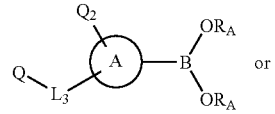

(XXVI)

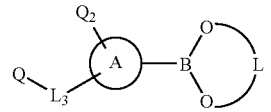

(XXVII)

wherein $R_A$ is H or $(C_1$-$C_6)$alkyl;

L is alkylene;

$L_3$ is a bond, —$(C_1$-$C_4)$alkyl-O—, —O—$(C_1$-$C_4)$alkyl, —$(C_1$-$C_4)$alkyl-, —$(C_2$-$C_6)$alkenyl-, —$C(O)$—, —$(C_1$-$C_4)$alkyl-O—, —$C(O)NH$—, or —$NHC(O)$—;

the A-ring is phenyl, naphthyl, isoindolyl, indolyl, pyridyl, thiazolyl, pyrimidyl, benzofuranyl, benzimidazolyl, or 1H-indazolyl each of which is optionally substituted with 1, 2, 3, or 4 groups that are independently, halogen, $C_1$-$C_4$ alkyl, $C_1$-$C_4$ alkoxy, $C_1$-$C_4$ haloalkyl, $C_1$-$C_4$ haloalkoxy, $NO_2$, $NH_2$, $NH(C_1$-$C_6)$alkyl, or $N(C_1$-$C_6)$alkyl$(C_1$-$C_6)$alkyl;

Q is -heteroaryl-$(C_1$-$C_4)$alkyl-aryl, -aryl-$(C_1$-$C_4)$alkyl-heteroaryl, heteroaryl, heterocycloalkyl, or aryl, each of which is optionally substituted with 1, 2, 3, 4, or 5 groups that are independently alkoxycarbonyl, $(C_1$-$C_6)$alkyl, $(C_1$-$C_6)$alkoxy, halogen, $(C_1$-$C_6)$alkanoyl, $(C_1$-$C_4)$haloalkyl, $(C_1$-$C_4)$haloalkoxy, $NH_2$, $NH(C_1$-$C_6)$alkyl, $N(C_1$-$C_6)$alkyl$(C_1$-$C_6)$alkyl, phenyl, $(C_1$-$C_6)$alkanoyl; and $Q_2$ is and H or aryl, wherein the aryl is optionally substituted with 1, 2, or 3 groups that are independently $(C_1$-$C_6)$alkyl, $(C_1$-$C_6)$alkoxy, or halogen.

In another aspect, the invention provides a compound of formula (XXVI) or formula (XXVII) wherein
$R_4$ is H or $(C_1-C_6)$alkyl;
L is alkylene;
A is phenyl;
$Q_2$ is H;
$L_3$ is a bond or $(C_1-C_4)$alkyl;
Q is heteroaryl or aryl wherein each is optionally substituted with alkoxycarbonyl, $C_1-C_6$ alkyl, $(C_1-C_6)$alkoxy, halogen, $(C_1-C_6)$alkanoyl, $(C_1-C_4)$haloalkyl, $(C_1-C_4)$haloalkoxy, $NH_2$, $NH(C_1-C_6)$alkyl, $(C_1-C_4)$phenyl, or $N(C_1-C_6)$alkyl$(C_1-C_6)$alky.

In another aspect, the invention provides a compound of formula (XXVI) or formula (XXVII) wherein
$R_4$ is H or $(C_1-C_6)$alkyl;
L is alkylene;
A is phenyl;
$Q_2$ is H;
$L_3$ is $(C_1-C_4)$alkyl; and
Q is 1,2,3,4,-tetrahydroquinolinyl.

In another aspect, the invention provides a compound of formula (XXVI) or formula (XXVII) wherein
$R_4$ is H or $(C_1-C_6)$alkyl;
L is alkylene;
A is phenyl;
$L_3$ is a bond;
Q is heteroaryl or aryl wherein each is optionally substituted with alkoxycarbonyl, $(C_1-C_6)$alkyl, $(C_1-C_6)$alkoxy, halogen, $(C_1-C_6)$alkanoyl, $(C_1-C_4)$haloalkyl, $(C_1-C_4)$haloalkoxy, $NH_2$, $NH(C_1-C_6)$alkyl, $(C_1-C_4)$phenyl, or $N(C_1-C_6)$alkyl$(C_1-C_6)$alky.

In another aspect, the invention provides a compound of formula (XXVI) or formula (XXVII) wherein
$R_4$ is H or $(C_1-C_6)$alkyl,
L is alkylene,
A is phenyl;
$Q_2$ is H;
$L_3$ is a bond; and
Q is dibenzofuranyl, dibenzothiophenyl, indolinyl, or 2-benzylbenzofuranyl.

In another aspect, the invention is a method of treating diabetes comprising administering a pharmaceutically acceptable amount of a compound of formula 1 to a patient in need of such treatment.

In another aspect, the invention is a pharmaceutical composition comprising a compound of embodiment 1 and at least one pharmaceutically acceptable solvent, carrier, adjuvant or excipient.

In another aspect, the invention provides a method of treating diabetes, comprising administering to a patient in need of such treatment a pharmaceutically acceptable amount of a compounds of formula I.

In another aspect, the invention encompasses a method of treating diabetes comprising administering to a patient in need thereof, a pharmaceutically acceptable amount of a compound or salt of formula I or a pharmaceutical composition comprising a compound or salt of formula I.

In another aspect, the invention encompasses a method of inhibiting PTP-1B comprising administering to a patient in need thereof, a pharmaceutically acceptable amount of a compound or salt of formula I or a pharmaceutical composition comprising a compound or salt of formula I.

In another aspect, the invention encompasses a method of treating cancer or neurodegenerative diseases comprising administering to a patient in need thereof, a pharmaceutically acceptable amount of a compound or salt of formula I or a pharmaceutical composition comprising a compound or salt of formula I.

In another aspect, the invention provides the use of a compound or salt of formula I for the manufacture of a medicament for treating cancer, neurodegenerative diseases diabetes, syndrome X, immunological disease, bleeding disorders, or cardiovascular diseases in a patient in need of such treatment.

In another aspect, the invention provides the use of a compound or a salt of formula I for the manufacture of a medicament for inhibiting PTP-1B in a patient in need thereof.

In another aspect, the invention provides the use of a pharmaceutical composition for the manufacture of a medicament comprising a compound of embodiment 1 and at least one pharmaceutically acceptable solvent, carrier, adjuvant or excipient.

Illustrative compounds of the invention include the following, which were named using ChemDraw v. 6.02, which is sold by Cambridgesoft.com in Cambridge, Mass., or using Name Pro IUPAC Naming Software, version 5.09, available from Advanced Chemical Development, Inc., 90 Adelaide Street West, Toronto, Ontario, M5H 3V9, Canada, or were derived therefrom.

| IDD# | Cmpd. No. | Structure | Name |
|------|-----------|-----------|------|
| | 1 | | 2-tert-Butoxycarbonylamino-3-[4-(5-dibenzofuran-4-yl-6-methyl-pyridin-2-yl)-benzylsulfanyl]-propionic acid |

-continued

| IDD# | Cmpd. No. | Structure | Name |
|---|---|---|---|
| | 2 | 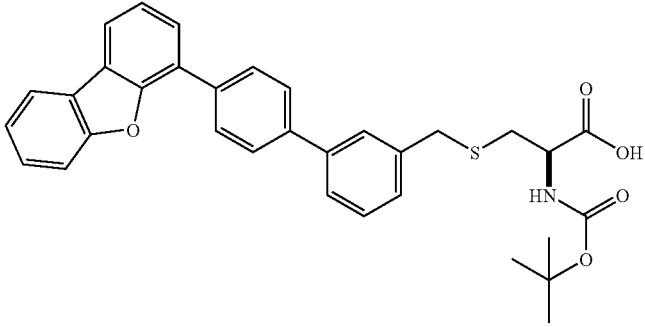 | 2-tert-Butoxycarbonylamino-3-(4'-dibenzofuran-4-yl-biphenyl-3-ylmethylsulfanyl)-propionic acid |
| | 3 | 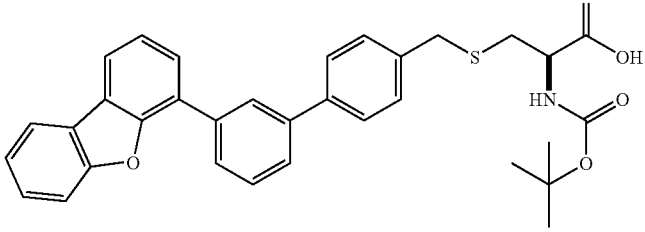 | 2-tert-Butoxycarbonylamino-3-(3'-dibenzofuran-4-yl-biphenyl-4-ylmethylsulfanyl)-propionic acid |
| | 4 | 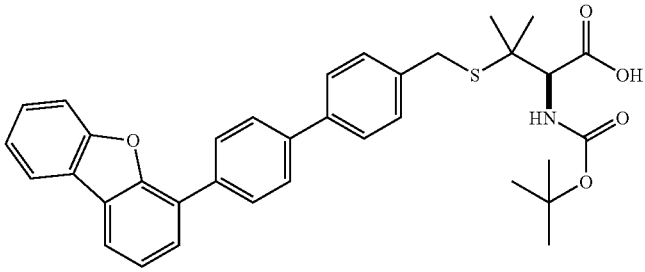 | 2-tert-Butoxycarbonylamino-3-(4'-dibenzofuran-4-yl-biphenyl-4-ylmethylsulfanyl)-3-methyl-butyric acid |
| | 5 | 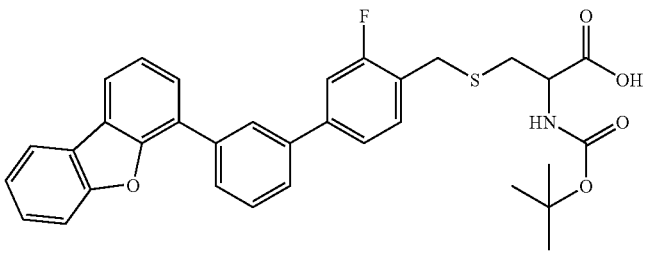 | 2-tert-Butoxycarbonylamino-3-(3'-dibenzofuran-4-yl-3-fluoro-biphenyl-4-ylmethylsulfanyl)-propionic acid |
| | 6 | 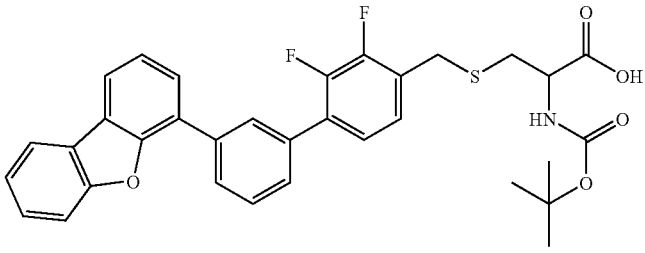 | 2-tert-Butoxycarbonylamino-3-(3'-dibenzofuran-4-yl-2,3-difluoro-biphenyl-4-ylmethylsulfanyl)-propionic acid |

-continued

| IDD# | Cmpd. No. | Structure | Name |
|---|---|---|---|
| | 7 | 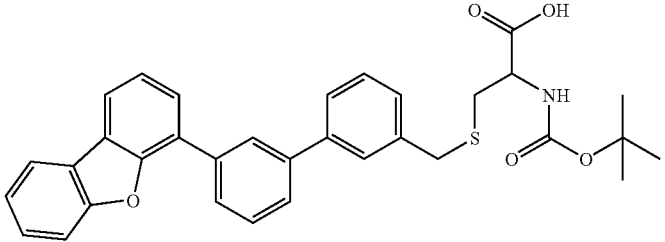 | 2-tert-Butoxycarbonylamino-3-(3'-dibenzofuran-4-yl-biphenyl-3-ylmethylsulfanyl)-propionic acid |
| | 8 | 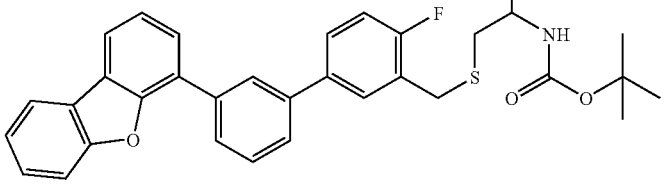 | 2-tert-Butoxycarbonylamino-3-(3'-dibenzofuran-4-yl-4-fluoro-biphenyl-3-ylmethylsulfanyl)-propionic acid |
| | 9 | 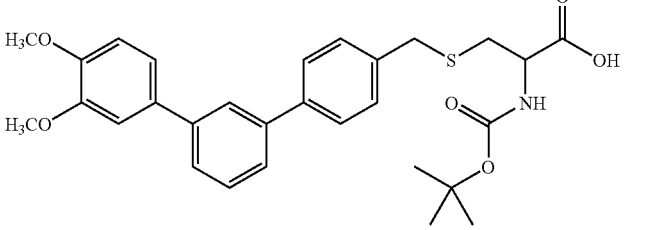 | 2-tert-Butoxycarbonylamino-3-(3,4-dimethoxy-[1,1';3',1'']terphenyl-4''-ylmethylsulfanyl)-propionic acid |
| | 10 | 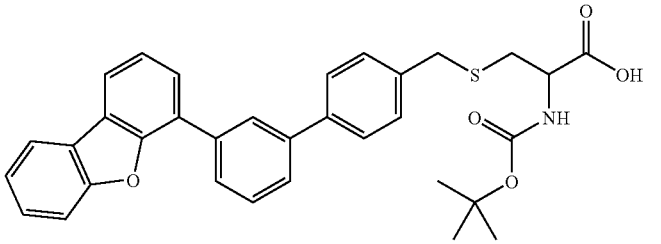 | 2-tert-Butoxycarbonylamino-4-(3'-dibenzofuran-4-yl-biphenyl-4-ylsulfanyl)-butyric acid |
| | 11 | 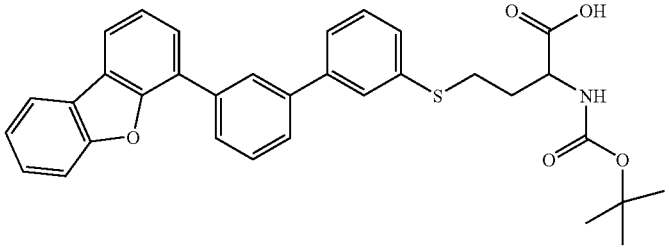 | 2-tert-Butoxycarbonylamino-4-(3'-dibenzofuran-4-yl-biphenyl-3-ylsulfanyl)-butyric acid |
| | 12 | 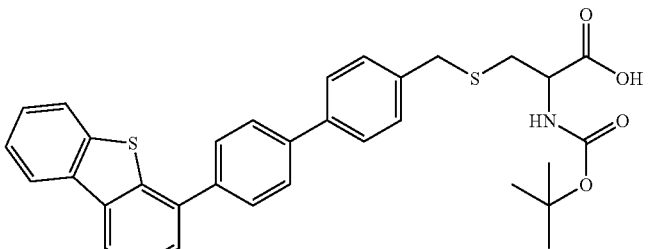 | 2-tert-Butoxycarbonylamino-3-(4'-dibenzothiophen-4-yl-biphenyl-4-ylmethylsulfanyl)-propionic acid |

| IDD# | Cmpd. No. | Structure | Name |
|---|---|---|---|
| | 13 | | 2-tert-Butoxycarbonylamino-3-(2-phenoxy-[1,1';3',1'']terphenyl-4''-ylmethylsulfanyl)-propionic acid |
| | 14 | | 2-tert-Butoxycarbonylamino-3-(2-phenoxy-[1,1';4',1'']terphenyl-4''-ylmethylsulfanyl)-propionic acid |
| | 15 | | 2-tert-Butoxycarbonylamino-3-(2-methoxy-[1,1';4',1'']terphenyl-4''-ylmethylsulfanyl)-propionic acid |
| | 16 | | 2-tert-Butoxycarbonylamino-3-(3,4-dimethoxy-[1,1';4',1'']terphenyl-4''-ylmethylsulfanyl)-propionic acid |
| | 17 | | 2-tert-Butoxycarbonylamino-3-(2-formyl-[1,1';3',1'']terphenyl-4''-ylmethylsulfanyl)-propionic acid |

-continued

| IDD# | Cmpd. No. | Structure | Name |
|---|---|---|---|
| | 18 | | 3-(2-Acetyl-[1,1';3',1'']terphenyl-4''-ylmethylsulfanyl)-2-tert-butoxycarbonylamino-propionic acid |
| | 19 | | 2-tert-Butoxycarbonylamino-3-[4-(4-dibenzofuran-4-yl-benzyloxy)-benzylsulfanyl]-propionic acid |
| | 20 | | 3-(2'-Adamantan-1-yl-4'-methyl-biphenyl-4-ylmethylsulfanyl)-2-tert-butoxycarbonylamino-propionic acid |
| | 21 | | 3-(4'-Adamantan-1-yl-3-fluoro-biphenyl-4-ylmethylsulfanyl)-2-tert-butoxycarbonylamino-propionic acid |
| | 22 | | 2-tert-Butoxycarbonylamino-5-(3'-dibenzofuran-4-yl-biphenyl-4-yl)-pent-4-enoic acid |

-continued

| IDD# | Cmpd. No. | Structure | Name |
|---|---|---|---|
| | 23 | 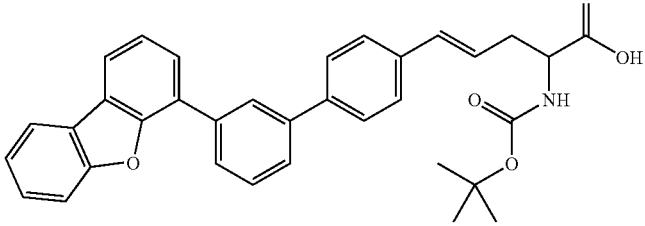 | 2-tert-Butoxycarbonylamino-5-(3'-dibenzofuran-4-yl-biphenyl-4-yl)-pent-4-enoic acid |
| | 24 | 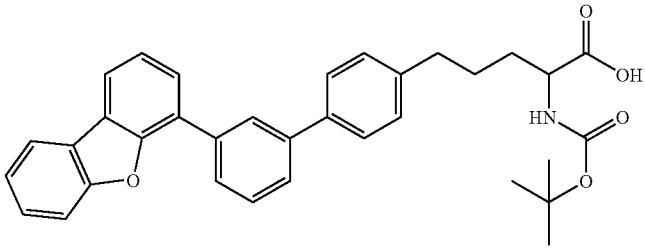 | 2-tert-Butoxycarbonylamino-5-(3'-dibenzofuran-4-yl-biphenyl-4-yl)-pentanoic acid |
| | 25 | 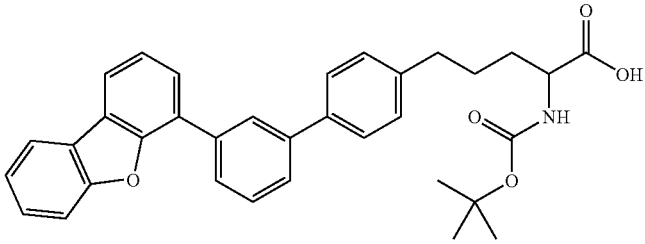 | 2-tert-Butoxycarbonylamino-5-(3'-dibenzofuran-4-yl-biphenyl-4-yl)-pentanoic acid |
| | 26 | 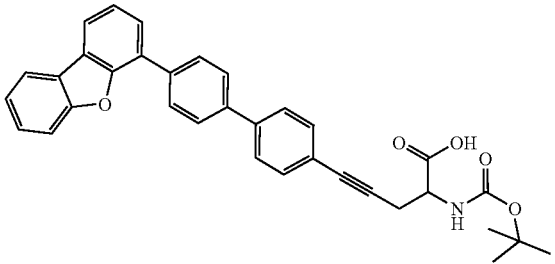 | 2-tert-Butoxycarbonylamino-5-(4'-dibenzofuran-4-yl-biphenyl-4-yl)-pent-4-ynoic acid |
| | 27 | 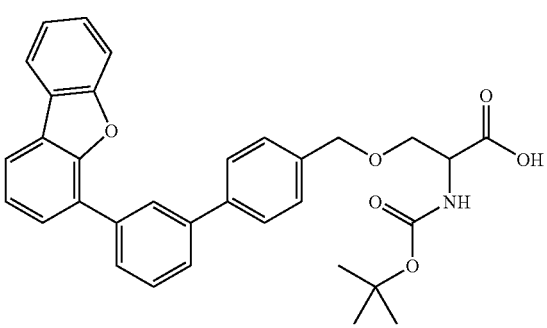 | 2-tert-Butoxycarbonylamino-3-(3'-dibenzofuran-4-yl-biphenyl-4-ylmethoxy)-propionic acid |

| IDD# | Cmpd. No. | Structure | Name |
|---|---|---|---|
| | 28 | | 2-tert-Butoxycarbonylamino-4-(3'-dibenzofuran-4-yl-biphenyl-3-yloxy)-butyric acid |
| | 29 | | 2-tert-Butoxycarbonylamino-4-(3'-dibenzofuran-4-yl-biphenyl-4-yloxy)-butyric acid |
| | 30 | | 2-tert-Butoxycarbonylamino-4-(4'-dibenzofuran-4-yl-biphenyl-3-yloxy)-butyric acid |

As noted above, the compounds of the invention bind to and preferably, inhibit PTP-1B. As a result that are useful in the treatment of various diseases, including controlling or treating Type 2 diabetes, improving glucose tolerance, and in improving insulin sensitivity in patients in need thereof. The compounds are also useful in treating or controlling other PTP-1B mediated diseases, such as the treatment of cancer, neurodegenerative diseases and the like.

The term "alkoxy" represents an alkyl group of indicated number of carbon atoms attached to the parent molecular moiety through an oxygen bridge. Examples of alkoxy groups include, for example, methoxy, ethoxy, propoxy and isopropoxy.

As used herein, the term "alkyl" includes those alkyl groups of a designed number of carbon atoms. Alkyl groups may be straight, or branched. Examples of "alkyl" include methyl, ethyl, propyl, isopropyl, butyl, iso-, sec- and tert-butyl, pentyl, hexyl, heptyl, 3-ethylbutyl, and the like.

The term "alkylene" means a divalent group derived from a straight or branched chain hydrocarbon of from 2 to 10 carbon atoms. Representative examples of alkylene include, but are not limited to, —$CH_2CH_2$—, —$C(CH_3)_2C(CH_3)_2$—, —$CH(CH_3)CH(CH_3)$—, —$CH_2CH_2CH_2$—, —$CH_2CH_2CH_2CH_2$—, and —$CH_2CH(CH_3)CH_2$—.

The term "aryl" refers to an aromatic hydrocarbon ring system containing at least one aromatic ring. The aromatic ring may optionally be fused or otherwise attached to other aromatic hydrocarbon rings or non-aromatic hydrocarbon rings. Examples of aryl groups include, for example, phenyl, naphthyl, 1,2,3,4-tetrahydronaphthalene and biphenyl. Preferred examples of aryl groups include phenyl, naphthyl, and anthracenyl. More preferred aryl groups are phenyl and naphthyl. Most preferred is phenyl.

The term "cycloalkyl" refers to a $C_3$-$C_8$ cyclic hydrocarbon. Examples of cycloalkyl include cyclopropyl, cyclobutyl, cyclopentyl, cyclohexyl, cycloheptyl and cyclooctyl.

The terms "halogen" or "halo" indicate fluorine, chlorine, bromine, and iodine.

The term "heterocycloalkyl," refers to a ring or ring system containing at least one heteroatom selected from nitrogen, oxygen, and sulfur, wherein said heteroatom is in a non-aromatic ring. The heterocycloalkyl ring is optionally fused to or otherwise attached to other heterocycloalkyl rings and/or non-aromatic hydrocarbon rings and/or phenyl rings. Preferred heterocycloalkyl groups have from 3 to 10 members. Examples of heterocycloalkyl groups include, for example, 1,2,3,4-tetrahydroquinolinyl, 1,2,3,4-tetrahydroisoquinolinyl, piperazinyl, morpholinyl, piperidinyl, tetrahydrofuranyl, pyrrolidinyl, pyridinonyl, and pyrazolidinyl. Preferred heterocycloalkyl groups include piperidinyl, piperazinyl, morpholinyl, pyrrolidinyl, pyridinonyl, dihydropyrrolidinyl, and pyrrolidinonyl.

The term "heteroaryl" refers to an aromatic ring system containing at least one heteroatom selected from nitrogen, oxygen, and sulfur. The heteroaryl ring may be fused or otherwise attached to one or more heteroaryl rings, aromatic or non-aromatic hydrocarbon rings or heterocycloalkyl rings. Examples of heteroaryl groups include, for example, pyridine, furan, thienyl, 5,6,7,8-tetrahydroisoquinoline and pyrimidine. Preferred examples of heteroaryl groups include thienyl, benzothienyl, pyridyl, quinolyl, pyrazolyl, pyrimidyl, imidazolyl, benzimidazolyl, furanyl, benzofuranyl, dibenzofuranyl, thiazolyl, benzothiazolyl, isoxazolyl, oxadiazolyl, isothiazolyl, benzisothiazolyl, triazolyl, pyrrolyl, indolyl, pyrazolyl, and benzopyrazolyl.

The compounds of this invention may contain one or more asymmetric carbon atoms, so that the compounds can exist in different stereoisomeric forms. These compounds can be, for example, racemates, chiral non-racemic or diastereomers. In these situations, the single enantiomers, i.e., optically active forms, can be obtained by asymmetric synthesis or by resolution of the racemates. Resolution of the racemates can be accomplished, for example, by conventional methods such as crystallization in the presence of a resolving agent; chromatography, using, for example a chiral HPLC column; or derivatizing the racemic mixture with a resolving reagent to generate diastereomers, separating the diastereomers via chromatography, and removing the resolving agent to generate the original compound in enantiomerically enriched form. Any of the above procedures can be repeated to increase the enantiomeric purity of a compound.

When the compounds described herein contain olefinic double bonds or other centers of geometric asymmetry, and unless otherwise specified, it is intended that the compounds include the cis, trans, Z- and E-configurations. Likewise, all tautomeric forms are also intended to be included.

The compounds of general Formula I may be administered orally, topically, parenterally, by inhalation or spray or rectally in dosage unit formulations containing conventional non-toxic pharmaceutically acceptable carriers, adjuvants and vehicles. The term parenteral as used herein includes percutaneous, subcutaneous, intravascular (e.g., intravenous), intramuscular, or intrathecal injection or infusion techniques and the like. In addition, there is provided a pharmaceutical formulation comprising a compound of general Formula I and a pharmaceutically acceptable carrier. One or more compounds of general Formula I may be present in association with one or more non-toxic pharmaceutically acceptable carriers and/or diluents and/or adjuvants, and if desired other active ingredients. The pharmaceutical compositions containing compounds of general Formula I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preservative agents in order to provide pharmaceutically elegant and palatable preparations. Tablets contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques. In some cases such coatings may be prepared by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules, wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Formulations for oral use may also be presented as lozenges.

Aqueous suspensions contain the active materials in admixture with excipients suitable for the manufacture of aqueous suspensions. Such excipients are suspending agents, for example sodium carboxymethylcellulose, methylcellulose, hydropropyl-methylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents or suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil or a mineral oil or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol, glucose or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents that have been mentioned above. The sterile injectable preparation may also be a sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of general Formula I may also be administered in the form of suppositories, e.g., for rectal administration of the drug. These compositions can be prepared by mixing the drug with a suitable non-irritating excipient that is solid at ordinary temperatures but liquid at the rectal temperature and will therefore melt in the rectum to release the drug. Such materials include cocoa butter and polyethylene glycols.

Compounds of general Formula I may be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

For disorders of the eye or other external tissues, e.g., mouth and skin, the formulations are preferably applied as a topical gel, spray, ointment or cream, or as a suppository, containing the active ingredients in a total amount of, for example, 0.075 to 30% w/w, preferably 0.2 to 20% w/w and most preferably 0.4 to 15% w/w. When formulated in an ointment, the active ingredients may be employed with either paraffinic or a water-miscible ointment base.

Alternatively, the active ingredients may be formulated in a cream with an oil-in-water cream base. If desired, the aqueous phase of the cream base may include, for example at least 30% w/w of a polyhydric alcohol such as propylene glycol, butane-1,3-diol, mannitol, sorbitol, glycerol, polyethylene glycol and mixtures thereof. The topical formulation may desirably include a compound which enhances absorption or penetration of the active ingredient through the skin or other affected areas. Examples of such dermal penetration enhancers include dimethylsulfoxide and related analogs. The compounds of this invention can also be administered by a transdermal device. Preferably topical administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane. The transdermal patch may include the compound in a suitable solvent system with an adhesive system, such as an acrylic emulsion, and a polyester patch. The oily phase of the emulsions of this invention may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. Emulsifiers and emulsion stabilizers suitable for use in the formulation of the present invention include Tween 60, Span 80, cetostearyl alcohol, myristyl alcohol, glyceryl monostearate, and sodium lauryl sulfate, among others. The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredients are dissolved or suspended in suitable carrier, especially an aqueous solvent for the active ingredients. The antiinflammatory active ingredients are preferably present in such formulations in a concentration of 0.5 to 20%, advantageously 0.5 to 10% and particularly about 1.5% w/w. For therapeutic purposes, the active compounds of this combination invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Dosage levels of the order of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient. The daily dose can be administered in one to four doses per day. In the case of skin conditions, it may be preferable to apply a topical preparation of compounds of this invention to the affected area two to four times a day.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

For administration to non-human animals, the composition may also be added to the animal feed or drinking water. It may be convenient to formulate the animal feed and drinking water compositions so that the animal takes in a therapeutically appropriate quantity of the composition along with its diet. It may also be convenient to present the composition as a premix for addition to the feed or drinking water. Preferred non-human animals include domesticated animals.

As noted above, the invention also provides methods and compositions for combination therapy of Type I and Type II diabetes. In one such aspect, the invention provides methods of using compounds of formula I in combination with one or more angiotensin converting enzyme (ACE) inhibitors for improving the cardiovascular risk profile in patients experiencing or subject to Syndrome X or type II diabetes (non-insulin-dependent diabetes mellitus), preferably in human type II diabetics. These methods may also be characterized as the reduction of risk factors for heart disease, stroke or heart attack in a type II diabetic.

These methods include the reduction of hyperlipidemia in a patients experiencing or subject to Syndrome X or type II diabetes. These methods include methods lowering low density lipoprotein (LDL) blood levels and to increase high density lipoprotein (HDL) blood levels. The methods herein may further be characterized as useful for inhibiting, preventing or reducing atherosclerosis in a type II diabetics, or for reducing the risk factors thereof.

These methods also include the lowering of free fatty acid blood levels and triglyceride levels in type II diabetics.

Among the ACE inhibitors which may be utilized with the invention described herein are quinapril, ramipril, verapamil, captopril, diltiazem, clonidine, hydrochlorthiazide, benazepril, prazosin, fosinopril, lisinopril, atenolol, enalapril, perindropril, perindropril tert-butylamine, trandolapril and moexipril, or a pharmaceutically acceptable salt form of one or more of these compounds.

The invention also provides methods of using PTPase inhibitors of formula I for improving the cardiovascular or cerebrovascular risk profile in patients experiencing or subject to type II diabetes (non-insulin-dependent diabetes mellitus), preferably in human type II diabetics or a patient experiencing or subject to Syndrome X. These methods may also be characterized as the reduction of risk factors for heart disease, stroke or heart attack in a type II diabetic or a patient experiencing or subject to Syndrome X.

The invention also provides methods of using a pharmacological combination of one or more PTPase inhibiting agents, one or more biguanide agents, and, optionally one or more sulfonlyurea agents for treatment of type II diabetes or Syndrome X in a patient in need of such treatment. Also provided are methodS of using these agents to treat or inhibit metabolic disorders mediated by insulin resistance or hyperglycemia in a patient in need thereof. Further included in this invention is a method of modulating blood glucose levels in a patient in need thereof.

Each of these methods comprises administering to a patient in need thereof pharmaceutically effective amounts of:
a) a PTPase inhibiting agent of formula I; and
b) a biguanide agent; and
c) optionally, a sulfonylurea agent.

Biguanide agents useful with this invention include metformin and its pharmaceutically acceptable salt forms. Sulfonylurea agents useful for the methods and combinations of this invention may be selected from the group of glyburide, glyburide, glipizide, glimepiride, chlorpropamide, tolbutamide, or tolazamide, or a pharmaceutically acceptable salt form of these agents.

This invention also provides pharmaceutical compositions and methods of using PTPase inhibitors of formula I in combination with one or more alpha-glucosidase inhibitors, such as miglitol or acarbose, for improving the cardiovascular risk profile in patients experiencing or subject to Syndrome X or type II diabetes (non-insulin-dependent diabetes mellitus), preferably in human type II diabetics. These methods may also be characterized as the reduction of risk factors for heart disease, stroke or heart attack in a patient in such need.

These methods include the reduction of hyperlipidemia in type II diabetics, including methods in type II diabetics for lowering low density lipoprotein (LDL) blood levels and to increase high density lipoprotein (HDL) blood levels. The methods herein may further be characterized as useful for inhibiting, preventing or reducing atherosclerosis in a type II diabetic or a patient experiencing or subject to Syndrome X, or the risk factors of either.

These methods also include the lowering free fatty acid blood levels and triglyceride levels in type II diabetics, or a patient experiencing or subject to Syndrome X.

Among the alpha-glucosidase inhibitors which may be utilized with the invention described herein are miglitol or acarbose, or a pharmaceutically acceptable salt form of one or more of these compounds.

This invention further provides methods for using a PTPase inhibitor of the invention and a sulfonylurea agent for the management of Syndrome X or type 2 diabetes and for improving the cardiovascular risk profile in patients experiencing or subject to those maladies. These methods may also be characterized as the reduction of risk factors in such patients for heart disease, stroke or heart attack in a type II diabetic. Such methods include the reduction of hyperlipidemia in a patients experiencing or subject to Syndrome X or type II diabetes and include methods for lowering low density lipoprotein (LDL) blood levels, high density lipoprotein (HDL) blood levels, and overall blood lipoprotein levels. The methods herein may further be characterized as inhibiting, preventing or reducing atherosclerosis in patients subject to or experiencing Syndrome X or type II diabetes, or the risk factors thereof. Such methods further include the lowering of free fatty acid blood levels and triglyceride levels in such patients.

Representative sulfonylurea agents include glipizide, glyburide (glibenclamide), chlorpropamide, tolbutamide, tolazamide and glimepriride, or the pharmaceutically acceptable salt forms thereof.

In addition, the invention provides combinations of a PTPase inhibitor of the invention and at least one thiazolidinedione agents. Such combinations are useful for treatment, inhibition or maintenance of Syndrome X or type II diabetes in patients in need of such treatment. Accordingly, methods of using such combinations are provided by the invention. Thus, the invention provides methods of using these agents to treat or inhibit metabolic disorders mediated by insulin resistance or hyperglycemia in patients in need thereof. Further included in this invention are methods of modulating blood glucose levels in a patient in need thereof.

Each of these methods comprises administering to a patient in need thereof pharmaceutically effective amounts of:
a) a thiazolidinedione agent, such as selected from the group of pioglitzone and rosiglitazone, or a pharmaceutically acceptable salt form of these agents; and
b) a compound of formula I.

The invention also provides pharmaceutical compositions and methods of using PTPase inhibitors in combination with one or more antilipemic agents. Such methods and compositions are useful for improving the cardiovascular risk profile in patients experiencing or subject to type II diabetes (non-insulin-dependent diabetes mellitus), preferably in type II diabetics or Syndrome X. These methods also include reducing the risk factors for heart disease, stroke or heart attack in a type II diabetic or a patient experiencing or subject to Syndrome X. Such methods further include the reduction of hyperlipidemia in type II diabetics, including such methods in type II diabetics for lowering low density lipoprotein (LDL) blood levels and to increase high density lipoprotein (HDL) blood levels. These compositions and methods are also useful for inhibiting, preventing or reducing atherosclerosis in a type II diabetic or a patient experiencing or subject to Syndrome X, or the risk factors thereof. In this aspect, the compositions and methods are useful for lowering of free fatty acid blood levels and triglyceride levels in type II diabetics, or patients experiencing or subject to Syndrome X.

Representative antilipemic or agents, also known as anti-hyperlipidemic agents, suitable for use in the invention are bile acid sequestrants, fibric acid derivatives, HMG-CoA reductase inhibitors and nicotinic acid compounds. Bile acid sequestrant agents useful with this invention include colestipol and colesevelam, and their pharmaceutically acceptable salt forms. Fibric acid derivatives which may be used with the present invention include clifofibrate, gemfibrozil and fenofibrate. HMG-CoA reductase inhibitors, also known as statins, useful with this invention include cerivastatin, fluvastatin, atorvastatin, lovastatin, pravastatin and simvastatin, or the pharmaceutically acceptable salt forms thereof. Niacin is an example of a nicotinic acid compound which may be used with the methods of this invention. Also useful are lipase inhibiting agents, such as orlistat.

This invention also provides pharmaceutical compositions that are a combination of a compound of Formula I and an aldose reductase inhibitor (ARI). Such combinations are useful in methods for treating, inhibiting or preventing type II diabetes, or its related and associated symptoms, disorders and maladies. These methods comprise administering to a patient in need of such therapy a pharmaceutically effective amount of a composition comprising a combination of pharmaceutically effective amounts of a compound of formula I and an ARI. These compositions and methods are useful for the treatment, prevention or inhibition of diabetic neuropathy, diabetic nephropathy, retinopathy, keratopathy, diabetic uveitis, cataracts.

Representative suitable ARIs are disclosed in U.S. Pat. Nos. 6,420,426 and 6,214,991.

Combinations of the compounds of Formula I and an ARI are also useful for inhibition or reduction of risk factors for heart disease, stroke or heart attack in a type II diabetic. Therefore, in this aspect the invention is useful for reducing hyperlipidemia and/or low density lipoprotein (LDL) blood levels in type II diabetics. Also included in this aspect are methods for inhibiting, preventing or reducing atherosclerosis or the risk factors thereof in type II diabetics. This aspect includes lowering of free fatty acid blood levels and triglyceride levels.

This invention also provides methods of using a compound of formula I and insulin(s) for the management of type I or type II diabetes. Accordingly, the invention provides for combination therapy, i.e., where a compound of Formula I is administered in combination with insulin. Such combination therapy encompasses simultaneous or sequential administration of the compound of Formula I and insulin. The insulins useful in this aspect include both naturally occurring and synthetic insulins.

Insulins useful with the methods and combinations of this invention include rapid acting insulins, intermediate acting insulins, long acting insulins and combinations of intermediate and rapid acting insulins.

Rapid acting commercially available insulin products include HUMALOG® Brand Lispro Injection (rDNA origin); HUMULIN® Regular Human Injection, USP [rDNA origin]; HUMULIN® Regular U-500 Concentrated Human Injection, USP [rDNA origin]; REGULAR ILETIN® II (insulin injection, USP, purified pork) available from Eli Lilly and Co.; and the NOVALIN® Human Insulin Injection and VENOSULIN® BR Buffered Regular Human Injection, each available from Novo Nordisk Pharmaceuticals.

Commercially available intermediate acting insulins useful with this invention include, but are not limited to, the HUMULIN® L brand LENTE® human insulin [rDNA origin] zinc suspension, HUMULIN® N NPH human insulin [rDNA origin] isophane suspension, LENTE® ILETIN®. II insulin zinc suspension, USP, purified pork, and NPH ILETIN® II isophane insulin suspension, USP, purified pork, available from Eli Lilly and Company, LANTUS® insulin glargine [rDNA origin] injection, available from Aventis Pharmaceuticals, and the NOVOLIN L Lente® human insulin zinc suspension (recombinant DNA origin), and NOVOLIN®. N NPH human insulin isophane suspension (recombinant DNA origin) products available from Novo Nordisk Pharmaceuticals, Inc, Princeton N.J.

Also useful with the methods and formulations of this invention are intermediate and rapid acting insulin combinations, such as the HUMALOG® Mix 75/25 (75% Insulin Lispro Protamine Suspension and 25% Insulin Lispro Injection), HUMULIN® 50/50 (50% Human Insulin Isophane Suspension and 50% Human Insulin Injection) and HUMULIN® 70/30 (70% Human Insulin Isophane Suspension and 30% Human Insulin Injection), each available from Eli Lilly and Company. Also useful are the NOVALIN® 70/30 (70% NPH, Human Insulin Isophane Suspension and 30% Regular, Human Insulin Injection) line of combination products available from Novo Nordisk Pharmaceuticals.

A commercially available long acting insulin for use with this invention is the HUMULIN® U Ultralente® human insulin [rDNA origin] extended zinc suspension, available from Eli Lilly and Company.

Also useful in the methods of this invention are inhaled insulin products, such as the EXUBERA® inhaled insulin product developed by Pfizer Inc. and Aventis SA.

Each of these insulin products can be administered as directed by a medical professional using administrations, dosages and regimens known in the art, such as those published for each product in the Physicians' Desk Reference, 55 Edition, 2001, published by Medical Economics Company, Inc. at Montvale, N.J., the relevant sections of which are incorporated herein by reference.

In this aspect, the invention includes, for example, methods for improving the cardiovascular and cerebrovascular risk profiles in patients experiencing or subject to type I or type II diabetes (non-insulin-dependent diabetes mellitus), preferably in human type II diabetics. These methods may also be characterized as the inhibition or reduction of risk factors for heart disease, stroke or heart attack in a type II diabetic.

The compounds of the present invention may be prepared by use of known chemical reactions and procedures. Representative methods for synthesizing compounds of the invention are presented below. It is understood that the nature of the substituents required for the desired target compound often determines the preferred method of synthesis. All variable groups of these methods are as described in the generic description if they are not specifically defined below.

Methods of Preparation

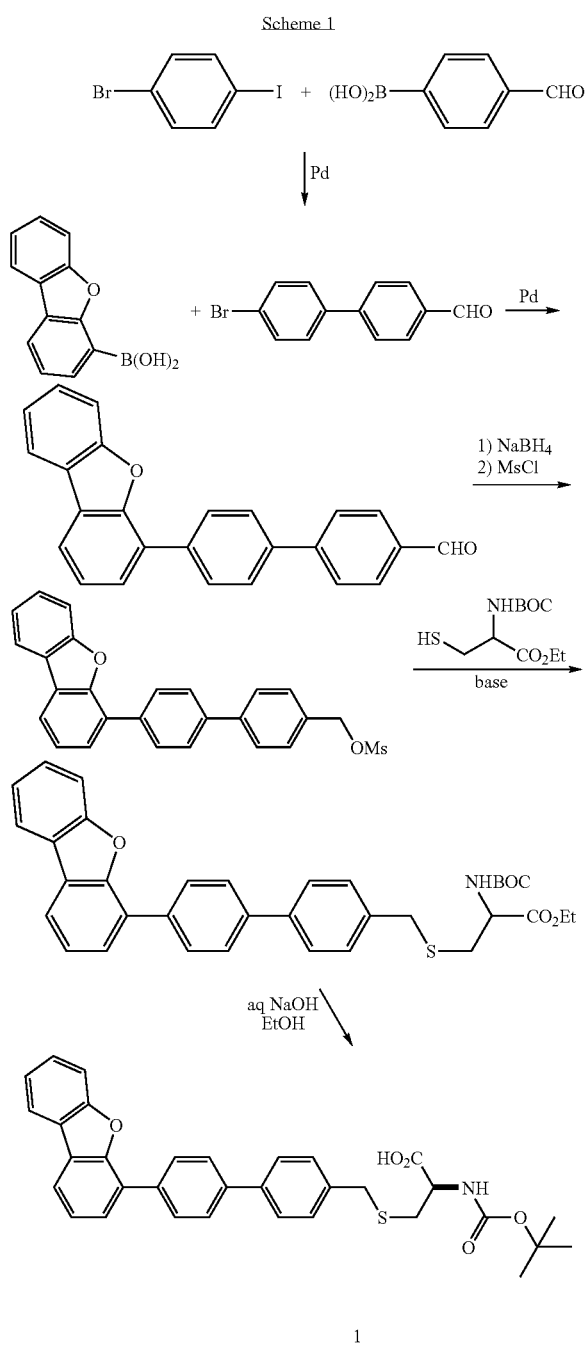

A method for preparing the compounds of the invention is outlined in scheme 1. Here, the biphenyl core is coupled to a Q-ring via a transition metal catalyzed reaction. The aldehyde in the resulting coupled product is reduced and then converted into a leaving group using methods known in the art. The leaving group is then displaced via a nucleophilic substitution. Depending on the desired final product, the $CO_2R_1$ group (wherein $R_1$ is $C_1$-$C_6$ alkyl) may be hydrolyzed to form a $CO_2H$ group, and any protecting groups may be removed using methods known in the art.

Additionally, if the nucleophile is a thiol (as shown above), then the resulting thioether linkage may be oxidized to the sulfoxide or sulfone using methods known in the art.

Furthermore, if there is an amine in the molecule, it may be elaborated by methods known in the art to form an amide, or sulfonamide, or the amine may be reacted with an aldehyde and a reducing agent to form an N-alkyl amine.

Those having skill in the art will recognize that the starting materials and reaction conditions may be varied, the sequence of the reactions altered, and additional steps employed to produce compounds encompassed by the present invention, as demonstrated by the following examples. In some cases, protection of certain reactive functionalities may be necessary to achieve some of the above transformations. In general, the need for such protecting groups as well as the conditions necessary to attach and remove such groups will be apparent to those skilled in the art of organic synthesis.

The disclosures of all articles and references mentioned in this application, including patents, are incorporated herein by reference in their entirety.

The preparation of the compounds of the present invention is illustrated further by the following examples, which are not to be construed as limiting the invention in scope or spirit to the specific procedures and compounds described in them. In all cases, unless otherwise specified, the column chromatography is performed using a silica gel solid phase.

Experimental Procedures

EXAMPLE 1

2-tert-Butoxycarbonylamino-3-(4'-dibenzofuran-4-yl-biphenyl-4-ylmethylsulfanyl)-propionic acid

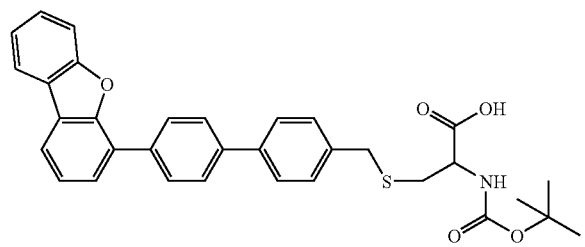

Step 1: Preparation of 4'-Dibenzofuran-4-yl-biphenyl-4-carbaldehyde

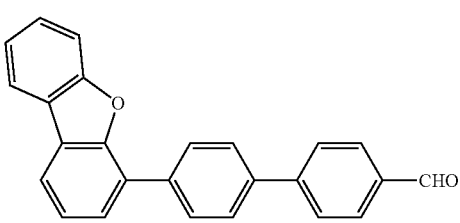

A solution of dibenzofuran-4-boronic acid (1.0 g, 4.7 mmol) in ethanol (10 mL) was added to a stirred solution of 1-bromo-4-iodobenzene (1.33 g, 4.7 mmol) and tetrakis-(triphenylphosphine)-palladium(0) (271 mg, 5 mol %) in toluene (40 mL). 2 N sodium carbonate (4.7 mL, 9.4 mmol) was added and then the reaction was heated to 90° C. (oil bath temp.) for 2-3 h until complete (TLC control). The reaction mixture was cooled to room temperature and partitioned between water and diethyl ether. The phases were separated, the aqueous phase being further extracted with diethyl ether (2×20 mL). The combined organic extracts were washed with water and sat'd aq NaCl. The ethereal solution was dried over anhyd MgSO$_4$, filtered and concentrated in vacuo to yield 4-(4-bromophenyl)-dibenzofuran as a yellow solid, which was used immediately without further purification.

A solution of 4-formylphenylboronic acid (0.9 g, 5.64 mmol) in ethanol (10 mL) was added to a stirred solution of the crude 4-(4-bromophenyl)-dibenzofuran (from the previous reaction) in toluene (40 mL). Tetrakis-(Triphenylphosphine)-palladium(0) (270 mg, 5 mol %) and 2 N sodium carbonate (4.7 mL, 9.4 mmol) were added and then the reaction was heated to 100° C. (oil bath temp.) for 2-3 h until complete (TLC control). The reaction mixture was cooled to room temperature and partitioned between water and ethyl acetate. The phases were separated, the aqueous phase being further extracted with ethyl acetate (2×20 mL). The combined organic extracts were washed with 0.5 N hydrochloric acid, water and sat'd aq NaCl and then dried over anhyd MgSO$_4$, filtered and concentrated in vacuo. Purification by flash column chromatography (10-20% ethyl acetate in heptane) afforded the title compound has a white solid (1.51 g).

Step 2: Preparation of (4'-Dibenzofran-4-yl-bipenyl-4-yl)methanol

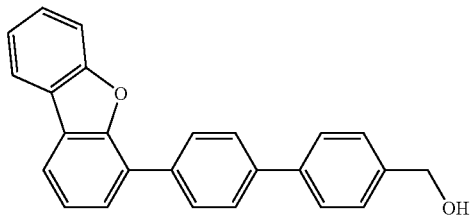

Sodium borohydride (322 mg, 8.4 mmol) was added portion-wise to a stirred solution of aldehyde (prepared in the previous step) (1.48 g, 4.2 mmol) in a mixture of anhyd THF and ethanol (1:2, 50 mL) at room temperature. The reaction mixture was stirred for 5-10 min at room temperature (TLC control), poured into water (50 mL) and acidified to pH 4 with 2 N hydrochloric acid, and then extracted with diethyl ether (3×30 mL). The combined organic extracts were washed with 0.5 N hydrochloric acid (2×10 mL), water and finally sat'd aq NaCl. The ethereal solution was dried over anhyd MgSO$_4$, filtered and concentrated in vacuo. Purification by flash column chromatography (30% ethyl acetate in heptane) afforded the title compound has a white solid (1.40 g).

Step 3: Preparation of Methanesulfonic acid, 4'-dibenzofuran-4-yl-biphenyl-4-ylmethyl ester

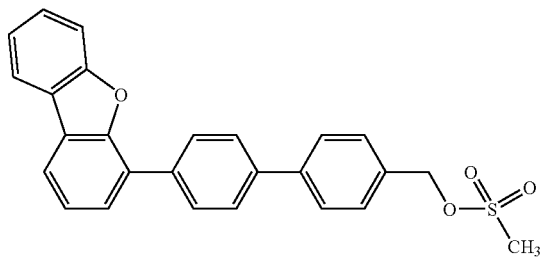

Methanesulfonyl chloride (490 mg, 330 μL, 4.3 mmol) was added dropwise to a cooled (0° C.) solution of alcohol (prepared in the previous step) (1.38 g, 3.9 mmol) and triethylamine (800 mg, 1.1 mL, 7.9 mmol) in anhyd methylene chloride (50 mL). The clear reaction mixture was stirred at 0° C. for 2-4 h (TLC control), then poured into water (50 mL), and extracted with diethyl ether (3×30 mL). The combined extract was washed with 0.5 N hydrochloric acid (2×10 mL), water and finally sat'd aq NaCl. The ethereal solution was dried over anhyd MgSO$_4$, filtered and concentrated in vacuo. The crude mesylate was used in the subsequent alkylation step without further purification.

Step 4: Preparation of (R)-Methyl-2-tert-butoxycarbonylamino-3-(4'-dibenzofuran-4-yl-biphenyl-4-ylmethylsulfanyl)-propionate

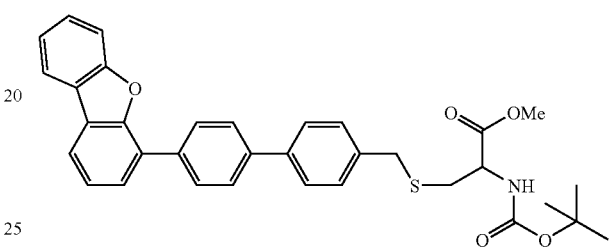

L-N-(tert)Butoxycarbonyl cysteine methyl ester (940 mg, 4.0 mmol) was added dropwise to a stirred suspension of mesylate (prepared in the previous step) (1.65 g, 3.8 mmol) and cesium carbonate (2.6 g, 8.0 mmol), in anhyd DMF (50 mL) at room temperature. The reaction mixture was stirred at room temperature for 2-3 h (TLC control) and then poured into water (50 mL) and extracted with diethyl ether (3×50 mL). The combined organic extracts were washed with water (2×30 mL), sat'd aq NaCl (3×30 mL), dried over anhyd MgSO$_4$, filtered and concentrated in vacuo. Purification by flash column chromatography (20-40% ethyl acetate in heptane) afforded the title compound has a pale yellow solid (1.96 g).

Step 5: Preparation of (R)-2-tert-Butoxycarbonyl-3-(4'-dibenzofuran-4-yl-biphenyl-4-ylmethylsulfanyl)-propionic acid

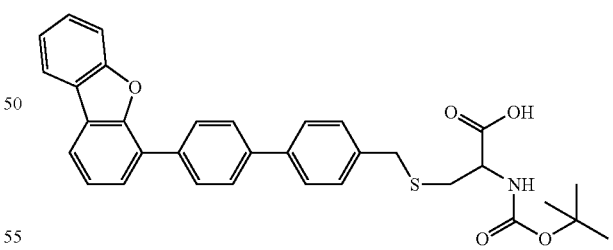

2 N Sodium hydroxide solution (1.32 mL, 2.64 mmol) was added dropwise to a stirred solution of methyl-2-tert-butoxycarbonylamino-3-(4'-dibenzofuran-4-yl-biphenyl-4-ylmethylsulfanyl)propionate (500 mg, 0.88 mmol) in tetrahydrofuran (15 mL) and methanol (3 mL). The clear reaction mixture was stirred at room temperature until the reaction was complete (TLC control), and then diluted with water (10 mL), and acidified to pH 3 with 2 N hydrochloric acid. The reaction mixture was extracted with ethyl acetate (2×20 mL). The combined organic extracts were washed with water, sat'd aq NaCl, dried over anhyd MgSO$_4$, filtered and concentrated in vacuo. Purification by flash column chromatography (5-10% methanol in methylene chloride) afforded the title compound has a white solid (420 mg), mp 205-206° C.

EXAMPLE 2

Preparation of 3-(4'-Dibenzofuran-4-yl-biphenyl-4-ylmethylsulfanyl)-2-(2-fluoro-5-trifluoromethyl-benzoylamino)-propionic acid

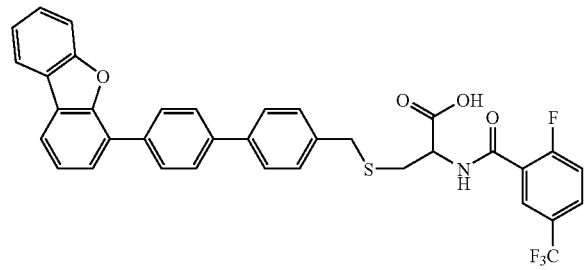

Step 1: Preparation of Methyl-2-amino-3-(4'-dibenzofuran-4-ylbipheny-4-ylmethylsulfanyl)-propionate

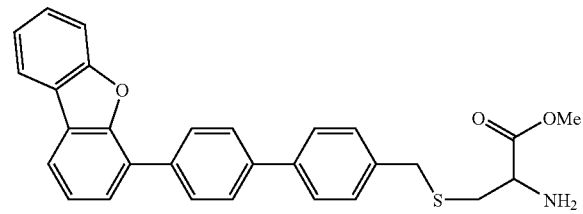

TMS-I (290 mg, 0.21 mL, 1.45 mmol) was added dropwise to a stirred solution of methyl-2-tert-butoxycarbonylamino-3-(4'-dibenzofuran-4-yl-biphenyl-4-ylmethyl-sulfanyl)-propionate (748 mg, 1.32 mmol) in anhyd methylene chloride (20 mL). The reaction mixture was stirred at room temperature for 20-30 min (TLC control), and then diluted with water (20 mL). Sat'd aq sodium bicarbonate solution was added to adjust the solution to pH 8-9. The reaction mixture was extracted with diethyl ether (2×30 mL). The combined organic extracts were washed with water, sat'd aq NaCl, dried over anhydrous MgSO₄, filtered and concentrated in vacuo. Purification by flash column chromatography (5% methanol in methylene chloride) afforded the title compound has a pale yellow solid (596 mg).

Step 2: Preparation of Methyl-3-(4'-dibenzofuran-4-yl-biphen-4ylmethylsulfanyl)-2(2-fluoro-5-trifluoromethylbenzoylamino)-propionate

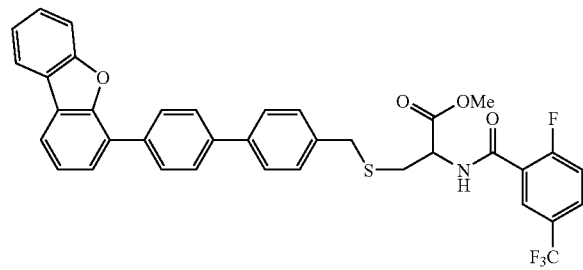

2-Fluoro-5-trifluoromethylbenzoic acid (49 mg, 0.24 mmol) was added to a stirred solution of methyl-2-amino-3-(4'-dibenzofuran-4-ylbipheny-4-ylmethylsulfanyl)-propionate (92 mg, 0.2 mmol), EDCI (58 mg, 0.3 mmol) and triethylamine (404 mg, 0.56 mL, 0.4 mmol) in anhyd methylene chloride (5 mL). The reaction mixture was stirred at room temperature for 4-6 h (TLC control) and then diluted with water (10 mL). The reaction mixture was extracted with ethyl acetate (2×20 mL). The combined organic extract were washed with water, sat'd aq NaCl, dried over anhydrous MgSO₄₁ filtered and concentrated in vacuo. Purification by flash column chromatography (30% ethyl acetate in heptane) afforded the title compound has a white solid (117 mg).

Step 3: Preparation of 3-(4'-Dibenzofuran-4-yl-biphen-4ylmethylsulfanyl)-2(2-fluoro-5-trifluoromethyl-benzoylamino)propionic acid 2 N Sodium hydroxide solution (0.25 mL, 0.5 mmol) was added dropwise to a stirred solution of methyl-3-(4'-dibenzofuran-4-yl-biphen-4ylmethylsulfanyl)-2(2-fluoro-5-trifluoromethylbenzoylamino)-propionate (110 mg, 0.17 mmol) in tetrahydrofuran (5 mL) and methanol (1 mL). The clear reaction mixture was stirred at room temperature until the reaction was complete (TLC control), and then diluted with water (5 mL), and acidified to pH 3 with 2 N hydrochloric acid. The reaction mixture was extracted with ethyl acetate (2×10 mL). The combined extract was washed with water, sat'd aq NaCl, dried over anhydrous MgSO₄, filtered and concentrated in vacuo. Purification by flash column chromatography (5-10% methanol in methylene chloride) afforded the title compound has a white solid (98 mg).

EXAMPLE 3

(4'-Indol-1-yl-biphen-4-yl)methanol

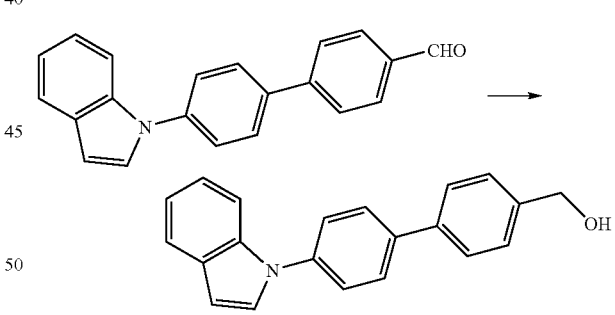

Sodium borohydride (783 mg, 20.6 mmol) was added portion-wise to a stirred solution of aldehyde (3.06 g, 10.3 mmol) in a mixture of anhydrous THF and ethanol (1:1; 100 mL) at room temperature. The reaction mixture was stirred for 10 minutes at room temperature (TLC control), poured into water (50 mL) and acidified to pH 4 with 2N hydrochloric acid, and then extracted with diethyl ether (3×20 mL). The combined extract was washed with 0.5 N hydrochloric acid (2×10 mL), water and finally brine. The ethereal solution was dried over anhydrous MgSO₄, filtered and concentrated in vacuo. Purification of the product by flash column chromatography, using 30% ethyl acetate/hexane as eluent, afforded the title compound has a white solid (2.80 g, 91%); ¹H NMR (CDCl₃, 300 MHz) δ 7.55-7.78 (7H, m, Ar—H), 7.52 (2H, d, J=8 Hz, Ar—H), 7.41 (1H, d, J=3.5 Hz, Ar—H), 7.22 (3H, m, Ar—H), 6.72 (1H, d, J=3.5 Hz, Ar—H), 4.79 (2H, d, J=5.5 Hz, CH₂O).

EXAMPLE 4

Methanesulfonic acid, (4'-Indol-1-yl-biphen-4-yl)methyl ester

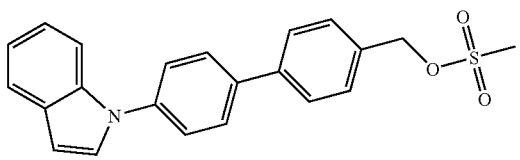

Methanesulfonyl chloride (194 mg, 131 µL, 1.7 mmol) was added dropwise to a cooled (0° C.) solution of alcohol (prepared in the previous step) (620 mg, 1.54 mmol) and triethylamine (311 mg, 0.43 mL, 3.08 mmol) in anhydrous methylene chloride (10 mL). The clear reaction mixture was stirred at 0° C. for 2-4 hrs (TLC control), then poured into water (50 mL), and extracted with diethyl ether (3×30 mL). The combined extract was washed with 0.5 N hydrochloric acid (2×10 mL), water and finally brine. The ethereal solution was dried over anhydrous MgSO₄, filtered and concentrated in vacuo. The crude mesylate was used in the subsequent alkylation step without further purification.

EXAMPLE 5

(2R)-Methyl-tert-butoxycarbonylamino-3-(4'-indol-1-ylbiphen-4-ylmethylsulfanyl)-propionate L-N-tert-Butoxycarbonyl cysteine methyl ester (3.0 g, 2.6 mL, 12.43 mmol) was added dropwise to a stirred suspension of mesylate (prepared according to the method in the previous step) (4.8 g, 12.43 mmol) and cesium carbonate (8.3 g, 25 mmol), in anhydrous DMF (100 mL) at room temperature. The reaction mixture was stirred at room temperature for 2-3 hrs (TLC control) and then poured into water (50 mL) and extracted with diethyl ether (3×100 mL). The combined extract was washed with water (2×30 mL), brine (3×30mL), dried over anhydrous MgSO₄, filtered and concentrated in vacuo. Purification of the product by flash column chromatography, using 30% ethyl acetate/hexane as eluent, afforded the title compound has a white solid (4.68 g, 75%). ¹H NMR (CDCl₃, 300 MHz): δ 7.69-7.82 (3H, m, Ar—H), 7.58 (5H, m, Ar—H), 7.42 (2H, d, J=8 Hz, , Ar—H), 7.38 (1H, d, J=3.5 Hz, Ar—H), 7.22 (2H, m, Ar—H), 6.72 (1H, d, J=3.5 Hz, Ar—H), 5.34 (1H, d, J=8 Hz, NH), 4.59 (1H, m, CHN), 3.80 (2H, s, PhCH2), 3.76 (3H, s, OMe), 2.97 (1H, dd, J=13, 5 Hz, CHHCHN), 2.86 (1H, dd, J=13, 5 Hz, CHHCHN), 1.47 (9H, s, CMe₃).

EXAMPLE 6

(2R)-tert-Butoxycarbonylamino-3-(4'-indol-1-ylbiphen-4-ylmethylsulfanyl)-propionic acid 1N Sodium hydroxide solution (2.14 mL, 2.14 mmol) was added dropwise to a stirred solution of (2R)-Methyl-tert-butoxycarbonylamino-3-(4'-indol-1-ylbiphen-4-ylmethylsulfanyl)-propionate (552 mg, 1.07 mmol) in tetrahydrofuran (15 mL) and methanol (3 mL). The clear reaction mixture was stirred at room temperature until the reaction was complete (TLC control), and then diluted with water (10 mL), and acidified to pH 3 with 2N hydrochloric acid. The reaction mixture was extracted with ethyl acetate (2×20 mL). The combined extract was washed with water, brine, dried over anhydrous MgSO₄, filtered and concentrated in vacuo. Purification of the product by flash column chromatography, using 5-10% methanol in methylene chloride as eluent, afforded the title compound has a white solid (486 mg, 90%), m.pt. 171-173° C. Rf: 0.35 (10% methanol in dichloromethane); ¹H NMR (DMSO-d6, 300 MHz): δ 7.86 (2H, d, J=8 Hz, Ar—H), 7.68 (6H, m, Ar—H), 7.61 (1H, d, J=8 Hz, , Ar—H), 7.43 (2H, d, J=8 Hz, Ar—H), 7.11-7.22 (2H, m, Ar—H), 6.80 (1H, br s, NH), 6.72 (1H, d, J=3.5 Hz, Ar—H), 4.06 (1H, m, CHN), 3.80 (2H, s, PhCH2), 2.86 (1H, dd, J=13, 5 Hz, CHHCHN), 2.72 (1H, dd, J=13, 8 Hz, CHHCHN), 1.40 (9H, s, CMe₃), ESI-LCMS e/z calcd for C₂₉H₃₀N₂O₄S: 502.632, found 503 (M+H)⁺, 525 (M+Na)⁺.

EXAMPLE 7

(2R)-tert-Butoxycarbonylamino-3-(4'-indol-1-ylbiphen-4-ylmethylsulfinyl)-propionic acid

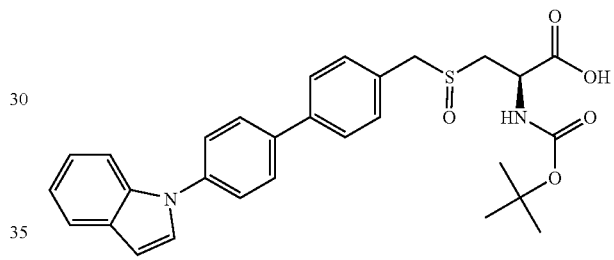

Sodium perborate tetrahydrate (151 mg, 0.95 mmol) was added as a solid to a stirred solution of (2R)-tert-Butoxycarbonylamino-3-(4'-indol-1-ylbiphen-4-ylmethylsulfanyl)-propionic acid (380 mg, 0.76 mmol) in acetic acid (10 mL) at 40° C. This solution was stirred at 40° C. for 2 hours (HPLC control) and then diluted with ethyl acetate (50 mL), washed with water, brine (2×), dried over anhydrous MgSO₄, filtered and concentrated in vacuo. Purification by trituration of the product with diethyl ether afforded the title compound as a 2:1 mix of diastereoisomers as an off-white solid (372 mg, 95%): mp. 169-170° C. Rf 0.65 (20% methanol in dichloromethane). ¹H NMR (DMSO-d6, 300 MHz): δ 7.88 (2H, d, J=8 Hz, Ar—H), 7.62-7.78 (7H, m, Ar—H), 7.44 (2H, d, J=8 Hz, Ar—H), 7.36 (1H, d, J=8 Hz, NH), 7.11-7.22 (2H, m, Ar—H), 6.72 (1H, d, J=3.5 Hz, Ar—H), 4.06-4.26 (3H, m, CHN+PhCH₂), 2.96-3.04 (2H, m, CH₂CHN), 1.39 (3H, s, CMe₃, minor isomer), 1.36 (6H, s, CMe₃, major isomer), ESI-LCMS e/z calcd for C₂₉H₃₀N₂O₅S: 518.631, found 519 (M+H)⁺, 541 (M+Na)⁺.

EXAMPLE 8

(2R)-Methyl-2-amino-3-[4'indol-1-yl-biphen-4-ylmethylsulfanyl]propionate

TMSI (1.56 mL, 10.63 mmol) was added dropwise to a stirred solution of (2R)-methyl-tert-butoxycarbonylamino-3-(4'-indol-1-ylbiphen-4-ylmethylsulfanyl)-propionate (4.47 g, 8.66 mmol) in anhydrous methylene chloride (50 mL). The reaction was stirred for 10 mins. and then poured into 1N sodium bicarbonate solution (50 mL), extracted with ethyl acetate (3×50 mL). The combined extract was washed with water, brine, dried over anhydrous MgSO$_4$, filtered and concentrated in vacuo. Purification of the product by flash column chromatography, using 5% methanol in methylene chloride as eluent, afforded the title compound as a yellow oil (3.43 g, 95%):. Rf=0.65 (10% methanol in dichloromethane). $^1$H NMR (DMSO-d6, 300 MHz): δ 7.86 (2H, d, J=8 Hz, Ar—H), 7.64-7.72 (6H, m, Ar—H), 7.61 (1H, d, J=8 Hz, , Ar—H), 7.42 (1H, d, J=8 Hz, Ar—H), 7.21 (1H, td, J=7, 2 Hz, Ar—H), 7.14 (1H, td, J=7, 2 Hz, Ar—H), 6.72 (1H, d, J=3.5 Hz, Ar—H), 3.80 (2H, s, PhCH$_2$), 3.62 (3H, s, OMe), 3.56 (1H, t, J=6.5 Hz, CHN), 2.68 (1H, dd, J=6.5, 3 Hz, CHHCHN), 2.63 (1H, dd, J=6.5, 3 Hz, CHHCHN), 2.04 (2H, br s, NH$_2$).

EXAMPLE 9

General Methods for the Synthesis 2-N-amido acids (N-acylation Plus Subsequent Ester Hydrolysis)

Method A:

To a solution of (2R)-methyl-2-amino-3-[4'indol-1-yl-biphen-4-ylmethylsulfanyl]-propionate (0.3 mmol) in a mixture of methylene chloride (5 mL) and dimethylformamide (1 mL) was added the required carboxylic acid (0.37 mmol), EDCI (85 mg, 0.43 mmol), HOBt (5 mg) and triethylamine (82 µL). The reaction mixture was stirred for 16 hours and then diluted with diethyl ether (25 mL), washed with water, brine (2×), dried over anhydrous MgSO$_4$, filtered and concentrated in vacuo to yield the crude amido-methyl ester compound.

2N Sodium hydroxide (0.5 mL) was added to a stirred solution of the amido methyl ester in a mixture of tetrahydrofuran (5 mL) and methanol (1 mL). The solution was stirred for 1 hour and then acidified to pH 3 with 2N hydrochloric acid. The reaction mixture was extracted with ethyl acetate (3×10 mL). The combined extract was washed with water, brine, dried over anhydrous MgSO$_4$, filtered and concentrated in vacuo. Purification of the product by flash column chromatography, using 5-20% methanol in methylene chloride as eluent, afforded the title compound.

Method B:

To a solution of (2R)-Methyl-2-Amino-3-[4'indol-1-yl-biphen-4-ylmethylsulfanyl]-propionate (0.3 mmol) in a 1,2-dichloroethane was added the required acid chloride, sulfonyl chloride, carbamoyl chloride or isocyanate (0.37 mmol). The reaction mixture was stirred for 4 hours and then diluted with diethyl ether (25 mL), washed with water, brine (2×), dried over anhydrous MgSO$_4$, filtered and concentrated in vacuo to yield the crude amido-methyl ester compounds.

2N Sodium hydroxide (0.5 mL) was added to a stirred solution of the amido methyl ester in a mixture of tetrahydrofuran (5 mL) and methanol (1 mL). The solution was stirred for 1 hour and then acidified to pH 3 with 2N hydrochloric acid. The reaction mixture was extracted with ethyl acetate (3×10 mL). The combined extract was washed with water, brine, dried over anhydrous MgSO$_4$, filtered and concentrated in vacuo. Purification of the product by flash column chromatography, using 5-20% methanol in methylene chloride as eluent, afforded the title compounds.

EXAMPLE 10

(2R)-3-(4'-Indol-1-ylbiphen-4-ylmethylsulfanyl)-2-[2-(3-nitrophenyl)acetylamino]-propionic acid (2R)-3-(4'-Indol-1-ylbiphen-4-ylmethylsulfanyl)-2-[2-(3-nitrophenyl)acetylamino]-propionic acid was prepared according to the method described in Example 9, Method A, using 3-nitrophenylacetic acid as the corresponding carboxylic acid. The title compound was isolated as a pale yellow solid: mp. 94° C. Rf=0.18 (10% methanol in dichloromethane). $^1$H NMR (DMSO-d6, 300 MHz) δ 8.46 (1H, d, J=8 Hz, NH), 8.21 (1H, t, J=2 Hz, Ar—H), 8.16 (1H, ddd, J=8, 2, 1 Hz, Ar—H), 7.84 (2H, d, J=8 Hz, Ar—H), 7.76 (1H, d, J=8 Hz, Ar—H), 7.58-7.69 (6H, m, Ar—H), 7.35 (2H, d, J=8 Hz, Ar—H), 7.21 (1H, td, J=7, 2 Hz, Ar—H), 7.14 (1H, td, J=7, 2 Hz, Ar—H), 6.72 (1H, dd, J=3, 1 Hz, Ar—H), 4.38 (1H, m, CHN), 3.72 (4H, m, PhCH$_2$CO+PhCH$_2$S), 2.89 (1H, dd, J=13, 5 Hz, CHHCHN, 2.71 (1H, dd, J=13, 8 Hz, CH HCHN); ESI-LCMS e/z calcd for C$_{32}$H$_{27}$N$_3$O$_5$S 565.647, found 566 (M+H)$^+$, 588 (M+Na)$^+$.

EXAMPLE 11

(2R)-3-(4'-Indol-1-ylbiphen-4-ylmethylsulfanyl)-2-phenylacetylamino-propionic acid

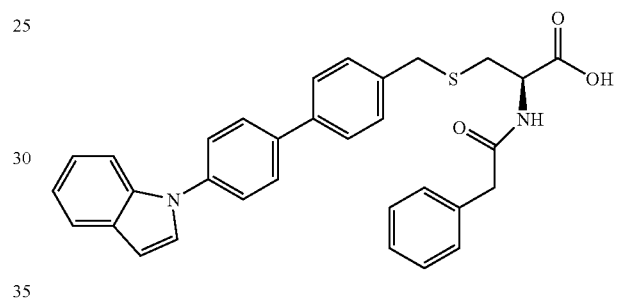

(2R)-3-(4'-Indol-1-ylbiphen-4-ylmethylsulfanyl)-2-phenylacetylamino-propionic acid was prepared according to the method described in Example 9, Method A, using phenylacetic acid as the corresponding carboxylic acid. The title compound was isolated as a pale pink solid: Rf=0.20 (10% methanol in dichloromethane). $^1$H NMR (DMSO-d6, 300 MHz) δ 8.40 (1H, d, J=8 Hz, NH), 7.86 (2H, d, J=8 Hz, Ar—H), 7.60-7.69 (7H, m, Ar—H), 7.38 (2H, d, J=8 Hz, Ar—H), 7.28 (4H, m, Ar—H), 7.12-7.25 (3H, m, Ar—H), 6.72 (1H, dd, J=3, 1 Hz, Ar—H), 4.41 (1H, m, CHN), 3.76 (2H, s, PhCH$_2$CO) 3.50 (2H, s, PhCH$_2$S), 2.86 (1H, dd, J=13, 5 Hz, CHHCHN, 2.73 (1H, dd, J=13, 8 Hz, CHHCHN); ESI-LCMS e/z calcd for C$_{32}$H$_{28}$N$_2$O$_3$S 520.650, found 521 (M+H)$^+$, 543 (M+Na)$^+$.

EXAMPLE 12

(2R)-3-(4'-Indol-1-ylbiphen-4-ylmethylsulfanyl)-2-methoxycarbonylamino-propionic acid (2R)-3-(4'-Indol-1-ylbiphen-4-ylmethylsulfanyl)-2-methoxycarbonylamino-propionic acid was prepared according to the method described in Example 9, Method B, using methyl chloro-formate as the corresponding acylating reagent. The title compound was isolated as a cream solid: mp. 81-82° C. Rf=0.45 (20% methanol in dichloromethane); $^1$H NMR (CDCl$_3$, 300 MHz): δ 7.58 (3H, m, Ar—H), 7.46 (5H, m, Ar—H), 7.26 (3H, m, Ar—H), 7.10 (2H, m, Ar—H), 6.72 (1H, s, Ar—H), 5.52 (1H, br s, NH), 4.32 (1H, m, CHN), 3.70

(2H, s, PhCH$_2$), 3.58 (3H, s, OMe), 2.88 (2H, s, CH$_2$CHN); ESI-LCMS e/z calcd for C$_{26}$H$_{24}$N$_2$O$_4$S: 460.552, found 461 (M+H)$^+$.

EXAMPLE 13

(2R)-3-(4'-Indol-1-ylbiphen-4-ylmethylsulfanyl)-2-isobutoxycarbonylamino-propionic acid

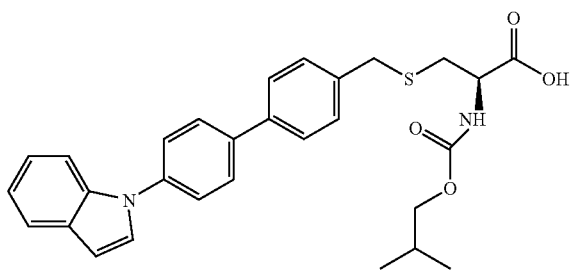

(2R)-3-(4'-Indol-1-ylbiphen-4-ylmethylsulfanyl)-2-isobutoxycarbonylamino-propionic acid was prepared according to the method described in Example 9, Method B, using isobutyl chloro-formate as the corresponding acylating reagent. The title compound was isolated as a beige solid: mp. 85-86° C. Rf=0.50 (20% methanol in dichloromethane); $^1$H NMR (CDCl$_3$, 300 MHz): δ 7.56 (3H, m, Ar—H), 7.52 (5H, m, Ar—H), 7.36 (3H, m, Ar—H), 7.17 (2H, m, Ar—H), 6.67 (1H, s, Ar—H), 5.62 (1H, br s, NH), 4.58 (1H, m, CHN), 3.86 (2H, m, OCH$_2$), 3.78 (2H, s, PhCH$_2$), 2.98 (2H, s, CH$_2$CHN) 1.92 (1H, m, CHMe$_2$), 0.91 (6H, d, J=6.5 Hz, CHMe$_2$); ESI-LCMS e/z calcd for C$_{29}$H$_{30}$N$_2$O$_4$S: 502.632, found 503 (M+H)$^+$.

EXAMPLE 14

(2R)-3-(4'-Indol-1-ylbiphen-4-ylmethylsulfanyl)-2-[(morpholine-4-carbonyl)-amino]-propionic acid (2R)-3-(4'-Indol-1-ylbiphen-4-ylmethylsulfanyl)-2-[(morpholine-4-carbonyl)-amino]-propionic acid was prepared according to the method described in Example 9, Method B, using 4-morpholinylcarbonyl chloride as the corresponding acylating reagent. The title compound was isolated as a beige solid: mp. 195° C. (dec.): Rf=0.30 (20% methanol in dichloromethane); $^1$H NMR (DMSO-d6, 300 MHz): δ 7.82 (3H, d, J=8 Hz, Ar—H), 7.60-7.69 (7H, m, Ar—H, NH), 7.42 (2H, d, J=8 Hz, Ar—H), 7.19 (1H, td, J=7, 2 Hz, Ar—H), 7.12 (1H, td, J=7, 2 Hz, Ar—H), 6.71 (1H, d, J=3 Hz, Ar—H), 4.00 (1H, m, CHN), 3.76 (2H, d, J=3.5 Hz, PhCH$_2$S), 3.56 (4H, m, CH$_2$OCH$_2$), 3.26 (4H, m, CH$_2$NCH$_2$), 2.91 (1H, dd, J=13, 5 Hz, CHHCHN); 2.79 (1H, dd, J=13, 8 Hz, CHHCHN); ESI-LCMS e/z calcd for C$_{29}$H$_{29}$N$_3$O$_4$S 515.631, found 516 (M+H)$^+$.

EXAMPLE 15

(2R)-2-(3,3-Dimethylureido)-3-(4'-indol-1-ylbiphen-4-ylmethylsulfanyl)-propionic acid (2R)-2-(3,3-Dimethylureido)-3-(4'-indol-1-ylbiphen-4-ylmethylsulfanyl)-propionic acid was prepared according to the method described in Example 9, Method B, using N,N-dimethyl-carbamoyl chloride as the corresponding acylating reagent. The title compound was isolated as a beige solid: mp: Rf=0.40 (15% methanol in dichloromethane); $^1$H NMR (CDCl$_3$, 300 MHz): δ 7.66 (2H, m, Ar—H), 7.48-7.62 (6H, m, Ar—H), 7.36 (3H, m, Ar—H), 7.17 (2H, m, Ar—H), 6.68 (1H, s, Ar—H), 5.42 (1H, br s, NH), 4.50 (1H, m, CHN), 3.80 (2H, s, PhCH$_2$), 3.05 (2H, s, CH$_2$CHN), 2.89 (6H, s, NMe$_2$); ESI-LCMS e/z calcd for C$_{27}$H$_{27}$N$_3$O$_3$S: 473.594, found 475 (M+H)$^+$.

EXAMPLE 16

(2R)-2-Benzyloxycarbonylamino-3-(4'-Indol-1-ylbiphen-4-ylmethylsulfanyl-propionic acid (2R)-2-Benzyloxycarbonylamino-3-(4'-Indol-1-ylbiphen-4-ylmethylsulfanyl-propionic acid was prepared according to the method described in Example 9, Method B, using benzylchloroformate as the corresponding acylating reagent. The title compound was isolated as a pale pink solid: Rf=0.50 (15% methanol in dichloromethane); $^1$H NMR (CDCl$_3$, 300 MHz): δ 7.70 (2H, d, J=8 Hz, Ar—H), 7.48-7.62 (6H, m, Ar—H), 7.17-7.36 (10H, m, Ar—H), 6.67 (1H, d, J=3 Hz, Ar—H), 5.80 (1H, br s, NH), 5.16 (2H, m, PhCH$_2$O), 4.60 (1H, m, CHN), 3.76 (2H, s, PhCH$_2$), 2.95 (2H, s, CH$_2$CHN); ESI-LCMS e/z calcd for C$_{32}$H$_{28}$N$_2$O$_4$S: 536.649, found 537 (M+H)$^+$.

EXAMPLE 17

(2R)-3-(4'-Indol-1-ylbiphen-4-ylmethylsulfinyl)-2-[2-(3-nitrophenyl)acetylamino]-propionic acid

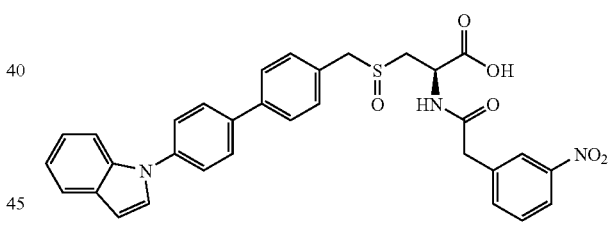

Sodium perborate tetrahydrate (97 mg, 0.63 mmol) was added as a solid to a stirred solution of (2R)-3-(4'-Indol-1-ylbiphen-4-ylmethylsulfanyl)-2-[2-(3-nitrophenyl)-acetylamino]-propionic acid (330 mg, 0.58 mmol) in acetic acid (10 mL) at 40° C. This solution was stirred at 40° C. for 2 hours (HPLC control) and then diluted with ethyl acetate (50 mL), washed with water, brine (2×), dried over anhydrous MgSO$_4$, filtered and concentrated in vacuo. Purification by trituration of the product with diethyl ether afforded the title compound as a light brown solid (206 mg, 61%): mp. 197-198° C. Rf 0.15 (15% methanol in dichloromethane): $^1$H NMR (DMSO-d6, 300 MHz) δ 8.46 (1H, d, J=8 Hz, NH), 8.18 (1H, t, J=2 Hz, Ar—H), 8.08 (1H, ddd, J=8, 2, 1 Hz, Ar—H), 7.87 (2H, d, J=8 Hz, Ar—H), 7.72 (2H, d, J=8 Hz, Ar—H), 7.54-7.69 (7H, m, Ar—H), 7.35 (2H, d, J=8 Hz, Ar—H), 7.21 (1H, td, J=7, 2 Hz, Ar—H), 7.14 (1H, td, J=7, 2 Hz, Ar—H), 6.71 (1H, d, J=3 Hz, Ar—H), 4.36 (1H, m, CHN), 4.20 (1H, d, J=13 Hz, PhCHHS), 3.84 (1H, d, J=13 Hz, PhCHHS), 3.66 (2H, m, PhCH$_2$CO), 3.11 (1H, dd, J=13, 5

Hz, CHHCHN), 2.99 (1H, dd, J=13, 8 Hz, CHHCHN); ESI-LCMS e/z calcd for $C_{32}H_{27}N_3O_6S$ 581.646, found 582 $(M+H)^+$, 604 $(M+Na)^+$.

EXAMPLE 18

(2R)-3-(4'-Indol-1-ylbiphen-4-ylmethylsulfinyl)-2-phenylacetylamino-propionic acid Sodium perborate tetrahydrate (97 mg, 0.63 mmol) was added as a solid to a stirred solution of (2R)-3-(4'-indol-1-ylbiphen-4-ylmethylsulfanyl)-2-phenylacetylamino-propionic acid (300 mg, 0.58 mmol) in acetic acid (10 mL) at 40° C. This solution was stirred at 40° C. for 2 hours (HPLC control) and then diluted with ethyl acetate (50 mL), washed with water, brine (2×), dried over anhydrous $MgSO_4$, filtered and concentrated in vacuo. Purification of the product by flash column chromatography, using 15% methanol in dichloromethane as eluent, afforded the title compound has an off-white solid (261 mg g, 84%) as a 1:1 mixture of diasereomers; $^1H$ NMR (DMSO-d6, 300 MHz) δ 12.98 (1H, s, COOH), 8.75 and 8.80 (both 0.5H, d, J=8 Hz, NH), 8.40 (1H, d, J=8 Hz, NH), 7.84 (2H, m, Ar—H), 7.60-7.78 (7H, m, Ar—H), 7.44 and 7.39 (both 1H, d, J=8 Hz, Ar—H), 7.12-7.28 (7H, m, Ar—H), 6.72 (1H, d, J=3 Hz, Ar—H), 4.68 and 4.48 (both 0.5H, m, CHN), 4.16 (2H, m, PhCH$_2$CO) 3.52 and 3.32 (both 1H, s, PhCH$_2$S), 3.09 (1H, m, CHHCHN), 2.96 (1H, m, CHHCHN); ESI-LCMS e/z calcd for $C_{32}H_{28}N_2O_4S$ 536.649, found 537 $(M+H)^+$.

EXAMPLE 19

4'-Dibenzofuran-4-yl-biphenyl-4-carbaldehyde

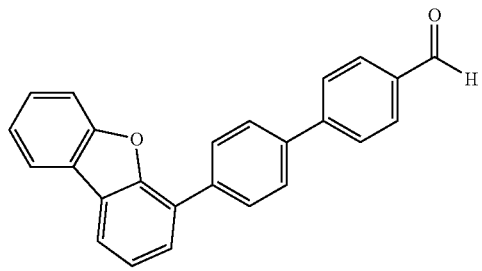

A solution of dibenzofuran-4-boronic acid (1.0 g, 4.7 mmol) in ethanol (10 mL) was added to a stirred solution of 1-bromo-4-iodobenzene (1.33 g, 4.7 mmol) and tetrakis-(triphenylphosphine)palladium(0) (271 mg, 5 mol %) in toluene (40 mL). 2N sodium carbonate (4.7 mL, 9.4 mmol) was added and the reaction was heated to 90° C. (oil bath temp.) for 2-3 hrs until complete (TLC control).

The reaction mixture was cooled to room temperature and partitioned between water and diethyl ether. The phases were separated, the aqueous phase being further extracted with diethyl ether (2×20 mL). The combined extract was washed with water and brine. The ethereal solution was dried over anhydrous $MgSO_4$, filtered and concentrated in vacuo to yield 4-(4-bromophenyl)-dibenzofuran as a yellow solid, which was used immediately without further purification.

A solution of 4-formylphenylboronic acid (0.9 g, 5.64 mmol) in ethanol (10 mL) was added to a stirred solution of the crude 4-(4-bromophenyl)-dibenzofuran (from the previous reaction) in toluene (40 mL). tetrakis-(Triphenylphosphine)palladium(0) (270 mg, 5 mol %) and 2N sodium carbonate (4.7 mL, 9.4 mmol) were added and the reaction was heated to 100° C. (oil bath temp.) for 2-3 hrs until complete (TLC control). The reaction mixture was cooled to room temperature and partitioned between water and ethyl acetate. The phases were separated, the aqueous phase being further extracted with ethyl acetate (2×20 mL). The combined extract was washed with 0.5 N hydrochloric acid, water and brine and then dried over anhydrous $MgSO_4$, filtered and concentrated in vacuo. Purification of the product by flash column chromatography, using 10-20% ethyl acetate in hexane as eluent, afforded the title compound has a white solid (1.51 g).

EXAMPLE 20

(4'-Dibenzofuran-4-yl-biphenyl-4-yl)methanol

Sodium borohydride (322 mg, 8.4 mmol) was added portion-wise to a stirred solution of aldehyde (prepared in the previous step) (1.48 g, 4.2 mmol) in a mixture of anhydrous THF and ethanol (1:2; 50 mL) at room temperature. The reaction mixture was stirred for 5-10 minutes at room temperature (TLC control), poured into water (50 mL) and acidified to pH 4 with 2N hydrochloric acid, and then extracted with diethyl ether (3×30 mL). The combined extract was washed with 0.5 N hydrochloric acid (2×10 mL), water and finally brine. The ethereal solution was dried over anhydrous $MgSO_4$, filtered and concentrated in vacuo. Purification of the product by flash column chromatography, using 30% ethyl acetate/hexane as eluent, afforded the title compound has a white solid (1.40 g).

EXAMPLE 21

Methanesulfonic acid, 4'-dibenzofuran-4-yl-biphenyl-4-yl-lmethyl ester

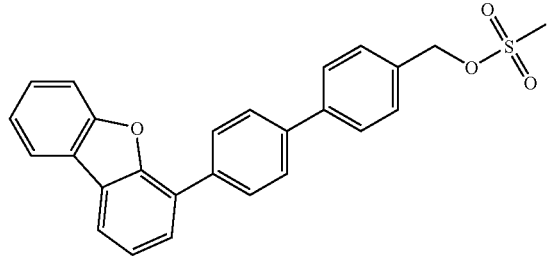

Methanesulfonyl chloride (490 mg, 330 μL, 4.3 mmol) was added dropwise to a cooled (0° C.) solution of alcohol (prepared in the previous step) (1.38 g, 3.9 mmol) and triethylamine (800 mg, 1.1 mL, 7.9 mmol) in anhydrous methylene chloride (50 mL). The clear reaction mixture was stirred at 0° C. for 2-4 hrs (TLC control), then poured into water (50 mL), and extracted with diethyl ether (3×30 mL). The combined extract was washed with 0.5 N hydrochloric acid (2×10 mL), water and finally brine. The ethereal solution was dried over anhydrous $MgSO_4$, filtered and concentrated in vacuo. The crude mesylate was used in the subsequent alkylation step without further purification.

EXAMPLE 22

(2R)-Methyl-2-tert-butoxycarbonylamino-3-(4'-dibenzofuran-4-yl-biphenyl-4-ylmethylsulfanyl)-propionate L-N-tert-Butoxycarbonyl cysteine methyl ester (940 mg, 4.0 mmol) was added dropwise to a stirred suspension of mesylate (prepared in the previous step) (1.65 g, 3.8 mmol) and cesium carbonate (2.6 g, 8.0 mmol), in anhydrous DMF (50 mL) at room temperature. The reaction mixture was stirred at room temperature for 2-3 hrs (TLC control) and then poured into water (50 mL) and extracted with diethyl ether (3×50 mL). The combined extract was washed with water (2×30 mL), brine (3×30 mL), dried over anhydrous $MgSO_4$, filtered and concentrated in vacuo. Purification of the product by flash column chromatography, using 20-40% ethyl acetate/hexane as eluent, afforded the title compound has a pale yellow solid (1.96 g, 91%): Rf: 0.4 (30% ethyl acetate in heptane).

EXAMPLE 23

(2R)-2-tert-Butoxycarbonyl-3-(4'-dibenzofuran-4-yl-biphenyl-4-ylmethylsulfanyl)-propionic acid 2N Sodium hydroxide solution (1.32 mL, 2.64 mmol) was added dropwise to a stirred solution of (2R)-methyl-2-tert-butoxycarbonylamino-3-(4'-dibenzofuran-4-yl-biphenyl-4-ylmethylsulfanyl)propionate (500 mg, 0.88 mmol) in tetrahydrofuran (15 mL) and methanol (3 mL). The clear reaction mixture was stirred at room temperature until the reaction was complete (TLC control), and then diluted with water (10 mL), and acidified to pH 3 with 2N hydrochloric acid. The reaction mixture was extracted with ethyl acetate (2×20 mL). The combined extract was washed with water, brine, dried over anhydrous $MgSO_4$, filtered and concentrated in vacuo. Purification of the product by flash column chromatography, using 5-10% methanol in methylene chloride as eluent, afforded the title compound has a white solid (420 mg, 87%), m.pt. 205-206° C.; Rf: 0.40 (10% methanol in dichloromethane); $^1$H NMR (MeOH-d4): δ 7.90 (4H, m, Ar—H), 7.67 (2H, d, J=9 Hz, Ar—H), 7.56 (2H, d, J=9 Hz, Ar—H), 7.53 (2H, d, J=8 Hz, Ar—H), 7.29-7.41 (5H, m, Ar—H), 4.34 (1H, m, CHN), 3.87 (2H, s, PhCH$_2$S), 2.95 (1H, dd, J=15, 5 Hz, CHHCHN), 2.86 (1H, dd, J=15, 7 Hz, CHHCHN), 1.42 (9H, s, CMe$_3$); ESI-LCMS e/z calcd for $C_{33}H_{31}NO_5S$ 553.676, found 554 (M+H)$^+$, 576 (M+Na)$^+$.

EXAMPLE 24

(2R)-2-tert-Butoxycarbonyl-3-(4'-dibenzofuran-4-yl-biphenyl-4-ylmethylsulfinyl)-propionic acid Sodium perborate tetrahydrate (42 mg, 0.27 mmol) was added as a solid to a stirred solution of (2R)-2-tert-Butoxycarbonyl-3-(4'-dibenzofuran-4-yl-biphenyl-4-ylmethylsulfanyl)-propionic acid (150 mg, 0.27 mmol), in acetic acid (5 mL) at 40° C. This solution was stirred at 40° C. for 1 hour (HPLC control) and then diluted with ethyl acetate (50 mL), washed with water, brine (2×), dried over anhydrous $MgSO_4$, filtered and concentrated in vacuo. Purification by trituration of the product with diethyl ether afforded the title compound as a 1:1 mix of diastereoisomers as a white solid (144 mg, 93%): Rf 0.25 (20% methanol in dichloromethane). $^1$H NMR (DMSO-d6, 300 MHz) δ 8.19 (1H, d, J=8 Hz, Ar—H), 8.15 (1H, dd, J=8, 1 Hz, Ar—H), 8.01 (2H, d, J=9 Hz, Ar—H), 7.87 (2H, d, J=9 Hz, Ar—H), 7.78 (4H, m, Ar—H), 7.52 (2H, m, Ar—H), 7.44 (4H, m, Ar—H, NH), 4.39 (1H, m, CHN), 4.05-4.27 (2H, m, PhCH$_2$), 3.04 (1H, m, CHHCHN), 2.92 (1H, m, CHHCHN), 1.39 and 1.37 (both 4.5H, s, CMe$_3$ diastereomers); ESI-LCMS e/z calcd for $C_{33}H_{31}NO_6S$ 569.675, found 570 (M+H)$^+$, 592 (M+Na)$^+$.

EXAMPLE 25

(2R)-2-tert-Butoxycarbonyl-3-(4'-dibenzofuran-4-yl-biphenyl-4-ylmethylsulfonyl)-propionic acid Sodium perborate tetrahydrate (105 mg, 0.68 mmol) was added as a solid to a stirred solution of (2R)-2-tert-Butoxycarbonyl-3-(4'-dibenzofuran-4-yl-biphenyl-4-ylmethyl-sulfanyl)-propionic acid (150 mg, 0.27 mmol), in acetic acid (10 mL) at 50° C. This solution was stirred at 40° C. for 2 hours (HPLC control) and then diluted with ethyl acetate (50 mL), washed with water, brine (2×), dried over anhydrous $MgSO_4$, filtered and concentrated in vacuo. Purification by trituration of the product with diethyl ether afforded the title compound as a white solid (138 mg, 87%): Rf 0.5 (20% methanol in dichloromethane). $^1$H NMR (MeOH-d4, 300 MHz): δ 7.90 (4H, m, Ar—H), 7.70 (4H, m, Ar—H), 7.53 (2H, m, Ar—H), 7.29-7.49 (5H, m, Ar—H), 4.62 (1H, m, CHN) 4.41 (2H, s, PhCH$_2$S), 3.42 (2H, m, CH$_2$CHN), 1.46 (9H, s, CMe$_3$); ESI-LCMS e/z calcd for $C_{33}H_{31}NO_7S$ 585.674, found 586 (M+H)$^+$, 608 (M+Na)$^+$.

EXAMPLE 26

(2R)-Methyl-3-(3-bromobenzylsulfanyl)-2-tert-butoxycarbonylamino-propionate

L-N-tert-Butoxycarbonyl cysteine methyl ester (1.0 g, 4.25 mmol) was added dropwise to a stirred suspension of 3-bromobenzyl chloride (1.31 g, 6.3 mmol), cesium carbonate (2.77 g, 8.50 mmol) and tetra-n-butyl ammonium iodide (10 mg) in anhydrous DMF (25 mL) at room temperature. The reaction mixture was stirred at room temperature for 2-3 hrs (TLC control) and then poured into water (50 mL) and extracted with diethyl ether (3×50 mL). The combined extract was washed with water (2×30 mL), brine (3×30 mL), dried over anhydrous $MgSO_4$, filtered and concentrated in vacuo. Purification of the product by flash column chromatography, using 20-40% ethyl acetate/hexane as eluent, afforded the title compound has a pale yellow oil (1.54 g, 90%): Rf: 0.4 (30% ethyl acetate in heptane); $^1$H NMR (CDCl$_3$, 300 MHz): δ 7.48 (1H, s, Ar—H), 7.38 (1H, d, J=8 Hz, Ar—H), 7.40 (2H, m, Ar—H), 5.30 (1H, d, J=8 Hz, NH), 4.56 (1H, m, CHN), 3.78 (3H, s, OMe), 3.71 (2H, s, PhCH$_2$S), 2.89 (1H, dd, J=13, 5 Hz, CHHCHN), 2.81 (1H, dd, J=13, 5 Hz, CHHCHN), 1.49 (9H, s, CMe$_3$).

EXAMPLE 27

(2R)-Methyl-3-(2-bromobenzylsulfanyl)-2-tert-butoxycarbonylamino-propionate

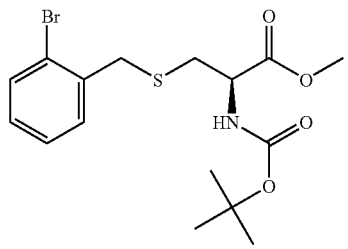

L-N-tert-Butoxycarbonyl cysteine methyl ester (1.0 g, 4.25 mmol) was added dropwise to a stirred suspension of 2-bromobenzyl bromide (1.06 g, 4.25 mmol) and cesium carbonate (2.77 g, 8.50 mmol) in anhydrous DMF (25 mL) at room temperature. The reaction mixture was stirred at room temperature for 2-3 hrs (TLC control) and then poured into water (50 mL) and extracted with diethyl ether (3×50 mL). The combined extract was washed with water (2×30 mL), brine (3×30 mL), dried over anhydrous MgSO$_4$, filtered and concentrated in vacuo. Purification of the product by flash column chromatography, using 20-40% ethyl acetate/hexane as eluent, afforded the title compound has a pale yellow oil (1.12 g, 66%): Rf: 0.4 (30% ethyl acetate in heptane); $^1$H NMR (CDCl$_3$, 300 MHz): δ 7.58 (1H, d, J=8 Hz, Ar—H), 7.38 (1H, d, J=8 Hz, Ar—H), 7.32 (1H, t, J=8 Hz, Ar—H), 7.12 (1H, t, J=8 Hz, Ar—H), 5.38 (1H, d, J=8 Hz, NH), 4.58 (1H, m, CHN), 3.86 (3H, s, OMe), 3.77 (2H, s, PhCH$_2$S), 2.97 (1H, dd, J=13, 5 Hz, CHHCHN), 2.89 (1H, dd, J=13, 5 Hz, CHHCHN), 1.46 (9H, s, CMe$_3$)

EXAMPLE 28

(2R)-Methyl-3-(4-bromo-2-fluorobenzylsulfanyl)-2-tert-butoxycarbonylamino-propionate L-N-tert-Butoxycarbonyl cysteine methyl ester (1.0 g, 4.25 mmol) was added dropwise to a stirred suspension of 2-fluoro-4-bromobenzyl bromide (1.14 g, 4.25 mmol) and cesium carbonate (2.77 g, 8.50 mmol) in anhydrous DMF (25 mL) at room temperature. The reaction mixture was stirred at room temperature for 2-3 hrs (TLC control) and then poured into water (50 mL) and extracted with diethyl ether (3×50 mL). The combined extract was washed with water (2×30 mL), brine (3×30 mL), dried over anhydrous MgSO$_4$, filtered and concentrated in vacuo. Purification of the product by flash column chromatography, using 20-40% ethyl acetate/hexane as eluent, afforded the title compound has a pale yellow oil (1.12 g, 66%): Rf: 0.25 (30% ethyl acetate in heptane); $^1$H NMR (CDCl$_3$, 300 MHz): δ 7.42 (4H, m, Ar—H), 5.32 (1H, d, J=8 Hz, NH), 4.58 (1H, m, CHN), 3.77 (3H, s, OMe), 3.72 (2H, s, PhCH$_2$S), 2.94 (1H, dd, J=13, 5 Hz, CHHCHN), 2.86 (1H, dd, J=13, 5 Hz, CHHCHN), 1.48 (9H, s, CMe$_3$).

EXAMPLE 29

Suzuki Coupling: General Methods

General Method A:

A solution of 4-(dibenzofuran-4-yl)phenyl boronic acid (5.0 mmol) in methanol (10 mL) was added to a stirred solution of the required aryl bromide (4.0 mmol) and tetrakis-(triphenylphosphine)palladium(0) (5 mol %) in toluene (40 mL). 2N sodium carbonate (4 mL, 8.0 mmol) was added and then the reaction was heated to 80° C. (oil bath temp.) for 2-3 hrs until complete (TLC control). The reaction mixture was cooled to room temperature and partitioned between water (30 mL) and diethyl ether (50 mL). The phases were separated, the aqueous phase being further extracted with diethyl ether (2×30 mL). The combined organic extract was washed with water and brine, dried over anhydrous MgSO$_4$, filtered and concentrated in vacuo to yield the coupled product. Purification of the product by flash column chromatography, using 20-50% ethyl acetate/hexane as eluent, afforded the corresponding methyl ester of the title compound.

2N Sodium hydroxide (1.0 mL) was added to a stirred solution of the amido methyl ester in a mixture of tetrahydrofuran (10 mL) and methanol (2 mL). The solution was stirred for 1 hour and then acidified to pH 3 with 2N hydrochloric acid. The reaction mixture was extracted with ethyl acetate (3×20 mL). The combined extract was washed with water, brine, dried over anhydrous MgSO$_4$, filtered and concentrated in vacuo. Purification of the product by flash column chromatography, using 5-20% methanol in methylene chloride as eluent, afforded the title compound.

General Method B:

A suspension of the required aryl bromide (1 mmol), 4-(dibenzofuran-4-yl)phenyl boronic acid (1.2 mmol), cesium carbonate (3.0 mmol), [1.1'-bis-(diphenylphodphino)-ferrocene]dichloropalladium(II), complex with dichloromethane (3 mol %) and 1.1'-bis-(diphenylphodphino)ferrocene (3 mol %) in anhydrous dioxane (20 mL) was heated at reflux for 4-6 hrs (TLC control). Upon reaction completion, the reaction mixture was cooled to room temperature, poured into water (25 mL) and extracted with diethyl ether (3×30 mL). The combined organic extract was washed with water and brine, dried over anhydrous MgSO$_4$, filtered and concentrated in vacuo to yield the coupled product. Purification of the product by flash column chromatography, using 20-50% ethyl acetate/hexane as eluent, afforded the corresponding methyl ester of the title compound.

2N Sodium hydroxide (1.0 mL) was added to a stirred solution of the amido methyl ester in a mixture of tetrahydrofuran (10 mL) and methanol (2 mL). The solution was stirred for 1 hour and then acidified to pH 3 with 2N hydrochloric acid. The reaction mixture was extracted with ethyl acetate (3×20 mL). The combined extract was washed with water, brine, dried over anhydrous MgSO$_4$, filtered and concentrated in vacuo. Purification of the product by flash column chromatography, using 5-20% methanol in methylene chloride as eluent, afforded the title compound.

EXAMPLE 30

(2R)-2-tert-Butoxycarbonyl-3-(4'-dibenzofuran-4-yl-biphenyl-3-ylmethylsulfanyl)-propionic acid (2R)-2-tert-Butoxycarbonyl-3-(4'-dibenzofuran-4-yl-biphenyl-3-ylmethylsulfanyl)-propionic acid was prepared according to the method described in Suzuki Coupling Method A, using (2R)-methyl-3-(3-bromobenzylsulfanyl)-2-tert-butoxycarbonylamino-propionate as the required aryl bromide. The title compound was isolated as a white solid: Rf: 0.30 (10% methanol in dichloromethane); $^1$H NMR (MeOH-d4, 300 MHz): δ 7.93 (4H, m, Ar—H), 7.72 (2H, d, J=9 Hz, Ar—H), 7.58 (4H, m, Ar—H), 7.29-7.41 (5H, m, Ar—H), 4.39 (1H, m, CHN), 3.80 (2H, s, PhCH$_2$S), 2.97 (1H, dd, J=15, 5 Hz, CHHCHN), 2.88 (1H, dd, J=15, 7 Hz, CH HCHN), 1.40 (9H, s, CMe₃); ESI-LCMS e/z calcd for C₃₃H₃₁NO₅S 553.676, found 576 (M+Na)⁺.

EXAMPLE 31

(2R)-2-tert-Butoxycarbonyl-3-(4'-dibenzofuran-4-yl-biphenyl-2-ylmethylsulfanyl)-propionic acid

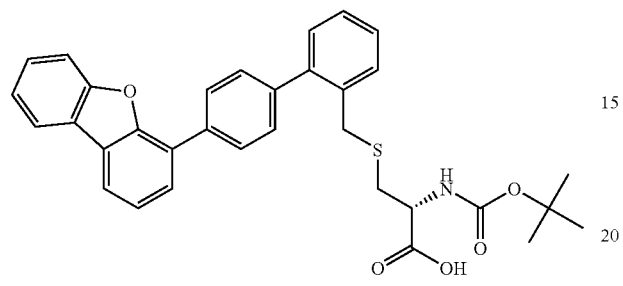

(2R)-2-tert-Butoxycarbonyl-3-(4'-dibenzofuran-4-yl-biphenyl-2-ylmethylsulfanyl)-propionic acid was prepared according to the method described in Suzuki Coupling Method A, using (2R)-methyl-3-(2-bromobenzylsulfanyl)-2-tert-butoxycarbonylamino-propionate as the required aryl bromide. The title compound was isolated as a white solid: Rf: 0.30 (10% methanol in dichloromethane); ¹H NMR (CDCl₃, 300 MHz): δ 7.97 (4H, q. J=9 Hz, Ar—H), 7.78 (4H, m, Ar—H), 7.42 (2H, m, Ar—H), 7.26-7.41 (5H, m, Ar—H), 4.41 (1H, m, CHN), 3.80 (2H, s, PhCH₂S), 2.95 (1H, dd, J=15, 5 Hz, CHHCHN), 2.84 (1H, dd, J=15, 7 Hz, CH HCHN), 1.38 (9H, s, CMe₃); ESI-LCMS e/z calcd for C₃₃H₃₁NO₅S 553.676, found 576 (M+Na)⁺.

EXAMPLE 32

(2R)-2-tert-Butoxycarbonyl-3-(4'-dibenzofuran-4-yl-3-fluorobiphenyl-4-ylmethyl-sulfanyl)-propionic acid (2R)-2-tert-Butoxycarbonyl-3-(4'-dibenzofuran-4-yl-3-fluorobiphenyl-4-ylmethyl-sulfanyl)-propionic acid was prepared according to the method described in Suzuki Coupling Method A, using (2R)-methyl-3-(4-bromo-2-fluorobenzyl-sulfanyl)-2-tert-butoxycarbonylamino-propionate as the required aryl bromide. The title compound was isolated as a white solid: Rf: 0.30 (10% methanol in dichloromethane); ¹H NMR (CDCl₃, 300 MHz): δ 7.83 (4H, m, Ar—H), 7.78 (2H, m, Ar—H), 7.64 (2H, m, Ar—H), 7.26-7.38 (7H, m, Ar—H), 4.43 (1H, m, CHN), 3.78 (2H, s, PhCH₂S), 3.02 (1H, dd, J=15, 5 Hz, CHHCHN), 2.91 (1H, dd, J=15, 7 Hz, CH HCHN), 1.39 (9H, s, CMe₃); ESI-LCMS e/z calcd for C₃₃H₃₀FNO₅S 571.666, found 594 (M+Na)⁺.

EXAMPLE 33

(2R)-Methyl-2-amino-3-(4'-dibenzofuran-4-ylbipheny-4-ylmethylsulfanyl)-propionate TMS-I (870 mg, 0.63 mL, 4.35 mmol) was added dropwise to a stirred solution of (2R)-methyl-2-tert-butoxycarbonylamino-3-(4'-dibenzofuran-4-yl-biphenyl-4-ylmethyl-sulfanyl)-propionate (2.24 g, 3.96 mmol) in anhydrous methylene chloride (50 mL). The reaction mixture was stirred at room temperature for 20-30 mins (TLC control), and then diluted with water (50 mL). Saturated sodium bicarbonate solution was added to adjust the solution to pH 8-9. The reaction mixture was extracted with diethyl ether (2×50 mL). The combined extract was washed with water, brine, dried over anhydrous MgSO₄, filtered and concentrated in vacuo. Purification of the product by flash column chromatography, using 5% methanol in methylene chloride as eluent, afforded the title compound has a pale yellow solid (1.76 g, 95%); Rf: 0.20 (5% methanol in dichloromethane); ¹H NMR (CDCl₃, 300 MHz): δ 8.00 (3H, d, J=8 Hz, Ar—H), 7.94 (1H, d, J=8 Hz, Ar—H), 7.76 (2H, d, J=9 Hz, Ar—H), 7.64 (4H, m, Ar—H), 7.34-7.51 (5H, m, Ar—H), 3.81 (2H, s, PhCH₂S), 3.75 (3H, s, OMe), 3.67 (1H, m CHN), 2.91 (1H, dd, J=15, 5 Hz, CHHCHN), 2.86 (1H, dd, J=15, 8 Hz, CHHCHN), 1.91 (2H, s, NH₂); ESI-LCMS e/z calcd for C₂₉H₂₅NO₃S 467.586, found 468 (M+H)⁺.

EXAMPLE 34

(2R)-2-Amino-3-(4'-dibenzofuran-4-ylbipheny-4-ylmethylsulfanyl)-propionic acid

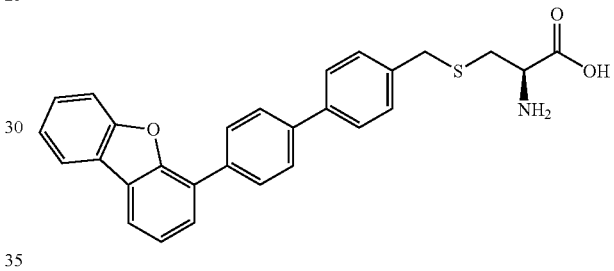

2N Sodium hydroxide (0.5 mL) was added to a stirred solution of the amino methyl ester, (2R)-Methyl-2-Amino-3-(4'-dibenzofuran-4-ylbipheny-4-ylmethylsulfanyl)-propionate (100 mg) in a mixture of tetrahydrofuran (5 mL) and methanol (1 mL). The solution was stirred for 1 hour and then acidified to pH 3 with 2N hydrochloric acid. The reaction mixture was extracted with ethyl acetate (3×10 mL). The combined extract was washed with water, brine, dried over anhydrous MgSO₄, filtered and concentrated in vacuo. Purification of the product by flash column chromatography, using 25% methanol in methylene chloride as eluent, afforded the title compound as a cream solid (83 mg, 86%); Rf: 0.10 (25% methanol in dichloromethane); ¹H NMR (DMSO-d6, 300 MHz): δ 11.20 (3H, br s, NH, OH), 7.94 (1H, d, J=9 Hz, Ar—H), 7.91 (1H, d, J=8 Hz, Ar—H), 7.86 (2H, d, J=9 Hz, Ar—H), 7.67 (2H, d, J=9 Hz, Ar—H), 7.48-7.57 (4H, m, Ar—H), 7.21-7.39 (5H, m, Ar—H), 4.02 (1H, dd, J=8, 5 Hz, CHN), 3.74 (2H, s, PhCH₂S), 2.94 (1H, dd, J=16, 5 Hz, C HHCHN), 2.86 (1H, dd, J=16, 8 Hz, CHHCHN); ESI-LCMS e/z calcd for C₂₈H₂₃NO₃S 453.560, found 454 (M+H)⁺.

EXAMPLE 35

General Procedure for the Formation of N-Acylated Acids: (N-Acylation and Subsequent Ester Hydrolysis)

Method A:

To a solution of (2R)-Methyl-2-amino-3-(4'-dibenzofuran-4-ylbipheny-4-ylmethyl-sulfanyl)-propionate (140 mg, 0.296 mmol) in a mixture of methylene chloride (5 mL) and dimethylformamide (1 mL) was added the carboxylic acid (0.37 mmol), EDCI (85 mg, 0.43 mmol), HOBt (5 mg) and triethylamine (82 µL). The reaction mixture was stirred for 16 hours and then diluted with diethyl ether (25 mL), washed with water, brine (2×), dried over anhydrous MgSO$_4$, filtered and concentrated in vacuo to yield the crude amido-methyl ester compound.

2N Sodium hydroxide (0.5 mL) was added to a stirred solution of the amido methyl ester in a mixture of tetrahydrofuran (5 mL) and methanol (1 mL). The solution was stirred for 1 hour and then acidified to pH 3 with 2N hydrochloric acid. The reaction mixture was extracted with ethyl acetate (3×10 mL). The combined extract was washed with water, brine, dried over anhydrous MgSO$_4$, filtered and concentrated in vacuo. Purification of the product by flash column chromatography, using 5-20% methanol in methylene chloride as eluent, afforded the title compound.

Method B:

To a solution of (2R)-Methyl-2-amino-3-(4'-dibenzofuran-4-ylbipheny-4-ylmethyl-sulfanyl)-propionate (140 mg, 0.296 mmol) and triethylamine (75 mg, 0.10 mL, 0.74 mmol) in a 1,2-dichloroethane was added the required acylating reagent (acid chloride, sulfonyl chloride, carbamoyl chloride or isocyanate) (0.37 mmol). The reaction mixture was stirred for 4 hours and then diluted with diethyl ether (25 mL), washed with water, brine (2×), dried over anhydrous MgSO$_4$, filtered and concentrated in vacuo to yield the crude amido-methyl ester compound.

2N Sodium hydroxide (0.5 mL) was added to a stirred solution of the amido methyl ester in a mixture of tetrahydrofuran (5 mL) and methanol (1 mL). The solution was stirred for 1 hour and then acidified to pH 3 with 2N hydrochloric acid. The reaction mixture was extracted with ethyl acetate (3×10 mL). The combined extract was washed with water, brine, dried over anhydrous MgSO$_4$, filtered and concentrated in vacuo. Purification of the product by flash column chromatography, using 5-20% methanol in methylene chloride as eluent, afforded the title compound.

EXAMPLE 36

(2R)-3-(4'-Dibenzofuran-4-yl-biphenyl-4-ylmethyl-sulfanyl)-2-(2,4-difluorobenzoyl-amino)-propionic acid (2R)-3-(4'-Dibenzofuran-4-yl-biphenyl-4-ylmethylsulfanyl)-2-(2,4-difluorobenzoyl-amino)-propionic acid was prepared according to the method described in Example 35, Method A, using 2,4-difluorobenzoic acid as the corresponding carboxylic acid. The title compound was isolated as a white solid: Rf=0.60 (20% methanol in dichloromethane). $^1$H NMR (DMSO-d6, 300 MHz): δ 8.21 (1H, d, J=8 Hz, Ar—H), 8.15 (1H, d, J=8 Hz, Ar—H), 7.98 (2H, d, J=9 Hz, Ar—H), 7.82 (2H, d, J=9 Hz, Ar—H), 7.74 (2H, d, J=8 Hz, Ar—H), 7.65 (2H, d, J=8 Hz, Ar—H), 7.50 (2H, m, Ar—H), 7.38 (5H, m, Ar—H, NH), 7.19 (2H, t, J=9 Hz, Ar—H), 4.30 (1H, m, CHN), 3.80 (1H, d, J=15 Hz, PhCHHS), 3.73 (1H, d, J=15 Hz, PhCHHS), 3.07 (1H, dd, J=15, 5 Hz, CHHCHN), 2.95 (1H, dd, J=15, 7 Hz, CHHCHN); ESI-LCMS e/z calcd for C$_{35}$H$_{25}$F$_2$NO$_4$S 593.648, found 594 (M+H)$^+$, 616 (M+Na)$^+$.

EXAMPLE 37

(2R)-3-(4'-Dibenzofuran-4-yl-biphenyl-4-ylmethyl-sulfanyl)-2-(4-nitrobenzoyl-amino)-propionic acid

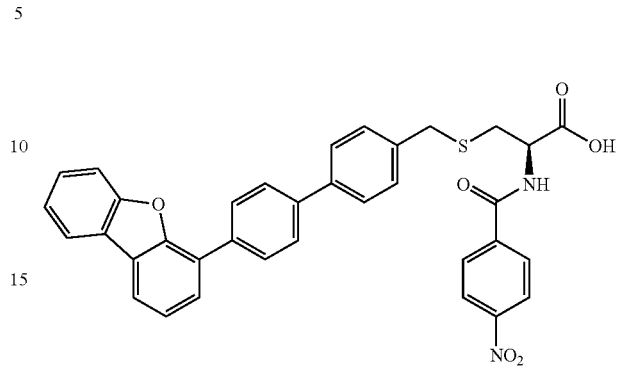

(2R)-3-(4'-Dibenzofuran-4-yl-biphenyl-4-ylmethylsulfanyl)-2-(4-nitrobenzoyl-amino)-propionic acid was prepared according to the method described in Example 35, Method A, using 4-nitrobenzoic acid as the corresponding carboxylic acid. The title compound was isolated as a pale yellow solid: Rf=0.40 (20% methanol in dichloromethane). $^1$H NMR (DMSO-d6, 300 MHz): δ 9.10 (1H, d, J=9 Hz, NH), 8.32 (2H, d, J=9 Hz, Ar—H), 8.17(2H, dd, J=13, 8 Hz, Ar—H), 8.10 (2H, d, J=9 Hz, Ar—H), 7.98 (2H, d, J=9 Hz, Ar—H), 7.84 (2H, d, J=9 Hz, Ar—H), 7.72 (4H, m, Ar—H), 7.50 (2H, q, J=9 Hz, Ar—H), 7.42 (3H, m, Ar—H), 4.62 (1H, m, CHN), 3.85 (2H, s, PhCH$_2$S), 3.01 (1H, dd, J=15, 5 Hz, CHHCHN), 2.89 (1H, dd, J=15, 11 Hz, CHHCHN); ESI-LCMS e/z calcd for C$_{35}$H$_{26}$N$_2$O$_6$S 602.664, found 603 (M+H)$^+$.

EXAMPLE 38

(2R)-3-(4'-Dibenzofuran-4-yl-biphenyl-4-ylmethyl-sulfanyl)-2-[(pyridine-3-carbonyl)-amino]-propionic acid (2R)-3-(4'-Dibenzofuran-4-yl-biphenyl-4-ylmethylsulfanyl)-2-[(pyridine-3-carbonyl)-amino]-propionic acid was prepared according to the method described in Example 35, Method A, using nicotinic acid as the corresponding carboxylic acid. The title compound was isolated as a white solid: Rf=0.40 (20% methanol in dichloromethane). $^1$H NMR (DMSO-d6, 300 MHz): δ 9.02 (2H, m, Ar—H, NH), 8.71 (2H, dd, J=5, 2 Hz, Ar—H), 8.19 (3H, m, Ar—H), 8.01 (2H, d, J=9 Hz, Ar—H), 7.84 (2H, d, J=9 Hz, Ar—H), 7.74 (4H, m, Ar—H), 7.52 (3H, m, Ar—H), 7.42 (3H, m, Ar—H), 4.65 (1H, m, CHN), 3.85 (2H, s, PhCH$_2$S), 3.00 (1H, dd, J=15, 5 Hz, CHHCHN), 2.89 (1H, dd, J=15, 11 Hz, CHHCHN); ESI-LCMS e/z calcd for C$_{34}$H$_{26}$N$_2$O$_4$S 558.655, found 559 (M+H)$^+$.

EXAMPLE 39

N-[1-Carboxy-2-(4'-dibenzofuran-4-ylbiphen-4-ylmethylsulfanyl)-ethyl]-tere-phthalamic acid N-[1-Carboxy-2-(4'-dibenzofuran-4-ylbiphen-4-ylmethylsulfanyl)-ethyl]-tere-phthalamic acid was prepared according to the method described in Example 35, Method A, using terephthalic acid as the corresponding carboxylic acid. The title compound was isolated as a white solid: Rf=0.10 (20% methanol in dichloromethane). $^1$H NMR (DMSO-d6, 300

MHz): δ 8.95 (1H, d, J=9 Hz, NH), 8.26 (2H, d, J=9 Hz, Ar—H), 8.10 (2H, dd, J=13, 8 Hz, Ar—H), 7.98 (4H, m, Ar—H), 7.84 (2H, d, J=9 Hz, Ar—H), 7.72 (3H, m, Ar—H), 7.45-7.58 (6H, m, Ar—H) 4.61 (1H, m, CHN), 3.83 (2H, s, PhCH$_2$S), 3.00 (1H, dd, J=15, 5 Hz, CHHCHN), 2.89 (1H, dd, J=15, 11 Hz, CHHCHN); ESI-LCMS e/z calcd for $C_{36}H_{27}NO_6S$ 601.676, found 602 (M+H)$^+$, 624 (M+Na)$^+$.

EXAMPLE 40

(2R)-2-Benzoylamino-3-(4'-Dibenzofuran-4-yl-biphenyl-4-ylmethylsulfanyl)-propionic acid (2R)-2-Benzoylamino-3-(4'-Dibenzofuran-4-yl-biphenyl-4-ylmethylsulfanyl)-propionic acid was prepared according to the method described in Example 35, Method A, using benzoic acid as the corresponding carboxylic acid. The title compound was isolated as a white solid: Rf=0.50 (20% methanol in dichloromethane). $^1$H NMR (DMSO-d6, 300 MHz): δ 8.18 (2H, d, J=8 Hz, Ar—H), 8.13 (1H, dd, J=8, 1 Hz, Ar—H), 7.97 (2H, d, J=9 Hz, Ar—H), 7.84 (4H, m, Ar—H), 7.74 (2H, m, Ar—H), 7.66 (2H, d, J=9 Hz, Ar—H), 7.38-7.56 (8H, m, Ar—H, NH), 4.39 (1H, m, CHN), 3.81 (1H, d, J=15 Hz, PhCHHS), 3.75 (1H, d, J=15 Hz, PhCHHS), 3.09 (1H, dd, J=13, 8 Hz, CHHCHN), 2.92 (1H, dd, J=15, 8 Hz, CHHCHN); ESI-LCMS e/z calcd for $C_{35}H_{27}NO_4S$ 557.667, found 558 (M+H)$^+$, 580 (M+Na)$^+$.

EXAMPLE 41

(2R)-3-(4'-Dibenzofuran-4-yl-biphenyl-4-ylmethyl-sulfanyl)-2-(2-fluoro-5-trifluoromethylbenzoylamino)-propionic acid

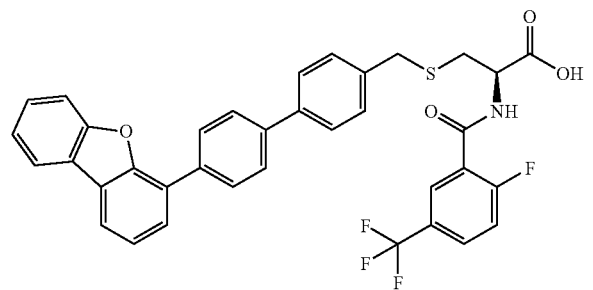

(2R)-3-(4'-Dibenzofuran-4-yl-biphenyl-4-ylmethylsulfanyl)-2-(2-fluoro-5-trifluoro-methylbenzoylamino)-propionic acid was prepared according to the method described in Example 35, Method A, using 2-fluoro-5-trifluoromethlybenzoic acid as the corresponding carboxylic acid. The title compound was isolated as a white solid: Rf=0.60 (20% methanol in dichloromethane). $^1$H NMR (DMSO-d6, 300 MHz): δ 8.45 (1H, t, J=7 Hz, Ar—H), 8.18 (1H, d, J=8 Hz, Ar—H), 8.13 (1H, d, J=8 Hz, Ar—H), 8.05 (1H, d, J=7 Hz, Ar—H), 7.97 (3H, m, Ar—H), 7.82 (2H, d, J=9 Hz, Ar—H), 7.74 (2H, d, J=9 Hz, Ar—H), 7.66 (2H, d, J=9 Hz, Ar—H), 7.54 (4H, m, Ar—H, NH), 7.42 (2H, m, Ar—H), 4.34 (1H, m, CHN), 3.80 (1H, d, J=15 Hz, PhCHHS), 3.76 (1H, d, J=15 Hz, PhCHHS), 3.09 (1H, dd, J=15, 7 Hz, CHHCHN), 2.92 (1H, dd, J=15, 7 Hz, CHHCHN); ESI-LCMS e/z calcd for $C_{36}H_{25}F_4NO_4S$ 643.654, found 644 (M+H)$^+$, 666 (M+Na)$^+$.

EXAMPLE 42

(2R)-3-(4'-Dibenzofuran-4-yl-biphenyl-4-ylmethyl-sulfanyl)-2-(2-fluoro-4-trifluoromethylbenzoylamino)-propionic acid (2R)-3-(4'-Dibenzofuran-4-yl-biphenyl-4-ylmethylsulfanyl)-2-(2-fluoro-4-trifluoromethylbenzoylamino)-propionic acid was prepared according to the method described in Example 35, Method A, using 2-fluoro-4-trifluoromethly-benzoic acid as the corresponding carboxylic acid. The title compound was isolated as a white solid: Rf=0.60 (20% methanol in dichloromethane). $^1$H NMR (DMSO-d6, 300 MHz): δ 8.41 (1H, t, J=7 Hz, Ar—H), 8.18 (1H, dd, J=8, 1 Hz, Ar—H), 8.15 (1H, d, J=9 Hz, Ar—H), 7.97-8.05 (3H, m, Ar—H), 7.82 (3H, m, Ar—H), 7.74 (2H, d, J=8 Hz, Ar—H), 7.66 (3H, m, Ar—H), 7.40-7.52 (5H, m, Ar—H, NH), 4.34 (1H, m, CHN), 3.81 (1H, d, J=15 Hz, PhCHHS), 3.76 (1H, d, J=15 Hz, PhCHHS), 3.10 (1H, dd, J=15, 5 Hz, CHHCHN), 2.92 (1H, dd, J=15, 7 Hz, CHHCHN); ESI-LCMS e/z calcd for $C_{36}H_{25}F_4NO_4S$ 643.654, found 666 (M+Na)$^+$.

EXAMPLE 43

(2R)-3-(4'-Dibenzofuran-4-yl-biphenyl-4-ylmethyl-sulfanyl)-2-(4-fluorophenylacetyl-amino)-propionic acid

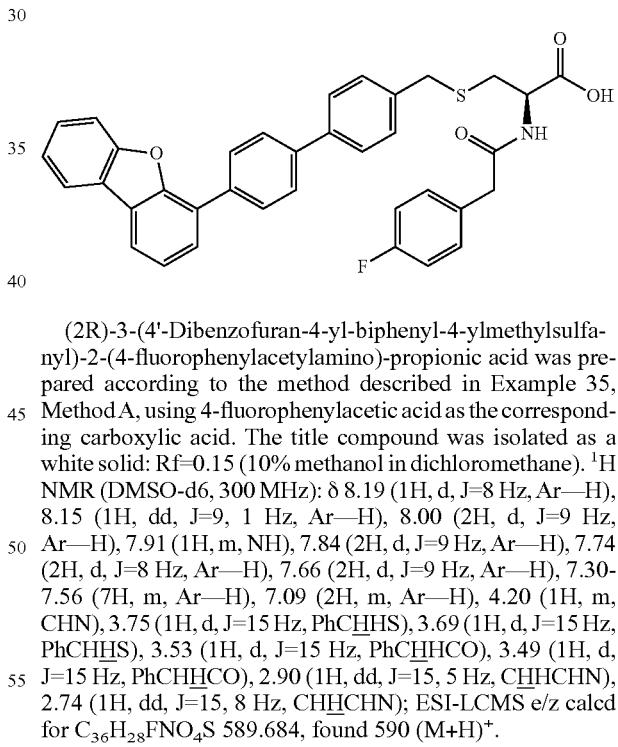

(2R)-3-(4'-Dibenzofuran-4-yl-biphenyl-4-ylmethylsulfanyl)-2-(4-fluorophenylacetylamino)-propionic acid was prepared according to the method described in Example 35, Method A, using 4-fluorophenylacetic acid as the corresponding carboxylic acid. The title compound was isolated as a white solid: Rf=0.15 (10% methanol in dichloromethane). $^1$H NMR (DMSO-d6, 300 MHz): δ 8.19 (1H, d, J=8 Hz, Ar—H), 8.15 (1H, dd, J=9, 1 Hz, Ar—H), 8.00 (2H, d, J=9 Hz, Ar—H), 7.91 (1H, m, NH), 7.84 (2H, d, J=9 Hz, Ar—H), 7.74 (2H, d, J=8 Hz, Ar—H), 7.66 (2H, d, J=9 Hz, Ar—H), 7.30-7.56 (7H, m, Ar—H), 7.09 (2H, m, Ar—H), 4.20 (1H, m, CHN), 3.75 (1H, d, J=15 Hz, PhCHHS), 3.69 (1H, d, J=15 Hz, PhCHHS), 3.53 (1H, d, J=15 Hz, PhCHHCO), 3.49 (1H, d, J=15 Hz, PhCHHCO), 2.90 (1H, dd, J=15, 5 Hz, CHHCHN), 2.74 (1H, dd, J=15, 8 Hz, CHHCHN); ESI-LCMS e/z calcd for $C_{36}H_{28}FNO_4S$ 589.684, found 590 (M+H)$^+$.

EXAMPLE 44

(2R)-3-(4'-Dibenzofuran-4-yl-biphenyl-4-ylmethyl-sulfanyl)-2-(4-methoxybenzoyl-amino)-propionic acid (2R)-3-(4'-Dibenzofuran-4-yl-biphenyl-4-ylmethylsulfanyl)-2-(4-methoxybenzoyl-amino)-propionic acid was prepared according to the method described in Example 35, Method A, using 4-methoxybenzoic acid as the corresponding carboxylic acid. The title compound was isolated as a white solid: Rf=0.20 (10% methanol in dichloromethane). $^1$H NMR (DMSO-d6, 300 MHz): δ 8.18 (1H, d, J=8 Hz, Ar—H), 8.13 (1H, dd, J=8, 1 Hz, Ar—H), 8.04 (1H, m, NH), 7.97 (2H, d, J=9 Hz, Ar—H), 7.82 (4H, t, J=10 Hz, Ar—H), 7.72 (2H, dd, J=9, 4 Hz, Ar—H), 7.64 (2H, d, J=9 Hz, Ar—H), 7.38-7.56 (5H, m, Ar—H), 6.99 (2H, d, J=9 Hz, Ar—H), 4.41 (1H, m, CHN), 3.79 (2H, s, PhCH$_2$S), 3.08 (1H, dd, J=15, 5 Hz, CHHCHN), 2.92 (1H, dd, J=15, 8 Hz, CHHCHN); ESI-LCMS e/z calcd for C$_{36}$H$_{29}$NO$_5$S 587.693, found 588 (M+H)$^+$, 610 (M+Na)$^+$.

EXAMPLE 45

(2R)-3-(4'-Dibenzofuran-4-yl-biphenyl-4-ylmethyl-sulfanyl)-2-(2,4,6-trifluoro-benzoyl-amino)-propionic acid (2R)-3-(4'-Dibenzofuran-4-yl-biphenyl-4-ylmethylsulfanyl)-2-(2,4,6-trifluoro-benzoyl-amino)-propionic acid was prepared according to the method described in Example 35, Method A, using 2,4,6-trifluorobenzoic acid as the corresponding carboxylic acid. The title compound was isolated as a white solid: Rf=0.15 (10% methanol in dichloromethane). $^1$H NMR (DMSO-d6, 300 MHz): δ 8.41 (1H, d, J=8 Hz, Ar—H), 8.18 (1H, d, J=8 Hz, Ar—H), 8.15 (1H, d, J=9 Hz, Ar—H), 7.98 (2H, d, J=8 Hz, Ar—H), 7.82 (2H, d, J=8 Hz, Ar—H), 7.72 (4H, m, Ar—H), 7.46 (5H, m, Ar—H, NH), 7.20 (2H, t, J=9 Hz, Ar—H), 4.38 (1H, m, CHN), 3.81 (1H, d, J=15 Hz, PhCHHS), 3.76 (1H, d, J=15 Hz, PhCHHS), 3.06 (1H, dd, J=15, 5 Hz, CHHCHN), 2.84 (1H, dd, J=15, 8 Hz, CHHCHN); ESI-LCMS e/z calcd for C$_{35}$H$_{24}$F$_3$NO$_4$S 611.638, found 612 (M+H)$^+$, 634 (M+Na)$^+$.

EXAMPLE 46

(2R,2'S)-2-[(1-Acetylpyrollidine-2-carbonyl)amino]-3-(4'-Dibenzofuran-4-yl-biphenyl-4-ylmethylsulfanyl)-propionic acid (2R,2'S)-2-[(1-Acetylpyrollidine-2-carbonyl)amino]-3-(4'-Dibenzofuran-4-yl-biphenyl-4-ylmethylsulfanyl)-propionic acid was prepared according to the method described in Example 35, Method A, using L-N-acetylproline as the corresponding carboxylic acid. The title compound was isolated as a white solid: Rf=0.05 (15% methanol in dichloromethane). $^1$H NMR (DMSO-d6, 300 MHz): δ 8.41 (1H, d, J=8 Hz, NH), 8.18 (1H, d, J=8 Hz, Ar—H), 8.15 (1H, d, J=9 Hz, Ar—H), 8.02 (2H, d, J=8 Hz, Ar—H), 7.82 (2H, d, J=8 Hz, Ar—H), 7.72 (4H, m, Ar—H), 7.58 (2H, m, Ar—H), 7.40 (3H, m, Ar—H), 4.40 (2H, m, 2×CHN), 3.81 (2H, s, PhCH$_2$S), 3.50 (2H, m, CH$_2$N), 2.96 (1H, dd, J=15, 5 Hz, CHHCHN), 2.84 (1H, dd, J=15, 8 Hz, CHHCHN), 2.21 (1H, m), 1.98 (3H, s, CH$_3$CO), 1.88 (3H, m); ESI-LCMS e/z calcd for C$_{35}$H$_{32}$N$_2$O$_5$S 592.713, found 593 (M+H)$^+$, 615 (M+Na)$^+$.

EXAMPLE 47

(2R)-3-(4'-Dibenzofuran-4-yl-biphenyl-4-ylmethyl-sulfanyl)-2-(2phenylamino-acetyl-amino)-propionic acid

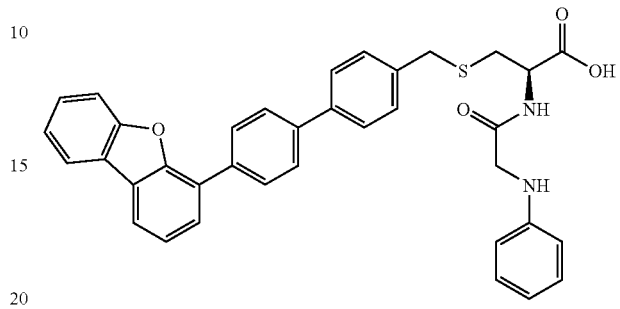

(2R)-3-(4'-Dibenzofuran-4-yl-biphenyl-4-ylmethylsulfanyl)-2-(2phenylamino-acetyl-amino)-propionic acid was prepared according to the method described in Example 35, Method A, using 2-phenylaminoacetic acid as the corresponding carboxylic acid. The title compound was isolated as a white solid: Rf=0.20 (20% methanol in dichloromethane). $^1$H NMR (DMSO-d6, 300 MHz): δ 8.18 (1H, d, J=8 Hz, Ar—H), 8.13 (1H, d, J=9 Hz, Ar—H), 7.99 (2H, d, J=9 Hz, Ar—H), 7.82 (3H, d, J=9 Hz, Ar—H), 7.74 (2H, d, J=7 Hz, Ar—H), 7.67 (2H, d, J=9 Hz, Ar—H), 7.52 (2H, m, Ar—H), 7.40 (4H, m, Ar—H, NH), 7.06 (2H, t, J=9 Hz, Ar—H), 6.58 (2H, d, J=9 Hz, Ar—H), 6.09 (1H, t, J=6 Hz, NH), 4.19 (1H, m, CHN), 3.75 (1H, d, J=15 Hz, PhCHHS), 3.71 (1H, d, J=15 Hz, PhCHHS), 3.62 (2H, m, CH$_2$N), 2.96 (1H, dd, J=15, 5 Hz, CHHCHN), 2.92 (1H, dd, J=15, 6 Hz, CHHCHN); ESI-LCMS e/z calcd for C$_{36}$H$_{30}$N$_2$O$_4$S 586.709, found 588 (M+H)$^+$, 609 (M+Na)$^+$.

EXAMPLE 48

(2R)-3-(4'-Dibenzofuran-4-yl-biphenyl-4-ylmethyl-sulfanyl)-2-[2-(3-(trifluoromethyl-phenyl)-acetylamino]-propionic acid (2R)-3-(4'-Dibenzofuran-4-yl-biphenyl-4-ylmethylsulfanyl)-2-[2-(3-(trifluoromethyl-phenyl)-acetylamino]-propionic acid was prepared according to the method described in Example 35, Method A, using 2-(3-trifluoromethylphenyl)acetic acid as the corresponding carboxylic acid. The title compound was isolated as a white solid: Rf=0.40 (10% methanol in dichloromethane). $^1$H NMR (DMSO-d6, 300 MHz): δ 8.17 (3H, dd, J=14, 9 Hz, Ar—H), 8.00 (2H, d, J=9 Hz, Ar—H), 7.82 (2H, d, J=9 Hz, Ar—H), 7.74 (2H, d, J=8 Hz, Ar—H), 7.66 (3H, m, Ar—H), 7.56 (5H, m, Ar—H, NH), 7.41 (1H, t, J=8 Hz, Ar—H), 7.32 (2H, d, J=9 Hz, Ar—H), 4.27 (1H, m, CHN), 3.70 (4H, m, PhCH$_2$S+PhCH$_2$CO), 2.91 (1H, dd, J=15, 5 Hz, CHHCHN), 2.76 (1H, dd, J=15, 8 Hz, CHHCHN); ESI-LCMS e/z calcd for C$_{37}$H$_{28}$F$_3$NO$_4$S 639.691, found 662 (M+Na)$^+$.

EXAMPLE 49

(2R)-3-(4'-Dibenzofuran-4-yl-biphenyl-4-ylmethyl-sulfanyl)-2-[(1,5-dimethyl-1H-pyrazole-3-carbonyl)-amino]-propionic acid

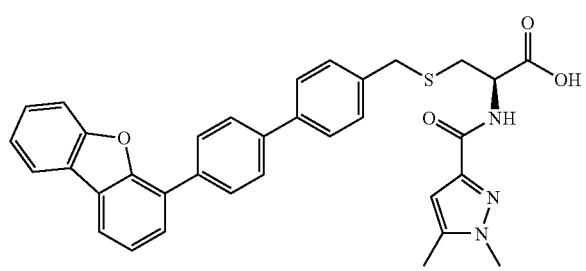

(2R)-3-(4'-Dibenzofuran-4-yl-biphenyl-4-ylmethylsulfanyl)-2-[(1,5-dimethyl-1H-pyrazole-3-carbonyl)-amino]-propionic acid was prepared according to the method described in Example 35, Method A, using 1,5-dimethyl-1H-pyrazole-3-carboxylic acid as the corresponding carboxylic acid. The title compound was isolated as a white solid: Rf=0.30 (10% methanol in dichloromethane). $^1$H NMR (DMSO-d6, 300 MHz): δ 8.18 (1H, d, J=9 Hz, Ar—H), 8.14 (1H, dd, J=9, 1 Hz, Ar—H), 7.99 (2H, d, J=9 Hz, Ar—H), 7.91 (1H, d, J=8 Hz, NH), 7.82 (2H, d, J=9 Hz, Ar—H), 7.74 (2H, m, Ar—H), 7.66 (2H, d, J=9 Hz, Ar—H), 7.52 (2H, m, Ar—H), 7.40 (3H, m, Ar—H), 6.41 (1H, s, pyrazole-CH), 4.36 (1H, m, CHN), 3.76 (5H, m, PhCH$_2$S+NMe), 3.10 (1H, dd, J=15, 5 Hz, CHHCHN), 2.95 (1H, dd, J=15, 8 Hz, CHHCHN), 2.26 (3H, s, Me); ESI-LCMS e/z calcd for $C_{34}H_{29}N_3O_4S$ 575.686, found 598 (M+Na)$^+$.

EXAMPLE 50

(1'R)-N-[2-(4'-Dibenzofuran-4-yl-biphenyl-4-ylmethylsulfanyl)-1-methoxycarbonyl-ethyl]-succinamic acid (1'R)-N-[2-(4'-Dibenzofuran-4-yl-biphenyl-4-ylmethylsulfanyl)-1-methoxycarbonyl-ethyl]-succinamic acid was prepared according to the method described in Example 35, Method B, using succinic anhydride as the corresponding acylating reagent. The title compound was isolated, as the mono-methyl ester, as an off-white solid: Rf=0.40 (10% methanol in dichloromethane). $^1$H NMR (DMSO-d6, 300 MHz): δ 8.45 (1H, d, J=9 Hz, NH), 8.19 (1H, d, J=9 Hz, Ar—H), 8.15 (1H, dd, J=9, 1 Hz, Ar—H), 8.01 (2H, d, J=9 Hz, Ar—H), 7.86 (2H, d, J=9 Hz, Ar—H), 7.74 (4H, m, Ar—H), 7.53 (2H, m, Ar—H), 7.42 (3H, m, Ar—H), 4.52 (1H, m, CHN), 3.82 (2H, s, PhCH$_2$S), 3.64 (3H, s, OMe), 2.82 (1H, dd, J=15, 7 Hz, CHHCHN), 2.71 (1H, dd, J=15, 8 Hz, CHHCHN), 2.41 (4H, m, CH$_2$CH$_2$); ESI-LCMS e/z calcd for $C_{33}H_{29}NO_6S$ 567.659, found 568 (M+H)$^+$, 590 (M+Na)$^+$.

EXAMPLE 51

(1'R)-N-[1-Carboxy-2-(4'-Dibenzofuran-4-yl-biphenyl-4-ylmethylsulfanyl)-1-ethyl]-succinamic acid (1'R)-N-[1-Carboxy-2-(4'-Dibenzofuran-4-yl-biphenyl-4-ylmethylsulfanyl)-1-ethyl]-succinamic acid was prepared by hydrolysis of (1'R)-N-[2-(4'-Dibenzofuran-4-yl-biphenyl-4-ylmethylsulfanyl)-1-methoxycarbonyl-ethyl]-succinamic acid (prepared above) according to the hydrolysis conditions described in Example 35, method B. The title compound was isolated as a white solid: Rf=0.20 (20% methanol in dichloromethane). $^1$H NMR (DMSO-d6, 300 MHz): δ 8.31 (1H, d, J=9 Hz, NH), 8.19 (1H, d, J=9 Hz, Ar—H), 8.15 (1H, dd, J=9, 1 Hz, Ar—H), 8.00 (2H, d, J=9 Hz, Ar—H), 7.85 (2H, d, J=9 Hz, Ar—H), 7.73 (4H, m, Ar—H), 7.53 (2H, m, Ar—H), 7.42 (3H, m, Ar—H), 4.47 (1H, m, CHN), 3.82 (2H, s, PhCH$_2$S), 3.64 (3H, s, OMe), 2.81 (1H, dd, J=15, 6 Hz, CHHCHN), 2.69 (1H, dd, J=15, 9 Hz, CHHCHN), 2.42 (4H, m, CH$_2$CH$_2$); ESI-LCMS e/z calcd for $C_{32}H_{27}NO_6S$ 553.632, found 554 (M+H)$^+$.

EXAMPLE 52

(2R)-3-(4'-Dibenzofuran-4-yl-biphenyl-4-ylmethyl-sulfanyl)-2-(4-fluorobenzoyl-amino)-propionic acid (2R)-3-(4'-Dibenzofuran-4-yl-biphenyl-4-ylmethylsulfanyl)-2-(4-fluorobenzoyl-amino)-propionic acid was prepared according to the method described in Example 35, Method A, using 4-fluorobenzoic acid as the corresponding carboxylic acid. The title compound was isolated as a white solid: Rf=0.30 (10% methanol in dichloromethane). $^1$H NMR (DMSO-d6, 300 MHz): δ 8.37 (1H, d, J=8 Hz, NH), 8.18 (1H, d, J=9 Hz, Ar—H), 8.15 (1H, d, J=8 Hz, Ar—H), 7.98 (4H, m, Ar—H), 7.82 (2H, d, J=9 Hz, Ar—H), 7.73 (2H, m, Ar—H), 7.66 (2H, d, J=9 Hz, Ar—H), 7.48 (3H, m, Ar—H, NH), 7.42 (2H, d, J=8 Hz, Ar—H), 7.28 (2H, t, J=9 Hz, Ar—H), 4.45 (1H, m, CHN), 3.78 (2H, s, PhCH$_2$S), 3.07 (1H, dd, J=15, 5 Hz, CHHCHN), 2.84 (1H, dd, J=15, 9 Hz, CHHCHN); ESI-LCMS e/z calcd for $C_{35}H_{26}FNO_4S$ 575.657, found 576 (M+H)$^+$.

EXAMPLE 53

(1'R)-N-[2-(4'-Dibenzofuran-4-yl-biphenyl-4-ylmethylsulfanyl)-1-methoxycarbonyl-ethyl]-phthalamic acid

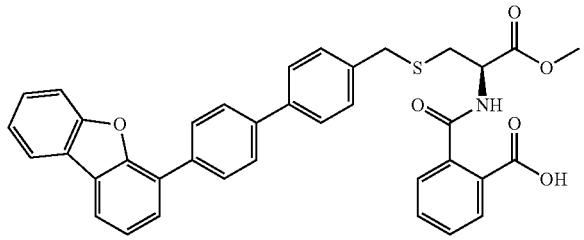

(1'R)-N-[2-(4'-Dibenzofuran-4-yl-biphenyl-4-ylmethyl-sulfanyl)-1-methoxycarbonyl-ethyl]-phthalamic acid was prepared according to the method described in Example 35, Method B, using phthalic anhydride as the corresponding acylating reagent. The title compound was isolated, as the mono-methyl ester, as a white solid: Rf=0.20 (5% methanol in dichloromethane). $^1$H NMR (CDCl$_3$, 300 MHz): δ 8.76 (4H, m, Ar—H), 7.64 (2H, d, J=9 Hz, Ar—H), 7.58 (4H, m, Ar—H), 7.42 (4H, m, Ar—H), 7.32 (5H, m, Ar—H), 4.98 (1H, m, CHN), 3.78 (2H, s, PhCH$_2$S), 3.62 (3H, s, OMe), 3.02

(1H, dd, J=15, 7 Hz, C<u>H</u>HCHN), 2.90 (1H, dd, J=15, 8 Hz, CH<u>H</u>CHN); ESI-LCMS e/z calcd for $C_{37}H_{29}NO_6S$ 615.703, found 617 (M+H)$^+$.

EXAMPLE 54

(1'R)-N-[1-Carboxy-2-(4'-dibenzofuran-4-yl-biphenyl-4-ylmethylsulfanyl)-ethyl]-phthalamic acid (1'R)-N-[1-Carboxy-2-(4'-dibenzofuran-4-yl-biphenyl-4-ylmethylsulfanyl)-ethyl]-phthalamic acid was prepared by hydrolysis of (1'R)-N-[2-(4'-Dibenzofuran-4-yl-biphenyl-4-ylmethylsulfanyl)-1-methoxycarbonyl-ethyl]-phthalamic acid (prepared above) according to the hydrolysis conditions described in Example 35, method B. The title compound was isolated as a white solid: Rf=0.05 (20% methanol in dichloromethane). $^1$H NMR (DMSO-d6, 300 MHz): δ 8.76 (1H, d, J=9 Hz, NH), 8.19 (1H, d, J=9 Hz, Ar—H), 8.15 (1H, dd, J=9, 1 Hz, Ar—H), 8.00 (2H, d, J=9 Hz, Ar—H), 7.86 (2H, d, J=9 Hz, Ar—H), 7.73 (5H, m, Ar—H), 7.56 (2H, m, Ar—H), 7.48 (6H, m, Ar—H), 4.62 (1H, m, CHN), 3.86 (2H, s, PhCH$_2$S), 2.92 (1H, dd, J=15, 6 Hz, C<u>H</u>HCHN), 2.69 (1H, dd, J=15, 9 Hz, CH<u>H</u>CHN); ESI-LCMS e/z calcd for $C_{36}H_{27}NO_6S$ 601.676, found 603 (M+H)$^+$.

EXAMPLE 55

(2R)-2-(4-Cyanobenzoylamino-3-(4'-Dibenzofuran-4-yl-biphenyl-4-ylmethyl-sulfanyl)-propionic acid (2R)-2-(4-Cyanobenzoylamino-3-(4'-Dibenzofuran-4-yl-biphenyl-4-ylmethyl-sulfanyl)-propionic acid was prepared according to the method described in Example 35, Method A, using 4-cyanobenzoic acid as the corresponding carboxylic acid. The title compound was isolated as a white solid: Rf=0.50 (20% methanol in dichloromethane). $^1$H NMR (DMSO-d6, 300 MHz): δ 8.59 (1H, d, J=8 Hz, NH), 8.26 (1H, s, Ar—H), 8.16 (2H, m, Ar—H), 8.10 (1H, d, J=8 Hz, Ar—H), 7.93 (3H, m, Ar—H), 7.76 (2H, d, J=9 Hz, Ar—H), 7.68 (2H, m, Ar—H), 7.62 (2H, d, J=9 Hz, Ar—H), 7.38-7.48 (3H, m, Ar—H), 7.34 (3H, m, Ar—H), 4.46 (1H, m, CHN), 3.77 (2H, s, PhCH$_2$S), 3.05 (1H, dd, J=15, 5 Hz, C<u>H</u>HCHN), 2.84 (1H, dd, J=15, 8 Hz, CH<u>H</u>CHN); ESI-LCMS e/z calcd for $C_{36}H_{26}N_2O_4S$ 582.677, found 605 (M+Na)$^+$.

EXAMPLE 56

(2R)-3-(4'-Dibenzofuran-4-yl-biphenyl-4-ylmethyl-sulfanyl)-2-(3,3-dimethylbutyryl-amino)-propionic acid (2R)-3-(4'-Dibenzofuran-4-yl-biphenyl-4-ylmethylsulfanyl)-2-(3,3-dimethylbutyryl-amino)-propionic acid was prepared according to the method described in Example 35, Method A, using 3,3-dimethylbutyric acid as the corresponding carboxylic acid. The title compound was isolated as a pale yellow solid: Rf=0.30 (10% methanol in dichloromethane). $^1$H NMR (DMSO-d6, 300 MHz): δ 8.24 (1H, d, J=8 Hz, NH), 8.17 (2H, t, J=9 Hz, Ar—H), 8.04 (2H, d, J=8 Hz, Ar—H), 7.90 (2H, d, J=9 Hz, Ar—H), 7.76 (4H, m, Ar—H), 7.56 (2H, q, J=9 Hz, Ar—H), 7.44 (3H, m, Ar—H), 4.48 (1H, m, CHN), 3.85 (2H, s, PhCH$_2$S), 2.86 (1H, dd, J=15, 5 Hz, C<u>H</u>HCHN), 2.71 (1H, dd, J=15, 9 Hz, CH<u>H</u>CHN), 2.06 (2H, s, CH$_2$CO), 0.99 (9H, s, CMe$_3$); ESI-LCMS e/z calcd for $C_{34}H_{33}NO_4S$ 551.704, found 552 (M+H)$^+$, 574 (M+Na)$^+$.

EXAMPLE 57

(2R)-2-(3-tert-Butyl-ureido)-3-(4'-dibenzofuran-4-yl-biphenyl-4-ylmethylsulfanyl)-propionic acid

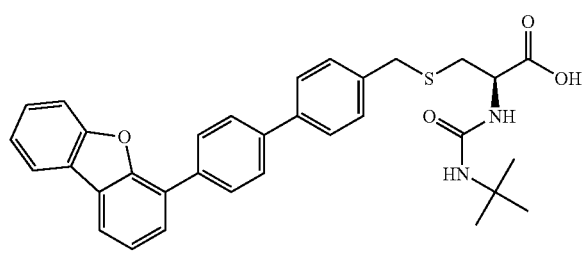

(2R)-2-(3-tert-Butyl-ureido)-3-(4'-dibenzofuran-4-yl-biphenyl-4-ylmethylsulfanyl)-propionic acid was prepared according to the method described in Example 35, Method B, using tert-butyl isocyanate as the corresponding acylating reagent. The title compound was isolated as a colorless foam: Rf=0.10 (10% methanol in dichloromethane). $^1$H NMR (DMSO-d6, 300 MHz): δ 8.19 (1H, d, J=8 Hz, Ar—H), 8.13 (1H, dd, J=9, 1 Hz, Ar—H), 7.98 (2H, d, J=9 Hz, Ar—H), 7.84 (2H, d, J=9 Hz, Ar—H), 7.74 (2H, m, Ar—H), 7.67 (2H, d, J=9 Hz, Ar—H), 7.53 (2H, m, Ar—H), 7.42 (3H, m, Ar—H), 6.28 (1H, s, NH), 6.06 (1H, d, J=8 Hz, NH), 4.13 (1H, m, CHN), 3.78 (2H, s, PhCH$_2$S), 2.86 (1H, dd, J=15, 5 Hz, C<u>H</u>HCHN), 2.75 (1H, dd, J=15, 6 Hz, CH<u>H</u>CHN), 1.24 (9H, s, CMe$_3$); ESI-LCMS e/z calcd for $C_{33}H_{32}N_2O_4S$ 552.692, found 553 (M+H)$^+$.

EXAMPLE 58

(2R)-2-[2,3-bis-(tert-Butoxycarbonyl)guanidino]-3-(4'-dibenzofuran-4-yl-biphenyl-4-ylmethylsulfanyl)-propionic acid (2R)-2-[2,3-bis-(tert-Butoxycarbonyl)guanadino)]-3-(4'-dibenzofuran-4-yl-biphenyl-4-ylmethylsulfanyl)-propionic acid was prepared according to the method described in Example 35, Method B, using N,N'-bis-(tert-butoxycarbonyl)-1H-pyrazole-1-carboxamidine as the corresponding acylating reagent. The title compound was isolated as an off-white solid: Rf=0.40 (10% methanol in dichloromethane). $^1$H NMR (CDCl$_3$, 300 MHz): δ 11.13 (1H, s, NH), 9.06 (1H, s, NH), 7.96 (4H, m, Ar—H), 7.74 (2H, d, J=9 Hz, Ar—H), 7.62 (4H, d, J=8 Hz, Ar—H), 7.46 (3H, m, Ar—H), 7.36 (2H, m, Ar—H), 4.65 (1H, m, CHN), 3.86 (2H, s, PhCH$_2$S), 3.10 (2H, m, C<u>H</u>$_2$CHN), 1.54 (9H, s, CMe$_3$), 1.48 (9H, s, CMe$_3$); ESI-LCMS e/z calcd for $C_{39}H_{41}N_3O_7S$ 695.833, found 696 (M+H)$^+$, 718 (M+Na)$^+$.

EXAMPLE 59

(2R)-3-(4'-Dibenzofuran-4-yl-biphenyl-4-ylmethyl-sulfanyl)-2-guanidino-propionic acid

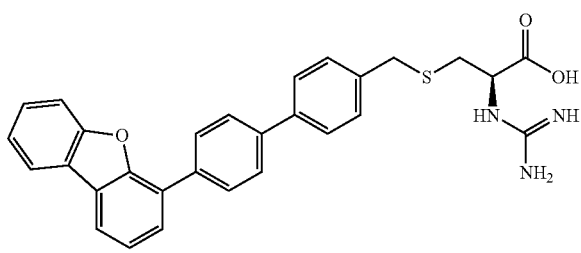

Trifluoroacetic acid (2 mL) was added to a stirred solution of (2R)-2-[2,3-bis-(tert-butoxycarbonyl)guanidino]-3-(4'-dibenzofuran-4-yl-biphenyl-4-ylmethylsulfanyl)-propionic acid (250 mg, 0.36 mmol) in anhydrous dichloromethane (10 mL). The reaction was stirred for 4 hours (HPLC control) and then concentrated in vacuo. The resultant brown oil was reconstituted and concentrated from methanol (3×10 mL) and then from dichloromethane (2×10 mL) to give the title compound as an off-white solid (175 mg, 99%): Rf=0.20 (10% methanol in dichloromethane). $^1$H NMR (DMSO-d6, 300 MHz): δ 8.19 (1H, d, J=8 Hz, Ar—H), 8.13 (1H, d, J=9 Hz, Ar—H), 8.02 (2H, d, J=9 Hz, Ar—H), 7.84 (3H, m, Ar—H), 7.74 (4H, m, 2×Ar—H, 2×NH), 7.53 (3H, m, Ar—H), 7.42 (3H, m, Ar—H), 7.26 (1H, d, J=9 Hz, NH), 7.10 (1H, br s, NH), 4.58 (1H, m, CHN), 3.86 (2H, s, PhCH$_2$S), 2.92 (1H, dd, J=15, 5 Hz, C$\underline{H}$HCHN), 2.75 (1H, dd, J=15, 7 Hz, CH$\underline{H}$CHN); ESI-LCMS e/z calcd for $C_{29}H_{25}N_3O_3S$ 495.600, found 496 (M+H)$^+$.

EXAMPLE 60

(2R)-3-(4'-Dibenzofuran-4-ylbiphen-4-ylmethylsulfanyl)-2-(4-trifluoromethylbenzyl-amino)-propionic acid Sodium nitrite (31 mg, 0.45 mmol) was added portion-wise to a stirred slurry of (2R)-methyl-2-amino-3-(4'-dibenzofuran-4-ylbipheny-4-ylmethylsulfanyl)-propionate (140 mg, 0.3 mmol) and potassium bromide (180 mg, 1.5 mmol) in 2N sulfuric acid (5 mL) at 0° C. The reaction was stirred at 0° C. for 3 hours (TLC control) and then diluted with water (20 mL) and extracted with diethyl ether (3×25 mL). The combined extract was washed with water (2×10 mL), brine, dried over anhydrous MgSO$_4$, filtered and concentrated in vacuo to afford crude methyl-2-bromo-3-(4'-dibenzofuran-4-ylbiphen-4-ylmethylsulfanyl)-2-(4-trifluoromethylbenzyl-amino)propionate, which was used immediately without purification.

To the bromide (prepared in the previous step) in anhydrous dimethylformamide (5 mL) was added 4-trifluoromethylbenzylamine (80 mg, 0.45 mmol) and triethylamine (0.5 mL). The reaction was stirred at room temperature for 16 hours and then poured into water, and extracted with diethyl ether (3×25 mL). The combined extract was washed with water (2×10 mL), brine, dried over anhydrous MgSO$_4$, filtered and concentrated in vacuo to afford methyl-3-(4'-dibenzofuran-4-ylbiphen-4-ylmethylsulfanyl)-2-(4-trifluoromethylbenzyl-amino)-propionate.

2N Sodium hydroxide (0.5 mL) was added to a stirred solution of the amino methyl ester in a mixture of tetrahydrofuran (5 mL) and methanol (1 mL). The solution was stirred for 1 hour and then acidified to pH 4 with 2N hydrochloric acid. The reaction mixture was extracted with ethyl acetate (3×20 mL). The combined extract was washed with water, brine, dried over anhydrous MgSO$_4$, filtered and concentrated in vacuo. Purification of the product by flash column chromatography, using 20% methanol in methylene chloride as eluent, afforded the title compound as a white solid. Rf: 0.40 (20% methanol in dichloromethane); $^1$H NMR (CDCl$_3$, 300 MHz): δ 7.87 (3H, m, Ar—H), 7.57 (3H, m, Ar—H), 7.56 (2H, d, J=9 Hz, Ar—H), 7.31-7.41 (6H, m, Ar—H), 7.29 (2H, t, J=9 Hz, Ar—H), 7.19 (3H, m, Ar—H), 3.98 (2H, s, PhCH$_2$S), 3.70 (3H, m, CHN+PhCH$_2$N), 3.09 (1H, m C$\underline{H}$HCHN), 2.89 (1H, m, CH$\underline{H}$CHN); ESI-LCMS e/z calcd for $C_{36}H_{28}F_3NO_3S$ 611.681, found 613 (M+H)$^+$.

EXAMPLE 61

Trifluoro-methanesulfonic acid 4-(2-benzyl-benzofuran-3-yl)-phenyl ester

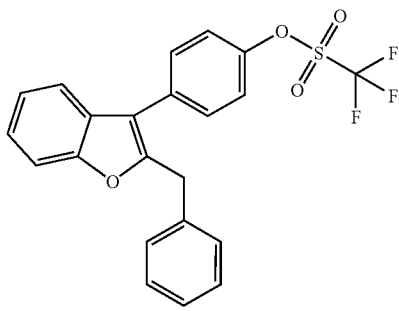

To a stirred solution of the known phenol, 4-(2-benzylbenzofuran-3-yl)-phenol, (7.2 g, 24 mmol) in anhydrous methylene chloride (100 mL), was added triethylamine (4.86 g, 6.7 mL, 48 mmol) and then N-phenyltrifluoromethanesulfonimide (9.4 g, 26.4 mmol) portionwise as a solid. The resulting solution was stirred for 2 hours at room temperature and then diluted with water, extracted with diethyl ether (3×100 mL). The combined extract was washed with water, brine, dried over anhydrous MgSO$_4$, filtered and concentrated in vacuo. Purification of the product by flash column chromatography, using 10% ethyl acetate in heptane as eluent, afforded the title compound as a white solid (9.35 g, 90%).

EXAMPLE 62

4'-(2-Benzylbenzofuran-3-yl)biphenyl-4-carbaldehyde

To a stirred solution of the triflate (from Example 61) (9.35 g, 21.6 mmol) and tetrakis-(triphenylphosphine)palladium (0) (750 mg, 0.65 mmol) in toluene (70 mL) was added a solution of 4-formylphenylboronic acid (4.06 g, 27.05 mmol) in ethanol (20 mL) and 2N sodium carbonate (21.6 mL, 43.2 mmol). The resulting suspension was stirred at 100° C. for 4 hrs (TLC control). The reaction was cooled, diluted with water (50 mL) and extracted with diethyl ether (3×100 mL). The combined extract was washed with water, brine, dried over anhydrous MgSO$_4$, filtered and concentrated in vacuo.

The resulting brown solid was redissolved in tetrahydrofuran (50 mL). 2N Hydrochloric acid (10 mL) was added and the resulting solution was stirred at room temperature for 1 hour, and then diluted with water (50 mL) and extracted with diethyl ether (3×100 mL). The combined extract was washed with water, brine, dried over anhydrous MgSO$_4$, filtered and concentrated in vacuo. Purification of the product by flash column chromatography, using 20% ethyl acetate in heptane as eluent, afforded the title compound as a white solid (7.34 g, 88%).

EXAMPLE 63

4'-(2-Benzylbenzofuran-3-yl)biphenyl-4-methanol

To a solution of 4'-(2-benzylbenzofuran-3-yl)biphenyl-4-carbaldehyde (5.0 g, 12.9 mmol) in ethanol (100 mL) and tetrahydrofuran (25 mL) was added sodium borohydride (980 mg, 25.8 mmol) as a solid in 3 portions. The reaction was stirred at room temperature for 1 hour (TLC control) and then poured into water (100 mL) and extracted with diethyl ether (3×100 mL). The combined extract was washed with water, brine, dried over anhydrous MgSO$_4$, filtered and concentrated in vacuo to afford the title compound as a white solid (5.02 g, 99%).

EXAMPLE 64

2-Benzyl-3-(4'-bromomethylbiphen-4-yl)benzofuran

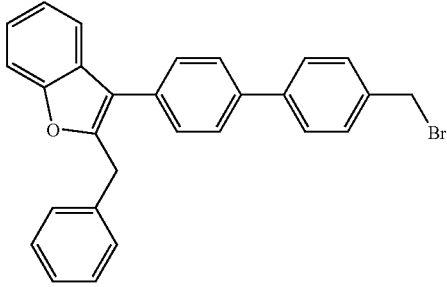

To a solution of 4'-(2-benzylbenzofuran-3-yl)biphenyl-4-methanol (5.01 g, 12.7 mmol) in anhydrous acetonitrile (75 mL) was added dibromotriphenylphosphorane (5.45 g, 12.7 mmol) as a solid portionwise over 15 mins. The reaction was stirred for 2 hours (TLC control) and then poured into water (100 mL) and extracted with diethyl ether (3×100 mL). The combined extract was washed with water, brine, dried over anhydrous MgSO$_4$, filtered and concentrated in vacuo to afford the title compound as an off-white solid (4.98 g, 87%): $^1$H NMR (CDCl$_3$, 300 MHz): δ 7.70 (2H, m, Ar—H), 7.63 (4H, m, Ar—H), 7.50 (3H, m, Ar—H), 7.30 (4H, m, Ar—H), 7.25 (4H, m, Ar—H), 4.57 (2H, s, CH$_2$Br), 4.26 (2H, PhCH$_2$).

EXAMPLE 65

(2R)-Methyl-3-[4'-(2-benzylbenzofuran-3-yl)biphen-4-ylmethylsulfanyl]-2-tert-butoxycarbonylaminopropionate N-Boc-L-Cysteine methyl ester (260 mg, 0.23 mL, 1.1 mmol) was added dropwise to a stirred suspension of 2-Benzyl-3-(4'-bromomethylbiphen-4-yl)benzofuran (500 mg, 1.1 mmol) and cesium carbonate (720 mg, 2.21 mmol) in anhydrous dimethylformamide (20 mL). The reaction was stirred at room temperature for 2 hrs (TLC control) and then poured into water (100 mL) and extracted with diethyl ether (3×100 mL). The combined extract was washed with water, brine (3×), dried over anhydrous MgSO$_4$, filtered and concentrated in vacuo. Purification using 30% ethyl acetate in heptane as eluent afforded the title compound as a white solid (620 mg, 92%): $^1$H NMR (CDCl$_3$, 300 MHz): δ 7.70 (2H, m, Ar—H), 7.64 (2H, m, Ar—H), 7.60 (3H, m, Ar—H), 7.48 (1H, m, Ar—H), 7.42 (2H, m, Ar—H), 7.26-7.36 (7H, m, Ar—H), 5.32 (1H, d, J=8 Hz, NH), 4.58 (1H, m, CHN), 4.26 (2H, PhCH$_2$), 3.79 (2H, s, PhCH2S), 3.76 (3H, s, OMe), 2.95 (1H, dd, J=13, 5 Hz, C<u>H</u>HCHN), 2.84 (1H, dd, J=13, 7 Hz, CH<u>H</u>CHN), 1.46 (9H, s, CMe$_3$); ESI-LCMS e/z calcd for C$_{37}$H$_{37}$NO$_5$S 607.760, found 608 (M+H)$^+$, 630 (M+Na)$^+$.

EXAMPLE 66

(2R)-3-[4'-(2-benzylbenzofuran-3-yl)biphen-4-ylmethylsulfanyl]-2-tert-butoxy-carbonylamino-propionic acid 1N Sodium hydroxide (2 mL) was added to a stirred solution of (2R)-methyl-3-[4'-(2-benzylbenzofuran-3-yl)biphen-4-ylmethylsulfanyl]-2-tert-butoxycarbonylamino-propionate (100 mg) in a mixture of tetrahydrofuran (6 mL) and methanol (2 mL). The solution was stirred for 1 hour and then acidified to pH 3 with 1N hydrochloric acid. The reaction mixture was extracted with ethyl acetate (3×10 mL). The combined extract was washed with water, brine, dried over anhydrous MgSO$_4$, filtered and concentrated in vacuo. Purification of the product by flash column chromatography, using 5% methanol in methylene chloride as eluent, afforded the title compound as a white solid (82 mg, 84%): mp. 89-90° C. Rf=0.50 (10% methanol in dichloromethane). $^1$H NMR (DMSO-d6, 300 MHz) δ 7.8 (2H, d, J=9 Hz, Ar—H), 7.6 (6H, m, Ar—H), 7.4 (2H, d, J=9 Hz, Ar—H), 7.28 (5H, m, Ar—H), 7.21 (2H, d, J=8 Hz, Ar—H), 6.42 (1H, d, J=8 Hz, NH), 4.26 (2H, s, PhCH2), 3.95 (1H, m, CHN), 3.75 (2H, s, PhCH2S), 2.9 (1H, dd, J=15, 5 Hz, C<u>H</u>HCHN), 2.74 (1H, dd, J=15, 8 Hz, CH<u>H</u>CHN), 1.39 (9H, s, tBu); ESI-LCMS e/z calcd for C$_{36}$H$_{35}$NO$_5$S 593.74, found 617 (M+Na)$^+$.

EXAMPLE 67

(2R,4RS)-3-[4'-(2-benzylbenzofuran-3-yl)biphen-4-ylmethylsulfinyl]-2-tert-butoxycarbonylaminopropionic acid

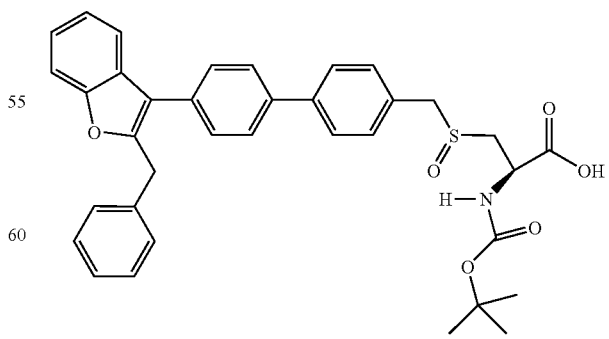

Sodium perborate tetrahydrate (18.3 mg, 0.12 mmol) was added as a solid to a stirred solution of (2R)-3-[4'-(2-benzylbenzofuran-3-yl)biphen-4-ylmethylsulfanyl]-2-tert-butoxycarbonylamino-propionic acid (70 mg, 0.12 mmol) in acetic acid (3 mL) at 40° C. This solution was stirred at 40° C. for 1 hour (HPLC control) and then diluted with ethyl acetate (50 mL), washed with water, brine (2×), dried over anhydrous MgSO$_4$, filtered and concentrated in vacuo. Purification by trituration of the product with diethyl ether afforded the title compound as a 1:1 mix of diastereoisomers as a white solid (68 mg, 93%): mp. 195-196° C. Rf 0.15 (20% methanol in dichloromethane). $^1$H NMR (DMSO-d6, 300 MHz) δ 7.82 (2H, m, Ar—H), 7.56-7.80 (6H, m, Ar—H), 7.4 (2H, d, m, Ar—H), 7.34-7.18 (7H, m, Ar—H), 6.42 (1H, br s, NH), 4.26 (2H, s, PhCH2), 4.20 (1H, m), 3.90 (2H, m, PhC$\underline{H}_2$S), 2.9 (2H, m C$\underline{HH}$CHN), 1.40 (9H, s, tBu); ESI-LCMS e/z calcd for C$_{36}$H$_{35}$NO$_6$S 609.730, found 610 (M+H)$^+$.

EXAMPLE 68

(2R)-3-[4'-(2-benzylbenzofuran-3-yl)biphen-4-ylmethylsulfonyl]-2-tert-butoxycarbonylaminopropionic acid Sodium perborate tetrahydrate (320 mg, 2.1 mmol) was added as a solid to a stirred solution of (2R)-3-[4'-(2-benzylbenzofuran-3-yl)biphen-4-ylmethylsulfanyl]-2-tert-butoxycarbonylamino-propionic acid (440 mg, 0.74 mmol) in acetic acid (10 mL) at 40° C. This solution was stirred at 40° C. for 2 hours (HPLC control) and then diluted with ethyl acetate (50 mL), washed with water, brine (2×), dried over anhydrous MgSO$_4$, filtered and concentrated in vacuo. Purification of the product by flash column chromatography, using 15% methanol in methylene chloride as eluent, afforded the title compound as a white solid (426 mg, 92%): mp. 202-203° C. Rf 0.40 (20% methanol in dichloromethane). $^1$H NMR (DMSO-d6, 300 MHz) δ 7.84 (2H, d, J=9 Hz, Ar—H), 7.74 (2H, d, J=9 Hz, Ar—H), 7.60 (4H, m, Ar—H), 7.48 (2H, d, J=9 Hz, Ar—H), 7.29 (5H, m, Ar—H), 7.22 (2H, d, J=8 Hz, Ar—H), 6.58 (1H, br s, NH), 4.51 (2H, s, PhCH2), 4.27 (2H, s, PhCH2S), 4.16 (1H, m, CHN), 3.56 (1H, dd, J=15, 5 Hz, C$\underline{HH}$CHN), 3.20 (1H, dd, J=15, 8 Hz, CH$\underline{H}$CHN), 1.37 (9H, s, tBu); ESI-LCMS e/z calcd for C$_{36}$H$_{35}$NO$_7$S 625.739, found 626 (M+H)$^+$.

EXAMPLE 69

(2R)-Methyl-2-Amino-3-[4'-(2-benzylbenzofuran-3-yl)biphen-4-ylmethylsulfanyl]-2-propionate TMSI (0.41 g, 0.29 mL, 2.06 mmol) was added dropwise to a stirred solution of (2R)-Methyl-3-[4'-(2-benzylbenzofuran-3-yl)biphen-4-ylmethylsulfanyl]-2-tert-butoxy-carbonylamino-propionate (1.0 g, 1.64 mmol) in anhydrous methylene chloride (10 mL). The reaction was stirred for 30 mins. and then poured into 1N sodium bicarbonate solution (10 mL), extracted with ethyl acetate (3×10 mL). The combined extract was washed with water, brine, dried over anhydrous MgSO$_4$, filtered and concentrated in vacuo. Purification of the product by flash column chromatography, using 5% methanol in methylene chloride as eluent, afforded the title compound as a pale yellow oil (790 mg, 95%). Rf=0.50 (5% methanol in dichloromethane). $^1$H NMR (DMSO-d6, 300 MHz) δ 7.7 (2H, m, Ar—H), 7.62 (5H, m, Ar—H), 7.44 (4H, m, Ar—H), 7.28 (6H, m, Ar—H), 4.26 (2H, s, PhCH$_2$), 3.80 (2H, s, PhC$\underline{H}_2$S), 3.74 (3H, s, OMe), 3.65 (1H, dd, J=7.5, 5 Hz, C$\underline{H}$N), 2.89 (1H, dd, J=15, 5 Hz, CH$\underline{H}$CHN), 2.73 (1H, dd, J=15, 7.5 Hz, C$\underline{HH}$CHN); ESI-LCMS e/z calcd for C$_{32}$H$_{29}$NO$_3$S 507.65, found 509 (M+H)$^+$.

EXAMPLE 70

(2R)-2-Benzoylamino-3-[4'-(2-benzylbenzofuran-3-yl)biphen-4-ylmethylsulfanyl]-propionic acid (2R)-2-Benzoylamino-3-[4'-(2-benzylbenzofuran-3-yl)biphen-4-ylmethylsulfanyl]-propionic acid was prepared according to the method described in Example 35, Method A, using benzoic acid as the corresponding carboxylic acid. The title compound was isolated as a white solid: mp. 138-139° C. Rf=0.25 (10% methanol in dichloromethane). $^1$H NMR (CDCl$_3$, 300 MHz) δ 7.74 (2H, d, J=9 Hz, Ar—H), 7.48-7.62 (6H, m, Ar—H), 7.30-7.42 (6H, m, Ar—H), 7.22 (8H, m, Ar—H), 6.90 (1H, d, J=8 Hz, NH), 4.88 (1H, d, J=8 Hz, CHN), 4.18 (2H, s, PhCH$_2$), 3.76 (2H, s, PhCH$_2$S), 3.06 (2H, d, J=8 Hz, C$\underline{H}_2$CHN); ESI-LCMS e/z calcd for C$_{38}$H$_{31}$NO$_4$S 597.732, found 599 (M+H)$^+$.

EXAMPLE 71

(2R)-2-Phenylacetylamino-3-[4'-(2-benzylbenzofuran-3-yl)biphen-4-ylmethyl-sulfanyl]-propionic acid

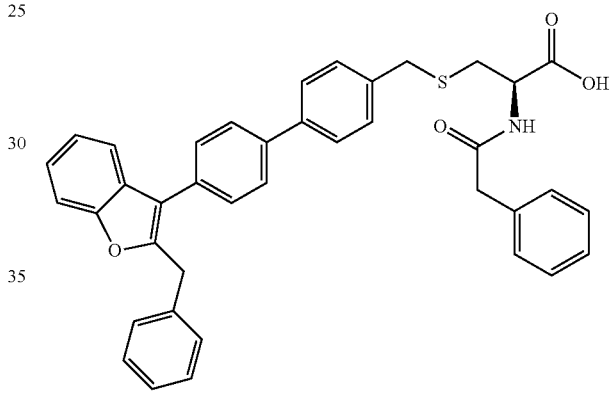

(2R)-2-Phenylacetylamino-3-[4'-(2-benzylbenzofuran-3-yl)biphen-4-ylmethylsulfanyl]-propionic acid was prepared according to the method described in Example 35, Method A, using phenylacetic acid as the corresponding carboxylic acid. The title compound was isolated as a white solid: mp. 77-78° C. Rf=0.25 (10% methanol in dichloromethane). $^1$H NMR (CDCl$_3$, 300 MHz) δ 7.56-7.72 (7H, m, Ar—H), 7.48 (1H, m, Ar—H), 7.20-7.40 (14H, m, Ar—H), 6.29 (1H, d, J=7 Hz, NH), 4.77 (1H, dd, J=13, 6 Hz, CHN), 4.25 (2H, s, PhCH$_2$), 3.66 (2H, s, PhC$\underline{H}_2$CO), 3.62 (2H, s, PhC$\underline{H}_2$S), 2.92 (2H, m, C$\underline{H}_2$CHN); ESI-LCMS e/z calcd for C$_{39}$H$_{33}$NO$_4$S 611.759, found 613 (M+H)$^+$.

EXAMPLE 72

(2R)-2-{3-Phenylpropionoylamino-3-[4'-(2-benzylbenzofuran-3-yl)biphen-4-ylmethylsulfanyl]}-propionic acid (2R)-2-{3-Phenylpropionoylamino-3-[4'-(2-benzylbenzofuran-3-yl)biphen-4-ylmethylsulfanyl]}-propionic acid was prepared according to the method described in Example 35, Method A, using 3-phenylpropionic acid as the corresponding carboxylic acid. The title compound was isolated as a white solid: mp. 158-159° C. Rf=0.28 (10% methanol in dichloromethane). $^1$H NMR (CDCl$_3$, 300 MHz) δ 7.58-7.66 (7H, m, Ar—H), 7.48 (1H, m, Ar—H), 7.38 (2H, m, Ar—H), 7.12-7.23 (12H, m, Ar—H), 6.16 (1H, d, J=8 Hz, NH), 4.76 (1H, dd, J=13, 6 Hz, CHN), 4.26 (2H, s, PhCH₂), 3.74 (2H, s, PhCH₂S), 2.94 (4H, m, C$\underline{H}_2$CHN+C$\underline{H}_2$CH₂CO) 2.52 (2H, m, C₂C$\underline{H}_2$CO); ESI-LCMS e/z calcd for C₄₀H₃₅NO₄S 625.786, found 626 (M+H)⁺.

EXAMPLE 73

(2R)-2-[(3H-Benzoimidazole-5-carbonyl)amino]-3-[4'-(2-benzylbenzofuran-3-yl)biphen-4-ylmethylsulfanyl]}-propionic acid

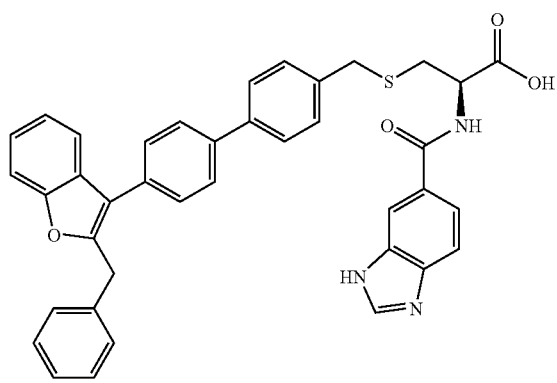

(2R)-2-[(3H-Benzoimidazole-5-carbonyl)amino]-3-[4'-(2-benzylbenzofuran-3-yl)biphen-4-ylmethylsulfanyl]}-propionic acid was prepared according to the method described in Example 35, Method A, using 3H-benzimidazole-5-carboxylic acid as the corresponding carboxylic acid. The title compound was isolated as an off-white solid: mp. 149-150° C. Rf=0.35 (15% methanol in dichloromethane). ¹H NMR (DMSO-d6, 300 MHz) δ 8.76 (1H, d, J=8 Hz, NH), 8.36 (1H, s, C$\underline{H}$N(=N)), 8.20 (1H, br s, NH), 7.76-7.82 (3H, m, Ar—H), 7.54-7.72 (8H, m, Ar—H), 7.42 (2H, d, J=8 Hz, Ar—H), 7.20-7.35 (7H, m, Ar—H), 4.65 (1H, m, CHN), 4.26 (2H, s, PhCH₂), 3.84 (2H, s, PhCH₂S), 2.94 (2H, m, C$\underline{H}_2$CHN); ESI-LCMS e/z calcd for C₃₉H₃₁N₃O₄S 637.757, found 638 (M+H)⁺.

EXAMPLE 74

(2R)-2-(4-Fluorophenylacetylamino)-3-[4'-(2-benzylbenzofuran-3-yl)biphen-4-ylmethylsulfanyl]-propionic acid (2R)-2-(4-Fluorophenylacetylamino)-3-[4'-(2-benzylbenzofuran-3-yl)biphen-4-ylmethylsulfanyl]-propionic acid was prepared according to the method described in Example 35, Method A, using 4-fluorophenylacetic acid as the corresponding carboxylic acid. The title compound was isolated as a white solid: mp. 82-84° C. Rf=0.15 (10% methanol in dichloromethane). ¹H NMR (CDCl₃, 300 MHz) δ 7.48-7.62 (7H, m, Ar—H), 7.42 (1H, d, J=8 Hz, Ar—H), 7.12-7.28 (11H, m, Ar—H), 6.94 (3H, m, Ar—H), 6.24 (1H, d, J=7 Hz, NH), 4.70 (1H, dd, J=13, 6 Hz, CHN), 4.18 (2H, s, PhCH₂), 3.62 (2H, s, PhC$\underline{H}_2$CO), 3.50 (2H, s, PhC$\underline{H}_2$S), 2.84 (2H, m, C$\underline{H}_2$CHN); ESI-LCMS e/z calcd for C₃₉H₃₂FNO₄S 629.749, found 630 (M+H)⁺.

EXAMPLE 75

(2R)-2-(3-Nitrophenylacetylamino)-3-[4'-(2-benzylbenzofuran-3-yl)biphen-4-ylmethylsulfanyl]-propionic acid (2R)-2-(3-Nitrophenylacetylamino)-3-[4'-(2-benzylbenzofuran-3-yl)biphen-4-ylmethylsulfanyl]-propionic acid was prepared according to the method described in Example 35, Method A, using 3-nitrophenylacetic acid as the corresponding carboxylic acid. The title compound was isolated as an off-white solid: mp. 108-109° C. Rf=0.10 (10% methanol in dichloromethane). ¹H NMR (CDCl₃, 300 MHz) δ 8.17 (1H, t, J=3 Hz, Ar—H), 8.12 (1H, dd, J=8, 3 Hz, Ar—H), 7.68 (2H, d, J=8 Hz, Ar—H), 7.56-7.62 (6H, m, Ar—H), 7.48 (2H, m, Ar—H), 7.36 (2H, d, J=8 Hz, Ar—H), 7.24-7.32 (7H, m, Ar—H), 6.36 (1H, d, J=7 Hz, NH), 4.80 (1H, dd, J=13, 6 Hz, CHN), 4.24 (2H, s, PhCH₂), 3.74 (2H, s, PhC$\underline{H}_2$CO), 3.66 (2H, s, PhC$\underline{H}_2$S), 2.90 (2H, d, J=6 Hz, C$\underline{H}_2$CHN); ESI-LCMS e/z calcd for C₃₉H₃₂N₂O₆S 656.756, found 657 (M+H)⁺.

EXAMPLE 76

(2R)-2-[(1H-Indole-5-carbonyl)amino]-3-[4'-(2-benzylbenzofuran-3-yl)biphen-4-ylmethylsulfanyl]}-propionic acid (2R)-2-[(1H-Indole-5-carbonyl)amino]-3-[4'-(2-benzylbenzofuran-3-yl)biphen-4-ylmethylsulfanyl]}-propionic acid was prepared according to the method described in Example 35, Method A, using 1H-indole-5-carboxylic acid as the corresponding carboxylic acid. The title compound was isolated as a white solid: mp. 181-182° C. Rf=0.40 (20% methanol in dichloromethane). ¹H NMR (DMSO-d6, 300 MHz) δ 11.36 (2H, br s, OH, NH), 8.16 (2H, s, Ar—H), 7.78 (2H, d, J=8 Hz, Ar—H), 7.54-7.66 (7H, m, Ar—H), 7.40 (4H, m, Ar—H), 7.18-7.36 (6H, m, Ar—H), 6.54 (1H, br s, Ar—H), 4.45 (1H, m, CHN), 4.26 (2H, s, PhCH₂), 3.78 (2H, dd, J=15, 13 Hz, PhCH₂S), 3.04 (1H, dd, J=13, 5 Hz, C$\underline{H}$HCHN) 2.95 (1H, dd, J=13, 7 Hz, CH$\underline{H}$CHN); ESI-LCMS e/z calcd for C₄₀H₃₂N₂O₄S 636.769, found 638 (M+H)⁺.

EXAMPLE 77

(2R)-2-(4-Nitrophenylacetylamino)-3-[4'-(2-benzylbenzofuran-3-yl)biphen-4-ylmethylsulfanyl]-propionic acid

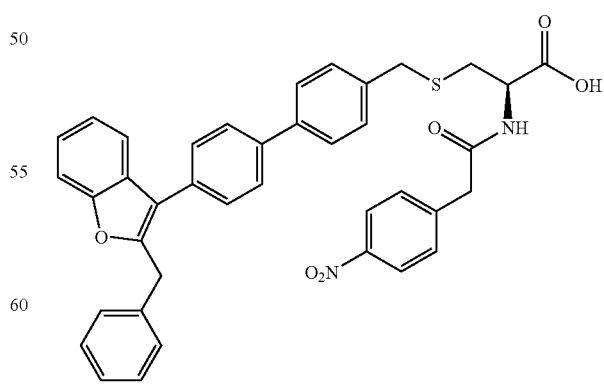

(2R)-2-(4-Nitrophenylacetylamino)-3-[4'-(2-benzylbenzofuran-3-yl)biphen-4-ylmethylsulfanyl]-propionic acid was prepared according to the method described in Example 35, Method A, using 4-nitrophenylacetic acid as the corresponding carboxylic acid. The title compound was isolated as an off-white solid: mp. 102-103° C. Rf=0.70 (20% methanol in dichloromethane). $^1$H NMR (DMSO-d6, 300 MHz) δ 8.68 (1H, d, J=8 Hz, NH), 8.16 (2H, d, J=9 Hz, Ar—H), 7.82 (2H, d, J=8 Hz, Ar—H), 7.64 (5H, m, Ar—H), 7.56 (3H, m, Ar—H), 7.31 (6H, m, Ar—H), 7.24 (3H, m, Ar—H), 4.46 (1H, ddd, J=13, 8, 5 Hz, CHN), 4.26 (2H, s, PhCH$_2$), 3.77 (2H, s, PhCH$_2$CO), 3.68 (2H, s, PhCH$_2$S), 2.82 (1H, dd, J=13, 5 Hz, CHHCHN), 2.70 (1H, dd, J=13, 8 Hz, CHHCHN); ESI-LCMS e/z calcd for $C_{39}H_{32}N_2O_6S$ 656.756, found 657 (M+H)$^+$.

EXAMPLE 78

(2R)-2-(2-Nitrophenylacetylamino)-3-[4'-(2-benzyl-benzofuran-3-yl)biphen-4-ylmethylsulfanyl]-propionic acid (2R)-2-(2-Nitrophenylacetylamino)-3-[4'-(2-benzylbenzofuran-3-yl)biphen-4-ylmethylsulfanyl]-propionic acid was prepared according to the method described in Example 35, Method A, using 2-nitrophenylacetic acid as the corresponding carboxylic acid. The title compound was isolated as an off-white solid: mp. 189-191° C. Rf=0.72 (20% methanol in dichloromethane). $^1$H NMR (DMSO-d6, 300 MHz) δ 8.16 (1H, d, J=8 Hz, NH), 7.97 (1H, d, J=8 Hz, Ar—H), 7.82 (2H, d, J=8 Hz, Ar—H), 7.64 (65H, m, Ar—H), 7.52 (3H, m, Ar—H), 7.38 (2H, d, J=9 Hz, Ar—H), 7.30 (4H, m, Ar—H), 7.24 (3H, m, Ar—H), 4.30 (3H, m, CHN+PhCH$_2$), 3.96 (2H, s, PhCH$_2$CO), 3.68 (2H, dd, J=16, 12 Hz, PhCH$_2$S), 2.85 (1H, dd, J=16, 5 Hz, CHHCHN), 2.70 (1H, dd, J=16, 7 Hz, CHHCHN); ESI-LCMS e/z calcd for $C_{39}H_{32}N_2O_6S$ 656.756, found 657 (M+H)$^+$.

EXAMPLE 79

(2R)-2-(4-Hydroxyphenylacetylamino)-3-[4'-(2-benzylbenzofuran-3-yl)biphen-4-ylmethylsulfanyl]-propionic acid

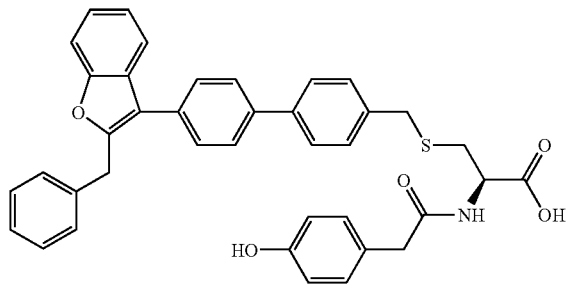

(2R)-2-(4-Hydroxyphenylacetylamino)-3-[4'-(2-benzylbenzofuran-3-yl)biphen-4-ylmethylsulfanyl]-propionic acid was prepared according to the method described in Example 35, Method A, using 4-hydroxyphenylacetic acid as the corresponding carboxylic acid. The title compound was isolated as a white solid: mp. 148-149° C. Rf=0.60 (20% methanol in dichloromethane). $^1$H NMR (DMSO-d6, 300 MHz) δ 9.30 (1H, br s, OH), 7.82 (2H, d, J=8 Hz, Ar—H), 7.70 (1H, d, J=8 Hz, NH), 7.62 (5H, m, Ar—H), 7.56 (1H, d, J=7 Hz, Ar—H), 7.30 (6H, m, Ar—H), 7.22 (3H, m, Ar—H), 7.18 (2H, d, J=8 Hz, Ar—H), 6.67 (1H, d, J=8 Hz, Ar—H), 4.26 (2H, s, PhCH$_2$), 4.18 (1H, m, CHN), 3.73 (2H, d, J=13 Hz, PhCHHCO), 3.66 (1H, d, J=13 Hz, PhCHHCO), 3.38 (2H, m, PhCH$_2$S), 2.88 (1H, dd, J=13, 5 Hz, CHHCHN), 2.76 (1H, dd, J=13, 7 Hz, CHHCHN); ESI-LCMS e/z calcd for $C_{39}H_{33}NO_5S$ 627.758, found 628 (M+H)$^+$.

EXAMPLE 80

(2R)-2-Acetylamino-3-[4'-(2-benzylbenzofuran-3-yl)biphen-4-ylmethylsulfanyl]-propionic acid (2R)-2-Acetylamino-3-[4'-(2-benzylbenzofuran-3-yl)biphen-4-ylmethylsulfanyl]-propionic acid was prepared according to the method described in Example 35, Method B, using acetyl chloride as the corresponding acylating reagent. The title compound was isolated as a white solid: mp. 131-132° C. Rf=0.60 (20% methanol in dichloromethane). $^1$H NMR (DMSO-d6, 300 MHz) δ 7.82 (2H, d, J=9 Hz, Ar—H), 7.64 (5H, m, Ar—H), 7.56 (1H, d, J=8 Hz, NH), 7.40 (2H, m, Ar—H), 7.31 (5H, m, Ar—H), 7.24 (3H, m, Ar—H), 4.26 (3H, m, CHN+PhCH$_2$), 3.77 (2H, s, PhCH$_2$S), 2.82 (1H, dd, J=13, 5 Hz, CHHCHN), 2.69 (1H, dd, J=13, 8 Hz, CHHCHN), 1.85 (3H, s, CH$_3$CO); ESI-LCMS e/z calcd for $C_{33}H_{29}NO_4S$ 536.661, found 537 (M+H)$^+$.

EXAMPLE 81

(2R)-2-(4-Methoxyphenylacetylamino)-3-[4'-(2-benzylbenzofuran-3-yl)biphen-4-ylmethylsulfanyl]-propionic acid (2R)-2-(4-Methoxyphenylacetylamino)-3-[4'-(2-benzyl-benzofuran-3-yl)biphen-4-ylmethylsulfanyl]-propionic acid was prepared according to the method described in Example 35, Method A, using 4-methoxyphenylacetic acid as the corresponding carboxylic acid. The title compound was isolated as a white solid: mp. 59-60° C. Rf=0.75 (20% methanol in dichloromethane). $^1$H NMR (DMSO-d6, 300 MHz) δ 8.40 (1H, d, J=8 Hz, NH), 7.84 (2H, d, J=8 Hz, Ar—H), 7.64 (5H, m, Ar—H), 7.30 (5H, m, Ar—H), 7.20 (5H, m, Ar—H), 6.84 (3H, m, Ar—H), 4.42 (1H, m, CHN), 4.27 (2H, s, PhCH$_2$), 3.76 (2H, s, PhCH$_2$CO), 3.71 (2H, s, PhCH$_2$S), 3.68 (3H, s, OMe), 2.84 (1H, dd, J=13, 5 Hz, CHHCHN), 2.68 (1H, dd, J=13, 7 Hz, CHHCHN); ESI-LCMS e/z calcd for $C_{40}H_{35}NO_5S$ 641.784, found 643 (M+H)$^+$.

EXAMPLE 82

(2R)-2-(4-Aminophenylacetylamino)-3-[4'-(2-benzylbenzofuran-3-yl)biphen-4-ylmethylsulfanyl]-propionic acid (2R)-2-(4-Aminophenylacetylamino)-3-[4'-(2-benzylbenzofuran-3-yl)biphen-4-ylmethylsulfanyl]-propionic acid was prepared according to the method described in Example 35, Method A, using 4-aminophenylacetic acid as the corresponding carboxylic acid. The title compound was isolated as a pale yellow solid: mp. 170-172° C. Rf=0.50 (20% methanol in dichloromethane). $^1$H NMR (DMSO-d6, 300 MHz) δ 7.81 (2H, d, J=8 Hz, Ar—H), 7.64 (6H, m, Ar—H), 7.52 (1H, m, NH), 7.30 (7H, m, Ar—H), 7.21 (2H, d, J=8 Hz, Ar—H), 6.84 (2H, d, J=8 Hz, Ar—H), 6.48 (2H, d, J=8 Hz, Ar—H), 4.26 (2H, s, PhCH$_2$), 4.16 (1H, m, CHN), 3.72 (1H, d, J=13 Hz, PhCHHCO), 3.68 (1H, d, J=13 Hz, PhCHHCO), 3.28 (2H, s, PhCH$_2$S), 2.89 (1H, dd, J=13, 5 Hz, CHHCHN), 2.76 (1H, dd, J=13, 7 Hz, CHHCHN); ESI-LCMS e/z calcd for C$_{39}$H$_{34}$N$_2$O$_4$S 626.774, found 627 (M+H)$^+$.

EXAMPLE 83

(2R)-3-[4'-(2-Benzylbenzofuran-3-yl)biphen-4-ylmethylsulfanyl]-2-methoxy-carbonylaminopropionic acid

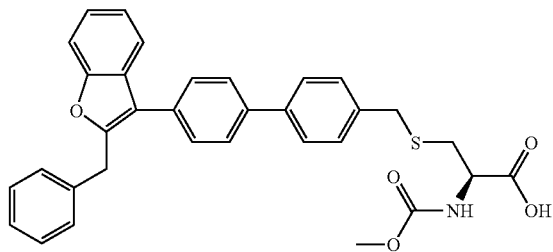

(2R)-3-[4'-(2-Benzylbenzofuran-3-yl)biphen-4-ylmethylsulfanyl]-2-methoxycarbonyl-aminopropionic acid was prepared according to the method described in Example 35, Method B, using methyl chloroformate as the corresponding acylating reagent. The title compound was isolated as a white solid: Rf=0.20 (10% methanol in dichloromethane). $^1$H NMR (DMSO-d6, 300 MHz) δ 7.84 (2H, d, J=9 Hz, Ar—H), 7.68 (2H, d, J=9 Hz, Ar—H), 7.60 (5H, m, Ar—H), 7.41 (2H, d, J=9 Hz, Ar—H), 7.26 (5H, m, Ar—H, NH), 7.20 (2H, d, J=8 Hz, Ar—H), 4.28 (2H, s, PhCH2), 4.18 (1H, m, CHN), 3.79 (2H, s, PhCH$_2$S), 3.55 (3H, s, OMe), 2.86 (1H, dd, J=13, 5 Hz, CHHCHN), 2.69 (1H, dd, J=13, 8 Hz, CHHCHN); ESI-LCMS e/z calcd for C$_{33}$H$_{29}$NO$_5$S 551.660, found 551: M$^+$.

EXAMPLE 84

(2R)-3-[4'-(2-Benzylbenzofuran-3-yl)biphen-4-ylmethylsulfanyl]-2-isobutoxy-carbonylaminopropionic acid (2R)-3-[4'-(2-Benzylbenzofuran-3-yl)biphen-4-ylmethylsulfanyl]-2-isobutoxy-carbonylaminopropionic acid was prepared according to the method described in Example 35, Method B, using isobutyl chloroformate as the corresponding acylating reagent. The title compound was isolated as a pale yellow solid: Rf=0.30 (10% methanol in dichloromethane). $^1$H NMR (DMSO-d6, 300 MHz) δ 7.82 (2H, d, J=9 Hz, Ar—H), 7.72 (2H, d, J=9 Hz, Ar—H), 7.64 (4H, m, Ar—H), 7.49 (1H, d, J=8 Hz, NH), 7.40 (2H, d, J=9 Hz, Ar—H), 7.31 (5H, m, Ar—H), 7.24 (2H, d, J=8 Hz, Ar—H), 4.26 (2H, s, PhCH2), 4.18 (1H, m, CHN), 3.79 (2H, s, PhCH$_2$S), 3.66 (2H, m, OCH$_2$), 2.82 (1H, dd, J=13, 5 Hz, CHHCHN), 2.71 (1H, dd, J=13, 8 Hz, CHHCHN), 1.84 (1H, m, CHMe$_2$), 0.87 (6H, d, J=7 Hz); ESI-LCMS e/z calcd for C$_{36}$H$_{35}$NO$_5$S 593.740, found 617: (M+Na)$^+$.

EXAMPLE 85

(2R)-3-[4'-(2-Benzylbenzofuran-3-yl)biphen-4-ylmethylsulfanyl]-2-[(morpholine-4-carbonyl)amino] propionic acid (2R)-3-[4'-(2-Benzylbenzofuran-3-yl)biphen-4-ylmethylsulfanyl]-2-[(morpholine-4-carbonyl)amino]propionic acid was prepared according to the method described in Example 35, Method B, using 4-morpholinylcarbonyl chloride as the corresponding acylating reagent. The title compound was isolated as an off-white solid: Rf=0.10 (10% methanol in dichloromethane). $^1$H NMR (DMSO-d6, 300 MHz) δ 7.84 (2H, d, J=9 Hz, Ar—H), 7.78 (2H, d, J=9 Hz, Ar—H), 7.64 (4H, m, Ar—H), 7.42 (2H, d, J=9 Hz, Ar—H), 7.32 (5H, m, Ar—H), 7.26 (2H, d, J=8 Hz, Ar—H), 6.82 (1H, d, J=8 Hz, NH), 4.30 (3H, m, PhCH$_2$+CHN), 3.79 (2H, s, PhCH$_2$S), 3.52 (4H, m, CH$_2$OCH$_2$), 3.31 (4H, m, CH$_2$NCH$_2$), 2.82 (1H, dd, J=13, 5 Hz, CHHCHN), 2.73 (1H, dd, J=13, 8 Hz, CHHCHN); ESI-LCMS e/z calcd for C$_{36}$H$_{34}$N$_2$O$_5$S 606.740, found 607: (M+H)$^+$.

EXAMPLE 86

(2R)-3-[4'-(2-Benzylbenzofuran-3-yl)biphen-4-ylmethylsulfanyl]-2-(3,3-dimethyl-ureido)-propionic acid (2R)-3-[4'-(2-Benzylbenzofuran-3-yl)biphen-4-ylmethylsulfanyl]-2-(3,3-dimethyl-ureido)-propionic acid was prepared according to the method described in Example 35, Method B, using N,N-Dimethylcarbamoyl chloride as the corresponding acylating reagent. The title compound was isolated as a pale yellow waxy solid: Rf=0.10 (10% methanol in dichloromethane). $^1$H NMR (DMSO-d6, 300 MHz) δ 7.83 (2H, d, J=9 Hz, Ar—H), 7.76 (2H, m, Ar—H), 7.62 (4H, m, Ar—H), 7.42 (2H, d, m, Ar—H), 7.30 (4H, m, Ar—H), 7.22 (3H, d, J=8 Hz, Ar—H), 6.48 (1H, d, J=8 Hz, NH), 4.26 (3H, m, PhCH$_2$+CHN), 3.80 (2H, s, PhCH$_2$S), 3.18 (2H, m CH$_2$CHN), 2.80 (6H, s, NMe$_2$); ESI-LCMS e/z calcd for C$_{34}$H$_{32}$N$_2$O$_4$S 564.703, found 565 (M+H)$^+$.

EXAMPLE 87

(2R)-3-[4'-(2-Benzylbenzofuran-3-yl)biphen-4-ylmethylsulfanyl]-2-benzyloxy-carbonylaminopropionic acid (2R)-3-[4'-(2-Benzylbenzofuran-3-yl)biphen-4-ylmethylsulfanyl]-2-benzyloxy-carbonylaminopropionic acid was prepared according to the method described in Example 35, Method B, using benzyl chloroformate as the corresponding acylating reagent. The title compound was isolated as an off-white solid: Rf=0.20 (10% methanol in dichloromethane). $^1$H NMR (DMSO-d6, 300 MHz) δ 7.84 (2H, d, J=9 Hz, Ar—H), 7.58-7.75 (6H, m, Ar—H, NH), 7.40 (2H, d, J=8 Hz, Ar—H), 7.26-7.36 (10H, m, Ar—H), 7.24 (3H, d, J=8 Hz, Ar—H), 5.06 (2H, s, OCH$_2$), 4.26 (2H, s, PhCH$_2$), 4.18 (1H, m, CHN), 3.82 (2H, s, PhCH$_2$S), 2.85 (1H, dd, J=13, 5 Hz, CHHCHN), 2.73 (1H, dd, J=13, 8 Hz, CHHCHN); ESI-LCMS e/z calcd for C$_{39}$H$_{33}$NO$_5$S 627.758, found 628: (M+H)$^+$.

EXAMPLE 88

(2R)-3-[4'-(2-Benzylbenzofuran-3-yl)biphen-4-ylmethylsulfanyl]-2-(4-methyl-3-nitrobenzenesulfonylamino)-propionic acid (2R)-3-[4'-(2-Benzylbenzofuran-3-yl)biphen-4-ylmethylsulfanyl]-2-(4-methyl-3-nitrobenzenesulfonylamino)-propionic acid was prepared according to the method described in Example 35, Method B, using 4-methyl-3-nitrobenzenesulfonyl chloride as the corresponding acylating reagent. The title compound was isolated as a white solid: Rf=0.45 (10% methanol in dichloromethane). $^1$H NMR (CDCl$_3$, 300 MHz)

δ 8.56 (1H, s, Ar—H), 7.99 (1H, d, J=9 Hz, Ar—H), 7.58-7.75 (7H, m, Ar—H), 7.42 (2H, m, Ar—H), 7.36 (2H, m, Ar—H), 7.21-7.36 (7H, m, Ar—H), 4.21 (3H, m, PhCH$_2$+CHN), 3.82 (2H, s, PhCH$_2$S), 2.95 (2H, m, CH$_2$CHN), 2.42 (3H, s, Me); ESI-LCMS e/z calcd for C$_{38}$H$_{32}$N$_2$O$_7$S$_2$ 692.810, found 693 (M+H)$^+$.

EXAMPLE 89

2-Chloro-4,6-diphenylpyrimidine

A mixture of 2,4,6-trichloropyrimidine, 2.76 g (15.0 mmol), phenylboronic acid, 3.66 g (30.0 mmol), Pd(OAc)$_2$, 86 mg (0.38 mmol), triphenylphosphine, 200 mg (0.76 mmol) in 150 mL of ethylene glycol dimethyl ether was heated to obtain a clear solution. To the solution was added 25 mL of 4.0M aq. Na$_2$CO$_3$. The reaction mixture was refluxed for 24 h at 70° C. The mixture was cooled to room temperature and diluted with 100 mL ethyl acetate. The organic layer was washed with water, sat. aq. NaCl, and dried (MgSO$_4$). After the solution was concentrated, the residue was recrystallized with Et$_2$O-Heptane (1:3) to afford the desired product in 1.64 g (41%) as a pale yellow solid. $^1$H NMR (CDCl$_3$) 8.15-8.12 (m, 4H), 8.02 (s, 1H), 7.57-7.51 (m, 6H).

EXAMPLE 90

[4-(4,6-Diphenylpyrimidin-2-yl)-phenyl]methanol

A mixture of 2-chloro-4,6-diphenylpryimidine, 0.79 g (2.96 mmol), 4-(hydroxylmethyl)phenylboronic acid, 0.45 g (2.96 mmol), Pd(PPh$_3$)$_4$, 342 mg (0.296 mmol), in 2 mL of toluene and 1 mL of methanol was heated to obtain a clear solution. To the solution was added 2 mL of 4.0M aq. Na$_2$CO$_3$. The reaction mixture refluxed for 16 h at 70° C. The mixture was cooled to room temperature and diluted with 100 mL ethyl acetate. The organic layer was washed with water, sat. aq. NaCl, and dried (MgSO$_4$). After the solution was concentrated, the residue was recrystallized with Et$_2$O-Heptane (1:1) to afford the desired product in 0.38 g (38%) as a yellow solid. $^1$H NMR (DMSO-d$_6$) 8.72 (d, 2H, J=9.0 Hz), 8.52-8.47 (m, 4H), 8.45 (s, 1H), 7.64-7.57 (m, 8H), 4.78 (d, 2H, J=6.7 Hz), 4.37 (t, 1H, J=6.7 Hz).

EXAMPLE 91

Methanesulfonic acid 4-(4,6-diphenylpyrimidin-2-yl)-benzyl ester

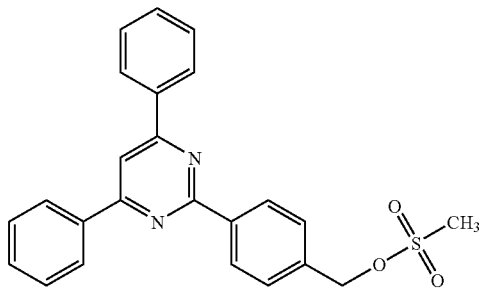

A solution of [4-(4,6-diphenylpyrimidin-2-yl)-phenyl] methanol, 0.38 g (1.11 mmol), triethylamine, 0.34 mL (2.45 mmol), and 6 mL of methylene chloride was cooled to 0° C. via ice-water bath. Methanesulfonyl chloride, 0.10 mL (1.23 mmol) was added dropwise over minutes. The solution stirred for 2 h at 0° C. The solution was quenched with 20 mL of water and diluted with 20 mL of ethyl acetate. The organic layer was washed with water, sat. aq. NaCl, and dried (MgSO$_4$). After the solution was concentrated, the residue was recrystallized with EtOAc-Heptane (1:2) to afford the desired product in 0.44 g (95%) as a yellow solid. $^1$H NMR (DMSO-d$_6$) 8.77 (d, 2H, J=9.0), 8.44-8.41 (m, 4H), 8.30 (s, 1H), 7.68-7.61 (m, 8H), 5.37 (s, 2H), 3.11 (s, 3H).

EXAMPLE 92

2-tert-Butoxy carbonylamino-3-[4-(4,6-diphenylpyrimidin-2-yl)-benzylsulfanyl] propionic acid methyl ester A mixture of Methanesulfonic acid 4-(4,6-diphenylpyrimidin-2-yl)-benzyl ester, 0.15 g (0.36 mmol), N-(tert-Butoxycarbonyl)-L-cysteine methyl ester, 0.08 mL (0.36 mmol), cesium carbonate, 235 mg (0.72 mmol), and 10 mL of N,N-dimethylformamide was stirred at room temperature for 4 h. The mixture was diluted with 10 mL of water and extracted with 2×50 mL of ethyl acetate. The organic layer was washed with 2×50 mL portions of aq. LiCl, sat. aq. NaHCO$_3$, sat. aq. NaCl, and dried (MgSO$_4$). After the solution was concentrated, the residue was purified by column chromatography (eluted with 7% EtOAc-Heptane) to afford the desired product in 0.18 g (90%) as a white solid. $^1$H NMR (CDCl$_3$) 8.67 (d, 2H, J=9.0 Hz), 8.30-8.27 (m, 4H), 8.02 (s, 1H), 7.61-7.55 (m, 6H), 7.47 (d, 2H, J=9.0 Hz), 5.30 (d, 1H, J=7.7 Hz), 4.63-4.52 (m, 1H), 3.82 (s, 2H), 3.76 (s, 3H), 2.93 (dd, 1H, J=15.7, 6.0 Hz), 2.84 (dd, 1H, J=15.7, 6.7 Hz), 1.47 (s, 9H).

EXAMPLE 93

2-tert-Butoxy carbonylamino-3-[4-(4,6-diphenylpyrimidin-2-yl)-benzylsulfanyl] propionic acid.

To a solution of 2-tert-Butoxy carbonylamino-3-[4-(4,6-diphenylpyrimidin-2-yl)-benzylsulfanyl]-propionic acid methyl ester, 0.18 g (0.32 mmol) in 10 mL of tetrahydrofuran and 5 mL of methanol was added 1.62 mL of 1.0M aq. KOH. The solution was stirred for 1 h at room temperature. The solution was diluted with 10 mL of water and acidified to pH 1-2. The aqueous was extracted with 3×30 mL portions of diethyl ether. The organic layers were combined, washed with sat. aq. NaHCO$_3$, sat. aq. NaCl, dried (MgSO$_4$). The solution was concentrated to the desired product in 0.10 g (57%) as an off-white solid. MP 250° C. decomp, R$_f$ 0.09 (100% Ethyl Acetate); $^1$H NMR (DMSO-d$_6$) 8.57 (d, 2H, J=9.3), 8.52-8.46 b (m, 5H), 7.60-7.58 (m, 6H), 7.51 (d, 2H, J=9.3), 4.11 (m, 1H), 3.86 (s, 3H), 2.81 (dd, 1H, J=14.8, 5.0 Hz), 2.67 (dd, 1H, J=15.3, 10.3), 1.39 (s, 9H). LCMS m/z calcd for C$_{31}$H$_{31}$N$_3$O$_4$S: 541.2 found 542.6(M+1)

EXAMPLE 94

2-Acetylmino-3-[4-(4,6-diphenylpyrimidin-2-yl)-benzylsulfanyl]-propionic acid methyl ester A mixture of Methanesulfonic acid 4-(4,6-diphenylpyrimidin-2-yl)-benzyl ester, 0.14 g (0.34 mmol), N-acetyl-L-cysteine methyl ester, 60 mg (0.346 mmol), cesium carbonate, 219 mg (0.67 mmol), and 10 mL of N,N-dimethylformamide was stirred at room temperature for 4 h. The mixture was diluted with 10 mL of water and extracted with 2×50 mL of ethyl acetate. The organic layer was washed with 2×50 mL portions of aq. LiCl, sat. aq. NaHCO$_3$, sat. aq. NaCl, and dried (MgSO$_4$). After the solution was concentrated, the residue was purified by column chromatography (eluted with 7% EtOAc-Heptane) to afford the desired product in 90 mg (54%) as a pale yellow solid. $^1$H NMR (CDCl$_3$) 8.67 (d, 2H, J=9.3 Hz), 8.30-8.25 (m, 4H), 8.02 (s, 1H), 7.61-7.55 (m, 6H), 7.46 (d, 2H, J=9.3 Hz), 6.16 (d, 1H, 7.7 Hz), 4.87-4.81 (m, 1H), 3.80 (s, 2H), 3.77 (s, 3H), 2.97 (dd, 1H, J=15.0, 5.3 Hz), 2.91 (dd, 1H, J=15.7, 6.3 Hz), 2.02 (s, 3H).

EXAMPLE 95

2-Acetylamino-3-[4-(4,6-diphenyl-pyrimidin-2-yl)-benzylsulfanyl]-propionic acid

To a solution of 2-acetylmino-3-[4-(4,6-diphenylpyrimidin-2-yl)-benzylsulfanyl]-propionic acid methyl ester, 90 mg (0.18 mmol) in 10 mL of tetrahydrofuran and 5 mL of methanol was added 0.90 mL of 1.0M aq. KOH. The solution was stirred for 1 h at room temperature. The solution was diluted with 10 mL of water and acidified to pH 1-2. The aqueous was extracted with 3×30 mL portions of diethyl ether. The organic layers were combined, washed with sat. aq. NaHCO$_3$, sat. aq. NaCl, dried (MgSO$_4$). The solution was concentrated to afford the desired product in 60 mg (69%) as a white solid. MP 223-226° C., R$_f$=0.07 (100% Ethyl Acetate); $^1$H NMR (CDCl$_3$) 8.55 (d, 2H, J=9.3), 8.20-8.15 (m, 4H), 7.93 (s, 1H), 7.52-7.45 (m, 6H), 7.40 (d, 2H, J=9.3), 6.13 (d, 1H, J=8.0 Hz), 4.63 (q, 1H, J=13.3, 5.8 Hz), 3.74 (s, 2H), 2.96 (dd, 1H, J=15.7, 6.0 Hz), 2.87 (dd, 1H, J=15.7, 6.3), 1.94 (s, 3H). LCMS m/z calcd for C$_{28}$H$_{25}$N$_3$O$_3$S: 483.2 found 484.4(M+1).

EXAMPLE 96

4'-Bromo-biphenyl-4-carboxylic acid methyl ester

A mixture of methyl 4-iodobenzoate, 9.38 g (35.8 mmol), 4-bromophenylboronic acid 7.18 g (35.8 mmol), Pd(PPh$_3$)$_4$, 2.07 g (1.79 mmol), in 180 mL of toluene and 100 mL of ethanol was heated to obtain a clear solution. To the solution was added 30 mL of 4.0M aq. Na$_2$CO$_3$. The reaction mixture refluxed for 4 h at 80° C. The mixture was cooled to room temperature and diluted with 300 mL ethyl acetate. The organic layer was washed with 2×300 mL portions of water, 2×300 mL portions of sat. aq. NaCl, and dried (MgSO$_4$). After the solution was concentrated, the residue was purified by column chromatography (eluted with 7% EtOAc-Heptane) to afford the desired product in 7.8 g (78%) as a white solid. $^1$H NMR (CDCl$_3$) 8.10 (d, 2H, J=9.0 Hz), 7.62 (d, 2H, J=9.0 Hz), 7.59 (d, 2H, J=9.3 Hz), 7.48 (d, 2H, J=9.3 Hz), 3.95 (s, 3H).

EXAMPLE 97

(4'-Bromo-biphenyl-4-yl)-methanol

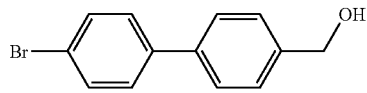

A solution of 4'-Bromo-biphenyl-4-carboxylic acid methyl ester, 7.8 g (27.9 mmol) in 150 mL of tetrahydrofuran was cooled to 0° C. via ice-water bath. Lithium aluminum hydride, 1.1 g (27.9 mmol) was added to the solution in one portion. The reaction mixture stirred at 0° C. for 1 h. The mixture was slowly quenched with 10 mL of isopropyl alcohol, then with 10 mL of water. The aqueous mixture was extracted with 3×50 mL portions of ethyl acetate. The organic layers were combined, washed with sat. aq. NaCl, and dried (MgSO$_4$). The solution was concentrated to afford the desired product in 7.01 g (100%) as a white solid. The material was taken to the next step without further purification.

EXAMPLE 98

4'-Bromo-4-bromomethyl-biphenyl

A solution of (4'-bromo-biphenyl-4-yl)-methanol, 7.01 g (27.9 mmol) and dibromo-triphenylphosphorane 11.8 g (27.9 mmol) in 150 mL of methylene chloride stirred at room temperature for 2 h. The solution was diluted with 100 mL of water and extracted with 2×200 mL portions of diethyl ether. The organic layers were combined, washed with sat. aq. NaCl, and dried (MgSO$_4$). After the solution was concentrated, the residue was purified through a short plug of silica gel (eluted with 50% EtOAc-Heptane) to afford the desired product in 9.1 g (100%) as a white solid. The material was taken to the next step without further purification.

EXAMPLE 99

3-(4'-Bromobiphenyl-4-ylmethylsulfanyl)-2-tert-butoxycarbonylamino-propionic acid methyl ester A mixture of 4'-Bromo-4-bromomethyl-biphenyl, 9.1 g (27.9 mmol), N-(tert-Butoxy-carbonyl)-L-cysteine methyl ester, 5.74 mL (27.9 mmol), cesium carbonate, 18.2 g (55.8 mmol), and 100 mL of N,N-dimethylformamide was stirred at room temperature for 4 h. The mixture was diluted with 200 mL of water and extracted with 2×200 mL of ethyl acetate. The organic layer was washed with 2×200 mL portions of aq. LiCl, sat. aq. NaHCO$_3$, sat. aq. NaCl, and dried (MgSO$_4$). After the solution was concentrated, the residue was purified through a short plug of silica gel (eluted with 20% EtOAc-Heptane) to afford the desired product in 8.8 g (66%) as a white solid. $^1$H NMR (CDCl$_3$) 7.55 (d, 2H, J=9.3 Hz), 7.50 (d, 2H, J=9.0 Hz), 7.43 (d, 2H, J=9.3 Hz), 7.37 (d, 2H, J=9.0 Hz), 5.31 (d, 1H, J=9.0 Hz), 4.62-4.51 (m, 1H), 3.76 (s, 5H), 2.93 (dd, 1H, 15.7, 5.7 Hz), 2.84 (dd, 1H, 15.7, 6.3 Hz), 1.47 (s, 9H).

EXAMPLE 100

3-(4'-Benzo[1,3]dioxol-5-yl-biphenyl-4-ylmethylsulfanyl)-2-tert-butoxycarbonyl amino-propionic acid methyl ester A mixture of 3-(4'-bromobiphenyl-4-ylmethylsulfanyl)-2-tert-butoxycarbonylamino-propionic acid methyl ester, 0.26 g (0.54 mmol), 3,4-methylenedioxyphenylboronic acid, 90 mg (0.54 mmol), Pd(PPh$_3$)$_4$, 63 mg (0.054 mmol), in 5 mL of toluene and 3 mL of ethanol was heated to obtain a clear solution. To the solution was added 5 mL of 0.4M aq. Na$_2$CO$_3$. The reaction mixture refluxed for 4 h at 80° C. The mixture was cooled to room temperature and diluted with 100 mL ethyl acetate. The organic layer was washed with 2×50 mL portions of water, 2×50 mL portions of sat. aq. NaCl, and dried (MgSO$_4$). After the solution was concentrated, the residue was purified by column chromatography (eluted with 7%

EtOAc-Heptane) to afford the desired product in 0.13 g (46%) as a white solid. $^1$H NMR (CDCl$_3$) 7.64-7.56 (m, 6H), 7.38 (d, 2H, J=9.3 Hz), 7.10 (dd, 2H, J=6.7, 2.0 Hz), 6.90 (d, 1H, J=9.3 Hz), 6.01 (s, 2H), 5.32 (d, 1H, J=8.0 Hz), 4.63-4.52 (m, 1H), 3.78 (s, 2H), 3.76 (s, 3H), 2.95 (dd, 1H, J=15.7, 5.3 Hz), 2.85 (dd, 1H, J=15.7, 6.3 Hz), 1.47 (s, 9H).

EXAMPLE 101

3-(4'-Benzo[1,3]dioxol-5-yl-biphenyl-4-ylmethylsulfanyl)-2-tert-butoxycarbonylamino-propionic acid

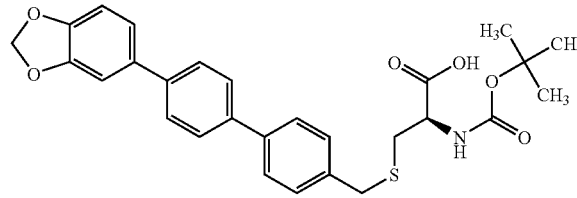

To a solution of 3-(4'-benzo[1,3]dioxol-5-yl-biphenyl-4-ylmethylsulfanyl)-2-tert-butoxycarbonyl amino-propionic acid, 130 mg (0.25 mmol) in 10 mL of tetrahydrofuran was added 1.25 mL of 6.0M aq. KOH. The solution was stirred for 1 h at room temperature. The solution was diluted with 10 mL of water and acidified to pH 1-2. The aqueous was extracted with 3×30 mL portions of diethyl ether. The organic layers were combined, washed with sat. aq. NaHCO$_3$, sat. aq. NaCl, dried (MgSO$_4$). The solution was concentrated to afford the desired product in 78 mg (61%) as an off-white solid. MP 178-180° C., R$_f$ 0.25 (10% Methanol-90% Methylene Chloride); $^1$H NMR (DMSO-d$_6$) δ 7.71-7.62 (m, 6H), 7.39 (d, 2H, J=9.3 Hz), 7.29 (d, 1H, J=2.0 Hz), 7.20-7.13 (m, 2H), 6.99 (d, 1H, J=9.3 Hz), 6.05 (s, 2H), 4.19-4.08 (m, 1H), 3.79 (s, 2H), 2.80 (dd, 1H, J=15.0, 5.7 Hz), 2.66 (dd, 1H, J=15.0, 10.3 Hz), 1.40 (s, 9H). LCMS m/z calcd for C$_{28}$H$_{29}$NO$_6$S: 507.2 found 508.0(M+1).

EXAMPLE 102

3-(2"-Acetyl-[1,1',4'1"]terphenyl-4-ylmethylsulfanyl)-2-tert-butoxycarbonylamino-propionic acid methyl ester A mixture of 3-(4'-bromobiphenyl-4-ylmethylsulfanyl)-2-tert-butoxycarbonylamino-propionic acid methyl ester, 0.26 g (0.54 mmol), 2-acetylphenylboronic acid, 89 mg (0.54 mmol), Pd(PPh$_3$)$_4$, 63 mg (0.054 mmol), in 5 mL of toluene and 3 mL of ethanol was heated to obtain a clear solution. To the solution was added 5 mL of 0.4M aq. Na$_2$CO$_3$. The reaction mixture refluxed for 4 h at 80° C. The mixture was cooled to room temperature and diluted with 100 mL ethyl acetate. The organic layer was washed with 2×50 mL portions of water, 2×50 mL portions of sat. aq. NaCl, and dried (MgSO$_4$). After the solution was concentrated, the residue was purified by column chromatography (eluted with 7% EtOAc-Heptane) to afford the desired product in 0.11 g (39%) as a yellow oil. $^1$H NMR (CDCl$_3$) δ 7.65 (d, 2H, J=9.3 Hz), 7.58 (t, 3H, J=9.3 Hz), 7.52 (d, 1H, J=7.7 Hz), 7.45-7.38 (m, 6H), 5.32 (d, 1H, J=8.3 Hz), 4.63-4.52 (m, 1H), 3.78 (s, 2H), 3.77 (s, 3H), 2.94 (dd, 1H, J=15.2, 5.3 Hz), 2.85 (dd, 1H, J=15.2, 6.3 Hz), 2.09 (s, 3H), 1.47 (s, 9H).

EXAMPLE 103

3-(2"-Acetyl-[1,1',4'1"]terphenyl-4-ylmethylsulfanyl)-2-tert-butoxycarbonylamino-propionic acid

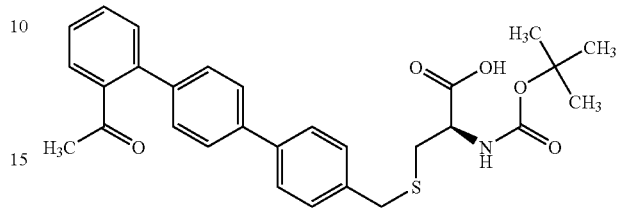

To a solution of 3-(2"-acetyl-[1,1',4'1"]terphenyl-4-ylmethylsulfanyl)-2-tert-butoxycarbonylamino-propionic acid methyl ester, 110 mg (0.21 mmol) in 10 mL of tetrahydrofuran was added 1.06 mL of 6.0M aq. KOH. The solution was stirred for 1 h at room temperature. The solution was diluted with 10 mL of water and acidified to pH 1-2. The aqueous was extracted with 3×30 mL portions of diethyl ether. The organic layers were combined, washed with sat. aq. NaHCO$_3$, sat. aq. NaCl, dried (MgSO$_4$). The solution was concentrated to afford the desired product in 60 mg (56%) as a pale yellow foam. R$_f$ 0.25 (10% Methanol-90% Methylene Chloride); $^1$H NMR (DMSO-d$_6$) 7.73 (dd, 2H, J=9.0 Hz), 7.67 (d, 2H, J=9.0 Hz), 7.59 (dd, 2H, J=10.0, 8.3 Hz), 7.47 (dd, 2H, J=10.0, 8.3 Hz), 7.40 (d, 2H, J=9.0 Hz), 7.37 (d, 2H, J=9.0 Hz), 4.18-4.08 (m, 1H), 3.80 (s, 2H), 2.81 (dd, 1H, J=15.2, 5.3 Hz), 2.66 (dd, 1H, J=15.2, 10.0 Hz), 2.20 (s, 3H), 1.40 (s, 9H). LCMS m/z calcd for C$_{29}$H$_{31}$NO$_5$S: 505.2 found 506.1(M+1).

EXAMPLE 104

2-tert-Butoxycarbonylamino-3-(2"-methoxy-[1,1',4',1"]terphenyl-4-ylmethylsulfanyl)-propionic acid methyl ester A mixture of 3-(4'-bromobiphenyl-4-ylmethylsulfanyl)-2-tert-butoxycarbonylamino-propionic acid methyl ester, 0.26 g (0.54 mmol), 2-methoxyphenylboronic acid, 83 mg (0.54 mmol), Pd(PPh$_3$)$_4$, 63 mg (0.054 mmol), in 5 mL of toluene and 3 mL of ethanol was heated to obtain a clear solution. To the solution was added 5 mL of 0.4M aq. Na$_2$CO$_3$. The reaction mixture refluxed for 4 h at 80° C. The mixture was cooled to room temperature and diluted with 100 mL ethyl acetate. The organic layer was washed with 2×50 mL portions of water, 2×50 mL portions of sat. aq. NaCl, and dried (MgSO$_4$). After the solution was concentrated, the residue was purified by column chromatography (eluted with 7% EtOAc-Heptane) to afford the desired product in 80 mg (29%) as a white solid. $^1$H NMR (CDCl$_3$) 7.61-7.57 (m, 6H), 7.39-7.30 (m, 4H), 7.06 (d, 1H, J=8.0 Hz), 7.00 (d, 1H, J=9.7 Hz), 5.35 (d, 1H, J=8.7 Hz), 4.63-4.52 (m, 1H), 3.85 (s, 3H), 3.78 (s, 2H), 3.76 (s, 3H), 2.95 (dd, 1H, J=15.3, 5.3 Hz), 2.85 (dd, 1H, J=15.3, 6.7), 1.48 (s, 9H).

EXAMPLE 105

2-tert-Butoxycarbonylamino-3-(2"-methoxy-[1,1',4',1"]terphenyl-4-ylmethylsulfanyl)-propionic acid To a solution of 2-tert-butoxycarbonylamino-3-(2"-methoxy-[1,1',4',1"]terphenyl-4-ylmethylsulfanyl)-propionic acid methyl ester, 80 mg (0.16 mmol) in 10 mL of tetrahydrofuran was added 0.79 mL of 6.0M aq. KOH. The solution was stirred for 1 h at room temperature. The solution was diluted with 10 mL of water and acidified to pH 1-2. The aqueous was extracted with 3×30 mL portions of diethyl ether. The organic layers were combined, washed with sat. aq. NaHCO$_3$, sat. aq. NaCl, dried (MgSO$_4$). The solution was concentrated to afford the desired compound in 17 mg (22%) as a pale yellow foam. R$_f$ 0.25 (10% Methanol-90% Methylene Chloride); $^1$H NMR (DMSO-d$_6$) 7.69-7.63 (m, 3H), 7.54 (d, 2H, J=9.0 Hz), 7.39 (d, 2H, J=9.0 Hz), 7.32 (d, 2H, 8.0 Hz), 7.17-7.10 (m, 2H), 7.03 (t, 1H, J=8.0 Hz), 4.19-4.08 (m, 1H), 3.80 (s, 2H), 3.78 (s, 3H), 2.81 (dd, 1H, J=15.3, 5.0 Hz), 2.67 (dd, 1H, J=15.3, 10.0 Hz), 1.40 (s, 9H). LCMS m/z calcd for C$_{28}$H$_{31}$NO$_5$S: 493.2 found 494.4(M+1).

EXAMPLE 106

2-tert-Butoxycarbonylamino-3-(4'-dibenzothiophen-4-yl-biphenyl-4-ylmethyl-sufanyl)-propionic acid methyl ester A mixture of 3-(4'-bromobiphenyl-4-ylmethylsulfanyl)-2-tert-butoxycarbonylamino-propionic acid methyl ester, 0.33 g (0.69 mmol), 4-dibenzothiopheneboronic acid, 0.19 g (0.82 mmol), Pd(PPh$_3$)$_4$, 80 mg (0.069 mmol), in 5 mL of toluene and 3 mL of ethanol was heated to obtain a clear solution. To the solution was added 5 mL of 0.4M aq. Na$_2$CO$_3$. The reaction mixture refluxed for 4 h at 80° C. The mixture was cooled to room temperature and diluted with 100 mL ethyl acetate. The organic layer was washed with 2×50 mL portions of water, 2×50 mL portions of sat. aq. NaCl, and dried (MgSO$_4$). After the solution was concentrated, the residue was purified by column chromatography (eluted with 7% EtOAc-Heptane) to afford the desired product in 300 mg (75%) as a white solid. $^1$H NMR (CDCl$_3$) 8.26-8.16 (m, 2H), 7.86-7.82 (m, 3H), 7.74 (d, 2H, J=9.3 Hz), 7.64 (d, 2H, J=9.3 Hz), 7.60-7.44 (m, 6H), 5.35 (d, 1H, J=12.5 Hz), 4.63-4.52 (m, 1H), 3.80 (s, 2H), 3.78 (s, 3H), 2.97 (dd, 1H, J=15.3, 5.3 Hz), 2.89 (dd, 1H, J=15.3, 6.3 Hz), 1.49 (s, 9H).

EXAMPLE 107

2-tert-Butoxycarbonylamino-3-(4'-dibenzothiophen-4-yl-biphenyl-4-ylmethyl-sufanyl)-propionic acid

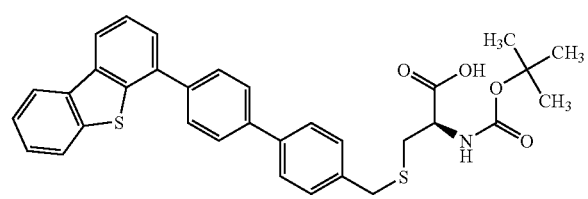

To a solution of 2-tert-Butoxycarbonylamino-3-(4'-dibenzothiophen-4-yl-biphenyl-4-ylmethyl-sufanyl)-propionic acid methyl ester, 0.27 g (0.51 mmol) in 10 mL of tetrahydrofuran was added 0.43 mL of 6.0M aq. KOH. The solution was stirred for 1 h at room temperature. The solution was diluted with 10 mL of water and acidified to pH 1-2. The aqueous was extracted with 3×30 mL portions of diethyl ether. The organic layers were combined, washed with sat. aq. NaHCO$_3$, sat. aq. NaCl, dried (MgSO$_4$), and filtered. The solution was concentrated to afford the desired compound in 0.21 g (72%) as a pale yellow solid. MP 108-110° C., R$_f$ 0.25 (10% Methanol-90% Methylene Chloride); $^1$H NMR (DMSO-d$_6$) 8.20-8.15 (m, 2H), 7.87-7.80 (m, 3H), 7.72 (d, 2H, J=9.3 Hz), 7.63 (d, 2H, J=9.3 Hz), 7.57-7.35 (m, 6H), 5.40 (d, 1H, J=7.0 Hz), 4.63-4.52 (m, 1H), 3.830 (s, 2H), 2.99 (dd, 1H, J=15.3, 5.3 Hz), 2.91 (dd, 1H, J=15.3, 6.3), 1.48 (s, 9H). LCMS m/z calcd for C$_{33}$H$_{31}$NO$_4$S$_2$: 569.2 found 570.4 (M+1).

EXAMPLE 108

(2R)-Methyl-3-(4-amino-benzylsulfanyl)-2-tert-butoxycarbonylamino-propionate

A mixture of 1-bromomethyl-4-nitro-benzene (2.15 g, 9.95 mmol), cesium carbonate (6.49 g, 19.9 mmol) and 2-tert-butoxycarbonylamino-3-mercapto-propionic acid methyl ester (2.46 g, 10.5 mmol) in DMF (25 mL) was stirred at room temperature. Upon completion of the reaction (TLC control: 30% ethyl acetate in heptane), the reaction mixture was quenched with water (50 mL) and extracted with diethyl ether (3×50 mL). The combined extract was washed sequentially with water and brine, dried over anhydrous MgSO$_4$, filtered and concentrated in vacuo. Purification by flash chromatography (SiO$_2$; 30% ethyl acetate in heptane as eluent) yielded the thioether as an off-white solid.

A mixture of (2R)-methyl-2-tert-butoxycarbonylamino-3-(4-nitro-benzylsulfanyl)-propionate (3.75 g, 10.1 mmol) and tin (II) chloride (5.76 g, 30.0 mmol) in methanol (50 mL) was stirred at 50° C. Upon completion (TLC: 5% methanol in dichloromethane), the mixture was cooled to room temperature, quenched with saturated potassium fluoride solution (75 mL) and extracted with diethyl ether (3×75 mL). The combined extract was washed sequentially with water and brine, dried over anhydrous MgSO$_4$, filtered and concentrated in vacuo. Flash chromatography purification (SiO$_2$; 1-2% methanol in dichloromethane as eluent) yielded the titled compound as an off-white solid. $^1$H NMR (CDCl$_3$, 300 MHz) δ 7.08 (2H, d, J=8 Hz, ArH), 6.25 (2H, d, J=8 Hz, ArH), 4.53 (1H, m, CHN), 3.75 (3H, s, OCH$_3$), 3.63 (2H, s, PhCH$_2$S), 2.84 (2H, m, C$\underline{H}_2$CHN), 1.46 (9H, s, CMe$_3$); ESI-LCMS e/z calculated for C$_{16}$H$_{24}$N$_2$O$_4$S 340.146, found 341 (M+H)$^+$, 363 (M+Na)$^+$.

EXAMPLE 109

Indol-1-yl-acetic acid 1H-indole (5.0 g, 42.7 mmol) in anhydrous DMF (10 mL) was added to a suspension of sodium hydride (1.13 g, 46.9 mmol) in anhydrous DMF (20 mL) in a flame dried flask at 0° C. stirred under nitrogen atmosphere. Fifteen minutes after gas evolution had ceased, bromo-acetic acid ethyl ester (5.7 mL, 51.2 mmol) was added and the reaction was heated to 70° C. and stirred under nitrogen. Upon completion (TLC: 50% dichloromethane in heptane), the reaction mixture was quenched with water (50 mL) and extracted with diethyl ether (3×50 mL). The combined extract was washed sequentially with water and brine, dried over anhydrous MgSO$_4$, filtered and concentrated in vacuo. To a solution of crude indol-1-yl-acetic acid ethyl ester (9.37 g, 46.2 mmol) in methanol (20 mL) and THF (80 mL) was added 6N NaOH solution (25 mL). Upon completion (TLC: 10% methanol in dichloromethane), the mixture was acidified with 6N HCl solution to pH 2, and extracted with ethyl acetate (3×75 mL). The combined extract was washed sequentially with water and brine, dried over anhydrous MgSO$_4$, filtered and concentrated in vacuo to yield the crude titled compound as a light brown solid. ¹H NMR (DMSO-d6, 300 MHz) δ 7.51 (1H, dd, J=8, 1 Hz, Ar—H), 7.35 (1H, dd, J=8, 1 Hz, Ar—H), 7.30 (1H, d, J=3 Hz, Ar—H), 7.09 (1H, td, J=7.5, 1 Hz, Ar—H), 6.99 (1H, td, J=7.5, 1 Hz, Ar—H), 6.41 (1H, dd, J=3, 1 Hz, Ar—H), 4.99 (2H, s, CH$_2$).

EXAMPLE 110

(5-Fluoro-indol-1-yl)-acetic acid (5-Fluoro-indol-1-yl)-acetic acid was prepared in analogous fashion to that exemplified in Example 109, except 5-fluoro-1H-indole was substituted for 1H-indole. ¹H NMR (CDCl$_3$, 300 MHz) δ 7.27 (1H, dd, J=9, 2 Hz, Ar—H), 7.14 (1H, dd, J=9, 4 Hz, Ar—H), 7.10 (1H, d, J=3 Hz, Ar—H), 6.97 (1H, td, J=9, 2.5 Hz, Ar—H), 6.53 (1H, d, J=3 Hz, Ar—H), 4.88 (2H, s, CH$_2$).

EXAMPLE 111

(5-Benzyloxy-indol-1-yl)-acetic acid (5-Benzyloxy-indol-1-yl)-acetic acid was prepared in analogous fashion to that exemplified in Example 109, except 5-benzyloxy-1H-indole was substituted for 1H-indole. ¹H NMR (DMSO-d6, 300 MHz) δ 7.45-7.24 (7H, m, Ar—H), 7.10 (1H, d, J=2 Hz, Ar—H), 6.82 (1H, dd, J=9, 2 Hz, Ar—H), 6.31 (1H, d, J=3 Hz, Ar—H), 5.07 (2H, d, J=4 Hz, PhCH$_2$O), 4.94 (2H, s, CH$_2$N).

EXAMPLE 112

(2R)-2-tert-Butoxycarbonylamino-3-[4-(2-indol-1-yl-acetylamino)-benzylsulfanyl]-propionic acid A solution of indol-1-yl-acetic acid (1.25 g, 7.14 mmol), (2R)-3-(4-amino-benzylsulfanyl)-2-tert-butoxycarbonylamino-propionic acid methyl ester (2.67 g, 7.85 mmol), EDC (1.71 g, 8.93 mmol), triethylamine (2.48 mL, 17.85 mmol) and DMAP (87 mg, 0.714 mmol) in DCM (50 mL) was stirred at ambient temperature. Upon completion (TLC: 2% methanol in dichloromethane), the reaction was quenched with water (75 mL) and extracted with ethyl acetate (3×50 mL). The combined extract was washed sequentially with water and brine, dried over anhydrous MgSO$_4$, filtered, concentrated in vacuo and purified by flash chromatography (SiO$_2$; 30-40% ethyl acetate/heptane as eluent) To a stirred solution of (2R)-2-tert-butoxycarbonylamino-3-[4-(2-indol-1-yl-acetylamino)-benzylsulfanyl]-propionic acid methyl ester (0.470 g, 0.945 mmol) in methanol (3 mL) and THF (12 mL) was added 2N NaOH solution (2.5 mL, 5.3 mmol). Upon completion (TLC 10% methanol in dichloromethane), the mixture was acidified to pH 2 with 2N HCl solution and extracted with ethyl acetate (3×20 mL). The combined extract was washed sequentially with water and brine, dried over anhydrous MgSO$_4$, filtered and concentrated in vacuo to yield the titled compound as a light yellow solid. R$_f$ 0.40 (20% methanol in dichloromethane); ¹H NMR (CDCl$_3$, 300 MHz) δ 7.71 (1H, d, J=7 Hz, Ar—H), 7.37-7.20 (6H, m, Ar—H), 7.16 (1H, d, J=3 Hz, Ar—H), 7.00 (1H, m, Ar—H), 6.69 (1H, d, J=3 Hz, Ar—H), 4.95 (2H, s, NCH$_2$CO), 4.38 (1H, m, CHN), 3.66 (2H, s, PhCH$_2$S), 2.85 (2H, m, CH$_2$CHN), 1.45 (9H, s, CMe$_3$); ESI-LCMS e/z calculated for C$_{25}$H$_{29}$N$_3$O$_5$S 483.183, found 484 (M+H)$^+$, 506 (M+Na)$^+$.

EXAMPLE 113

(2R)-2-tert-Butoxycarbonylamino-3-{4-[2-(5-fluoro-indol-1-yl)-acetylamino]-benzylsulfanyl}-propionic acid (2R)-2-tert-Butoxycarbonylamino-3-{4-[2-(5-fluoro-indol-1-yl)-acetylamino]-benzylsulfanyl}-propionic acid was prepared in analogous fashion to that exemplified in Example 112, except (5-fluoro-indol-1-yl)-acetic acid was substituted for indol-1-yl-acetic acid. R$_f$ 0.35 (20% methanol in dichloromethane); ¹H NMR (CDCl$_3$, 300 MHz) δ 7.32 (1H, dd, J=9, 2.5 Hz, Ar—H), 7.23-7.11 (6H, m, Ar—H), 7.00 (1H, td, J=9, 2.5 Hz, Ar—H), 6.61 (1H, d, J=3 Hz, Ar—H), 4.90 (2H, s, NCH$_2$CO), 4.44 (1H, m, CHN), 3.64 (2H, s, PhCH$_2$S), 2.82 (2H, m, CH$_2$CHN), 1.44 (9H, s, CMe$_3$); ESI-LCMS e/z calculated for C$_{25}$H$_{28}$FN$_3$O$_5$S 501.173, found 502 (M+H)$^+$, 524 (M+Na)$^+$.

EXAMPLE 114

(2R)-3-{4-[2-(5-Benzyloxy-indol-1-yl)-acetylamino]-benzylsulfanyl}-2-tert-butoxycarbonylamino-propionic acid (2R)-3-{4-[2-(5-Benzyloxy-indol-1-yl)-acetylamino]-benzylsulfanyl}-2-tert-butoxycarbonylamino-propionic acid was prepared in analogous fashion to that exemplified in Example 112, except (5-benzyloxy-indol-1-yl)-acetic acid was substituted for indol-1-yl-acetic acid. R$_f$ 0.58 (20% methanol in dichloromethane); ¹H NMR (DMSO-d6, 300 MHz) δ 10.33 (1H, s, COOH), 7.52-7.20 (10H, m, Ar—H), 7.12 (1H, d, J=2 Hz, Ar—H), 6.83 (1H, dd, J=9, 2 Hz, Ar—H), 6.33 (1H, d, J=3 Hz, Ar—H), 5.08 (2H, s), 4.97 (2H, s), 4.03 (1H, m, CHN), 3.68 (2H, s, PhCH$_2$S), 2.67 (2H, m, CH$_2$CHN), 1.38 (9H, s, CMe$_3$); ESI-LCMS e/z calculated for C$_{32}$H$_{35}$N$_3$O$_6$S 589.225, found 590 (M+H)$^+$, 612 (M+Na)$^+$.

EXAMPLE 115

(2R)-2-tert-Butoxycarbonylamino-3-{4-[2-(5-fluoro-indol-1-yl)-acetylamino]-phenylmethanesulfinyl}-propionic acid.

To a stirred solution of (2R)-2-tert-butoxycarbonylamino-3-{4-[2-(5-fluoro-indol-1-yl)-acetylamino]-benzylsulfanyl}-propionic acid (460 mg, 0.917 mmol) in acetic acid (20 mL) was added sodium perborate tetrahydrate (148 mg, 0.963 mmol). This solution was stirred at 40° C. until complete (TLC: 20% methanol in dichloromethane), then cooled to room temperature, diluted with ethyl acetate (100 mL), washed sequentially with water and brine, dried over anhydrous MgSO$_4$, filtered and concentrated in vacuo. Purification by flash chromatography (SiO$_2$; 10-20% methanol in dichloromethane as eluent) yielded the titled compound as a 1:1 mixture of diastereomers as an off-white solid. $R_f$ 0.09 (20% methanol in dichloromethane); $^1$H NMR (DMSO-d6, 300 MHz) δ 7.32 (2H, d, J=9 Hz, Ar—H), 7.44-7.34 (2H, m, Ar—H), 7.31-7.19 (3H, m, Ar—H), 6.94 (1H, td, J=9, 2.5 Hz, 6.43 (1H, d, J=3 Hz, Ar—H), 5.07 (2H, s, NCH$_2$CO), 4.23-3.80 (3H, m, PhCH$_2$S and CHN), 2.87 (2H, m, C$\underline{H}_2$CHN), 1.37 and 1.35 (both 4.5H, s, CMe$_3$ diastereomers); ESI-LCMS e/z calculated for C$_{25}$H$_{28}$FN$_3$O$_6$S 517.168, found 518 (M+H)$^+$, 540 (M+Na)$^+$.

EXAMPLE 116

N-[4'-(2-Butyl-benzofuran-3-ylmethyl)-4-(3-phenyl-propoxy)-biphenyl-3-yl]-oxalamic acid Step 1: (4-Bromo-phenyl)-(2-butyl-benzofuran-3-yl)-methanone

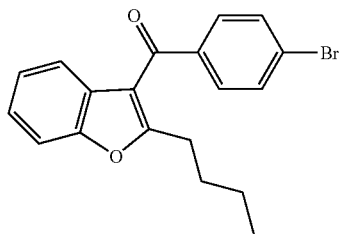

A solution of 2-n-butylbenzofurane (19.8 g, 114 mmol) and 4-bromobenzoyl chloride (25.0 g, 114 mmol) in dry dichloromethane (300 mL, 0.4 M) was cooled to 0° C. and treated with AlCl$_3$ (16.6 g, 1.1 equiv., 125.4 mmol) in 3 portions. After the additions were complete, the solution was stirred for 3 h and carefully added to ice water. After separation, the aqueous layer was extracted with dichloromethane (2×200 mL) and the combined organic layers were washed with water, sat'd aq NaCl, dried over anhydrous MgSO$_4$, filtered and concentrated in vacuo. Purification by flash column chromatography (1-2% ethyl acetate in heptane) afforded (4-bromo-phenyl)-(2-butyl-benzofuran-3-yl)-methanone (14.6 g, 36%).

Step 2: 3-(4-Bromo-benzyl)-2-butyl-benzofuran

A solution of (4-bromo-phenyl)-(2-butyl-benzofuran-3-yl)-methanone (2.25 g, 6.32 mmol) in ethanol (20 mL, 0.3 M) was cooled to 0° C. and treated with NaBH$_4$ (0.263 g, 1.1 equiv, 6.95 mmol) After stirring for 1 h, the mixture was poured into a 50% ether in water solution (200 mL). After separation, the aqueous layer was extracted with ether (50 mL) and the combined organic layers were washed with water, sat'd aq NaCl, dried over anhydrous MgSO$_4$, filtered and concentrated in vacuo.

The resulting alcohol was subsequently disolved in dry dichloromethane (50 mL), cooled to 0° C. and treated with triethylsilane (2.0 mL, 2.0 equiv., 12.64 mmol) dropwise via syringe. After stirring an additional 5 min, trifluoroacetic acid (2.43 mL, 5.0 equiv., 31.6 mmol) was added over 2 min and the mixture was stirred for 3 h. Once complete, the solution was washed with water, sat'd aq NaCl, dried over anhydrous MgSO$_4$, filtered and concentrated in vacuo. Purification by flash column chromatography (0-2% ethyl acetate in heptane) afforded 3-(4-bromo-benzyl)-2-butyl-benzofuran as a pale yellow oil (1.34 g, 63%).

Step 3: 2-Butyl-3-[4-(4,4,5,5-tetramethyl-[1,3,2]dioxaborolan-2-yl)-benzyl]-benzofuran

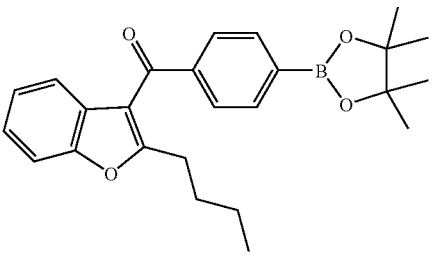

A solution of 3-(4-bromo-benzyl)-2-butyl-benzofuran (14.03 g, 41.5 mmol), bis(pinacolato)diborane (11.60 g, 1.1 equiv., 45.7 mmol), potassium acetate (12.2 g, 3.0 equiv., 125 mmol) in DMSO (100 mL, 0.4 M) was treated with PdCl$_2$(dppf).CH$_2$Cl$_2$ (4.15 g, 0.1 equiv., 4.15 mmol) and heated to 80° C. After compete by TLC, the solution was coled to room temperature, diluted with water (150 mL) and filtered through celite (washed with ether, 500 mL). After separation, the aqueous layer was extracted with ether (2×150 mL). The combined organic layers were washed with water, sat'd aq NaCl, dried over anhydrous MgSO$_4$, filtered and concentrated in vacuo. Purification by flash column chromatography (2-5% ethyl acetate in heptane) afforded 2-butyl-3-[4-(4,4,5,5-tetramethyl-[1,3,2]dioxaborolan-2-yl)-benzyl]-benzofuran as a pale yellow oil (11.2 g, 69%).

Step 4: 2-Butyl-3-[3'-nitro-4'-(3-phenyl-propoxy)-biphenyl-4-ylmethyl]-benzofuran A solution of 2-butyl-3-[4-(4,4,5,5-tetramethyl-[1,3,2]dioxaborolan-2-yl)-benzyl]-benzofuran (100 mg, 0.256 mmol), 4-bromo-2-nitro-1-(3-phenylpropylox)-benzene (95 mg, 1.1 equiv., 0.282 mmol) and K$_2$CO$_3$ (136 mg, 3.5 equiv., 0.987 mmol) in water (1 mL) and DMF (2 mL) was treated with PdCl$_2$(dppf).CH$_2$Cl$_2$ (23 mg, 0.1 equiv., 0.0282 mmol) and heated to 120° C. After complete (by TLC) the solution was cooled to room temperature, acidified to pH<4 with 10% aq HCl and diluted with water (20 mL). After separation, the aqueous layer was extracted with ether (3×20 mL) and the combined organic layers were washed with water, sat'd aq NaCl, dried over anhydrous MgSO$_4$, filtered and concentrated in vacuo. Purification by prep thin layer chromatography afforded 2-butyl-3-[3'-nitro-4'-(3-phenyl-propoxy)-biphenyl-4-ylmethyl]-benzofuran (53 mg, 41%).

Step 5: 4'-(2-Butyl-benzofuran-3-ylmethyl)-4-(3-phenyl-propoxy)-biphenyl-3-ylamine A solution of 2-butyl-3-[3'-nitro-4'-(3-phenyl-propoxy)-biphenyl-4-ylmethyl]-benzofuran (53 mg, 0.105 mmol) in ethanol (1 mL) and acetic acid (1 mL) was treated with Fe (26.4 mg, 4.5 equiv., 0.472 mmol) and heated to 120° C. for 3 h. After cooling to room temperature, the solution was poured into a 20% aq NaOH/ice water solution (Ph>8) and extracted with ether (3×20 mL). The combined organic layers were washed with water, sat'd aq NaCl, dried over anhydrous MgSO$_4$, filtered and concentrated in vacuo. Purification by prep thin layer chromatography (25% ethyl acetate in heptane) afforded 4'-(2-butyl-benzofuran-3-ylmethyl)-4-(3-phenyl-propoxy)-biphenyl-3-ylamine (14.5 mg, 29%).

Step 6: N-[4'-(2-Butyl-benzofuran-3-ylmethyl)-4-(3-phenyl-propoxy)-biphenyl-3-yl]-oxalamic acid ethyl ester

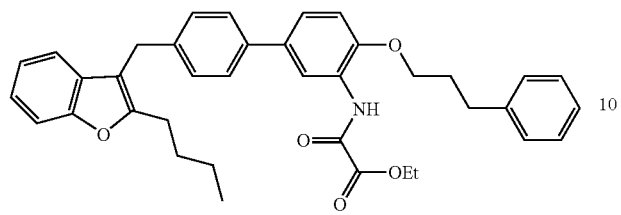

A solution of 4'-(2-butyl-benzofuran-3-ylmethyl)-4-(3-phenyl-propoxy)-biphenyl-3-ylamine (129 mg, 0.264 mmol) and diisopropylethylamine (0.115 mL, 2.5 equiv., 0.66 mmol) in dichloromethane (5 mL) was treated with a solution of ethyl chlorooxoacetate (44 mg, 1.2 equiv., 0.317 mmol) in dichloromethane (1 mL). After stirring for 2 h, the solution was diluted with water and extracted with dichloromethane (2×15 mL). The combined organic layers were washed with water, sat'd aq NaCl, dried over anhydrous $MgSO_4$, filtered and concentrated in vacuo. Purification by prep thin layer chromatography (25% ethyl acetate in heptane) afforded N-[4'-(2-butyl-benzofuran-3-ylmethyl)-4-(3-phenyl-propoxy)-biphenyl-3-yl]-oxalamic acid ethyl ester (120 mg, 77%).

Step 7: N-[4'-(2-Butyl-benzofuran-3-ylmethyl)-4-(3-phenyl-propoxy)-biphenyl-3-yl]-oxalamic acid A solution of N-[4'-(2-butyl-benzofuran-3-ylmethyl)-4-(3-phenyl-propoxy)-biphenyl-3-yl]-oxalamic acid ethyl ester (120 mg, 0.204 mmol) in ethanol (3 mL) was treated with aq 1 N NaOH (0.3 mL, 1.5 equiv., 0.306 mmol) and stirred at room temperature. After stirring 1 h, the solution was acidified to pH<4 with 10% HCl, concentrated and purified by prep thin layer chromatography (10% methanol in dichloromethane) afforded N-[4'-(2-Butyl-benzofuran-3-ylmethyl)-4-(3-phenyl-propoxy)-biphenyl-3-yl]-oxalamic acid (32 mg, 28%).

EXAMPLE 117

4-Dibenzofuran-4-yl-phenyl-boronic acid

Step 1:
(4-Dibenzofuran-4-yl-phenyl)-trimethyl-silane

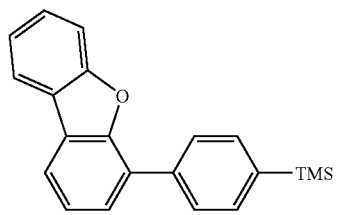

A solution of dibenzofuran-4-yl-boronic acid (20.0 g, 94.3 mmol), (4-bromo-phenyl)-trimethyl-silane (21.62 g, 94.3 mmol), $K_2CO_3$ (39.1 g, 3 equiv., 283 mmol) in toluene (100 mL), ethanol (60 mL) and water (30 mL) was purged with nitrogen for 5 min (bubbled into solution) and treated with $Pd(PPh_3)_4$ (3.59 g, 2.9 mmol). After heating to 80° C. for 4 h, the solution was cooled to room temperature, poured into water (300 mL) and extracted with ethyl acetate (300 mL). The organic phase was washed with sat'd aq NaCl, dried over anhydrous $MgSO_4$, filtered and concentrated in vacuo. Purification by flash column chromatography (5-20% ethyl acetate in heptane) afforded (4-dibenzofuran-4-yl-phenyl)-trimethyl-silane as a colorless oil (28.9 g, 96%).

Step 2: 4-Dibenzofuran-4-yl-phenyl-boronic acid

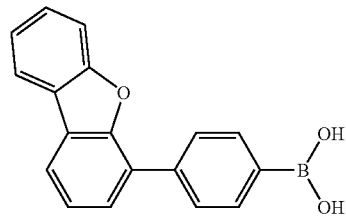

A solution of (4-dibenzofuran-4-yl-phenyl)-trimethylsilane (28 6 g, 90.2 mmol) in dichloromethane (350 mL, 0.26 M) was cooled to −78° C. and carefully treated with boron-tribromide (135 mL, 1.5 equiv., 135 mmol). After the addition was complete, the solution was warmed to room temperature and stirred for 3 h. Next, the reaction mixture was re-cooled to −78° C., treated with dry methanol (30 mL), slowly warmed to room temperature and stirred for 1.5 h. Next, the solution was re-cooled to −78° C., carefully quenched with 10% aq HCl (50 mL), warmed to room temperature and stirred for 1 h (solids form). The resulting solution was poured into water (500 mL) and extracted with ethyl acetate (3×700 mL). The combined organic layers were washed with sat'd aq NaCl, dried over anhydrous $MgSO_4$, filtered and concentrated in vacuo. The crude product was suspended in a 10% ethyl acetate in heptane solution, filtered and washed with the same solution (5×60 mL) to give 4-dibenzofuran-4-yl-phenyl-boronic acid as a white solid (20.2 g, 77%).

EXAMPLE 118

The following compounds were prepared essentially according to the methods and schemes described above.

2-tert-Butoxycarbonylamino-3-[4-(6-dibenzofuran-4-yl-pyridin-3-yl)-benzylsulfanyl]-propionic acid $R_f$ 0.70 (50% methanol in ethyl acetate)

2-tert-Butoxycarbonylamino-3-[4-(2-dibenzofuran-4-yl-thiazol-5-yl)-benzylsulfanyl]-propionic acid

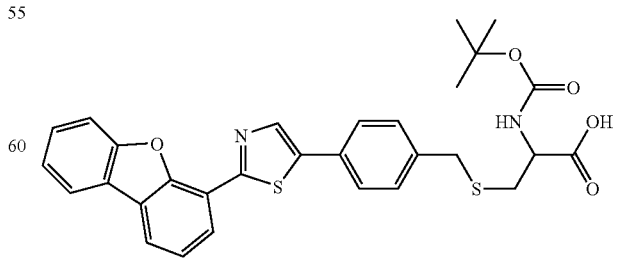

$R_f$ 0.81 (50% methanol in ethyl acetate).

EXAMPLE 119

2-tert-Butoxycarbonylamino-3-[4-(5-dibenzofuran-4-yl-6-methyl-pyridin-2-yl)-benzylsulfanyl]-propionic acid

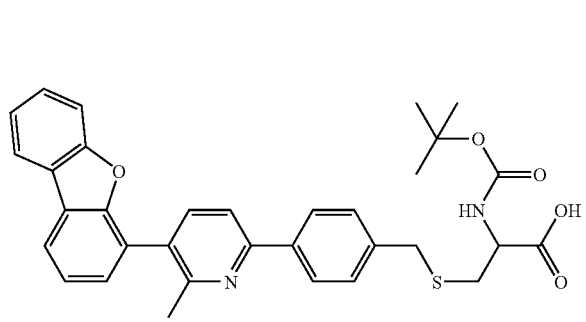

$R_f$ 0.64 (20% methanol in ethyl acetate)

EXAMPLE 120

2-tert-Butoxycarbonylamino-4-(4'-dibenzofuran-4-yl-biphenyl-4-yloxy)butyric acid

1. (L)-N-tert-Butoxycarbonylhomoserine

A solution of homoserine (5.0 g, 42 mmol) and triethylamine (8.8 mL, 63 mmol) in 50% aq acetone (25 mL) was cooled to 0° C. and treated with di-tert-butyl dicarbonate (10.1 g, 46.4 mmol). After stirring 16 h, the reaction mixture was concentrated to give crude (L)-N-tert-butoxycarbonylhomoserine triethylamine salt (13.4 g). The crude product was used without further purification.

2. (L)-N-tert-Butoxycarbonylhomoserine methyl ester

A solution of crude (L)-N-tert-butoxycarbonylhomoserine triethylamine salt (13.4 g, 42 mmol) in DMF (25 mL) was treated with methyliodide (3.2 mL, 46 mmol). After stirring for 16 h, the reaction mixture was diluted with ethyl acetate (100 mL), washed successively with 5% citric acid, sat. aq NaHCO$_3$, sat. aq NaCl, dried over MgSO$_4$, filltered and concentrated. Purification by flash column chromatography (25% ethyl acetate in heptane) gave (L)-N-tert-butoxycarbonylhomoserine methyl ester (7.8 g, 80% two-steps). $^1$H NMR (CDCl$_3$) 5.32 (d, J=12 Hz, 1H), 4.56 (m, 1 H), 4.09 (T, J=10 Hz, 2 H), 3.79 (s, 3 H), 2.38 (m, 2 H), 1.61 (s, 9 H).

3. (L)-2-tert-Butoxycarbonylamino-4-bromobutyric acid methyl ester

A solution of (L)-N-tert-butoxycarbonylhomoserine methyl ester (1.2 g, 5.14 mmol) and carbontetrabromide (2.52 g, 7.71 mmol) in dichloromethane (20 mL) was treated with a second solution of triphenylphosphine (1.34 g, 5.14 mmol) in dichloromethane (15 mL). After stirring at room temperature for 16 h, the solution was diluted with heptane (50 mL). The resulting precipitate was filtered and successively washed with heptane, 5% NaHCO$_3$, sat. aq NaCl, dried over MgSO$_4$ and concentrated. Purification by by flash column chromatography (10% ethyl acetate in heptane) gave (L)-2-tert-butoxycarbonylamino-4-bromobutyric acid methyl ester as white solid (1.19 g, 78%). $^1$H NMR (CDCl$_3$), δ 5.10 (d, J=5 Hz, 1H), 4.38 (t, J=15 Hz, 1 H), 3.77 (s, 3 H), 3.44 (t, J=13 Hz, 2 H), 2.40 (m, 1H), 2.21 (m, 1H), 1.42 (s, 9H).

4. 4-(4'-bromobiphen-4-yloxy)-2-tert-butoxycarbonylaminobutyric acid methyl ester

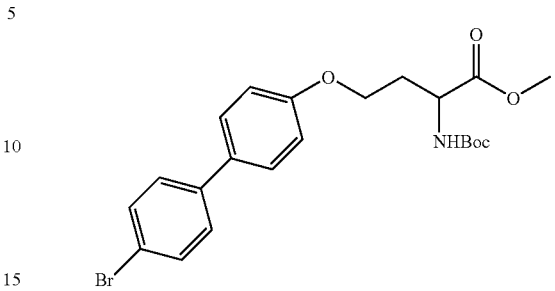

A solution of 4'-bromobipheny-4-ol (883 mg, 3.55 mmol) in DMF (10 mL) was treated with NaH (148 mg, 3.72 mmol). After stirring for 10 min, (L)-4-bromo-2-tert-butoxycarbonylamino-butyric acid methyl ester (1 g, 3.38 mmol) was added and the reaction mixture was stirred an additional 16 h. Once complete, the reaction mixture was diluted with ethyl acetate (100 mL), washed successively with sat. aq NH$_4$Cl and sat. aq NaCl, dried over MgSO$_4$, filtered, and concentrated. Purification by flash column chromatography (10% ethyl acetate in heptane) provided 4-(4'-bromobiphen-4-yloxy)-2-tert-butoxycarbonylaminobutyric acid methyl ester as white solid (0.79 g, 50%). $^1$H NMR (CDCl$_3$), δ 7.50 (d, J=8 Hz, 2 H), 7.44 (d, J=8 Hz, 2 H), 7.38 (d, J=8 Hz, 2 H), 6.92 (d, J=8 Hz, 2 H), 5.28 (m, 1 H), 4.51 (m, 1 H), 4.08 (t, J=8 Hz, 2 H), 3.77 (s, 3H), 2.34 (m, 2 H), 1.44 (s, 9 H). LCMS, 466 (M$^+$+1).

5. 2-tert-Butoxycarbonylamino-4-(4'-dibenzofuan-4-yl-biphenyl-4-yloxy)butryic acid methyl ester A solution of 4-(4'-bromobiphen-4-yloxy)-2-tert-butoxycarbonylaminobutyric acid methyl ester (464 mg, 1 mmol), 4-dibenzofuranboronic acid (222 mg, 1.1 mmol) and Pd(PPh$_3$)$_4$ (52 mg, 5% mol) in toluene (10 mL) and ethanol (3 mL) was heated until the solution became clear and subsequently treated with 2 M K$_2$CO$_3$ (1.5 mL). The reaction mixture was heated to reflux for 2 h, cooled to room temperature, diluted with ethyl acetate (100 mL). The organic layer was washed successively with sat. aq NH$_4$Cl and sat. aq NaCl, dried over MgSO$_4$ and concentrated. Purification by flash column chromatography (2-10% ethyl acetate in heptane) provided 2-tert-Butoxycarbonylamino-4-(4'-dibenzofuan-4-yl-biphenyl-4-yloxy)butryic acid methyl ester as white solid (374 mg, 69%). $^1$H NMR (CDCl$_3$), 7.95 (m, 4 H), 7.70 (d, J=8 Hz, 2 H), 7.62 (m, 4 H), 7.43 (m, 3 H), 6.96 (d, J=8 Hz, 2 H), 5.33 (d, J=8 Hz, 1 H), 4.53 (m, 1H), 4.11 (t, J=8 Hz, 2 H), 3.78 (s, 3 H), 2.34 (m, 2 H), 1.45 (s, 9 H). LCMS 552 (M$^+$+1).

6. 2-tert-Butoxycarbonylamino-4-(4'-dibenzofuran-4-yl-biphenyl-4-yloxy)butyric acid A solution of 2-tert-Butoxycarbonylamino-4-(4'-dibenzofuan-4-yl-biphenyl-4-yloxy)butryic acid methyl ester (280 mg, 0.51 mmol) in THF (2 mL) and methanol (2 mL) was cooled to 0° C. and treated with 2 N KOH (1.25 mL). After stirring 1 h, the solution was quenched with 10% HCl (to pH 2) and diluted with ethyl acetate (25 mL). After organic layer was seperated the aqueous layer was extracted with ethyl acetate (3×15 mL) and the combined organic layers were dried over MgSO$_4$ and concentrated. Purification by flash column chromatography (2-5% methanol in dichloromethane) provided 2-tert-Butoxycarbonylamino-4-(4'-dibenzofuan-4-yl-biphenyl-4-yloxy)butyric acid as white solid (250 mg, 91%). ° C., $^1$H NMR (DMSO-d$_6$), 8.15 (q, J=8 Hz, 2 H), 7.95 (d, J=8 Hz, 2 H), 7.71 (m, 6 H), 7.49 (m, 3 H), 7.01 (d, J=8 Hz, 2 H), 6.83 (m, 1 H), 4.04 (t, J=6 Hz, 2 H), 2.15 (m, 1 H), 2.00 (m, 1 H), 1.36 (s, 9 H). LCMS 538 (M$^+$+1).

EXAMPLE 121

2-tert-Butoxycarbonylamino-4-(4'-dibenzofuan-4-yl-biphenyl-4-ylsulfanyl)-butyric acid 1. 4-(4'-bromophenylsulfanyl)-2-tert-Butoxycarbonylaminobutryic acid methyl ester A solution of 4-bromobenzenethiol (670 mg, 3.55 mmol) and (L)-4-bromo-2-tert-butoxycarbonylamino-butyric acid methyl ester (1 g, 3.38 mmol) in DMF (15 mL) was cooled to 0° C. and treated with Cs$_2$CO$_3$ (1.2 g, 3.7 mmol). Once the addition was complete, the reaction mixture was warmed to room temperature, stirred for 2 h, diluted with ethyl acetate (100 mL) and washed sucssevely with sat. aq NH$_4$Cl and sat. aq NaCl. The resulting solution was dried over MgSO$_4$ concentrated and purified by flash column chromatography (10% ethyl acetate in heptane) to give 4-(4'-bromophenylsulfanyl)-2-tert-Butoxycarbonylaminobutryic acid methyl ester (1.37 g, 100%) as solid. $^1$H NMR (CDCl$_3$), δ 7.38 (d, J=12 Hz, 2 H), 7.18 (d, J=12 Hz, 2 H), 5.08 (d, J=8 Hz, 1 H), 4.43 (m, 1 H), 3.73 (s, 3 H), 2.92 (m, 2 H), 2.21 (m, 2 H), 1.45 (s, 9 H).

2. 2-tert-Butoxycarbonylamino-4-(4'-dibenzofuan-4-yl-biphenyl-4-ylsulfanyl)-butryic acid methyl ester

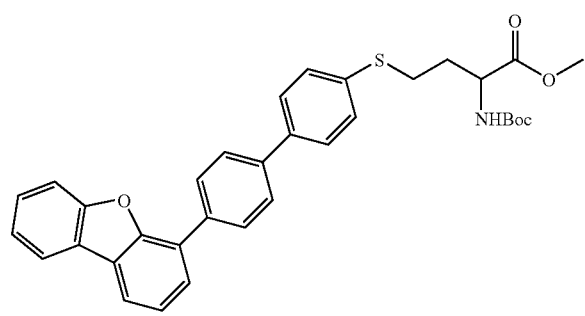

A solution of 4-(4'-bromophen-4-ylsulfanyl)-2-tert-butoxycarbonylaminobutyric acid methyl ester (404 mg, 1 mmol), (4-Dibenzofuran-4-yl-phenyl)boronic acid (302 mg, 1.05 mmol), Pd(PPh$_3$)$_4$ (52 mg, 5% mol) in toluene (10 mL) and ethanol (3 mL) was heated until the solution became clear and subsequently treated with 2 M K$_2$CO$_3$ (1.5 mL). The reaction mixture was heated to reflux for 2 h, cooled to room temperature, diluted with ethyl acetate (100 mL). The organic layer was washed successively with sat. aq NH$_4$Cl and sat. aq NaCl, dried over MgSO$_4$ and concentrated. Purification by flash column chromatography (2-10% ethyl acetate in heptane) to give 2-tert-Butoxycarbonylamino-4-(4'-dibenzofuan-4-yl-biphenyl-4-ylsulfanyl)-butryic acid methyl ester (340 mg, 60%) as white solid. $^1$H NMR (CDCl$_3$), 7.95 (m, 4 H), 7.75 (m, 2 H), 7.62 (m, 4 H), 7.41 (m, 5 H), 5.11 (d, J=12 Hz, 1 H), 4.47 (m, 1 H), ), 3.78 (s, 3 H), 3.01 (t, J=8 Hz, 2 H), 2.24 (m, 1 H), 2.01 (m, 1 H), 1.45 (s, 9H). LCMS 569 (M$^+$+1).

3. 2-tert-Butoxycarbonylamino-4-(4'-dibenzofuan-4-yl-biphenyl-4-ylsulfanyl)-butryic acid A solution of 2-tert-Butoxycarbonylamino-4-(4'-dibenzofuan-4-yl-biphenyl-4-ylsulfanyl)butryic acid methyl ester (190 mg, 0.335 mmol) in THF (2 mL) and methanol (2 mL) was cooled to 0° C. and treated with 2 N KOH (1.25 mL). After stirring 1 h, the solution was quenched with 10% HCl (to pH 2) and diluted with ethyl acetate (25 mL). After organic layer was seperated the aqueous layer was extracted with ethyl acetate (3×15 mL) and the combined organic layers were dried over MgSO$_4$ and concentrated. Purification by flash column chromatography (2-5% methanol in dichloromethane) gave 2-tert-Butoxycarbonylamino-4-(4'-dibenzofuan-4-yl-biphenyl-4-ylsulfanyl)-butryic acid (180 mg, 97%) as pale solid. $^1$H NMR (DMSO), 8.15 (dd, J=7, 12 Hz, 2 H), 7.98 (d, J=9 Hz, 2 H), 7.83 (d, J=9, 2 H), 7.69 (d J=9 Hz, 4 H), 7.47 (m, 5 H), 7.23 (d, J=8 Hz, 1 H), 4.07 (m, 1 H), 3.01 (m, 2 H), 1.95 (m, 2 H), 1.37 (s, 9 H). LCMS 554 (M$^+$+1).

EXAMPLE 122

2-tert-Butoxycarbonylamino-5-(4'-dibenzofuran-4-yl-biphen-4-yl)-5-pentenoic acid 1. 2-tert-Butoxycarbonylamino-5-pentenoic acid methyl ester A solution of di-tert-butyl dicarbonate (11.4 g, 52.1 mmol) in 1,4-dioxane (15 mL) was slowly added to a second solution of 2-amino-5-pentenoic acid (5 g, 43.4 mmol) in 1 N NaOH (55 mL) at 0° C. After stirring for 16 h, the solution was acidified with 5% HCl to pH 2, and the resulting mixture was extracted with ethyl acetate (3×80 mL). The combined organic layers were dried over MgSO$_4$ and concentrated. The resulting residue was dissolved in DMF (50 mL) and treated with K$_2$CO$_3$ (7 g, 51 mmol). After stirring for 15 min, the solution was cooled to 0° C. and treated with iodomethane (3.4 mL, 51 mmol). After the addition was complete, the reaction mixture was stirred at room temperature for another 4 h, filtered and the resulting solid was washed with ethyl acetate (200 mL). The filtrate was washed successively with 5% aq HCl, sat. aq NaCl, dried over MgSO$_4$ and concented. Purification by flash column chromatography (5% ethyl acetate in heptane) provided 2-tert-Butoxycarbonylamino-5-pentenoic acid methyl ester (9.03 g, 94%) as an oil. $^1$H NMR (CDCl$_3$), δ 5.73 (m, 1 H), 5.12 (m, 1 H), 5.03 (m, 1H), 4.38 (dd, J=6, 12 Hz, 1 H), 3.74 (s, 3 H), 2.51 (m, 2 H), 1.46 (s, 9 H).

2. 5-(4-Bromophenyl)-2-tert-butoxycarbonylamino-5-pentenoic acid methyl ester

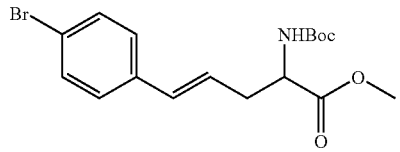

A sealed tube charged with 4-bromoiodobenzene (2.83 g, 10 mmol), 2-tert-butoxycarbonylamino-5-pentenoic acid methyl ester (2.52 g, 11 mmol), triethylamine (1.55 mL, 11 mmol) and Pd(OAc)$_2$ (90 mg, 4 mol %) in acetonitrile (2 mL) was degased with nitrogen, sealed and heated at 100° C. for 16 h. After cooling, the reaction mixture was flitered through celite and concentrated. Purification by flash column chromatography (10% ethyl acetate in heptane) gave 5-(4-Bromophenyl)-2-tert-butoxycarbonylamino-5-pentenoic acid methyl ester (2.61 g, 69%) as an oil. $^1$H NMR (CDCl$_3$), δ 7.40 (m, 2 H), 7.20 (m, 2 H), 6.38 (d, J=15 Hz, 1 H), 6.06 (ddd, J=8, 8, 15 Hz, 1H), 5.08 (d, J=8 Hz, 1 H), 4.45 (m, 1 H), 3.76 (s, 3 H), 2.67 (m, 2 H), 1.45 (s, 9 H).

3. 2-tert-Butoxycarbonylamino-5-(4'-dibenzofuran-4-yl-biphen-4-yl)-5-pentenoic acid methyl ester A solution of 5-(4-bromophenyl)-2-tert-butoxycarbonylamino-5-pentenoic acid methyl ester (0.384 g, 1 mmol), 4-(4-dibenzofuranyl)benzeneboronic acid (0.302 g, 1.05 mmol) and Pd(PPh$_3$)$_4$ (0.052 g, 5% mol) in toluene (10 mL) and ethanol (2.5 mL) was heated until the solution became clear and subsequently treated with 2 M K$_2$CO$_3$ (1.5 mL). The reaction mixture was heated to reflux for 2 h, cooled to room temperature, diluted with ethyl acetate (100 mL). The organic layer was washed successively with 2% aq HCl and sat. aq NaCl, dried over MgSO$_4$ and concentrated. Purification by flash column chromatography (2-10% ethyl acetate in heptane) gave 2-tert-Butoxycarbonylamino-5-(4'-dibenzofuran-4-yl-biphen-4-yl)-5-pentenoic acid methyl ester (422 mg, 77%) as a oil. $^1$H NMR (CDCl$_3$), δ 7.98 (d, J=9 Hz, 2 H), 7.94 (d, J=8 Hz, 2 H), 7.76 (d, J=8 Hz, 2 H), 7.66 (m, 4 H), 7.42 (m, 5 H), 6.53 (d, J=15 Hz, 1 H), 6.14 (ddd, J=8, 8, 15 Hz, 1 H), 5.11 (d, J=8 Hz, 1 H), 4.84 (m, 1 H), 3.79 (s, 3 H), 2.72 (m, 2 H), 1.52 (s, 9 H). LCMS 448 (M$^+$−100).

4. 2-tert-Butoxycarbonylamino-5-(4'-dibenzofuran-4-yl-biphen-4-yl)-5-pentenoic acid A solution of 2-tert-butoxycarbonylamino-5-(4'-dibenzofuran-4-yl-biphen-4-yl)-5-pentenoic acid methyl ester (0.2 g, 0.365 mmol) in THF (2 mL) and methanol (2 mL) was cooled to 0° C. and treated with 2 N KOH (1.0 mL). After stirring at room temperature for 1 h the solution was acidified with 10% HCl to pH 2 and diluted with 25 ml of ethyl acetate. After being seperated, the aqueous layer was extracted with ethyl acetate (3×15 mL) and the combined organic layers were dried over MgSO$_4$ and concentrated. Purification by flash column chromatography (2-5% methanol in dichloromethane) provided 2-tert-Butoxycarbonylamino-5-(4'-dibenzofuran-4-yl-biphen-4-yl)-5-pentenoic acid (160 mg, 82%) as white solid. MP 180-182° C.; $^1$H NMR (CDCl$_3$), § 7.90 (d, J=9 Hz, 2 H), 7.84 (d, J=8 Hz, 2 H), 7.67 (d, J=9 Hz, 2 H), 7.55 (m, 4 H), 7.32 (m, 5 H), 6.50 (d, J=15 Hz, 1H), 6.12 (ddd, J=8, 8, 15 Hz, 1 H), 5.01 (d, J=8 Hz, 1 H), 4.4 (m, 1 H), 2.72 (m, 2 H), 1.38 (s, 9 H). LCMS 434 (M$^+$−100).

EXAMPLE 123

2-tert-Butoxycarbonylamino-5-(4'-dibenzofuran-4-yl-biphen-4-yl)-pentanoic acid

1. 2-tert-Butoxycarbonylamino-5-(4'-dibenzofuran-4-yl-biphen-4-yl)-pentanoic acid methyl ester A solution of 2-tert-Butoxycarbonylamino-5-(4'-dibenzofuran-4-yl-biphen-4-yl)-5-pentenoic acid methyl ester (0.225 g, 0.5 mmol) and 10% Pd/C (25 mg, 5 mol %) in ethyl acetate (15 mL) was hydrogenated in a Parr apperatous at 20 psi for 1 h. After the reaction was complete, the solution was filtered and the solid was washed with ethyl acetate (50 mL), dried over MgSO$_4$ and concentrated. Purification by flash column chromatography (5% ethyl acetate in heptane) gave 2-tert-Butoxycarbonylamino-5-(4'-dibenzofuran-4-yl-biphen-4-yl)-pentanoic acid methyl ester (222 mg, 98%) as a foam. $^1$H NMR (CDCl$_3$), δ 7.98 (d, J=9 Hz, 2 H), 7.95 (d, J=8 Hz, 2 H), 7.75 (d, J=9 Hz, 2 H), 7.63 (m, 4 H), 7.37 (m, 5 H), 5.01 (d, J=9 Hz, 1 H), 4.38 (m, 1 H), 3.71 (s, 3 H), 2.72 (m, 2 H), 1.80 (m, 4 H), 1.46 (s, 9 H). LCMS 450 (M$^+$−100).

2. 2-tert-Butoxycarbonylamino-5-(4'-dibenzofuran-4-yl-biphen-4-yl)-pentanoic acid A solution of 2-tert-butoxycarbonylamino-5-(4'-dibenzofuran-4-yl-biphen-4-yl)-5-pentanoic acid methyl ester (250 mg, 0.454 mmol) in THF (2 mL) and methanol (2 mL) was cooled to 0° C. and treated with 2 N KOH (1.0 mL). After stirring at room temperature for 1 h the solution was acidified with 10% HCl to pH 2 and diluted with 25 ml of ethyl acetate. After being seperated, the aqueous layer was extracted with ethyl acetate (3×15 mL) and the combined organic layers were dried over MgSO$_4$ and concentrated. Purification by flash column chromatography (2-5% methanol in dichloromethane) provided the desired product (210 mg, 87%) as a white solid. $^1$H NMR (CDCl$_3$), 7.98 (d, J=9 Hz, 2 H), 7.94 (d, J=8 Hz, 2 H), 7.74 (d, J=9, 2H), 7.62 (m, 4 H), 7.41 (m, 5 H), 5.01 (d, J=9 Hz, 1 H), 4.39 (m, 1 H), 2.72 (m, 2 H), 1.85 9 m, 4 H), 1.47 (s, 9 H). LCMS 436 (M$^+$−100).

EXAMPLE 124

2-tert-Butoxycarbonylamino-3-(4'-dibenzofuran-4-yl-biphen-4-yl)-propanoic acid

1. 2-tert-Butoxycarbonylamino-3-(4-iodophenyl)-propanoic acid methyl ester

A solution of 2-tert-butoxycarbonylamino-3-(4-iodophenyl)-propanoic acid (5.0 g, 12.8 mmol) in DMF (50 mL) was treated with K$_2$CO$_3$ (2.2 g, 15.4 mmol). After stirring for 15 min, the solution was cooled to 0° C. and treated with iodomethane (1.0 mL, 15.4 mmol) After the addition was complete, the reaction mixture was stirred at room temperature for another 16 h, filtered and the resulting solid was washed with ethyl acetate (200 mL). The filtrate was washed successively with 5% aq HCl, sat. aq NaCl, dried over MgSO$_4$ and concented. Purification by flash column chromatography (5% ethyl acetate in heptane) provided the desired product (5.74 g, 98%) as an oil. $^1$H NMR (CDCl$_3$), δ 7.61 (d, J=9 Hz, 2 H), 7.74 (d, J=9, 2H), 4.97 (d, J=7 Hz, 1 H), 4.56 (m, 1 H), 3.73 (s, 3 H), 3.02 (ddd, J=7, 7, 12 Hz, 2 H), 1.47 (s, 9 H)

2. 2-tert-Butoxycarbonylamino-3-(4'-dibenzofuran-4-yl-biphen-4-yl)-propanoic acid methyl ester A solution of 2-tert-Butoxycarbonylamino-3-(4-iodophenyl)-propanoic acid methyl ester (1.22 g, 3 mmol), 4-(4-dibenzofuranyl)benzeneboronic acid (0.906 g, 3.15 mmol) and Pd(PPh$_3$)$_4$ (160 mg, 5 mol %) in toluene (25 mL) and ethanol (6.0 mL) was treated with 2 M K$_2$CO$_3$ (4.5 mL). The reaction mixture was heated to reflux for 2 h, cooled to room temperature, diluted with ethyl acetate (100 mL). The organic layer was washed successively with 2% aq HCl and sat. aq NaCl, dried over MgSO$_4$ and concentrated. Purification by flash column chromatography (2-10% ethyl acetate in heptane) gave 2-tert-Butoxycarbonylamino-3-(4'-dibenzofuran-4-yl-biphen-4-yl)-propanoic acid methyl ester (1.1 g, 70%) as an oil. $^1$H NMR (CDCl$_3$), δ 7.98 (d, J=9 Hz, 2 H), 7.96 (d, J=8 Hz, 2 H), 7.74 (d, J=9, 2H), 7.66 (m, 4 H), 7.42 (m, 5 H), 5.04 (d, J=9 Hz, 1 H), 4.66 (m, 1 H), 3.73 (s, 3 H), 3.15 (m, 2 H), 1.57 (s, 9 H). LCMS 422 (M$^+$−100).

3. 2-tert-Butoxycarbonylamino-3-(4'-dibenzofuran-4-yl-biphen-4-yl)-propanoic acid A solution of 2-tert-butoxycarbonylamino-3-(4'-dibenzofuran-4-yl-biphen-4-yl)-propanoic acid methyl ester (125 mg, 0.24 mmol) in THF (2 mL) and methanol (2 mL) was cooled to 0° C. and treated with 2 N KOH (1.0 mL). After stirring at room temperature for 1 h the solution was acidified with 10% HCl to pH 2 and diluted with ethyl acetate (25 mL). After being seperated, the aqueous layer was extracted with ethyl acetate (3×15 mL) and the combined organic layers were dried over $MgSO_4$ and concentrated. Purification by flash column chromatography (2-5% methanol in dichloromethane) provided 2-tert-Butoxycarbonylamino-3-(4'-dibenzofuran-4-yl-biphen-4-yl)-propanoic acid (80 mg, 67%) as white solid. $^1H$ NMR ($CDCl_3$), 7.98 (d, J=9 Hz, 2 H), 7.93 (d, J=8 Hz, 2 H), 7.74 (d, J=9, 2 H), 7.59 (m, 4 H), 7.41 (m, 5 H), 5.01 (d, J=8 Hz, 1 H), 4.66 (m, 1H), 3.30 (m, 2 H), 1.47 (s, 9 H). LCMS 408 ($M^+$−100).

EXAMPLE 125

2-tert-Butoxycarbonylamino-3-(4'-dibenzofuran-4-yl-biphen-4-ylsulfanyl)-propanoic acid

1. 2-tert-Butoxycarbonylamino-3-methylsulfonylpropanoic acid methyl ester

A solution of N-tert-butoxycarbonylserine (1.1 g, 5.0 mmol) and triethylamine (0.84 mL, 6.0 mmol) in dichloromethane (50 mL) was cooled to 0° C. and treated with methylsulfonyl chloride (0.44 mL, 5.8 mmol)). After stirring an additional 2 h, the reaction mixture was acidified with 2% HCl (20 mL) and extracted with dichloromethane (3×20 mL). The combined organic layers were washed successively with sat. aq $NaHCO_3$, and sat. aq NaCl, dried over $MgSO_4$ and concentrated. Purification by flash column chromatography (5% ethyl acetate in heptane) gave the desired product (1.25 g, 84%) as an oil. $^1H$ NMR ($CDCl_3$), 5.71 (d, J=7 Hz, 1 H), 4.56 (m, 3 H), 3.82 (s, 3 H), 3.02 (s, 3 H), 1.44 (s, 9 H).

2. 2-tert-Butoxycarbonylamino-3-(4-bromophenylsulfanyl)-propanoic acid methyl ester

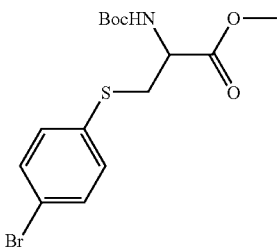

Solution of 2-tert-Butoxycarbonylamino-3-methylsulfonylpropanoic acid methyl ester (0.86 g, 2.89 mmol) and 4-bromobenzenthiol (0.56 g, 2.89 mmol) in DMF (10 mL) was cooled to at 0° C. and treated with $Cs_2CO_3$ (1.1 g, 3.2 mmol). After stirring at room temperature for 2 h, the reaction was acidified with 5% HCl (15 mL) and diluted with ethyl acetate (25 mL). After separation, the aqueous layer was extracted with ethyl acetate (3×15 mL) and the combined organic layers were washed with sat. aq NaCl, dried over $MgSO_4$, filtered, and concentrated. Purification by flash column chromatography (5% ethyl acetate in heptane) gave the desired product (857 mg, 76%) as a white solid. $^1H$ NMR ($CDCl_3$), δ 7.40 (d, J=9 Hz, 2 H), 7.27 (d, J=9, 2 H), 5.30 (d, J=7 Hz, 1 H), 4.56 (m, 1 H), 3.59 (s, 3 H), 3.35 (ddd, J=7, 7, 12 Hz, 2 H), 1.47 (s, 9 H)

3. 2-tert-Butoxycarbonylamino-3-(4'-dibenzofuran-4-yl-biphen-4-ylsulfanyl)-propanoic acid methyl ester A solution of 2-tert-Butoxycarbonylamino-3-(4-bromophenylsulfanyl)-propanoic acid methyl ester (0.55 g, 1.41 mmol), 4-(4-dibenzofuranyl)benzeneboronic acid (0.44 g, 1.52 mmol) and $Pd(PPh_3)_4$ (0.073 g, 5 mol %) in toluene (15 mL) and ethanol (3.0 mL) was treated with 2 M $K_2CO_3$ (2.2 mL). The reaction mixture was heated to reflux for 2 h, cooled to room temperature, diluted with ethyl acetate (100 mL). The organic layer was washed successively with 2% aq HCl and sat. aq NaCl, dried over $MgSO_4$ and concentrated. Purification by flash column chromatography (2-10% ethyl acetate in heptane) gave the desired product (552 mg, 72%) as a white solid. $^1H$ NMR ($CDCl_3$), δ 8.01 (d, J=6 Hz, 2 H), 7.96 (dd, J=4 Hz, 8 Hz, 2H), 7.74 (d, J=9 Hz, 2 H), 7.66 (m, 4 H), 7.42 (m, 5 H), 5.41 (d, J=7 Hz, 1 H), 4.62 (m, 1 H), 3.73 (s, 3 H), 3.45 (d, J=4 Hz, 2H), 1.57 (s, 9 H). LCMS 454 ($M^+$−100).

4. 2-tert-Butoxycarbonylamino-3-(4'-dibenzofuran-4-yl-biphen-4-ylsulfanyl)-propanoic acid A solution of 2-tert-Butoxycarbonylamino-3-(4'-dibenzofuran-4-yl-biphen-4-ylsulfanyl)-propanoic acid methyl ester (0.150 g, 0.27 mmol) in THF (2 mL) and methanol (2 mL) was cooled to 0° C. and treated with 2 N KOH (1.0 mL). After stirring at room temperature for 1 h the solution was acidified with 10% HCl to pH 2 and diluted with ethyl acetate (25 mL). After being seperated, the aqueous layer was extracted with ethyl acetate (3×15 mL) and the combined organic layers were dried over $MgSO_4$ and concentrated. Purification by flash column chromatography (2-5% methanol in dichloromethane) provided 2-tert-Butoxycarbonylamino-3-(4'-dibenzofuran-4-yl-biphen-4-ylsulfanyl)-propanoic acid (110 mg, 75%) as white solid. $^1H$ NMR ($CDCl_3$), δ 8.18 (d, J=7 Hz, 2 H), 8.14 (dd, J=1, 7 Hz, 2 H), 7.98 (d, J=9 Hz, 2 H), 7.82 (d, J=9 Hz, 2 H), 7.72 (m, 4 H), 7.51 (m, 3 H), 3.90 (m, 1 H), 3.48 (dd, J=4, 12 Hz, 1 H), 3.30 (m, 1H), 1.47 (s, 9 H). LCMS 440 ($M^+$−100).

EXAMPLE 126

2-tert-Butoxycarbonylamino-3-(4'-dibenzofuran-4-yl-biphen-4-ylmethylsulfanyl)-3,3-dimethylpropanoic acid

1. 2-tert-butoxycarbonylamino-3-(4-bromophenylmethylsulfanyl)-3,3-dimethylpropanoic acid methyl ester

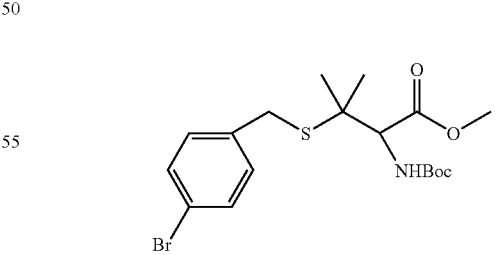

A solution of 4-bromobenzyl alcohol (1.87 g, 10 mmol) in $CF_3CO_{2H}$ (19 mL) and $CF_3SO_{3H}$ (1 mL) was treated with pencilamine (1.49 g, 10 mmol). The reaction mixture was stirred for another 4 h then concentrated. The resulting residue was dissolved in 2 M NaOH (20 mL), cooled to 0° C. and treated with a second solution of di-tert-butyl dicarbonate in 1,4-dioxane (10 mL) in a dropwise manner. After stirring for 16 h 3 N HCl was added until the solution became pH 2 and the resulting solution was extracted with ethyl acetate (3×50 mL). The combined organic layers were washed with sat. aq NaCl, dried over MgSO$_4$ and concentrated. The remaining residue was dissolved in DMF (15 mL) and treated with K$_2$CO$_3$ (2 g, 14.4 mmol) and MeI (1 mL, 16 mmol). After the addition was complete, the reaction mixture was stirred for 16 h and filtered to remove solid, which was washed by ethyl acetate (200 mL). The filtrate was washed with sat. aq NaCl, dried over MgSO$_4$ and concentrated. Purification by flash column chromatography (10% ethyl acetate in heptane) provided the desired product (2.5 g, 58%, 3 steps) as an oil. $^1$H NMR (CDCl$_3$), δ 7.43 (d, J=8 Hz, 2 H), 7.18 (d, J=8 Hz, 2 H), 5.36 (d, J=7 Hz, 1 H), 4.35 (dd, J=9, 30 Hz, 1 H), 3.75 (m, 5 H), 1.36 (s, 9 H).

2. 2-Butoxycarbonylamino-3-(4'-dibenzofuran-4-yl-biphen-4-ylmethylsulfanyl)-3,3-dimethylpropanoic acid methyl ester A solution of 2-tert-butoxycarbonylamino-3-(4-bromophenylmethylsulfanyl)-3,3-dimethylpropanoic acid methyl ester (0.432 g, 1 mmol), 4-(4-dibenzofuranyl)benzeneboronic acid (0.305 g, 1.05 mmol) and Pd(PPh$_3$)$_4$ (0.052 g, 5 mol %) in toluene (10 mL) and ethanol (3.0 mL) was treated with 2 M K$_2$CO$_3$ (1.5 mL). The reaction mixture was heated to reflux for 2 h, cooled to room temperature, diluted with ethyl acetate (100 mL). The organic layer was washed successively with 2% aq HCl and sat. aq NaCl, dried over MgSO$_4$ and concentrated. Purification by flash column chromatography (2-10% ethyl acetate in heptane) gave the desired product (430 mg, 72%) as an oil. $^1$H NMR (CDCl$_3$), δ 8.01 (d, J=8 Hz, 2 H), 7.94 (d, J=8 Hz, 2 H), 7.78 (d, J=8 Hz, 2 H), 7.66 (m, 4 H), 7.42 (m, 5 H), 5.44 (d, J=9 Hz, 1 H), 4.46 (d, J=9 Hz, 1 H), 3.87 (s, 2 H), 3.81 (s, 3 H), 1.44 (s, 9 H). LCMS 618 (M$^+$+23).

3. 2-tert-Butoxycarbonylamino-3-(4'-dibenzofuran-4-yl-biphen-4-ylmethylsulfanyl)-3,3-dimethylpropanoic acid A solution of 2-tert-butoxycarbonylamino-3-(4'-dibenzofuran-4-yl-biphen-4-yl)-propanoic acid methyl ester (0.250 g, 0.42 mmol) in THF (2 mL) and methanol (2 mL) was cooled to 0° C. and treated with 2 N KOH (1.0 mL). After stirring at room temperature for 1 h the solution was acidified with 10% HCl to pH 2 and diluted with ethyl acetate (25 mL). After being seperated, the aqueous layer was extracted with ethyl acetate (3×15 mL) and the combined organic layers were dried over MgSO$_4$ and concentrated. Purification by flash column chromatography (2-5% methanol in dichloromethane) provided the desired product (160 mg, 66%) as a white solid. $^1$H NMR (CDCl$_3$), δ 8.01 (d, J=8 Hz, 2 H), 7.94 (d, J=8 Hz, 2 H), 7.78 (d, J=8 Hz, 2 H), 7.66 (m, 4 H), 7.42 (m, 5 H), 5.44 (d, J=9 Hz, 1 H), 4.46 (d, J=9 Hz, 1 H), 3.90 (m, 2 H), 1.44 (s, 9 H). LCMS 6041 (M$^+$+23).

EXAMPLE 127

2-tert-Butoxycarbonylamino-3-(4'-dibenzofuran-4-yl-biphen-4-ylmethoxy)propanoic acid 1. Aziridine-N-butoxycarbonyl-2-carboxylic acid methyl ester A solution of aziridine-2-carboxylic acid methyl ester (1.5 g, 15 mmol) in THF (50 mL) was treated with Boc anhydride (3.9 g, 18 mmol) and DMAP (100 mg). After stirring for 16 h the reaction mixture was filtered through a short pad of silica gel which was subsequently washed with ethyl acetate (200 mL). The filtrate was concentrated to give crude aziridine-N-butoxycarbonyl-2-carboxylic acid methyl ester as oil. $^1$H NMR (CDCl$_3$), 3.77 (s, 3 H), 3.03 (dd, J=3, 8 Hz, 1 H), 2.52 (dd, J=1, 3 z, 1 H), 2.41 (dd, J=1, 8 Hz, 1 H), 1.45 (s, 9 H).

2. 2-tert-butoxycarbonyl-3-(4-bromophen-4-yl-methoxy)propanoic acid methyl ester

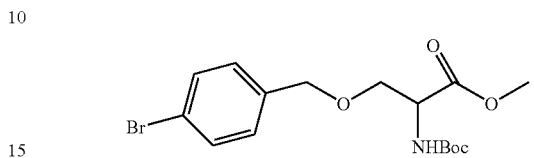

A solution of 4-bromobenyl alcohol (3.7 g, 20 mmol) in toluene (15 mL) was treated with BF$_3$ OEt$_2$ (150 µL). After stirring 15 min, aziridine-N-tert-butoxy-carbonyl-2-carboxylic acid methyl ester (2 g, 10 mmol) was added and stirring was continued for 16 h. Once complete, the solution was diluted with ethyl acetate (100 mL) and washed with sat.aq NaCl, dried over MgSO$_4$ and concentrated. Purification by flash column chromatography (2-10% ethyl acetate in heptane) provided the desired product (1.2 g, 31%) as a white solid. $^1$H NMR (CDCl$_3$), δ 7.43 (d, J=8 Hz, 2 H), 7.18 (d, J=8 Hz, 2 H), 5.36 (d, J=9 Hz, 1 H), 4.47 (m, 3 H), 3.86 (dd, J=1, 6 Hz, 1 H), 3.75 (s, 3 H), 3.66 (dd, J=1, 6 Hz, 1 H), 1.45 (s, 9 H).

3. 2-tert-Butoxycarbonylamino-3-(4'-dibenzofuran-4-yl-biphen-4-ylmethyloxy)-propanoic acid methyl ester A solution of 2-tert-butoxycarbonyl-3-(4-bromophen-4-ylmethoxy)propanoic acid methyl ester (0.388 g, 1 mmol), 4-(4-dibenzofuranyl)benzeneboronic acid (0.305 g, 1.05 mmol) and Pd(PPh$_3$)$_4$ (0.052 g, 5% mol) in toluene (10 mL) and ethanol (3.0 mL) was treated with 2 M K$_2$CO$_3$ (1.5 mL). The reaction mixture was heated to reflux for 2 h, cooled to room temperature, diluted with ethyl acetate (100 mL). The organic layer was washed successively with 2% aq HCl and sat. aq NaCl, dried over MgSO$_4$ and concentrated. Purification by flash column chromatography (2-10% ethyl acetate in heptane) gave the desired product (369 mg, 67%) as an oil. $^1$H NMR (CDCl$_3$), δ 8.01 (d, J=8 Hz, 2 H), 7.94 (d, J=8 Hz, 2 H), 7.78 (d, J=8 Hz, 2 H), 7.66 (m, 4 H), 7.42 (m, 5 H), 5.44 (d, J=9 Hz, 1H), 4.58 (dd, J=9, 21 Hz, 2 H), 4.05 (m, 1 H), 3.93 (dd, J=1, 6 Hz, 1 H), 3.78 (m, 4 H), 1.44 (s, 9 H). LCMS 574 (M$^+$+23).

4. 2-Butoxycarbonylamino-3-(4'-dibenzofuran-4-yl-biphen-4-ylmethyloxy)-propanoic acid A solution of 2-tert-butoxycarbonylamino-3-(4'-dibenzofuran-4-yl-biphen-4-yl)-propanoic acid methyl ester (0.125 g, 0.24 mmol) in THF (2 mL) and methanol (2 mL) was cooled to 0° C. and treated with 2 N KOH (1.0 mL). After stirring at room temperature for 1 h the solution was acidified with 10% HCl to pH 2 and diluted with ethyl acetate (25 mL). After being seperated, the aqueous layer was extracted with ethyl acetate (3×15 mL) and the combined organic layers were dried over MgSO$_4$ and concentrated. Purification by flash column chromatography (2-5% methanol in dichloromethane) provided the desired product (80 mg, 67%) as a white solid. $^1$H NMR (CDCl$_3$), δ 8.01 (d, J=8 Hz, 2 H), 7.94 (d, J=8 Hz, 2 H), 7.78 (d, J=8 Hz, 2 H), 7.66 (m, 4 H), 7.42 (m, 5 H), 5.44 (d, J=9 Hz, 1 H), 4.62 (s, 2 H), 4.53 (m, 1 H), 4.02 (dd, J=1, 6 Hz, 1 H), 3.78 (dd, J=1, 6 Hz, 1 H), 1.44 (s, 9 H). LCMS 560 (M$^+$+23).

EXAMPLE 128

2-Benzyl-3-[4-(4,4,5,5-tetramethyl-[1,3,2]-dioxaborolan-2-yl)phenyl]-benzofuran

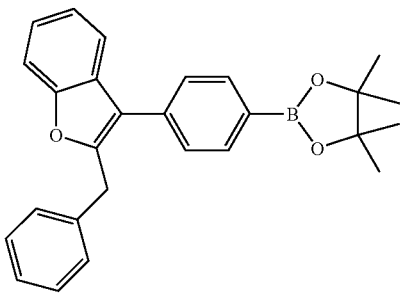

A solution of bis-(pinacolato)diboron (2.64 g, 10.41 mmol) in anhydrous DMSO (20 mL) was added to a stirred suspension of the known triflate, trifluoromethanesulfonic acid-4-(2-benzylbenzofuran-3 yl)phenyl ester, (4.09 g, 9.47 mmol) and potassium acetate (3.71 g, 37.9 mmol) in anhydrous DMSO (20 mL). [1,1'-bis-(Diphenylphosphino)-ferrocene]dichloropalladium(II)-DCM complex (770 mg, 0.95 mmol) was added as a solid, and the resulting suspension was heated to 80° C. for 4 hrs. The reaction mixture was cooled to room temperature, diluted with diethyl ether (150 mL), washed with water (2×50 mL), brine (3×50 mL), dried over anhydrous MgSO$_4$, filtered and concentrated in vacuo. Purification of the product by flash column chromatography, using 10% ethyl acetate/heptane as eluent, afforded the title compound as a white solid (2.96 g).

EXAMPLE 129

2-tert-Butoxycarbonylamino-3-(3'-dibenzofuran-4-yl-biphen-3-ylmethoxy)propanoic acid

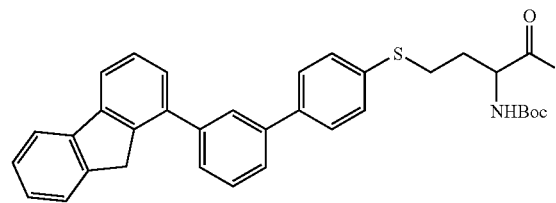

Step 1. Aziridine-N-butoxycarbonyl-2-carboxylic acid methyl ester

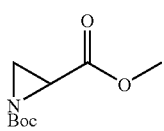

Solution of aziridine-2-carboxylic acid methyl ester (1.5 g, 15 mmol) in 50 ml THF was treated with Boc anhydride (3.9, 18 mmol) and DMAP (100 mg). The reaction mixture was stirred for 16 hr before being filtered through a short silica gel. The silica gel was washed with 200 ml ethyl acetate and the filtrate was concentrated to the title compound as an oil (3 g, ~100% yield, 95% purity). $^1$H NMR (CDCl$_3$): ☐ 3.77 (s, 3H), 3.03 (dd, J=8, 3 Hz, 1H), 2.52 (dd, J=3, 1 z, 1H), 2.41 (dd, J=8, 1 Hz, 1H), 1.45 (s, 9H).

Step 2. Methyl-2-tert-butoxycarbonylamino-3-(3'-dibenzofuran-4-yl-biphen-3-ylmethoxy)propionate

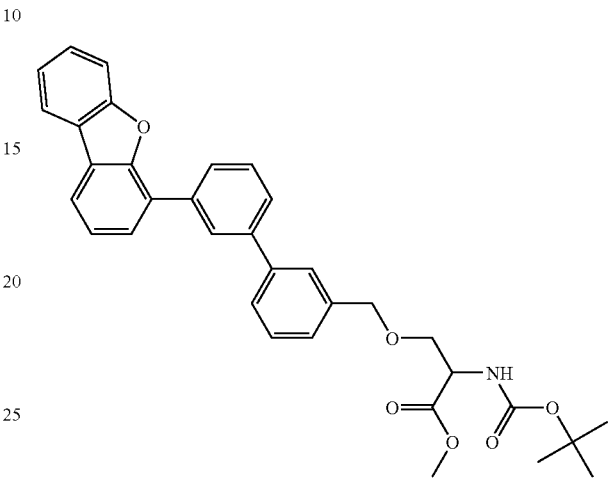

A solution of (3'-dibenzofuran-4-ylbiphen-3-yl)methanol (200 mg, 0.57 mmol) in 10 ml toluene was treated with catalytic amount BF$_3$ OEt$_2$ (1-2 drops). After 15 mine stirring, aziridine-N-tert-butoxy-carbonyl-2-carboxylic acid methyl ester (116 mg, 0.57 mmol) was introduced to the mixture. The reaction was continued for 16 hr before diluted with 100 ml ethyl acetate. The mixture was washed by sat.NaCl and dried over MgSO$_4$. After concentration, the residue was purified by flash column purification with 10-20% ethyl acetate in heptane to give the title compound as a colorless oil (154 mg, 49% yield).

Step 3. 2-tert-Butoxycarbonylamino-3-(3'-dibenzofuran-4-yl-biphen-3-ylmethoxy)propanoic acid

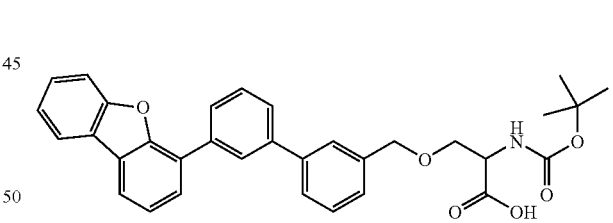

2N Sodium hydroxide solution (0.38 mL, 0.76 mmol) was added dropwise to a stirred solution of methyl-2-(3'-dibenzofuran-4-yl-biphen-3-ylmethylsulfanyl)-propionate (140 mg, 0.25 mmol) in tetrahydrofuran (5 mL) and methanol (1 mL). The clear reaction mixture was stirred at room temperature until the reaction was complete (TLC control), and then diluted with water (5 mL), and acidified to pH 3 with 2N hydrochloric acid. The reaction mixture was extracted with ethyl acetate (2×20 mL). The combined extract was washed with water, brine, dried over anhydrous MgSO$_4$, filtered and concentrated in vacuo. Purification of the product by flash column chromatography, using 5-10% methanol in methylene chloride as eluent, afforded the title compound has a white solid (126 mg, 92%); Rf: 0.30 (10% methanol in dichloromethane); $^1$H NMR (DMSO-d6): ☐ 8.18 (2H, d, J=8 Hz), 8.00 (2H, d, J=8 Hz), 7.84 (2H, d, J=8 Hz), 7.70 (5H, m), 7.48 (4H, m), 7.36 (2H, m), 6.34 (1H, m, NH), 4.54 (s, 2H), 3.94 (1H, m), 3.70 (2H, m), 1.38 (s, 9H); ESI-LCMS e/z calcd for $C_{33}H_{31}NO_6$ 537.60, found 560 (M+Na)$^+$.

EXAMPLE 130

(L)-2-tert-Butoxycarbonylamino-4-(3'-dibenzofuran-4-yl-biphenyl-4-yloxy)-butyric acid

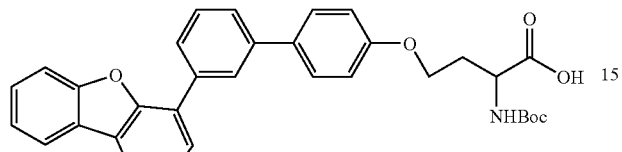

Step 1. 4-(3-Bromo-phenyl)-dibenzofuran

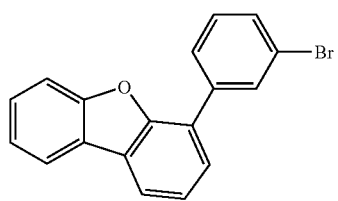

A mixture of 4-dibenzofuranboronic acid (51 mmol), 1-Bromo-3-iodo-benzene (51 mmol), and Pd(PPh$_3$)$_4$, (4 mmol) in 250 mL of toluene and 150 mL of ethanol was heated to obtain a clear solution, then Na$_2$CO$_3$ (155 mmol) in 250 mL water was added. The reaction mixture refluxed for 4 h at 80° C. The mixture was cooled to room temperature and diluted with 300 mL ethyl acetate. The organic layer was washed with 2×300 mL portions of water, 2×300 mL portions of sat. aq. NaCl, and dried (MgSO$_4$). After the solution was concentrated, the residue was purified by column chromatography (eluted with 2% EtOAc-Heptane) to afford 4-(3-Bromo-phenyl)-dibenzofuran.

Step 2. 4-[3-(4,4,5,5-Tetramethyl-[1,3,2]dioxaborolan-2-yl)-phenyl]-dibenzofuran

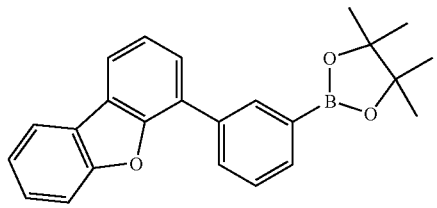

4-(3-Bromo-phenyl)-dibenzofuran (5.76 g, 17.8 mmol), bis(pinacolato)diboron (5.43 g, 21.4 mmol), Pd(dppf)Cl$_2$.CH$_2$Cl$_2$ (0.582 g, 4% mol) and 1,1'-bis(diphenylphosphino)ferrocene (0.395 g, 4% mol) were dissolved with heating in 100 ml 1,4-dioxane and then treated with KOAc (5.25 g, 53.5 mmol). The reaction mixture was stirred at reflux for 16 hr., cooled to ambient temperature and diluted with ethyl acetate. The organic layer was washed sequentially with 2% HCl and sat. NaCl., dried over MgSO$_4$, filtered and concentrated in vacuo. The residue was purified by flash column chromatography with 2-10% ethyl acetate in heptane as eluent to yield the titled compound as a white solid (4.81 g, 73% yield).

Step 3. 3'-Dibenzofuran-4-yl-biphenyl-4-ol

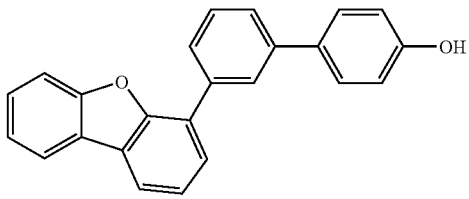

A mixture of 4-(3-bromo-phenyl)-dibenzofuran (0.62 mmol), 4-hydroxyphenyl boronic acid (0.62 mmol), and Pd(PPh$_3$)$_4$, (0.05 mmol) in 2 mL of toluene and 1 mL ethanol was heated to obtain a clear solution, then Na$_2$CO$_3$ (1.9 mmol) in 2 mL water was added. The reaction mixture refluxed for 5 h at 80° C. The mixture was cooled to room temperature and the aqueous layer was acidified with 2N HCl. The entire reaction mixture was diluted with 25 mL ethyl acetate. The organic layer was washed with 2×30 mL portions of water, 2×30 mL portions of sat. aq. NaCl, and dried (MgSO$_4$). After the solution was concentrated, the residue was purified by column chromatography (eluted with 5-10% EtOAc-Heptane) to afford 3'-Dibenzofuran-4-yl-biphenyl-4-ol.

Step 4. (L)-2-tert-Butoxycarbonylamino-4-(3'-dibenzofuran-4-yl-biphenyl-4-yloxy)-butyric acid methyl ester

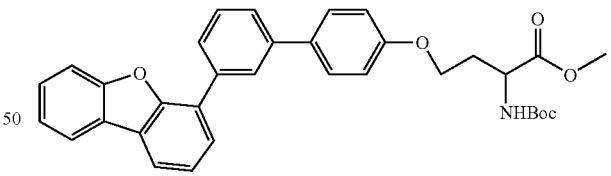

3'-Dibenzofuran-4-yl-biphenyl-4-ol (0.27 mmol) in 3 mL DMF was treated with NaH (0.32 mmol) for 10 minutes at room temperature. Then the known (L)-2-tert-Butoxycarbonyl-amino-4-bromobutyric acid methyl ester (0.27 mmol) was added to the reaction mixture. The reaction was stirred for 4 hours then was diluted with 25 mL ethyl acetate. The organic layer was washed with sat. NH$_4$Cl, sat. NaCl, and dried over MgSO$_4$. After the solution was concentrated, the residue was purified by column chromatography (eluted with 10-20% EtOAc-Heptane) to afford (L)-2-tert-Butoxycarbonylamino-4-(3'-dibenzofuran-4-yl-biphenyl-4-yloxy)-butyric acid methyl ester.

Step 5. (L)-2-tert-Butoxycarbonylamino-4-(3'-dibenzofuran-4-yl-biphenyl-4-yloxy)-butyric acid

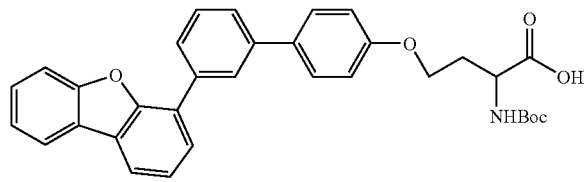

(L)-2-tert-Butoxycarbonylamino-4-(3'-dibenzofuran-4-yl-biphenyl-4-yloxy)-butyric acid methyl ester (0.50 mmol) was dissolved in 2 mL of THF and 2 mL of methanol. The solution was treated with 5 equivalents of 2N NaOH. The reaction was stirred at room temperature for 3 hours and then was acidified with 2N HCl to a pH 2. The reaction was extracted with 3×25 mL ethyl acetate and dried over MgSO$_4$. The residue was purified by column chromatography (eluted with 5% methanol-dichloromethane) to afford (L)-2-tert-Butoxycarbonylamino-4-(3'-dibenzofuran-4-yl-biphenyl-4-yloxy)-butyric acid as a white solid. $^1$H NMR (DMSO): □ 8.17 (2H, t, J=8 Hz), 8.05 (1H, s), 7.81 (1H, t, J=7 Hz), 7.77-7.48 (8H, m), 7.41 (1H, t, J=7 Hz), 7.22 (1H, d, J=8 Hz), 7.03 (2H, d, J=9 Hz), 4.09 (3H, m), 2.17 (1H, m), 1.99 (1H, m), 1.36 (9H, s). ESI-LCMS m/z calcd for $C_{33}H_{31}NO_6$: 537.6; found 560.3 (M+Na)$^+$.

EXAMPLE 131

(L)-2-tert-Butoxycarbonylamino-4-(3'-dibenzofuran-4-yl-biphenyl-3-yloxy)-butyric acid was prepared in a manner analogous to that set forth in Example 130 steps 1-4.

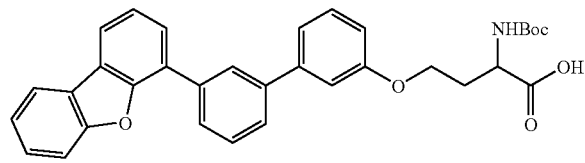

EXAMPLE 132

(L)-2-tert-Butoxycarbonylamino-4-(4'-dibenzofuran-4-yl-biphenyl-3-yloxy)-butyric acid was prepared in a manner analogous to that set forth in Example 130 steps 1-4.

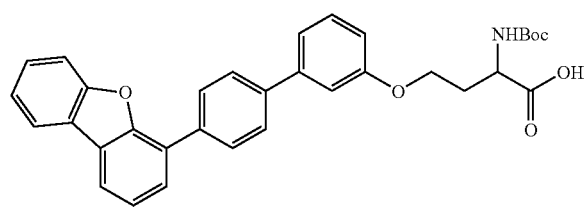

EXAMPLE 133

(L)-2-tert-Butoxycarbonylamino-4-(3'-dibenzofuran-4-yl-biphenyl-4-ylsulfanyl)-butyric acid

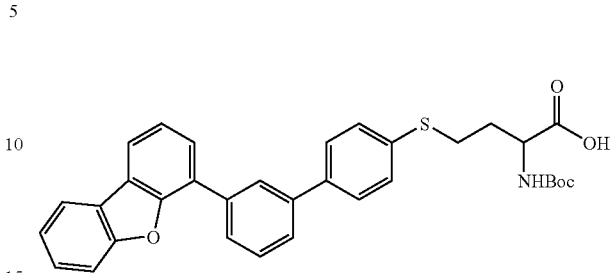

Step 1. (L)-2-tert-Butoxycarbonylamino-4-(3'-dibenzofuran-4-yl-biphenyl-4-ylsulfanyl)-butyric acid methyl ester

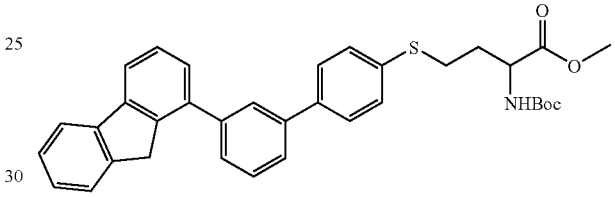

The known compound 4-[3-(4,4,5,5-tetramethyl-[1,3,2dioxaborolan-2-yl)-phenyl]-dibenzofuran (0.30 mmol) and 4-(4'-bromo-phenylsulfanyl)-(L)-2-tert-butoxycarbonylamino-butyric acid methyl ester (0.30 mmol) were dissolved in 5 mL dioxane. To this solution was added tripotassium phosphate (0.60 mmol), [1,1'-bis(diphenylphosphino)ferrocene] dichloropalladium(II) complex with dichloromethane (0.009 mmol), and 1,1'-bis(diphenylphosphino)ferrocene (0.009 mmol). The reaction mixture was refluxed at 100° C. for 8 hours. The reaction was then diluted with 25 mL water and extracted with 3×50 mL ethyl acetate and dried over MgSO$_4$. After the solution was concentrated, the residue was purified by column chromatography (eluted with 5-15% EtOAc-Heptane) to afford (L)-2-tert-Butoxycarbonylamino-4-(3'-dibenzofuran-4-yl-biphenyl-4-ylsulfanyl)-butyric acid methyl ester.

Step 2. (L)-2-tert-Butoxycarbonylamino-4-(3'-dibenzofuran-4-yl-biphenyl-4-ylsulfanyl)-butyric acid

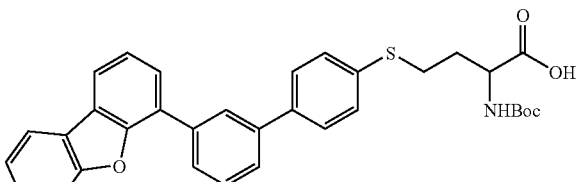

(L)-2-tert-Butoxycarbonylamino-4-(3'-dibenzofuran-4-yl-biphenyl-4-ylsulfanyl)-butyric acid methyl ester (0.50 mmol) was dissolved in 2 mL of THF and 2 mL of methanol. The solution was treated with 5 equivalents of 2N NaOH. The reaction was stirred at room temperature for 3 hours and then was acidified with 2N HCl to a pH 2, and extracted with 3×25 mL ethyl acetate and dried over MgSO$_4$. The residue was purified by column chromatography (eluted with 5% methanol-dichloromethane) to afford (L)-2-tert-butoxycarbonylamino-4-(3'-dibenzofuran-4-yl-biphenyl-4-ylsulfanyl)-butyric acid as a white solid. $^1$H NMR (DMSO) δ 8.17 (2H, t, J=8 Hz), 8.09 (1H, s), 7.88 (1H, d, J=8 Hz), 7.80-7.70 (4H, m), 7.63 (2H, t, J=8 Hz), 7.51 (2H, m), 7.41 (3H, m), 7.09 (1H, m), 4.01 (1H, m), 3.03 (2H, m), 1.94 (2H, m), 1.37 (9H, s). ESI-LCMS m/z calcd for C$_{33}$H$_{31}$NO$_5$S: 553.7; found 576.3 (M+Na)$^+$.

EXAMPLE 134

(L)-2-tert-Butoxycarbonylamino-4-(3'-dibenzofuran-4-yl-biphenyl-3-ylsulfanyl)-butyric acid was prepared in a manner analogous to that set forth in example 133 steps 1-2.

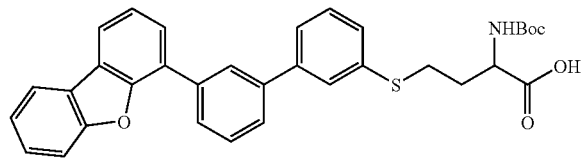

EXAMPLE 135

(L)-2-tert-Butoxycarbonylamino-5-(3'-dibenzofuran-4-yl-biphenyl-3-yl)-pent-4-enoic acid

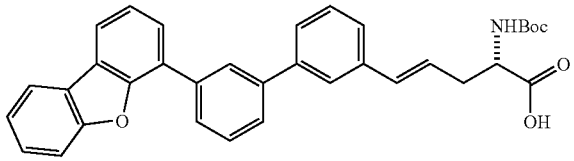

Step 1. (L)-2-tert-Butoxycarbonylamino-5-pentenoic acid methyl ester

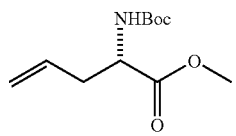

A solution of di-tert-butyl dicarbonate (4.64 g, 21.3 mmol) in 10 ml 1,4-dioxane was slowly added to a stirred solution of 2.04 g of (L)-2-amino-5-pentenoic acid (17.7 mmol) in 25 ml of 1N NaOH at 0° C. The reaction mixture was stirred for 16 hr before the pH was adjusted to 2. The mixture was then extracted with ethyl acetate (3×), dried over MgSO$_4$, filtered and concentrated in vacuo to yield 4.21 g of crude product. The crude product was dissolved in 25 ml DMF and treated with K$_2$CO$_3$ (3.24 g, 23.5 mmol) for 15 min at ambient temperature. Iodomethane (1.46 mL, 23.5 mmol) was introduced at 0° C. The reaction mixture was stirred for 4 hr. at ambient temperature, filtered and washed with 150 ml ethyl acetate. The filtrate was washed sequentially with 5% HCl and sat. NaCl, dried over MgSO$_4$ and filtered. After concentration in vacuo, the residue was purified by flash column chromatography with 5% ethyl acetate in heptane as eluent to yield the titled compound as an oil (3.87 g, 95% yield).

Step 2. (L)-5-(3-Bromophenyl)-2-tert-butoxycarbonylamino-5-pentenoic acid methyl ester

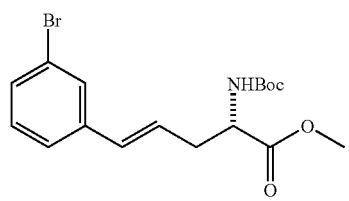

A sealed tube was charged with 3-bromoiodobenzene (1.96 mL, 15.4 mmol), (L)-2-tert-butoxycarbonylamino-5-pentenoic acid methyl ester (3.87 g, 16.9 mmol), triethylamine (2.35 mL, 16.9 mmol) and Pd(OAc)$_2$ (138 mg, 4% mol) in 2 ml acetonitrile. The tube was purged with N$_2$, sealed and heated at 100° C. for 16 hr. The reaction mixture was cooled to ambient temperature and filtered through celite. The filtrate was concentrated in vacuo and purified by flash column chromatography with 10% ethyl acetate in heptane as eluent to yield the titled compound as an oil (4.20 g, 71% yield).

Step 3. (L)-2-tert-Butoxycarbonylamino-5-(3'-dibenzofuran-4-yl-biphenyl-3-yl)-pent-4-enoic acid methyl ester

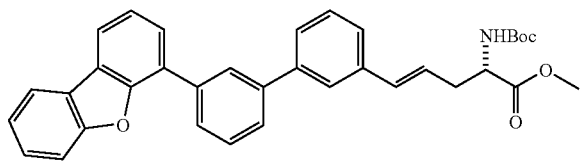

(L)-5-(3-Bromophenyl)-2-tert-butoxycarbonylamino-5-pentenoic acid methyl ester (1.41 g, 3.67 mmol), 4-[3-(4,4,5,5-tetramethyl-[1,3,2]dioxaborolan-2-yl)-phenyl]-dibenzofuran (1.63 g, 4.40 mmol), Pd(dppf)Cl$_2$.CH$_2$Cl$_2$ (0.120 g, 4% mol) and 1,1'-bis(diphenylphosphino)ferrocene (0.081 g, 4% mol) were dissolved with heating in 25 ml 1,4-dioxane and then treated with K$_3$PO$_4$ (1.56 g, 7.34 mmol). The reaction mixture was stirred at reflux for 2 hr., cooled to ambient temperature and diluted with 100 ml ethyl acetate. The organic layer was washed sequentially with 2% HCl and sat. NaCl., dried over MgSO$_4$, filtered and concentrated in vacuo. The residue was purified by flash column chromatography with 2-10% ethyl acetate in heptane as eluent to yield the titled compound as an oil (1.31 g, 65% yield).

Step 4. (L)-2-tert-Butoxycarbonylamino-5-(3'-dibenzofuran-4-yl-biphenyl-3-yl)-pent-4-enoic acid

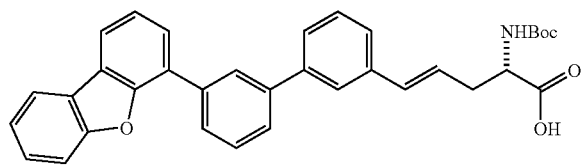

To a stirred solution of (L)-2-tert-butoxycarbonylamino-5-(3'-dibenzofuran-4-yl-biphenyl-3-yl)-pent-4-enoic acid methyl ester (0.074 g, 0.135 mmol) in methanol (1 mL) and THF (4 mL) was added 2M NaOH solution (0.68 mL, 1.35 mmol). Upon completion (TLC 10% methanol in dichloromethane), the mixture was acidified with 2M HCl solution (pH≈2) and extracted with ethyl acetate (3×). The combined extract was washed sequentially with water and brine, dried over anhydrous MgSO$_4$, filtered and concentrated in vacuo. Purification by flash column chromatography with 2-5% methanol in dichloromethane as eluent yielded the titled compound as a white solid (0.070 g, 97%). $R_f$=0.16 (5% methanol in dichloromethane); 1H NMR (CDCl$_3$, 300 MHz) δ 7.98 (1H, s, ArH), 7.91-7.80 (3H, m, ArH), 7.56-7.45 (6H, m, ArH), 7.39-7.24 (5H, m, ArH), 6.47 (1H, d, J=17 Hz, CH), 6.10 (1H, m, CH), 4.39 (1H, m, CHN), 1.33 (9H, s, C(CH$_3$)$_3$); ESI-LCMS e/z calculated for C$_{34}$H$_{31}$NO$_5$ 533.220, found 456 (M+Na-Boc)$^+$, 556 (M+Na)$^+$.

EXAMPLE 136

(L)-2-tert-Butoxycarbonylamino-5-(3'-dibenzofuran-4-yl-biphenyl-3-yl)-pentanoic acid

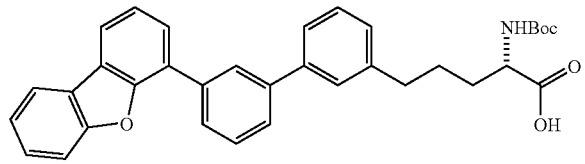

Hydrogenation of (L)-2-tert-butoxycarbonylamino-5-(3'-dibenzofuran-4-yl-biphenyl-3-yl)-pent-4-enoic acid methyl ester (0.249 g, 0.455 mmol) was carried out in 15 ml ethyl acetate with 10% Pd/C (5% mol) at 20 psi for 1 hr. Solids were removed by filtration through celite and washed with 50 ml ethyl acetate. The filtrate was concentrated in vacuo and purified by flash column chromatography with 5% ethyl acetate in heptane as eluent.

To a stirred solution of (L)-2-tert-butoxycarbonylamino-5-(3'-dibenzofuran-4-yl-biphenyl-3-yl)-pentanoic acid methyl ester (0.241 g, 0.438 mmol) in methanol (2 mL) and THF (8 mL) was added 2M NaOH solution (2.2 mL, 4.38 mmol). Upon completion (TLC 10% methanol in dichloromethane), the mixture was acidified with 2M HCl solution (pH≈2) and extracted with ethyl acetate (3×). The combined extract was washed sequentially with water and brine, dried over anhydrous MgSO$_4$, filtered and concentrated in vacuo. Purification by flash column chromatography with 2-5% methanol in dichloromethane as eluent yielded the titled compound as a white solid (0.075 g, 32%). Rf=0.14 (5% methanol in dichloromethane); $^1$H NMR (DMSO-d6, 300 MHz) δ 8.17 (2H, t, J=9 Hz, ArH), 8.06 (1H, s, ArH), 7.87 (1H, d, J=8 Hz, ArH), 7.79-7.35 (10H, m, ArH), 7.19 (1H, d, J=8 Hz, ArH), 3.76 (1H, m, CHN), 2.64 (2H, m, PhCH$_2$CH$_2$C<u>H</u>$_2$), 1.62 (4H, m, PhC<u>H</u>$_2$C<u>H</u>$_2$CH$_2$), 1.31 (9H, s, C(CH$_3$)$_3$); ESI-LCMS e/z calculated for C$_{34}$H$_{33}$NO$_5$ 535.236, found 458 (M+Na-Boc)$^+$, 558 (M+Na)$^+$.

EXAMPLE 137

(L)-2-tert-Butoxycarbonylamino-3-(3'-dibenzofuran-4-yl-biphenyl-3-ylsulfanyl)-propionic acid

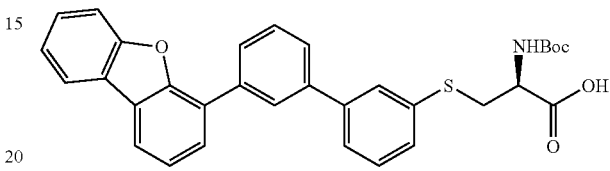

Step 1. (L)-2-tert-Butoxycarbonylamino-3-methanesulfonyloxy-propionic acid methyl ester

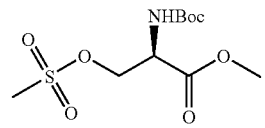

A solution of (L)-N-tert-butoxycarbonylserine (2.12 g, 9.67 mmol) and triethylamine (1.60 mL, 11.6 mmol) in 50 ml dichloromethane was treated with methylsulfonyl chloride (0.864 mL, 11.1 mmol) at 0° C. The reaction mixture was stirred for another 2 hr at 0° C. before it was quenched with 2% HCl. The organic layer was separated and the aqueous layer was extracted with dichloromethane (3×). The combined organic layers were washed sequentially with sat. NaHCO$_3$ and sat. NaCl, dried over MgSO$_4$, filtered and concentrated in vacuo.

Step 2. (L)-3-(3-Bromo-phenylsulfanyl)-2-tert-butoxycarbonylamino-propionic acid methyl ester

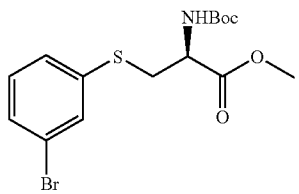

A solution of crude (L)-2-tert-butoxycarbonylamino-3-methylsulfonylpropanoic acid methyl ester (0.960 g, 3.23 mmol) and 3-bromobenzenthiol (0.300 mL, 2.91 mmol) in 10 ml DMF was treated with Cs$_2$CO$_3$ (1.16 g, 3.55 mmol) at 0° C. The reaction mixture was stirred at ambient temperature for 2 hr and then quenched with 15 ml of 5% HCl and 25 ml of ethyl acetate. After separation, the aqueous layer was extracted with ethyl acetate (3×). The combined organic layers were washed with sat. NaCl, dried over MgSO$_4$, filtered and concentrated in vacuo. Purification by flash column chromatography with 5% ethyl acetate in heptane as eluent yielded the titled compound as a white solid (0.851 g, 67% over 2 steps).

Step 3. (L)-2-tert-Butoxycarbonylamino-3-(3'-dibenzofuran-4-yl-biphenyl-3-ylsulfanyl)-propionic acid methyl ester

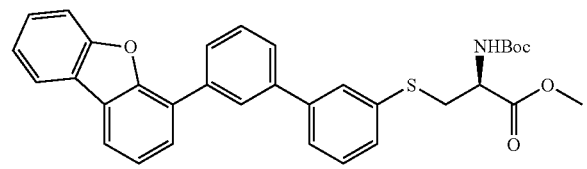

(L)-3-(3-Bromo-phenylsulfanyl)-2-tert-butoxycarbonylamino-propionic acid methyl ester (0.353 g, 0.904 mmol), 4-[3-(4,4,5,5-tetramethyl-[1,3,2]dioxaborolan-2-yl)-phenyl]-dibenzofuran (0.402 g, 1.09 mmol), Pd(dppf)Cl$_2$·CH$_2$Cl$_2$ (0.030 g, 4% mol) and 1,1'-bis(diphenylphosphino)ferrocene (0.020 g, 4% mol) were dissolved with heating in 10 ml 1,4-dioxane and then treated with K$_3$PO$_4$ (0.384 g, 1.81 mmol). The reaction mixture was stirred at reflux for 2 hr., cooled to ambient temperature and diluted with ethyl acetate. The organic layer was washed sequentially with 2% HCl and sat. NaCl., dried over MgSO$_4$, filtered and concentrated in vacuo. The residue was purified by flash column chromatography with 2-10% ethyl acetate in heptane as eluent to yield the titled compound as white solid (0.340 g, 68% yield.

Step 4. (L)-2-tert-Butoxycarbonylamino-3-(3'-dibenzofuran-4-yl-biphenyl-3-ylsulfanyl)-propionic acid

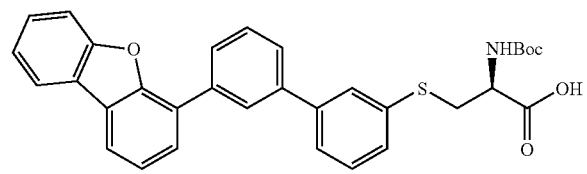

To a stirred solution of (L)-2-tert-butoxycarbonylamino-3-(3'-dibenzofuran-4-yl-biphenyl-3-ylsulfanyl)-propionic acid methyl ester (0.150 g, 0.271 mmol) in methanol (2 mL) and THF (8 mL) was added 2M NaOH solution (1.35 mL, 2.71 mmol). Upon completion (TLC 10% methanol in dichloromethane), the mixture was acidified with 2M HCl solution (pH≈2) and extracted with ethyl acetate (3×). The combined extract was washed sequentially with water and brine, dried over anhydrous MgSO$_4$, filtered and concentrated in vacuo. Purification by flash column chromatography with 2-5% methanol in dichloromethane as eluent yielded the titled compound as a white solid (0.075 g, 32%). Rf=0.32 (10% methanol in dichloromethane) $^1$H NMR (DMSO-d6, 300 MHz) δ 8.18 (2H, t, J=8 Hz, ArH), 8.11 (1H, s, ArH), 7.91 (1H, d, J=8 Hz, ArH), 7.81-7.72 (4H, m, ArH), 7.67-7.60 (2H, m, ArH), 7.55-7.36 (5H, m, ArH), 4.05 (1H, m, CHN), 3.46 (1H, m, CH), 3.17 (1H, m, CH), 1.32 (9H, s, C(CH$_3$)$_3$); ESI-LCMS e/z calculated for C$_{32}$H$_{29}$NO$_5$S 539.177, found 462 (M+Na-Boc)$^+$, 562 (M+Na)$^+$.

EXAMPLE 138

2-tert-Butoxycarbonylamino-3-[3'-(7-trifluoromethyl-3,4-dihydro-2H-quinolin-1-ylmethyl)-biphenyl-4-ylmethylsulfanyl]-propionic acid

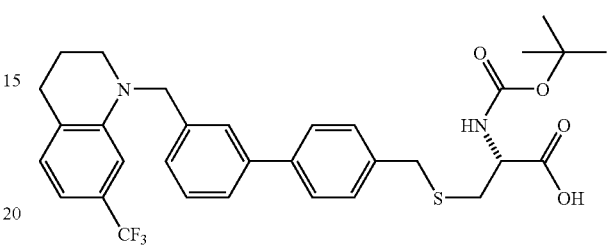

Step 1. 1-(3-bromo-benzyl)-7-trifluoromethyl-1,2,3,4-tetrahydro-quinoline

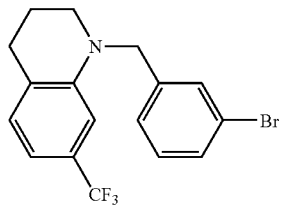

Under a nitrogen atmosphere, a solution of bromo-3-bromomethyl-benzene (3.47 g, 13.p mmol) and 7-trifluoromethyl-1,2,3,4-tetrahydro-quinoline (2.93 g, 14.6 mmol) in ethanol (15 mL, 1 M) was treated with sodium acetate (5.69 g, 69.3 mmol) and heated to 80° C. After stirring 2 h, the solution was cooled to room temperature, diluted with water, extracted with ethyl acetate and washed with saturated aq sodium chloride. The organic layer was dried over MgSO$_4$, filtered and concentrated. Purification by column chromatography (10% ethyl acetate in heptane) provided 1-(3-bromo-benzyl)-7-trifluoromethyl-1,2,3,4-tetrahydro-quinoline 4.21 g (82%) as a colorless oil.

Step 2. [3'-(7-trifluoromethyl-3,4-dihydro-2H-quinolin-1-ylmethyl)-biphenyl-4-yl]-methanol

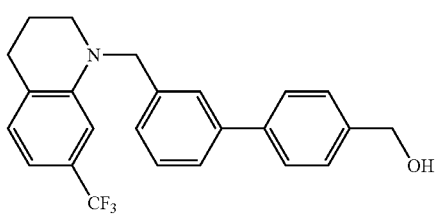

Under a nitrogen atmosphere, a solution of 1-(3-bromo-benzyl)-7-trifluoromethyl-1,2,3,4-tetrahydro-quinoline (2.36 g, 6.37 mmol), 4-(hydroxymethyl)phenyl boronic acid (1.07 g, 7.01 mmol), and 2 M Na$_2$CO$_3$ (7 mL, 12.7 mmol) in 16 mL of toluene and 4 mL ethanol (0.3 M) was treated with tetrakistriphenylphosphine palladium (Pd(Ph$_3$)$_4$) (0.37 g, 0.32 mmol) and heated to 80° C. for 2 hours. After cooling to room temperature the solution was extracted with ethyl acetate, dried over MgSO$_4$, and concentrated. Purification by flash chromatography (30% ethyl acetate in heptane) provided [3'-(7-trifluoromethyl-3,4-dihydro-2H-quinolin-1-ylmethyl)-biphenyl-4-yl]-methanol. $^1$H NMR (CDCl$_3$, 300 MHz) δ 7.49-7.32 (m, 6 H), 7.16-7.13 (m, 2 H), 6.95 (d, J=8.4 Hz, 1 H), 6.73-6.60 (m, 2 H), 4.66 (s, 2 H), 4.48 (s, 2 H), 3.30 (t, J=5.7 Hz, 2 H), 2.76 (t, J=6.3 Hz, 2 H), 1.98-1.90 (m, 2 H); ESI-LCMS m/z calcd for C$_{24}$H$_{22}$F$_3$NO: 397.4; found 398.7 (M+1)$^+$.

Step 3. 2-tert-butoxycarbonylamino-3-[3'-(7-trifluoromethyl-3,4-dihydro-2H-quinolin-1-ylmethyl)-biphenyl-4-ylmethylsulfanyl]-propionic acid methyl ester

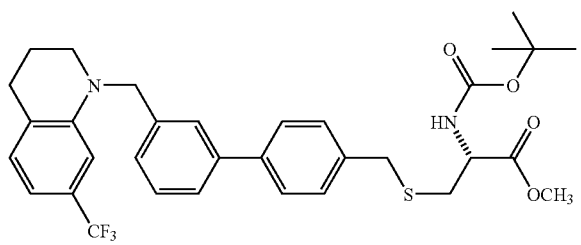

Under a nitrogen atmosphere, a solution of [3'-(7-trifluoromethyl-3,4-dihydro-2H-quinolin-1-ylmethyl)-biphenyl-4-yl]-methanol (0.257 g, 0.65 mmol), 2-tert-butoxycarbonylamino-3-mercapto-propionic acid methyl ester (0.304 g, 1.29 mmol), 1,1'-(azodicarbonyl)dipiperidine (0.343 g, 1.36 mmol), and imidazole (0.92 g, 1.36 mmol) in dichloromethane (10 mL, 0.07 M) was treated with trimethylphosphine (1 M in toluene; 1.4 mL, 1.36 mmol) in a dropwise manner at room temperature. After stirring for 1 hour, an equal volume of heptane was added and the resulting precipitate was removed by filtration. The filtrate was concentrated and purified by flash chromatography (20% ethyl acetate in heptane) to give 2-tert-butoxycarbonylamino-3-[3'-(7-trifluoromethyl-3,4-dihydro-2H-quinolin-1-ylmethyl)-biphenyl-4-ylmethylsulfanyl]-propionic acid methyl ester as a white solid.

Step 4. 2-tert-butoxycarbonylamino-3-[3'-(7-trifluoromethyl-3,4-dihydro-2H-quinolin-1-ylmethyl)-biphenyl-4-ylmethylsulfanyl]-propionic acid

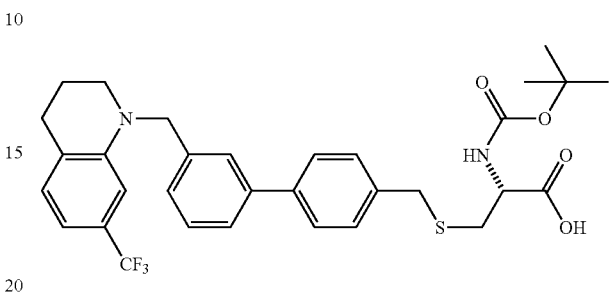

Under a nitrogen atmosphere, a solution of 2-tert-butoxycarbonylamino-3-[3'-(7-trifluoromethyl-3,4-dihydro-2H-quinolin-1-ylmethyl)-biphenyl-4-ylmethylsulfanyl]-propionic acid methyl ester (0.173 g, 0.281 mmol) in 4 mL of THF and 1 mL of methanol was treated with 2 N NaOH (1.5 mL, 2.81 mmol). After stirring at room temperature for 3 hours, the solution was acidified with 2 N HCl to a pH 3. The resulting solution was extracted with ethyl acetate (2×50 mL), dried over MgSO$_4$ and concentrated. The resulting residue was purified by flash chromatography (5% methanol in dichloromethane) to afford 2-tert-butoxycarbonylamino-3-[3'-(7-trifluoromethyl-3,4-dihydro-2H-quinolin-1-ylmethyl)-biphenyl-4-ylmethylsulfanyl]-propionic acid. $^1$H NMR (DMSO, 300 MHz) δ 7.58-7.49 (m, 4 H), 7.44-7.36 (m, 3 H), 7.21 (d, J=7.8 Hz, 1 H), 7.09 (d, J=7.5 Hz, 1 H), 6.76-6.70 (m, 2 H), 4.62 (s, 2 H), 4.14-4.07 (m, 1 H), 3.79 (s, 2 H), 3.47 (t, J=5.4 Hz, 2 H), 2.81-2.72 (m, 3 H), 1.99-1.91 (m, 1 H), 1.40 (s, 9 H); ESI-LCMS m/z calcd for C$_{32}$H$_{35}$F$_3$N$_2$O$_4$S: 600.7; found 601.3 (M+1)$^+$.

EXAMPLE 139

The following compounds are prepared essentially according to the methods and procedures set forth above.

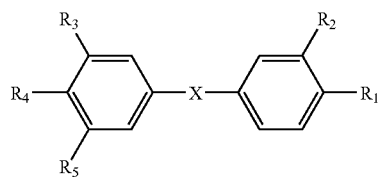

A.

OR

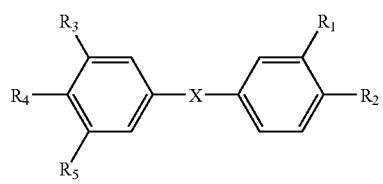

B.

-continued

| Cmpd. No. A | B | X | R₁ | R₂ | R₃ | R₄ | R₅ |
|---|---|---|---|---|---|---|---|
| 31 | 32 | bond | S-CH(NHBoc)-COOH | H | adamantyl | H | H |
| 33 | 34 | bond | S-CH(NHBoc)-COOH | F | adamantyl | H | H |
| 35 | 36 | CO | S-CH(NHBoc)-COOH | H | adamantyl | H | H |
| 37 | 38 | CO | S-CH(NHBoc)-COOH | F | adamantyl | H | H |
| 39 | 40 | SO₂ | S-CH(NHBoc)-COOH | H | adamantyl | H | H |
| 41 | 42 | SO₂ | S-CH(NHBoc)-COOH | F | adamantyl | H | H |
| 43 | 44 | —CH₂O— | S-CH(NHBoc)-COOH | H | adamantyl | H | H |
| 45 | 46 | —CH₂O— | S-CH(NHBoc)-COOH | F | adamantyl | H | H |

-continued

| | | | | | | |
|---|---|---|---|---|---|---|
| 47 | 48 | bond | [Cys(Boc) thioether] | H | [dibenzofuran-4-yl] | H |
| 49 | 50 | bond | [Cys(Boc) thioether] | F | [dibenzofuran-4-yl] | H |
| 51 | 52 | CO | [Cys(Boc) thioether] | H | [dibenzofuran-4-yl] | H |
| 53 | 54 | CO | [Cys(Boc) thioether] | F | [dibenzofuran-4-yl] | H |
| 55 | 56 | SO$_2$ | [Cys(Boc) thioether] | H | [dibenzofuran-4-yl] | H |
| 57 | 58 | SO$_2$ | [Cys(Boc) thioether] | F | [dibenzofuran-4-yl] | H |
| 59 | 60 | —CH$_2$O— | [Cys(Boc) thioether] | H | [dibenzofuran-4-yl] | H |
| 61 | 62 | —CH$_2$O— | [Cys(Boc) thioether] | F | [dibenzofuran-4-yl] | H |
| 63 | 64 | bond | [Cys(Boc) thioether] | t-Bu | [dibenzofuran-4-yl] | H |

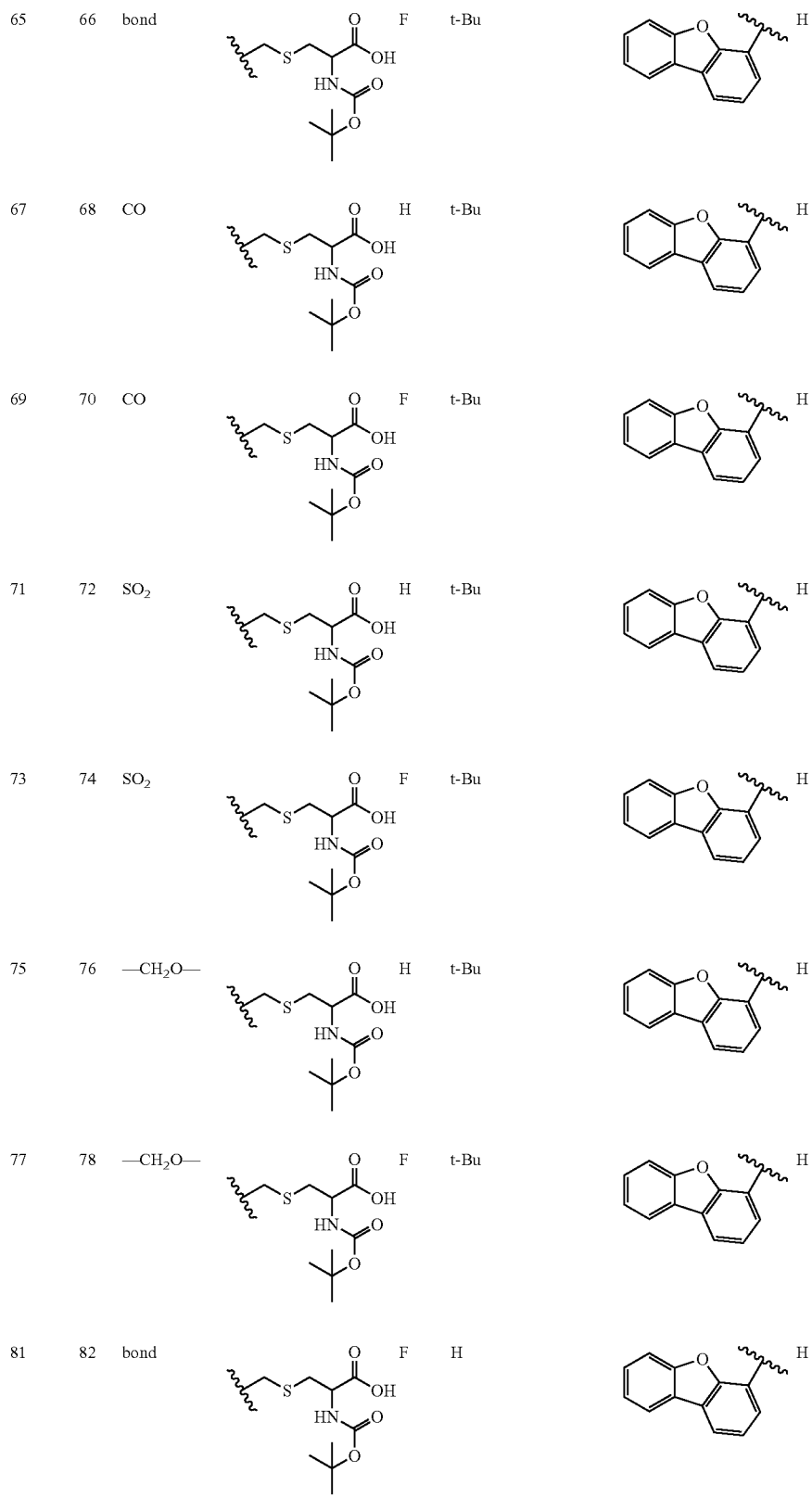

-continued

| | | | | | | |
|---|---|---|---|---|---|---|
| 83 | 84 | CO | [Cys(S-)-Boc structure] | H | H | [dibenzofuran] H |
| 85 | 86 | CO | [Cys(S-)-Boc structure] | F | H | [dibenzofuran] H |
| 87 | 88 | SO$_2$ | [Cys(S-)-Boc structure] | H | H | [dibenzofuran] H |
| 89 | 90 | SO$_2$ | [Cys(S-)-Boc structure] | F | H | [dibenzofuran] H |
| 91 | 92 | —CH$_2$O— | [Cys(S-)-Boc structure] | H | H | [dibenzofuran] H |
| 93 | 94 | —CH$_2$O— | [Cys(S-)-Boc structure] | F | H | [dibenzofuran] H |
| 95 | 96 | bond | [Cys(S-)-Boc structure] | H | F | [dibenzofuran] H |
| 97 | 98 | bond | [Cys(S-)-Boc structure] | F | F | [dibenzofuran] H |
| 99 | 100 | CO | [Cys(S-)-Boc structure] | H | F | [dibenzofuran] H |

-continued
| | | | | | | | |
|---|---|---|---|---|---|---|---|
| 101 | 102 | CO | 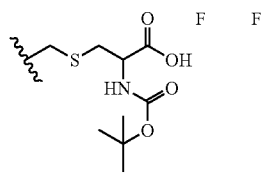 | F | F | 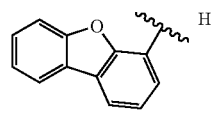 | H |
| 103 | 104 | SO$_2$ | 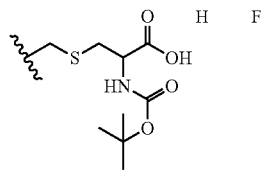 | H | F | 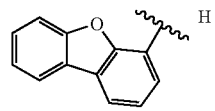 | H |
| 105 | 106 | SO$_2$ | 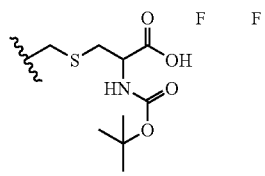 | F | F | 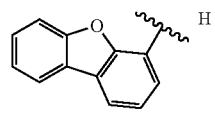 | H |
| 107 | 108 | —CH$_2$O— | 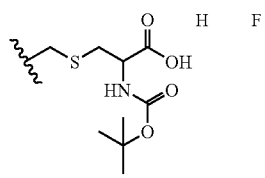 | H | F | 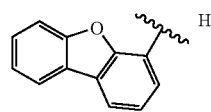 | H |
| 109 | 110 | —CH$_2$O— | 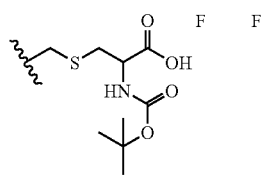 | F | F | 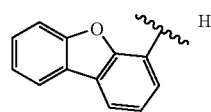 | H |
| 111 | 112 | bond | 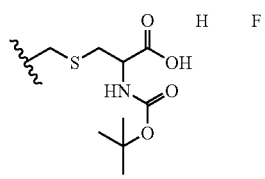 | H | F | 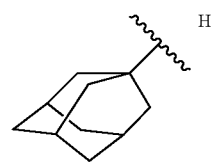 | H |
| 113 | 114 | bond | 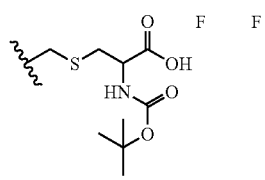 | F | F | 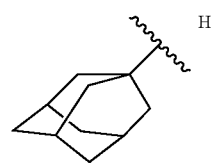 | H |
| 115 | 116 | CO | 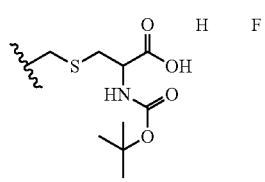 | H | F | 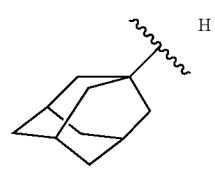 | H |

-continued

| | | | | | | | |
|---|---|---|---|---|---|---|---|
| 117 | 118 | CO | [Cys(S-)-Boc structure] | F | F | [adamantyl] | H |
| 119 | 120 | SO₂ | [Cys(S-)-Boc structure] | H | F | [adamantyl] | H |
| 121 | 122 | SO₂ | [Cys(S-)-Boc structure] | F | F | [adamantyl] | H |
| 123 | 124 | —CH₂O— | [Cys(S-)-Boc structure] | H | F | [adamantyl] | H |
| 125 | 126 | —CH₂O— | [Cys(S-)-Boc structure] | F | F | [adamantyl] | H |
| 127 | 128 | bond | [Cys(S-)-Boc structure] | H | t-Bu | [adamantyl] | H |
| 129 | 130 | bond | [Cys(S-)-Boc structure] | F | t-Bu | [adamantyl] | H |
| 131 | 132 | CO | [Cys(S-)-Boc structure] | H | t-Bu | [adamantyl] | H |
| 133 | 134 | CO | [Cys(S-)-Boc structure] | F | t-Bu | [adamantyl] | H |

-continued
| | | | | | | | |
|---|---|---|---|---|---|---|---|
| 135 | 136 | SO$_2$ | 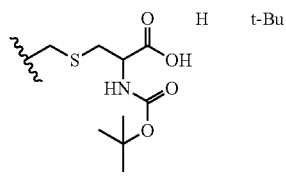 | H | t-Bu | 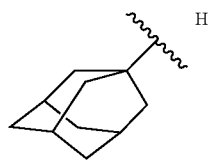 | H |
| 137 | 138 | SO$_2$ | 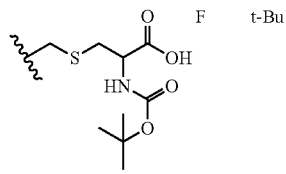 | F | t-Bu | 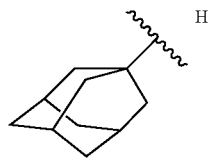 | H |
| 139 | 140 | —CH$_2$O— | 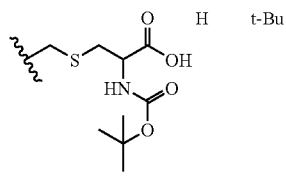 | H | t-Bu | 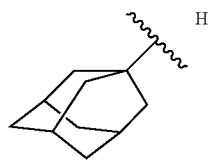 | H |
| 141 | 142 | —CH$_2$O— | 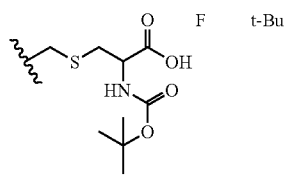 | F | t-Bu | 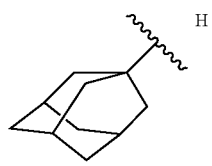 | H |
| 143 | 144 | bond | 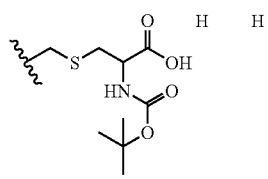 | H | H | t-Bu | 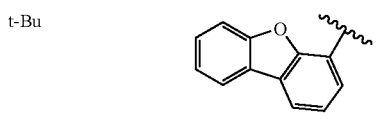 |
| 145 | 146 | bond | 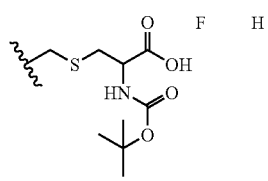 | F | H | t-Bu | 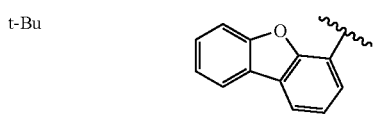 |
| 147 | 148 | CO | 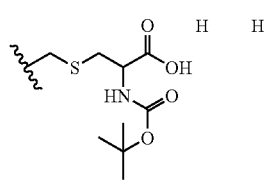 | H | H | t-Bu | 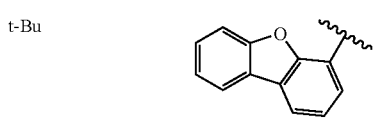 |
| 149 | 150 | CO | 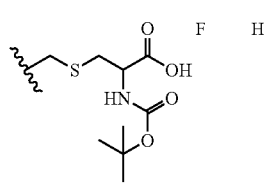 | F | H | t-Bu | 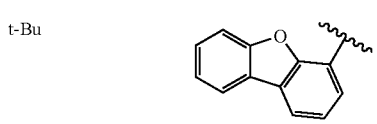 |

-continued

| | | | | | | | |
|---|---|---|---|---|---|---|---|
| 151 | 152 | SO₂ | S-CH₂-CH(COOH)-NH-C(O)-O-tBu | H | H | t-Bu | dibenzofuran |
| 153 | 154 | SO₂ | S-CH₂-CH(COOH)-NH-C(O)-O-tBu | F | H | t-Bu | dibenzofuran |
| 155 | 156 | —CH₂O— | S-CH₂-CH(COOH)-NH-C(O)-O-tBu | H | H | t-Bu | dibenzofuran |
| 157 | 158 | —CH₂O— | S-CH₂-CH(COOH)-NH-C(O)-O-tBu | F | H | t-Bu | dibenzofuran |
| 159 | 160 | bond | S-CH₂-CH(COOH)-NH-C(O)-O-tBu | H | F | t-Bu | dibenzofuran |
| 161 | 162 | bond | S-CH₂-CH(COOH)-NH-C(O)-O-tBu | F | F | t-Bu | dibenzofuran |
| 163 | 164 | CO | S-CH₂-CH(COOH)-NH-C(O)-O-tBu | H | F | t-Bu | dibenzofuran |
| 165 | 166 | CO | S-CH₂-CH(COOH)-NH-C(O)-O-tBu | F | F | t-Bu | dibenzofuran |
| 167 | 168 | SO₂ | S-CH₂-CH(COOH)-NH-C(O)-O-tBu | H | F | t-Bu | dibenzofuran |

-continued
| | | | | | | | |
|---|---|---|---|---|---|---|---|
| 169 | 170 | SO₂ | 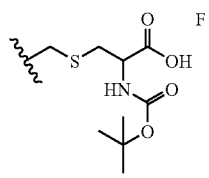 | F | F | t-Bu | 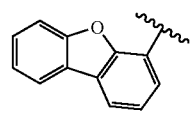 |
| 171 | 172 | —CH₂O— | 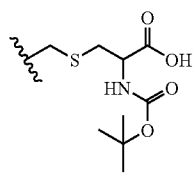 | H | F | t-Bu | 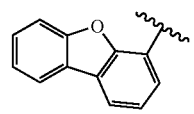 |
| 173 | 174 | —CH₂O— | 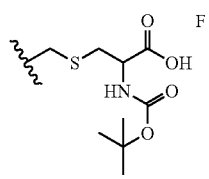 | F | F | t-Bu | 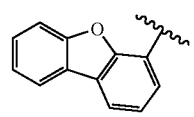 |
| 175 | 176 | bond | 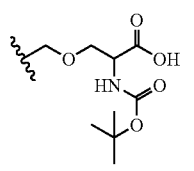 | H | 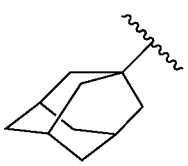 | H | H |
| 177 | 178 | bond | 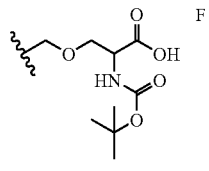 | F | 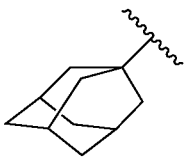 | H | H |
| 179 | 180 | CO | 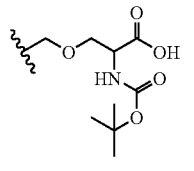 | H | 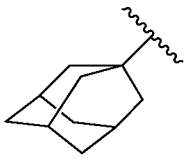 | H | H |
| 181 | 182 | CO | 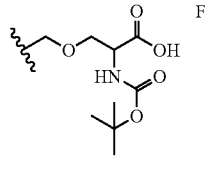 | F | 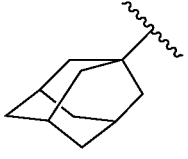 | H | H |
| 183 | 184 | SO₂ | 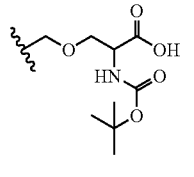 | H | 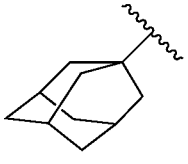 | H | H |
| 185 | 186 | SO₂ | 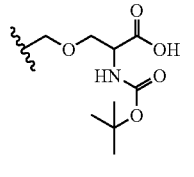 | F | 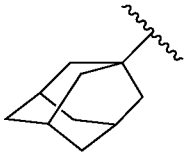 | H | H |

-continued
| | | | | | | | |
|---|---|---|---|---|---|---|---|
| 187 | 188 | —CH₂O— | 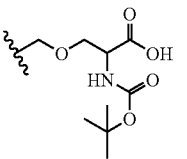 | H | 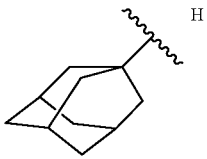 | H | H |
| 189 | 190 | —CH₂O— | 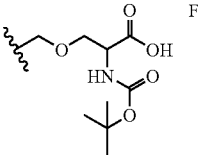 | F | 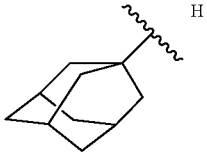 | H | H |
| 191 | 192 | bond | 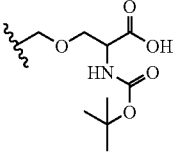 | H | 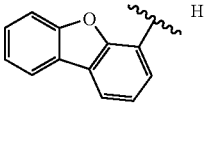 | H | H |
| 193 | 194 | bond | 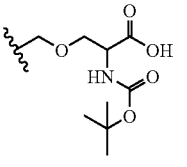 | F | 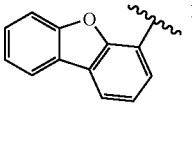 | H | H |
| 195 | 196 | CO | 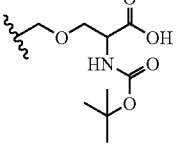 | H | 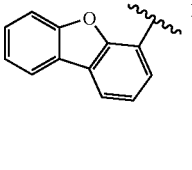 | H | H |
| 197 | 198 | CO | 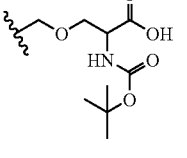 | F | 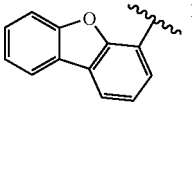 | H | H |
| 199 | 200 | SO₂ | 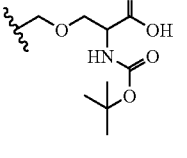 | H | 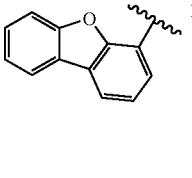 | H | H |
| 201 | 202 | SO₂ | 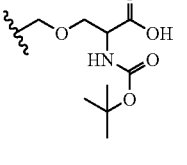 | F | 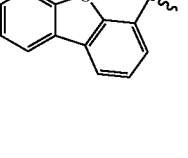 | H | H |
| 203 | 204 | —CH₂O— | 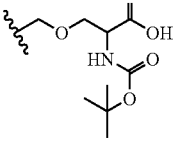 | H | 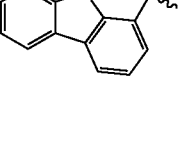 | H | H |

-continued
| | | | | | | | |
|---|---|---|---|---|---|---|---|
| 205 | 206 | —CH₂O— | 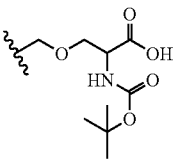 | F | 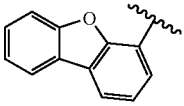 | H | H |
| 207 | 208 | bond | 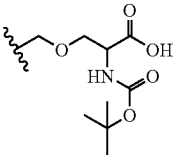 | H | t-Bu | 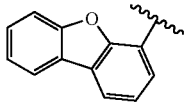 | H |
| 209 | 210 | bond | 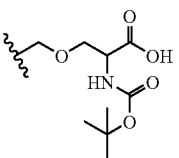 | F | t-Bu | 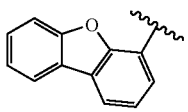 | H |
| 211 | 212 | CO | 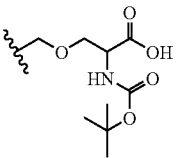 | H | t-Bu | 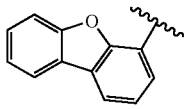 | H |
| 213 | 214 | CO | 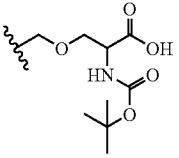 | F | t-Bu | 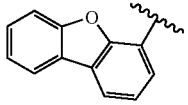 | H |
| 215 | 216 | SO₂ | 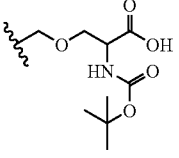 | H | t-Bu | 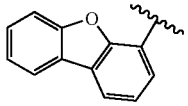 | H |
| 217 | 218 | SO₂ | 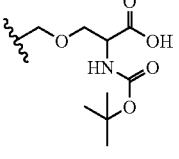 | F | t-Bu | 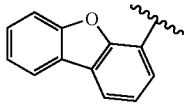 | H |
| 219 | 220 | —CH₂O— | 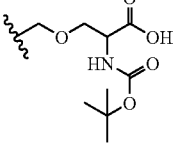 | H | t-Bu | 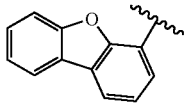 | H |
| 221 | 222 | —CH₂O— | 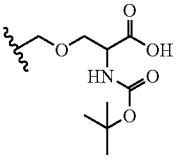 | F | t-Bu | 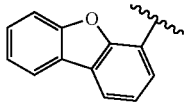 | H |

-continued
| | | | | | | | |
|---|---|---|---|---|---|---|---|
| 223 | 224 | bond | 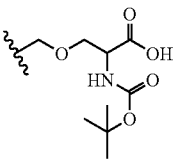 | H | H | 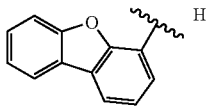 | H |
| 225 | 226 | bond | 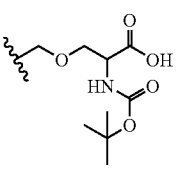 | F | H | 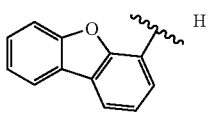 | H |
| 227 | 228 | CO | 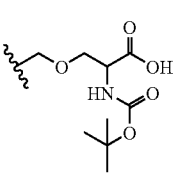 | H | H | 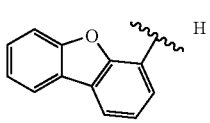 | H |
| 229 | 230 | CO | 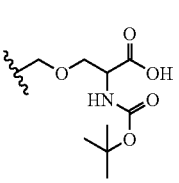 | F | H | 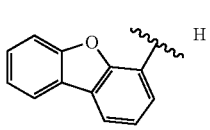 | H |
| 231 | 232 | SO$_2$ | 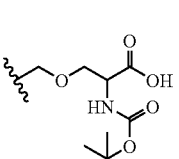 | H | H | 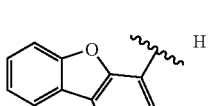 | H |
| 233 | 234 | SO$_2$ | 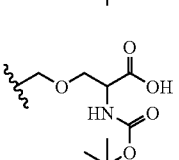 | F | H | 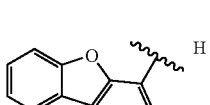 | H |
| 235 | 236 | —CH$_2$O— | 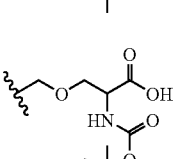 | H | H | 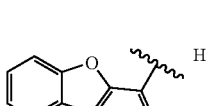 | H |
| 237 | 238 | —CH$_2$O— | 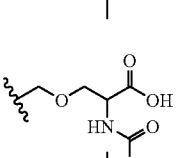 | F | H | 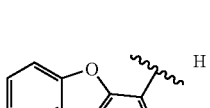 | H |
| 239 | 240 | bond | 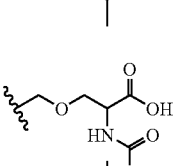 | H | F | 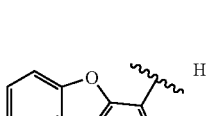 | H |

-continued
| | | | | | | | |
|---|---|---|---|---|---|---|---|
| 241 | 242 | bond | 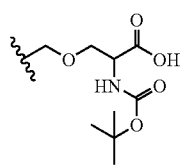 | F | F | 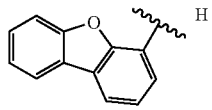 | H |
| 243 | 244 | CO | 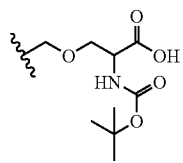 | H | F | 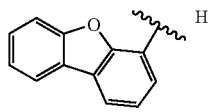 | H |
| 245 | 246 | CO | 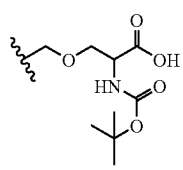 | F | F | 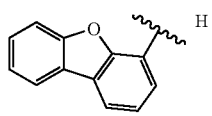 | H |
| 247 | 248 | SO$_2$ | 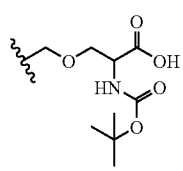 | H | F | 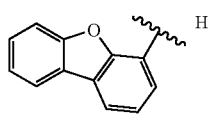 | H |
| 249 | 250 | SO$_2$ | 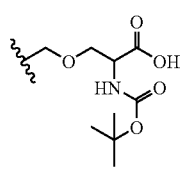 | F | F | 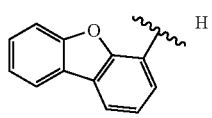 | H |
| 251 | 252 | —CH$_2$O— | 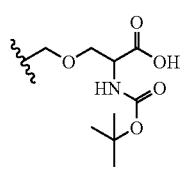 | H | F | 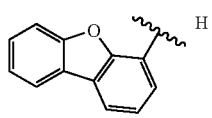 | H |
| 253 | 254 | —CH$_2$O— | 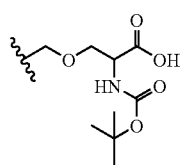 | F | F | 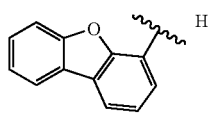 | H |
| 255 | 256 | bond | 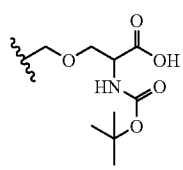 | H | F | 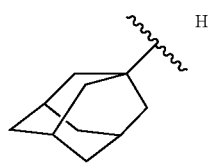 | H |
| 257 | 258 | bond | 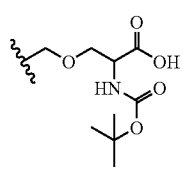 | F | F | 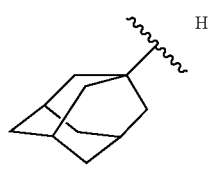 | H |

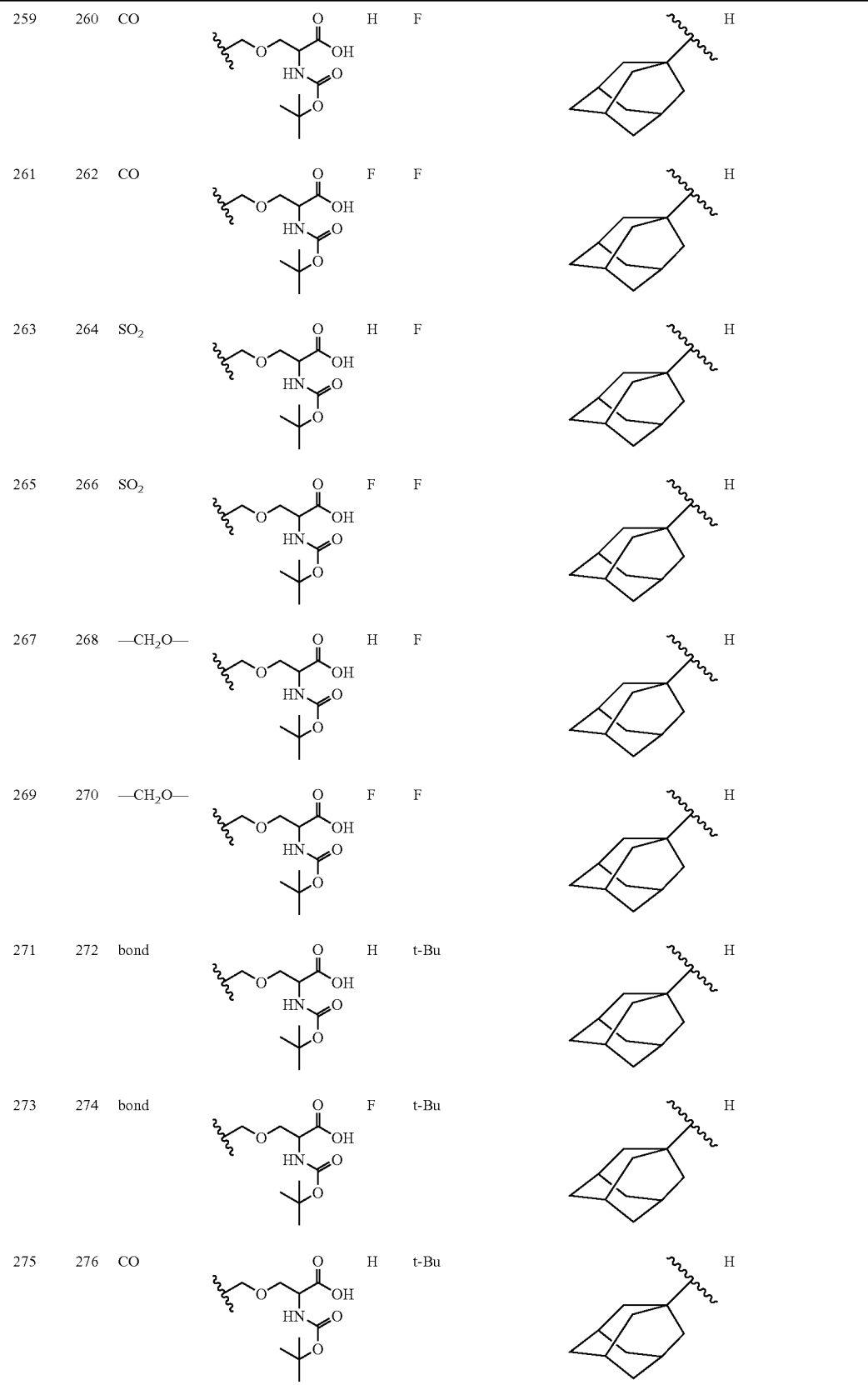

-continued
| | | | | | | | |
|---|---|---|---|---|---|---|---|
| 277 | 278 | CO | 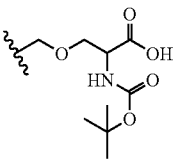 | F | t-Bu | 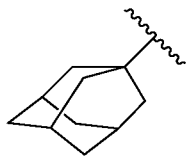 | H |
| 279 | 280 | SO$_2$ | 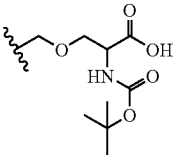 | H | t-Bu | 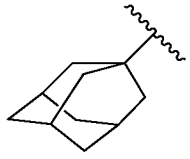 | H |
| 281 | 282 | SO$_2$ | 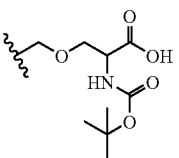 | F | t-Bu | 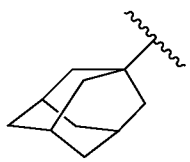 | H |
| 283 | 284 | —CH$_2$O— | 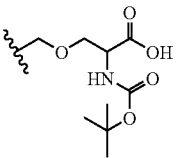 | H | t-Bu | 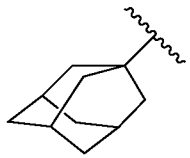 | H |
| 285 | 286 | —CH$_2$O— | 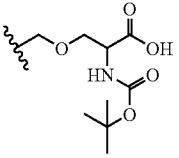 | F | t-Bu | 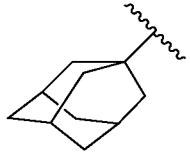 | H |
| 287 | 288 | bond | 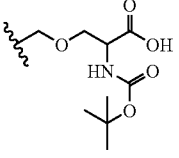 | H | H | t-Bu | 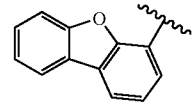 |
| 289 | 290 | bond | 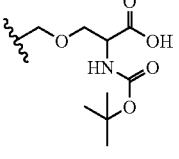 | F | H | t-Bu | 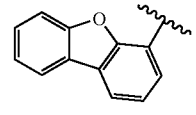 |
| 291 | 292 | CO | 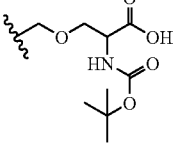 | H | H | t-Bu | 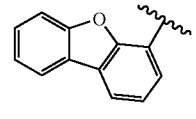 |
| 293 | 294 | CO | 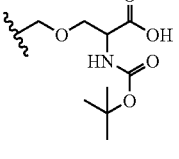 | F | H | t-Bu | 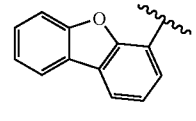 |

-continued

| | | | | | | | |
|---|---|---|---|---|---|---|---|
| 295 | 296 | SO$_2$ | [Ser(O-)-Boc structure] | H | H | t-Bu | [dibenzofuran] |
| 297 | 298 | SO$_2$ | [Ser(O-)-Boc structure] | F | H | t-Bu | [dibenzofuran] |
| 299 | 300 | —CH$_2$O— | [Ser(O-)-Boc structure] | H | H | t-Bu | [dibenzofuran] |
| 301 | 302 | —CH$_2$O— | [Ser(O-)-Boc structure] | F | H | t-Bu | [dibenzofuran] |
| 303 | 304 | bond | [Ser(O-)-Boc structure] | H | F | t-Bu | [dibenzofuran] |
| 305 | 306 | bond | [Ser(O-)-Boc structure] | F | F | t-Bu | [dibenzofuran] |
| 307 | 308 | CO | [Ser(O-)-Boc structure] | H | F | t-Bu | [dibenzofuran] |
| 309 | 310 | CO | [Ser(O-)-Boc structure] | F | F | t-Bu | [dibenzofuran] |
| 311 | 312 | SO$_2$ | [Ser(O-)-Boc structure] | H | F | t-Bu | [dibenzofuran] |

-continued
| | | | | | | | |
|---|---|---|---|---|---|---|---|
| 313 | 314 | SO$_2$ | 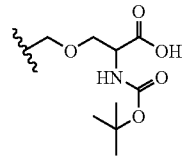 | F | F | t-Bu | 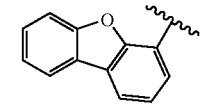 |
| 315 | 316 | —CH$_2$O— | 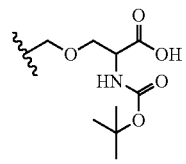 | H | F | t-Bu | 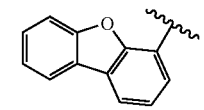 |
| 317 | 318 | —CH$_2$O— | 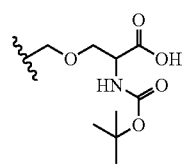 | F | F | t-Bu | 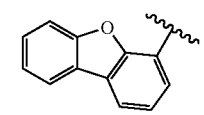 |
| 319 | 320 | bond | 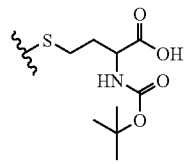 | H | 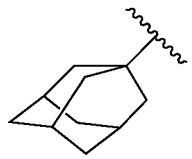 | H | H |
| 321 | 322 | bond |  | F | 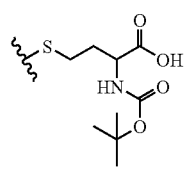 | H | H |
| 323 | 324 | CO | 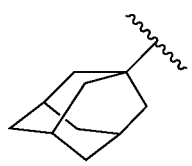 | H |  | H | H |
| 325 | 326 | CO | 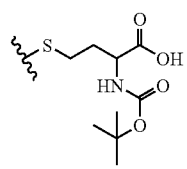 | F | 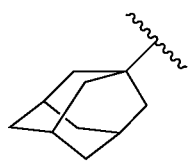 | H | H |
| 327 | 328 | SO$_2$ |  | H | 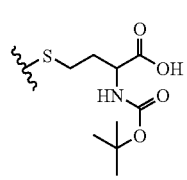 | H | H |
| 329 | 330 | SO$_2$ | 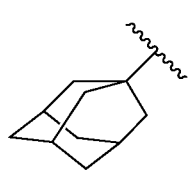 | F |  | H | H |

-continued

| | | | | | | | |
|---|---|---|---|---|---|---|---|
| 331 | 332 | —CH₂O— | (Boc-homocysteine-S) | H | (adamantyl) | H | H |
| 333 | 334 | —CH₂O— | (Boc-homocysteine-S) | F | (adamantyl) | H | H |
| 335 | 336 | bond | (Boc-homocysteine-S) | H | (dibenzofuranyl) | H | H |
| 337 | 338 | bond | (Boc-homocysteine-S) | F | (dibenzofuranyl) | H | H |
| 339 | 340 | CO | (Boc-homocysteine-S) | H | (dibenzofuranyl) | H | H |
| 341 | 342 | CO | (Boc-homocysteine-S) | F | (dibenzofuranyl) | H | H |
| 343 | 344 | SO₂ | (Boc-homocysteine-S) | H | (dibenzofuranyl) | H | H |
| 345 | 346 | SO₂ | (Boc-homocysteine-S) | F | (dibenzofuranyl) | H | H |
| 347 | 348 | —CH₂O— | (Boc-homocysteine-S) | H | (dibenzofuranyl) | H | H |

-continued

| | | | | | | |
|---|---|---|---|---|---|---|
| 349 | 350 | —CH₂O— | (Boc-homocysteine-S) | F | (dibenzofuran-4-yl) | H | H |
| 351 | 352 | bond | (Boc-homocysteine-S) | H | t-Bu | (dibenzofuran-4-yl) | H |
| 353 | 354 | bond | (Boc-homocysteine-S) | F | t-Bu | (dibenzofuran-4-yl) | H |
| 355 | 356 | CO | (Boc-homocysteine-S) | H | t-Bu | (dibenzofuran-4-yl) | H |
| 357 | 358 | CO | (Boc-homocysteine-S) | F | t-Bu | (dibenzofuran-4-yl) | H |
| 359 | 360 | SO₂ | (Boc-homocysteine-S) | H | t-Bu | (dibenzofuran-4-yl) | H |
| 361 | 362 | SO₂ | (Boc-homocysteine-S) | F | t-Bu | (dibenzofuran-4-yl) | H |
| 363 | 364 | —CH₂O— | (Boc-homocysteine-S) | H | t-Bu | (dibenzofuran-4-yl) | H |
| 365 | 366 | —CH₂O— | (Boc-homocysteine-S) | F | t-Bu | (dibenzofuran-4-yl) | H |

-continued

| | | | | | | | |
|---|---|---|---|---|---|---|---|
| 369 | 370 | bond | ![structure] | F | H | ![dibenzofuran] | H |
| 371 | 372 | CO | ![structure] | H | H | ![dibenzofuran] | H |
| 373 | 374 | CO | ![structure] | F | H | ![dibenzofuran] | H |
| 375 | 376 | SO₂ | ![structure] | H | H | ![dibenzofuran] | H |
| 377 | 378 | SO₂ | ![structure] | F | H | ![dibenzofuran] | H |
| 379 | 380 | —CH₂O— | ![structure] | H | H | ![dibenzofuran] | H |
| 381 | 382 | —CH₂O— | ![structure] | F | H | ![dibenzofuran] | H |
| 383 | 384 | bond | ![structure] | H | F | ![dibenzofuran] | H |
| 385 | 386 | bond | ![structure] | F | F | ![dibenzofuran] | H |

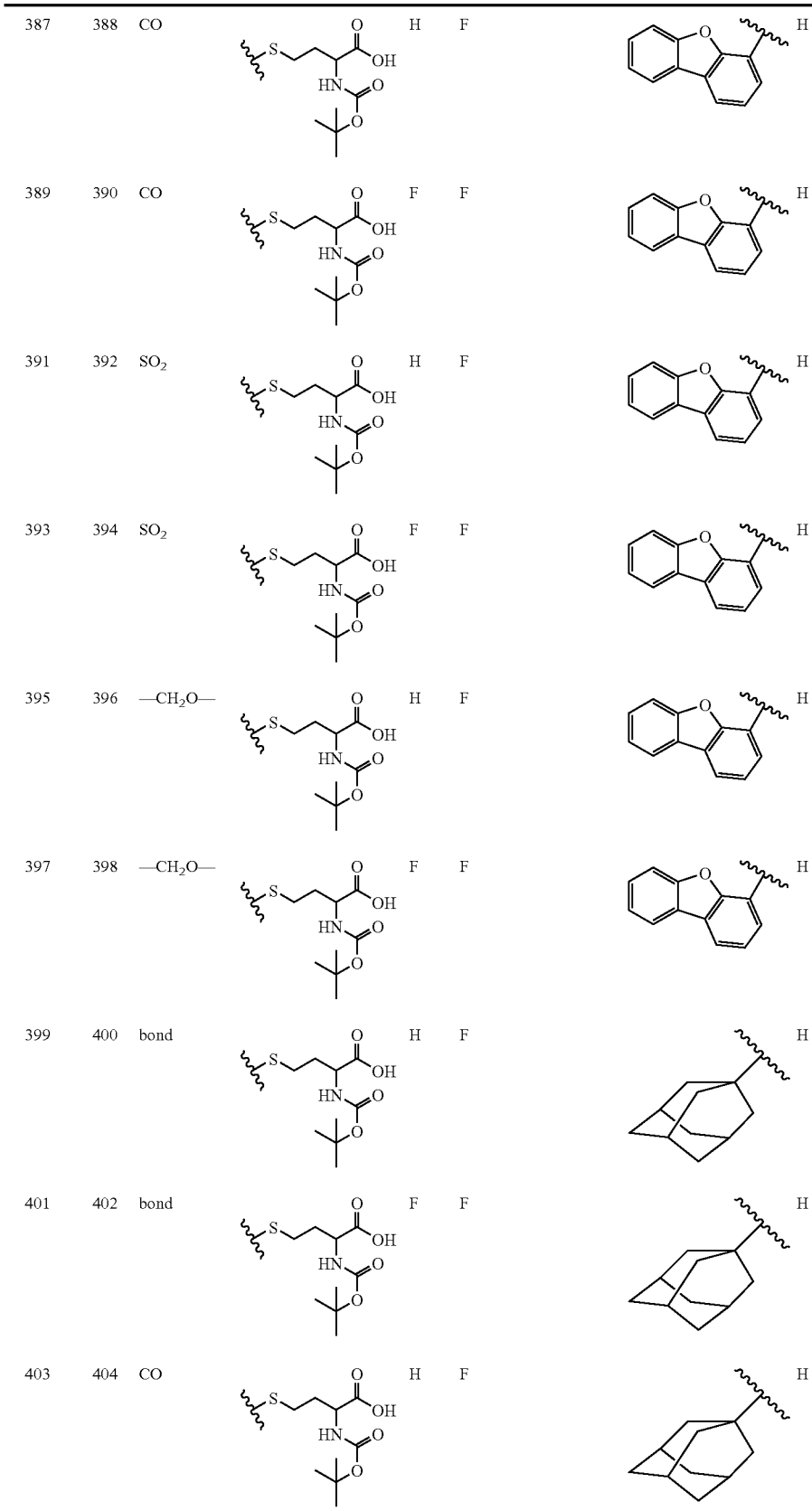

-continued
| | | | | | | | |
|---|---|---|---|---|---|---|---|
| 405 | 406 | CO | 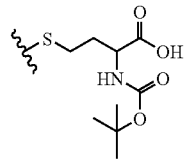 | F | F | 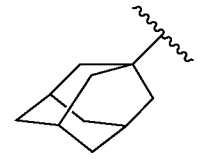 | H |
| 407 | 408 | SO$_2$ | 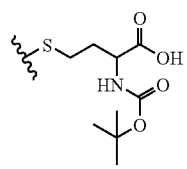 | H | F | 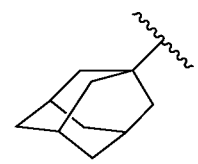 | H |
| 409 | 410 | SO$_2$ | 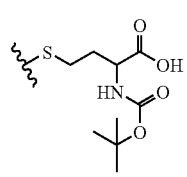 | F | F | 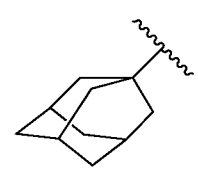 | H |
| 411 | 412 | —CH$_2$O— | 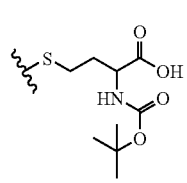 | H | F | 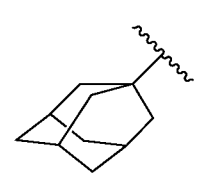 | H |
| 413 | 414 | —CH$_2$O— | 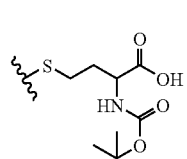 | F | F | 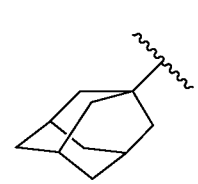 | H |
| 415 | 416 | bond | 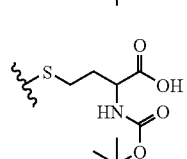 | H | t-Bu | 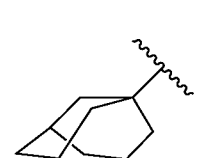 | H |
| 417 | 418 | bond | 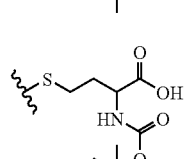 | F | t-Bu | 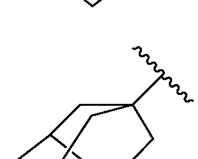 | H |
| 419 | 420 | CO | 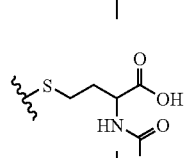 | H | t-Bu | 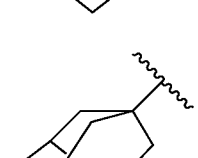 | H |
| 421 | 422 | CO | 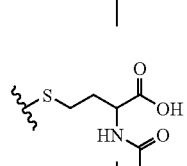 | F | t-Bu | 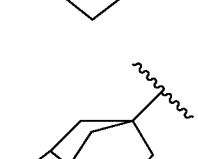 | H |

-continued

| | | | | | | | |
|---|---|---|---|---|---|---|---|
| 423 | 424 | SO$_2$ | (Boc-homocysteine-OH, S-linked) | H | t-Bu | (adamantyl) | H |
| 425 | 426 | SO$_2$ | (Boc-homocysteine-OH, S-linked) | F | t-Bu | (adamantyl) | H |
| 427 | 428 | —CH$_2$O— | (Boc-homocysteine-OH, S-linked) | H | t-Bu | (adamantyl) | H |
| 429 | 430 | —CH$_2$O— | (Boc-homocysteine-OH, S-linked) | F | t-Bu | (adamantyl) | H |
| 431 | 432 | bond | (Boc-homocysteine-OH, S-linked) | H | H | t-Bu | (dibenzofuranyl) |
| 433 | 434 | bond | (Boc-homocysteine-OH, S-linked) | F | H | t-Bu | (dibenzofuranyl) |
| 435 | 436 | CO | (Boc-homocysteine-OH, S-linked) | H | H | t-Bu | (dibenzofuranyl) |
| 437 | 438 | CO | (Boc-homocysteine-OH, S-linked) | F | H | t-Bu | (dibenzofuranyl) |
| 439 | 440 | SO$_2$ | (Boc-homocysteine-OH, S-linked) | H | H | t-Bu | (dibenzofuranyl) |

| | | | | | | | |
|---|---|---|---|---|---|---|---|
| 441 | 442 | SO₂ | (Boc-homocysteine-S) | F | H | t-Bu | (dibenzofuran-4-yl) |
| 443 | 444 | —CH₂O— | (Boc-homocysteine-S) | H | H | t-Bu | (dibenzofuran-4-yl) |
| 445 | 446 | —CH₂O— | (Boc-homocysteine-S) | F | H | t-Bu | (dibenzofuran-4-yl) |
| 447 | 448 | bond | (Boc-homocysteine-S) | H | F | t-Bu | (dibenzofuran-4-yl) |
| 449 | 450 | bond | (Boc-homocysteine-S) | F | F | t-Bu | (dibenzofuran-4-yl) |
| 451 | 452 | CO | (Boc-homocysteine-S) | H | F | t-Bu | (dibenzofuran-4-yl) |
| 453 | 454 | CO | (Boc-homocysteine-S) | F | F | t-Bu | (dibenzofuran-4-yl) |
| 455 | 456 | SO₂ | (Boc-homocysteine-S) | H | F | t-Bu | (dibenzofuran-4-yl) |
| 457 | 458 | SO₂ | (Boc-homocysteine-S) | F | F | t-Bu | (dibenzofuran-4-yl) |

-continued
| | | | | | | | |
|---|---|---|---|---|---|---|---|
| 459 | 460 | —CH₂O— | 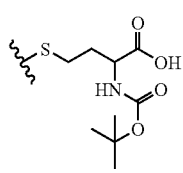 | H | F | t-Bu | 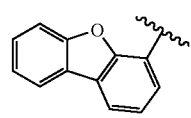 |
| 461 | 462 | —CH₂O— | 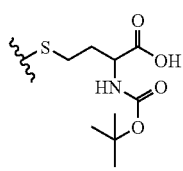 | F | F | t-Bu | 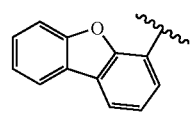 |
| 463 | 464 | bond | 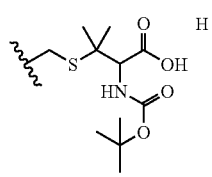 | H | 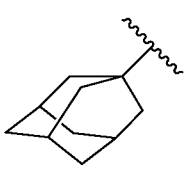 | H | H |
| 465 | 466 | bond | 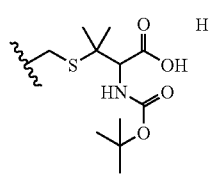 | H | 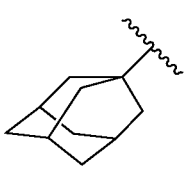 | H | H |
| 467 | 468 | CO | 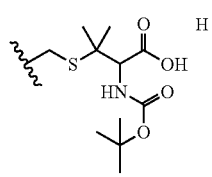 | H | 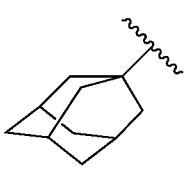 | H | H |
| 469 | 470 | CO | 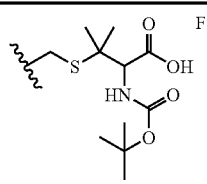 | F | 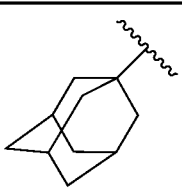 | H | H |
| 471 | 472 | SO₂ | 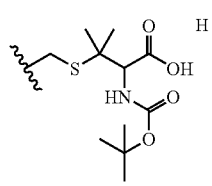 | H | 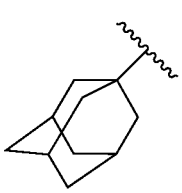 | H | H |
| 473 | 474 | SO₂ | 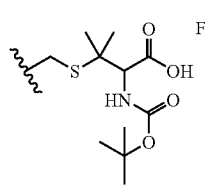 | F | 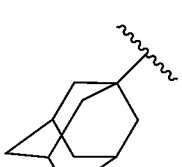 | H | H |

-continued
| | | | | | | | |
|---|---|---|---|---|---|---|---|
| 475 | 476 | —CH₂O— | 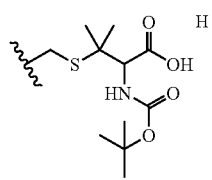 | H | 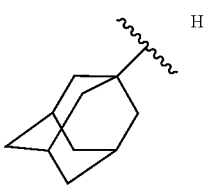 | H | H |
| 477 | 478 | —CH₂O— | 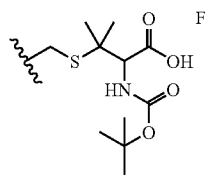 | F | 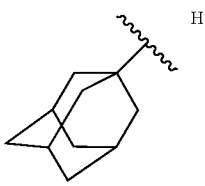 | H | H |
| 479 | 480 | bond | 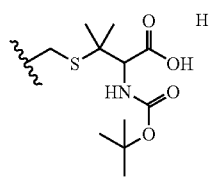 | H | 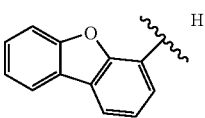 | H | H |
| 481 | 482 | bond | 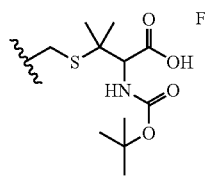 | F | 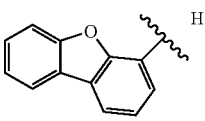 | H | H |
| 483 | 484 | CO | 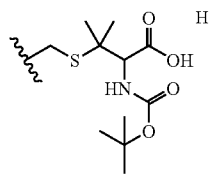 | H | 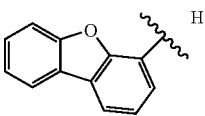 | H | H |
| 485 | 486 | CO | 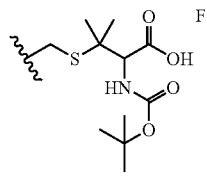 | F | 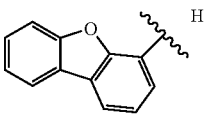 | H | H |
| 487 | 488 | SO₂ | 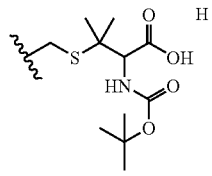 | H | 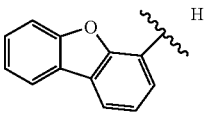 | H | H |
| 489 | 490 | SO₂ | 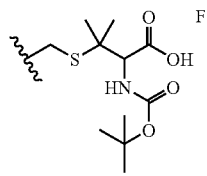 | F | 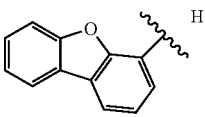 | H | H |

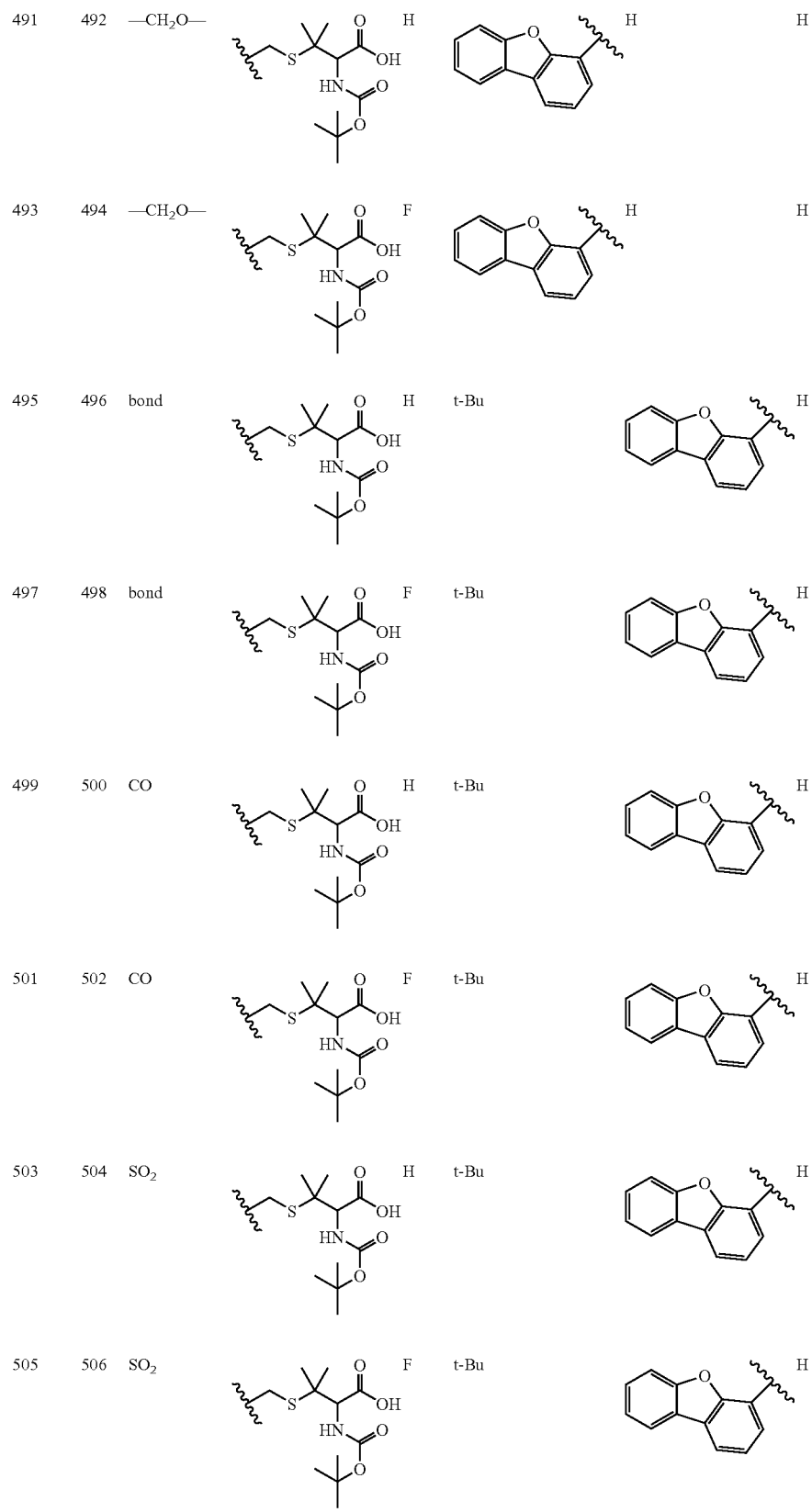

-continued

| | | | | | | | |
|---|---|---|---|---|---|---|---|
| 507 | 508 | —CH₂O— | (structure) | H | t-Bu | (dibenzofuran) | H |
| 509 | 510 | —CH₂O— | (structure) | F | t-Bu | (dibenzofuran) | H |
| 511 | 512 | | | | | | |
| 513 | 514 | bond | (structure) | F | H | (dibenzofuran) | H |
| 515 | 516 | CO | (structure) | H | H | (dibenzofuran) | H |
| 517 | 518 | CO | (structure) | F | H | (dibenzofuran) | H |
| 519 | 520 | SO₂ | (structure) | H | H | (dibenzofuran) | H |
| 521 | 522 | SO₂ | (structure) | F | H | (dibenzofuran) | H |
| 523 | 524 | —CH₂O— | (structure) | H | H | (dibenzofuran) | H |

-continued
| | | | | | | | |
|---|---|---|---|---|---|---|---|
| 525 | 526 | —CH₂O— | 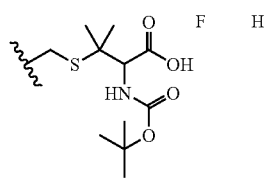 | F | H | 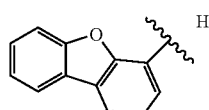 | H |
| 527 | 528 | bond | 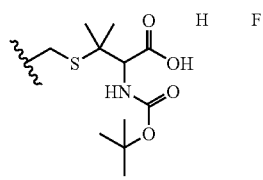 | H | F | 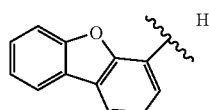 | H |
| 529 | 530 | bond | 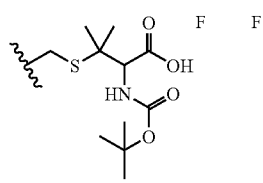 | F | F | 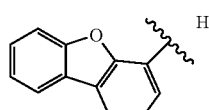 | H |
| 531 | 532 | CO | 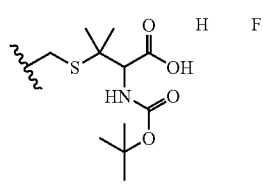 | H | F | 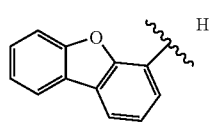 | H |
| 533 | 534 | CO | 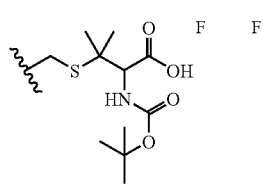 | F | F | 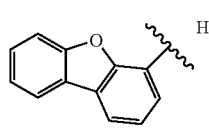 | H |
| 535 | 536 | SO₂ | 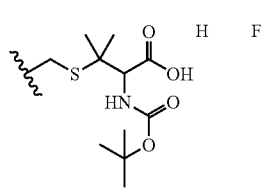 | H | F | 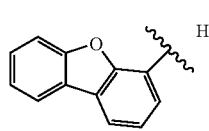 | H |
| 537 | 538 | SO₂ | 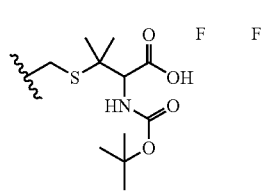 | F | F | 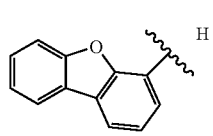 | H |
| 539 | 540 | —CH₂O— | 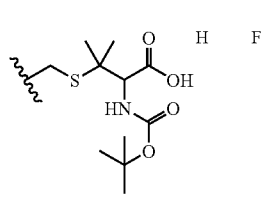 | H | F | 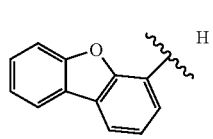 | H |

-continued
| | | | | | | | |
|---|---|---|---|---|---|---|---|
| 541 | 542 | —CH₂O— | 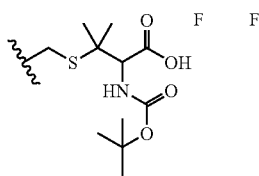 | F | F | 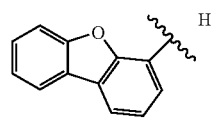 | H |
| 543 | 544 | bond | 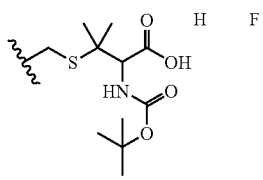 | H | F | 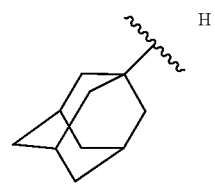 | H |
| 545 | 546 | bond | 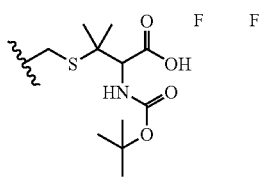 | F | F | 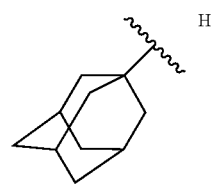 | H |
| 547 | 548 | CO | 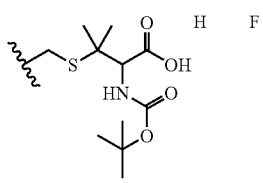 | H | F | 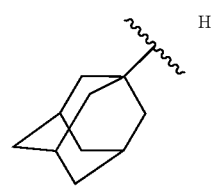 | H |
| 549 | 550 | CO | 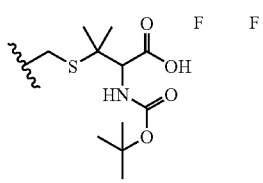 | F | F | 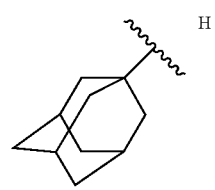 | H |
| 551 | 552 | SO₂ | 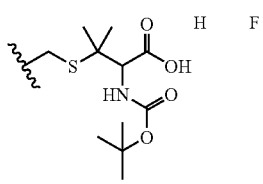 | H | F | 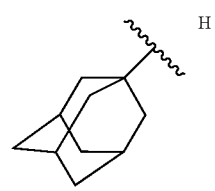 | H |
| 553 | 554 | SO₂ | 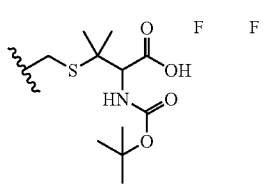 | F | F | 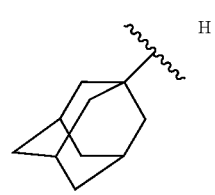 | H |
| 555 | 556 | —CH₂O— | 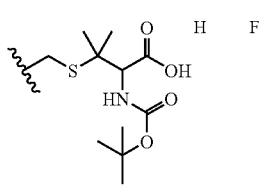 | H | F | 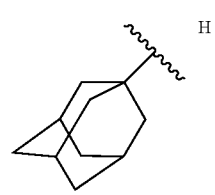 | H |

-continued
| | | | | | | | |
|---|---|---|---|---|---|---|---|
| 557 | 558 | —CH₂O— | 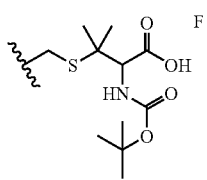 | F | F | 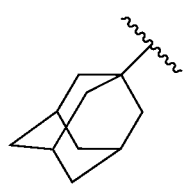 | H |
| 559 | 560 | bond | 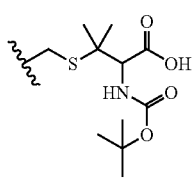 | H | t-Bu | 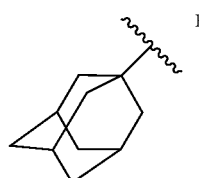 | H |
| 561 | 562 | bond | 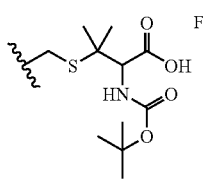 | F | t-Bu | 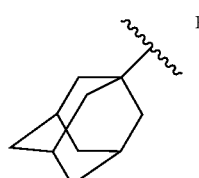 | H |
| 563 | 564 | CO | 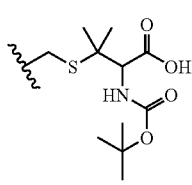 | H | t-Bu | 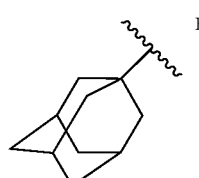 | H |
| 565 | 566 | CO | 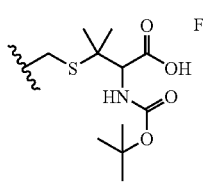 | F | t-Bu | 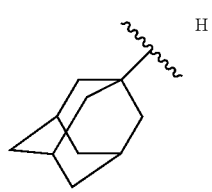 | H |
| 567 | 568 | SO₂ | 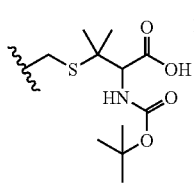 | H | t-Bu | 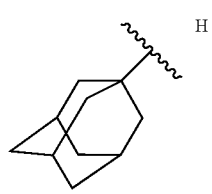 | H |
| 569 | 570 | SO₂ | 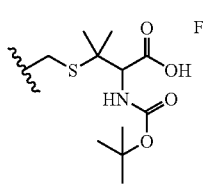 | F | t-Bu | 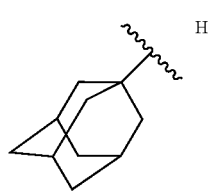 | H |
| 571 | 572 | —CH₂O— | 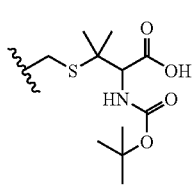 | H | t-Bu | 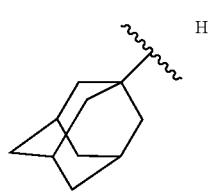 | H |

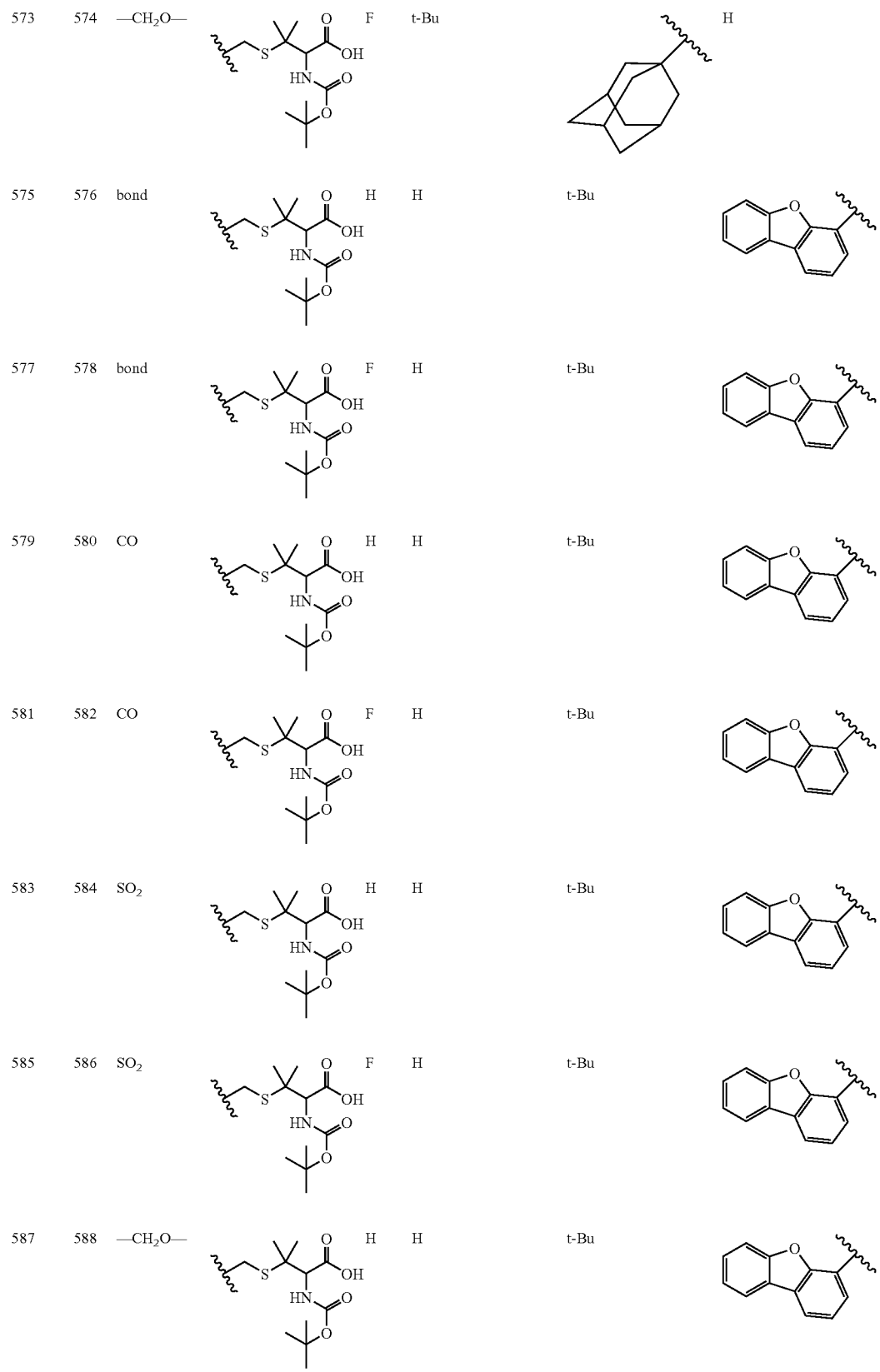

-continued

| | | 211 | | | | | 212 |
|---|---|---|---|---|---|---|---|
| 589 | 590 | —CH₂O— | (structure) | F | H | t-Bu | (dibenzofuran) |
| 591 | 592 | bond | (structure) | H | F | t-Bu | (dibenzofuran) |
| 593 | 594 | bond | (structure) | F | F | t-Bu | (dibenzofuran) |
| 595 | 596 | CO | (structure) | H | F | t-Bu | (dibenzofuran) |
| 597 | 598 | CO | (structure) | F | F | t-Bu | (dibenzofuran) |
| 599 | 600 | SO₂ | (structure) | H | F | t-Bu | (dibenzofuran) |
| 601 | 602 | SO₂ | (structure) | F | F | t-Bu | (dibenzofuran) |
| 603 | 604 | —CH₂O— | (structure) | H | F | t-Bu | (dibenzofuran) |

-continued

| | | | | | | | |
|---|---|---|---|---|---|---|---|
| 605 | 606 | —CH₂O— | [cysteine-S-CH₂ with Boc-NH, COOH, gem-dimethyl] | F | F | t-Bu | [dibenzofuran-4-yl] |
| 607 | 608 | bond | [sulfonyl-CH₂-CH(NHBoc)COOH] | H | [adamantyl] | H | H |
| 609 | 610 | bond | [sulfonyl-CH₂-CH(NHBoc)COOH] | F | [adamantyl] | H | H |
| 611 | 612 | CO | [sulfonyl-CH₂-CH(NHBoc)COOH] | H | [adamantyl] | H | H |
| 613 | 614 | CO | [sulfonyl-CH₂-CH(NHBoc)COOH] | F | [adamantyl] | H | H |
| 615 | 616 | SO₂ | [sulfonyl-CH₂-CH(NHBoc)COOH] | H | [adamantyl] | H | H |
| 617 | 618 | SO₂ | [sulfonyl-CH₂-CH(NHBoc)COOH] | F | [adamantyl] | H | H |
| 619 | 620 | —CH₂O— | [sulfonyl-CH₂-CH(NHBoc)COOH] | H | [adamantyl] | H | H |

-continued
| | | | | | | | |
|---|---|---|---|---|---|---|---|
| 621 | 622 | —CH₂O— | 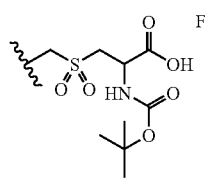 | F | 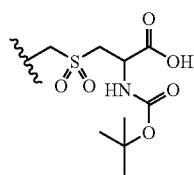 | H | H |
| 623 | 624 | bond | 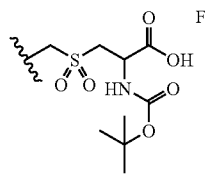 | H | 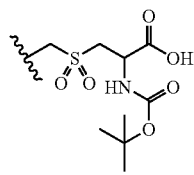 | H | H |
| 625 | 626 | bond | | F | | H | H |
| 627 | 628 | CO | 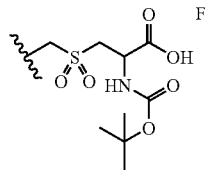 | H | | H | H |
| 629 | 630 | CO | | F | 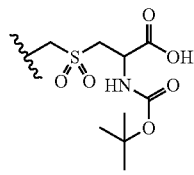 | H | H |
| 631 | 632 | SO₂ | 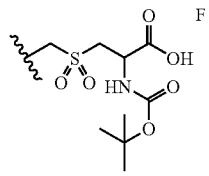 | H | | H | H |
| 633 | 634 | SO₂ | | F | | H | H |
| 635 | 636 | —CH₂O— | 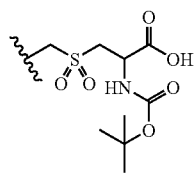 | H | | H | H |

-continued
| | | | | | | | |
|---|---|---|---|---|---|---|---|
| 637 | 638 | —CH₂O— | 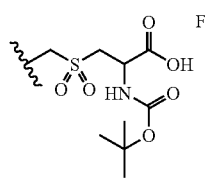 | F | 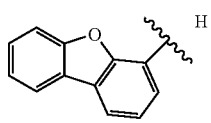 | H | H |
| 639 | 640 | bond | 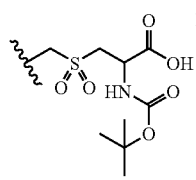 | H | t-Bu | 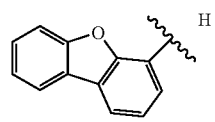 | H |
| 641 | 642 | bond | 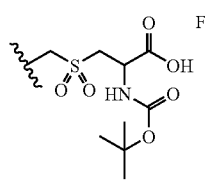 | F | t-Bu | 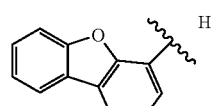 | H |
| 643 | 644 | CO | 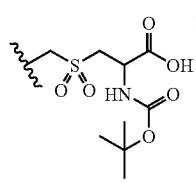 | H | t-Bu | 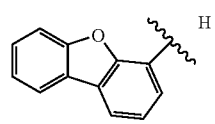 | H |
| 645 | 646 | CO | 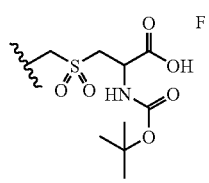 | F | t-Bu | 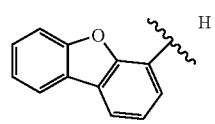 | H |
| 647 | 648 | SO₂ | 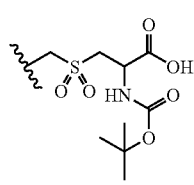 | H | t-Bu | 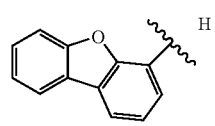 | H |
| 649 | 650 | SO₂ | 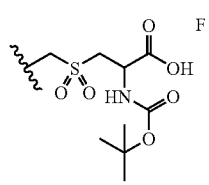 | F | t-Bu | 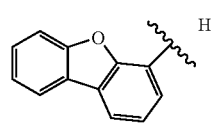 | H |
| 651 | 652 | —CH₂O— | 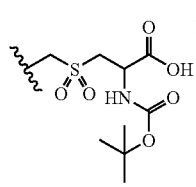 | H | t-Bu | 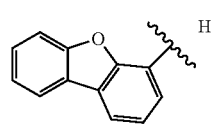 | H |

-continued
| | | | | | | | |
|---|---|---|---|---|---|---|---|
| 653 | 654 | —CH₂O— | 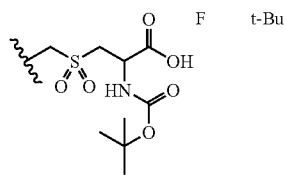 | F | t-Bu | 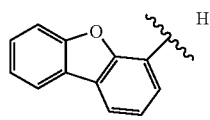 | H |
| 657 | 658 | bond | 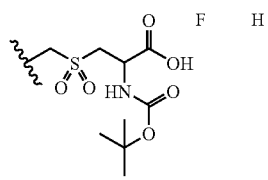 | F | H | 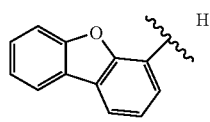 | H |
| 659 | 660 | CO | 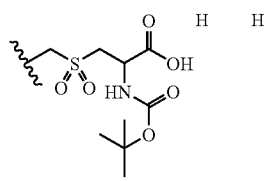 | H | H | 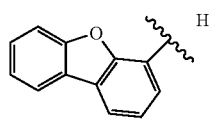 | H |
| 661 | 662 | CO | 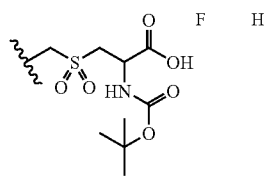 | F | H | 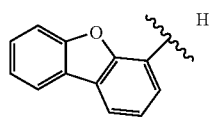 | H |
| 663 | 664 | SO₂ | 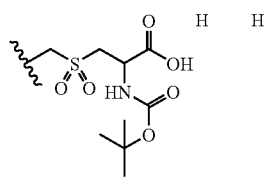 | H | H | 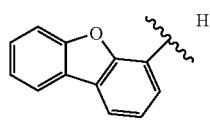 | H |
| 665 | 666 | SO₂ | 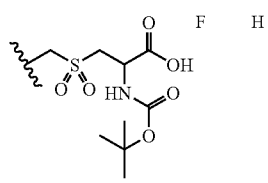 | F | H | 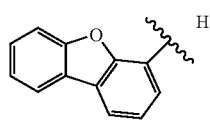 | H |
| 667 | 668 | —CH₂O— | 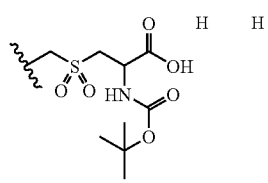 | H | H | 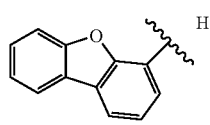 | H |
| 669 | 670 | —CH₂O— | 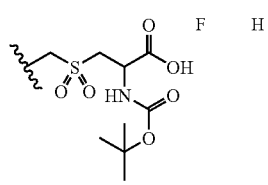 | F | H | 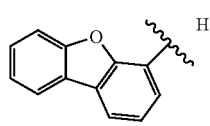 | H |

-continued
| | | | | | | | |
|---|---|---|---|---|---|---|---|
| 671 | 672 | bond | 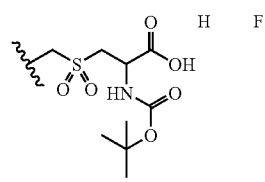 | H | F | 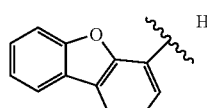 | H |
| 673 | 674 | bond | 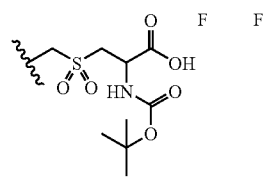 | F | F | 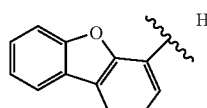 | H |
| 675 | 676 | CO | 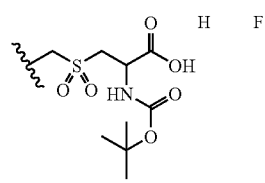 | H | F | 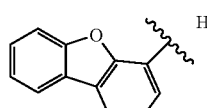 | H |
| 677 | 678 | CO | 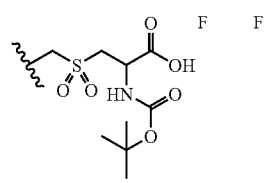 | F | F | 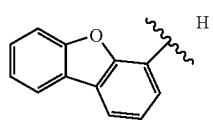 | H |
| 679 | 680 | SO$_2$ | 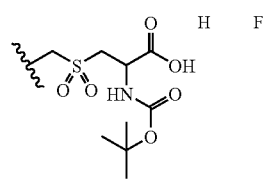 | H | F | 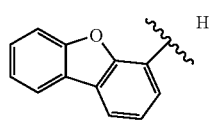 | H |
| 681 | 682 | SO$_2$ | 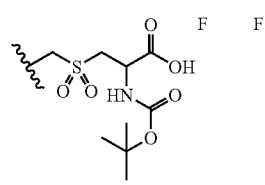 | F | F | 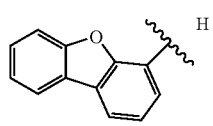 | H |
| 683 | 684 | —CH$_2$O— | 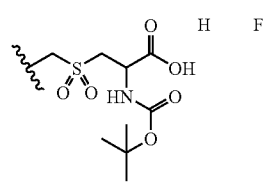 | H | F | 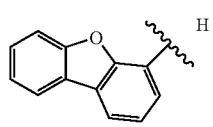 | H |
| 685 | 686 | —CH$_2$O— | 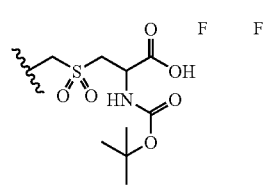 | F | F | 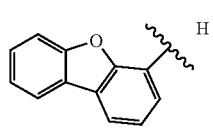 | H |

-continued
| | | | | | | | |
|---|---|---|---|---|---|---|---|
| 687 | 688 | bond | 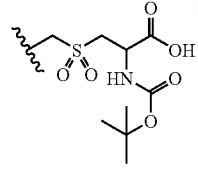 | H | F | 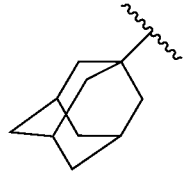 | H |
| 689 | 690 | bond | 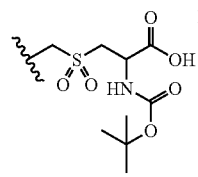 | F | F | 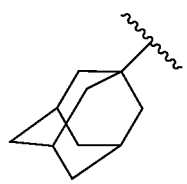 | H |
| 691 | 692 | CO | 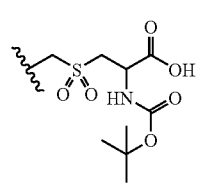 | H | F | 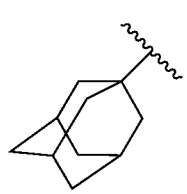 | H |
| 693 | 694 | CO | 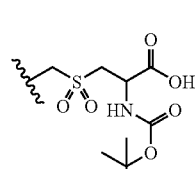 | F | F | 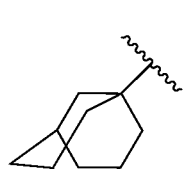 | H |
| 695 | 696 | $SO_2$ | 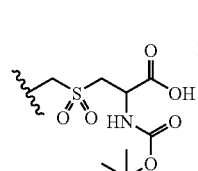 | H | F | 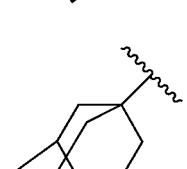 | H |
| 697 | 698 | $SO_2$ | 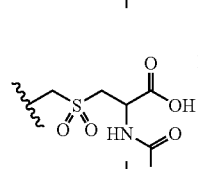 | F | F | 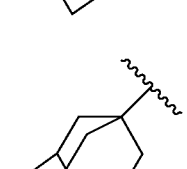 | H |
| 699 | 700 | —$CH_2O$— | 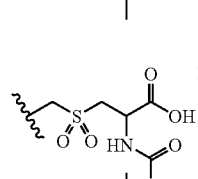 | H | F | 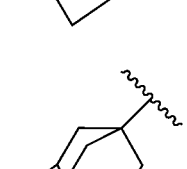 | H |
| 701 | 702 | —$CH_2O$— | 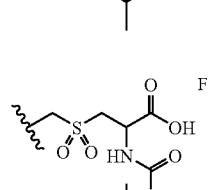 | F | F | 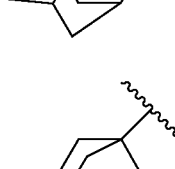 | H |

-continued
| | | | | | | | |
|---|---|---|---|---|---|---|---|
| 703 | 704 | bond | 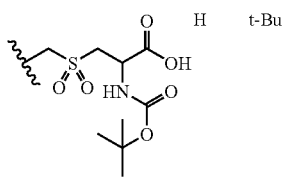 | H | t-Bu | 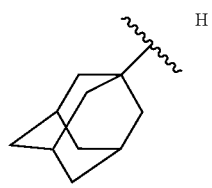 | H |
| 705 | 706 | bond | 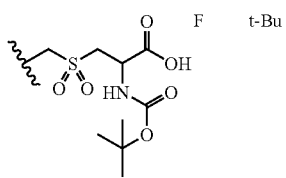 | F | t-Bu | 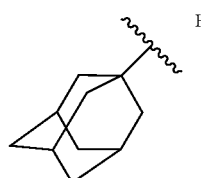 | H |
| 707 | 708 | CO | 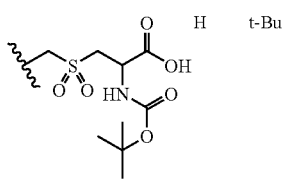 | H | t-Bu | 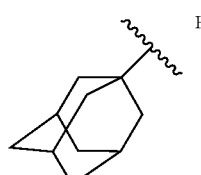 | H |
| 709 | 710 | CO | 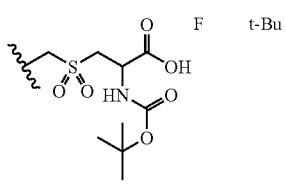 | F | t-Bu | 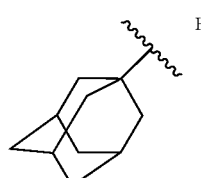 | H |
| 711 | 712 | $SO_2$ | 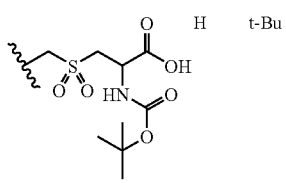 | H | t-Bu | 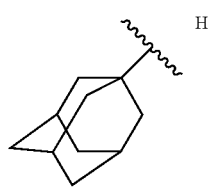 | H |
| 713 | 714 | $SO_2$ | 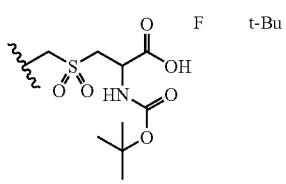 | F | t-Bu | 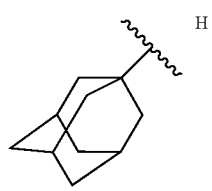 | H |
| 715 | 716 | —$CH_2O$— | 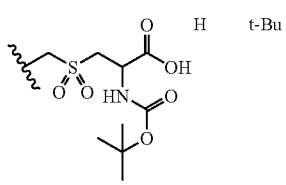 | H | t-Bu | 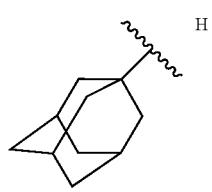 | H |
| 717 | 718 | —$CH_2O$— | 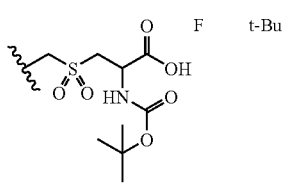 | F | t-Bu | 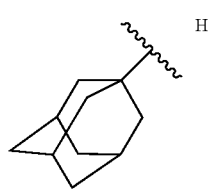 | H |

| | | | | | | | |
|---|---|---|---|---|---|---|---|
| 719 | 720 | bond | 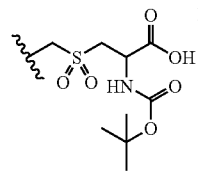 | H | H | t-Bu | 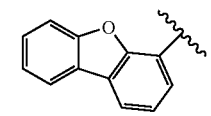 |
| 721 | 722 | bond | 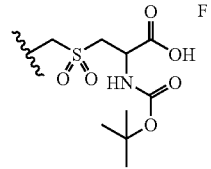 | F | H | t-Bu | 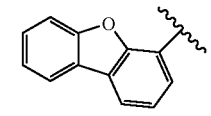 |
| 723 | 724 | CO | 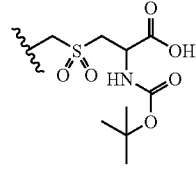 | H | H | t-Bu | 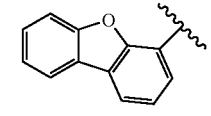 |
| 725 | 726 | CO | 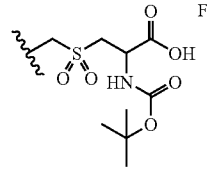 | F | H | t-Bu | 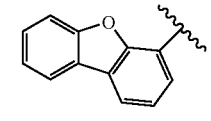 |
| 727 | 728 | SO₂ | 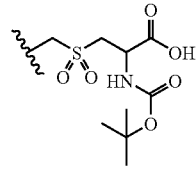 | H | H | t-Bu | 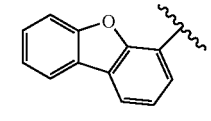 |
| 729 | 730 | SO₂ | 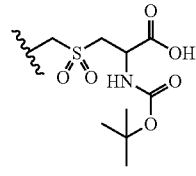 | F | H | t-Bu | 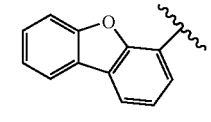 |
| 731 | 732 | —CH₂O— | 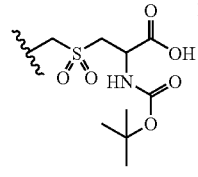 | H | H | t-Bu | 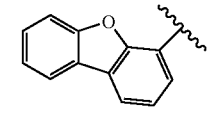 |
| 733 | 734 | —CH₂O— | 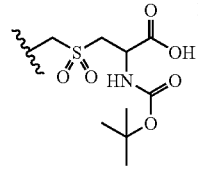 | F | H | t-Bu | 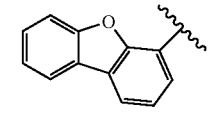 |

-continued
| | | | | | | | |
|---|---|---|---|---|---|---|---|
| 735 | 736 | bond | 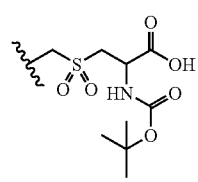 | H | F | t-Bu | 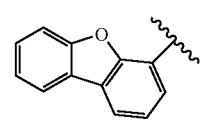 |
| 737 | 738 | bond | 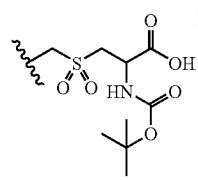 | F | F | t-Bu | 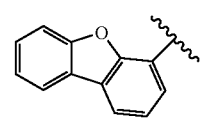 |
| 739 | 740 | CO | 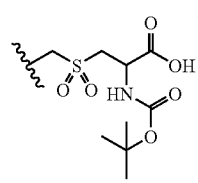 | H | F | t-Bu | 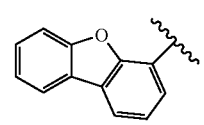 |
| 741 | 742 | CO | 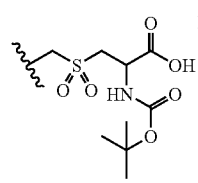 | F | F | t-Bu | 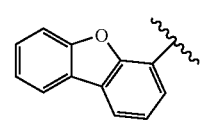 |
| 743 | 744 | $SO_2$ | 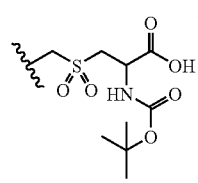 | H | F | t-Bu | 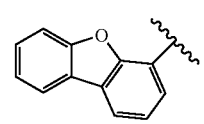 |
| 745 | 746 | $SO_2$ | 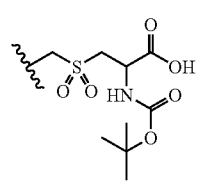 | F | F | t-Bu | 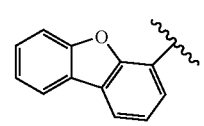 |
| 747 | 748 | —$CH_2O$— | 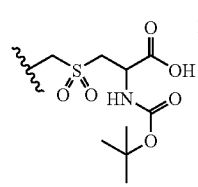 | H | F | t-Bu | 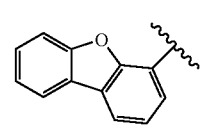 |
| 749 | 750 | —$CH_2O$— | 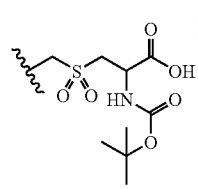 | F | F | t-Bu | 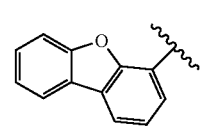 |

EXAMPLE 139

The following compounds are prepared essentially according to the methods and procedures set forth above.

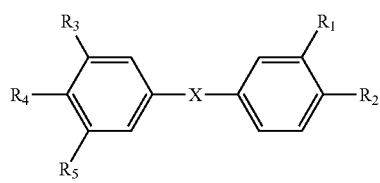

| Cmpd. No. | X | R₁ | R₂ | R₃ | R₄ | R₅ |
|---|---|---|---|---|---|---|
| 751 | bond | (homocysteine-S-linked, N-Boc, COOH) | H | H | (dibenzofuran-4-yl) | H |
| 752 | bond | (cysteine sulfone-S-linked via CH₂, N-Boc, COOH) | H | H | (dibenzofuran-4-yl) | H |
| 753 | bond | (cysteine-S-linked via CH₂, N-Boc, COOH) | H | H | (dibenzofuran-4-yl) | H |
| 754 | bond | (serine-O-linked via CH₂CH₂, N-Boc, COOH) | H | H | (dibenzofuran-4-yl) | H |

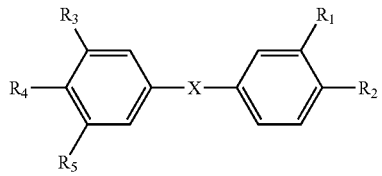

| Cmpd. No. | X | R₁ | R₂ | R₃ | R₄ | R₅ |
|---|---|---|---|---|---|---|
| 755 | bond | 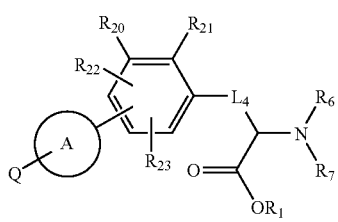 | H | H | dibenzofuranyl | H |

EXAMPLE 140

Method for Measuring PTP-1B Activity

The test compounds are evaluated for their in vitro inhibitory activity against recombinant human PTP1B with phosphotyrosyl dodecapeptide TRDI(P)YETD(P)Y(P)YRK. This corresponds to the 1142-1153 insulin receptor kinase regulatory domain, phosphorylated on the 1146, 1150 and 1151 tyrosine residues; IR-triphosphopeptide as a source of substrate. Enzyme reaction progression is monitored via the release of inorganic phosphate as detected by the malachite green—ammonium molybdate method for the phosphopeptide.

Preferred compounds of the invention exhibit $IC_{50}$ values of less than 10 μM; more preferred compounds of the invention exhibit $IC_{50}$ values of less than 1 μM. Particularly preferred compounds exhibit $IC_{50}$ values of less than 300 nM.

All references disclosed herein are hereby incorporated by reference for all purposes.

The invention and the manner and process of making and using it, are now described in such full, clear, concise and exact terms as to enable any person skilled in the art to which it pertains, to make and use the same. It is to be understood that the foregoing describes preferred embodiments of the invention and that modifications may be made therein without departing from the spirit or scope of the invention.

What is claimed is:

1. A compound of the formula or a pharmaceutically acceptable salt thereof, wherein
$R_1$ is H, $C_1$-$C_6$ alkyl, or phenyl ($C_1$-$C_6$)alkyl;
$R_6$ is hydrogen or $C_1$-$C_6$ alkyl;
$R_7$ is ($C_2$-$C_6$) alkanoyl, ($C_1$-$C_6$) alkoxycarbonyl, —C(O)NH$_2$, —C(O)NH($C_1$-$C_6$)alkyl, or —C(O)N($C_1$-$C_6$)alkyl($C_1$-$C_6$)alkyl;
$R_{20}$, $R_{21}$, $R_{22}$, and $R_{23}$ are independently selected from H, arylalkoxy, arylalkyl, halogen, alkyl, OH, alkoxy, NO$_2$, NH$_2$, NH ($C_1$-$C_6$)alkyl, N($C_1$-$C_6$)alkyl ($C_1$-$C_6$)alkyl, NH-aryl, N($C_1$-$C_4$)alkyl-aryl, —NHSO$_2$-aryl, —N($C_1$-$C_4$alkyl)SO$_2$aryl, wherein the aryl group is optionally substituted with 1, 2, 3, or 4 groups that are independently $C_1$-$C_6$ alkyl, $C_1$-$C_6$ alkoxy, halogen, OH, NO$_2$, $C_1$-$C_4$ haloalkyl, $C_1$-$C_4$ haloalkoxy;
$L_4$ is —($C_1$-$C_6$)alkyl-, —O—$C_1$-$C_6$ alkyl-, or $C_1$-$C_6$ alkyl-O—;
the A-ring is phenyl optionally substituted with 1, 2, 3, or 4 groups that are independently, halogen, $C_1$-$C_4$ alkyl, $C_1$-$C_4$ alkoxy, $C_1$-$C_4$ haloalkyl, $C_1$-$C_4$ haloalkoxy, NO$_2$, NH$_2$, NH($C_1$-$C_6$)alkyl, or N($C_1$-$C_6$)alkyl ($C_1$-$C_6$)alkyl; and
Q is -heteroaryl-($C_1$-$C_4$)alkyl-aryl, heteroaryl, heterocycloalkyl, each of which is optionally substituted with 1, 2, 3, 4, or 5 groups that are independently alkoxycarbonyl, $C_1$-$C_6$ alkyl, $C_1$-$C_6$ alkoxy, halogen, $C_1$-$C_6$ alkanoyl, $C_1$-$C_4$ haloalkyl, $C_1$-$C_4$ haloalkoxy, NH$_2$, NH($C_1$-$C_6$)alkyl, N($C_1$-$C_6$)alkyl($C_1$-$C_6$)alkyl, phenyl, $C_1$-$C_6$ alkanoyl.

2. A compound according to claim 1, wherein
Q is -benzofuranyl-($C_1$-$C_4$)alkyl-phenyl, -pyridyl-($C_1$-$C_4$)alkyl-phenyl, -dibenzofuranyl-($C_1$-$C_4$)alkyl-phenyl, indolyl-($C_1$-$C_4$)alkyl-phenyl, benzo[b]thienyl-($C_1$-$C_4$)alkyl-phenyl, indolyl benzo[d][1,3]dioxolyl, 2,3-dihydrobenzo[b][1,4]dioxinyl, dibenzothienyl, indolinyl, benzofuranyl, benzimidazolyl, 1,2,3,4-tetrahydroquinolinyl, 1,2,3,4-tetrahydroisoquinolinyl, or dibenzofuranyl, each of which is optionally substituted with 1, 2, 3, 4, or 5 groups that are independently alkoxycarbonyl, $C_1$-$C_6$ alkyl, $C_1$-$C_6$ alkoxy, halogen, $C_1$-$C_4$ haloalkyl, $C_1$-$C_4$ haloalkoxy, NH$_2$, NH($C_1$-$C_6$)alkyl, N($C_1$-$C_6$)alkyl($C_1$-$C_6$)alkyl, phenyl or $C_1$-$C_6$ alkanoyl.

3. A compound according to claim 2, wherein
$R_1$ is H, $C_1$-$C_6$ alkyl, or benzyl;
$R_{20}$, $R_{21}$, $R_{22}$, and $R_{23}$ are independently selected from H, benzyloxy, benzyl, halogen, $C_1$-$C_6$ alkyl, OH, $C_1$-$C_6$ alkoxy, NO$_2$, NH$_2$, NH($C_1$-$C_6$)alkyl, N($C_1$-$C_6$)alkyl($C_1$-

$C_6$)alkyl, NH-aryl, N($C_1$-$C_4$)alkyl-aryl, —$NHSO_2$-phenyl, —N($C_1$-$C_4$ alkyl)$SO_2$phenyl, wherein the phenyl group is optionally substituted with 1, 2, 3, or 4 groups that are independently $C_1$-$C_6$ alkyl, $C_1$-$C_6$ alkoxy, halogen, OH, $NO_2$, $C_1$-$C_2$ haloalkyl, $C_1$-$C_2$ haloalkoxy.

4. A compound according to claim 1, of the formula

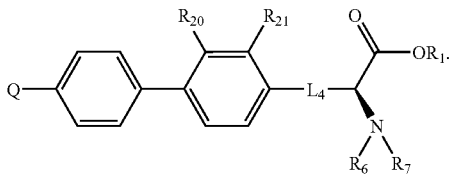

5. A compound according to claim 4, wherein
Q is -benzofuranyl-($C_1$-$C_4$)alkyl-phenyl, -dibenzofuranyl-($C_1$-$C_4$)alkyl-phenyl, indolyl, benzofuranyl, benzimidazolyl, 1,2,3,4-tetrahydroquinolinyl, 1,2,3,4-tetrahydroisoquinolinyl, or dibenzofuranyl, each of which is optionally substituted with 1, 2, 3, 4, or 5 groups that are independently $C_1$-$C_6$ alkoxycarbonyl, $C_1$-$C_6$ alkyl, $C_1$-$C_6$ alkoxy, halogen, $CF_3$, $OCF_3$, $NH_2$, NH($C_1$-$C_6$)alkyl, N($C_1$-$C_6$)alkyl($C_1$-$C_6$)alkyl, or phenyl.

6. A compound according to claim 5, wherein
Q is -benzofuranyl-($C_1$-$C_4$)alkyl-phenyl, indolyl, 1,2,3,4-tetrahydroquinolinyl, 1,2,3,4-tetrahydroisoquinolinyl, or dibenzofuranyl, each of which is optionally substituted with 1, 2, 3, 4, or 5 groups that are independently $C_1$-$C_6$ alkoxycarbonyl, $C_1$-$C_6$ alkyl, $C_1$-$C_6$ alkoxy, halogen, $CF_3$, $OCF_3$, $NH_2$, NH($C_1$-$C_6$)alkyl, or N($C_1$-$C_6$)alkyl($C_1$-$C_6$)alkyl.

7. A compound according to claim 4, wherein
$R_{20}$, and $R_{21}$ are independently selected from H, benzyloxy, benzyl, halogen, $C_1$-$C_6$ alkyl, OH, $C_1$-$C_6$ alkoxy, $NO_2$, $NH_2$, NH($C_1$-$C_6$)alkyl, or N($C_1$-$C_6$)alkyl($C_1$-$C_6$) alkyl.

8. A pharmaceutical composition comprising a compound of claim 1 and at least one pharmaceutically acceptable solvent, carrier, adjuvant or excipient.

9. A compound according to claim 1 that is selected from the group consisting of
2-tert-Butoxycarbonylamino-3-(3'-dibenzofuran-4-yl-biphen-3-ylmethoxy)propanoic acid;
(L)-2-tert-Butoxycarbonylamino-4-(3'-dibenzofuran-4-yl-biphenyl-4-yloxy)-butyric acid;
(L)-2-tert-Butoxycarbonylamino-4-(3'-dibenzofuran-4-yl-biphenyl-3-yloxy)-butyric acid;
(L)-2-tert-Butoxycarbonylamino-4-(4'-dibenzofuran-4-yl-biphenyl-3-yloxy)-butyric acid;
(L)-2-tert-Butoxycarbonylamino-5-(3'-dibenzofuran-4-yl-biphenyl-3-yl)-pent-4-enoic acid;
(L)-2-tert-Butoxycarbonylamino-5-(3'-dibenzofuran-4-yl-biphenyl-3-yl)-pentanoic acid;
and pharmaceutically acceptable salts thereof.

10. A method for treating a disease selected from Type 2 diabetes, and obesity, comprising administering to a patient in need of such treatment an effective amount of a compound according to claim 1.

11. A method according to claim 10, wherein the disease is Type 2 diabetes.

\* \* \* \* \*